United States Patent
Kimmelman et al.

(10) Patent No.: US 10,350,264 B2
(45) Date of Patent: Jul. 16, 2019

(54) COMPOSITIONS AND METHODS FOR MODULATING NCOA4-MEDIATED AUTOPHAGIC TARGETING OF FERRITIN

(71) Applicants: Dana-Farber Cancer Institute, Inc., Boston, MA (US); President and Fellows of Harvard College, Cambridge, MA (US); Beth Israel Deaconess Medical Center, Inc., Boston, MA (US); Brigham & Women's Hospital, Inc., Boston, MA (US)

(72) Inventors: Alec C. Kimmelman, Weston, MA (US); Joseph D. Mancias, Boston, MA (US); Jeffrey Wade Harper, Wellesley, MA (US)

(73) Assignees: Dana-Farber Cancer Institute, Inc., Boston, MA (US); President and Fellows of Harvard College, Cambridge, MA (US); Beth Israel Deaconess Medical Center, Inc., Boston, MA (US); The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/126,350

(22) PCT Filed: Mar. 27, 2015

(86) PCT No.: PCT/US2015/023142
§ 371 (c)(1),
(2) Date: Sep. 15, 2016

(87) PCT Pub. No.: WO2015/149006
PCT Pub. Date: Oct. 1, 2015

(65) Prior Publication Data
US 2017/0182119 A1     Jun. 29, 2017

Related U.S. Application Data

(60) Provisional application No. 61/971,419, filed on Mar. 27, 2014, provisional application No. 61/990,544, filed on May 8, 2014.

(51) Int. Cl.
| | | |
|---|---|---|
| A61K 38/17 | (2006.01) | |
| A61K 31/713 | (2006.01) | |
| C12N 15/11 | (2006.01) | |
| G01N 33/50 | (2006.01) | |

(52) U.S. Cl.
CPC ........ A61K 38/1709 (2013.01); A61K 31/713 (2013.01); C12N 15/11 (2013.01); G01N 33/5008 (2013.01); A61K 2121/00 (2013.01)

(58) Field of Classification Search
CPC ............ A61K 38/1709; A61K 39/0011; C07K 16/22; C07K 2317/622; C12N 2310/3513
See application file for complete search history.

(56) References Cited

U.S. PATENT DOCUMENTS

| | | |
|---|---|---|
| 4,046,722 A | 9/1977 | Rowland |
| 4,046,784 A | 9/1977 | Gipson |
| 4,331,647 A | 5/1982 | Goldenberg |
| 4,348,376 A | 9/1982 | Goldenberg |
| 4,361,544 A | 11/1982 | Goldenberg |
| 4,444,744 A | 4/1984 | Goldenberg |
| 4,460,459 A | 7/1984 | Shaw et al. |
| 4,460,561 A | 7/1984 | Goldenberg |
| 4,468,457 A | 8/1984 | Goldenberg |
| 4,624,846 A | 11/1986 | Goldenberg |
| 4,671,958 A | 6/1987 | Rodwell et al. |
| 4,814,470 A | 3/1989 | Colin et al. |
| 4,818,709 A | 4/1989 | Primus |
| 4,857,653 A | 7/1989 | Colin |
| 4,924,011 A | 5/1990 | Denis |
| 5,034,506 A | 7/1991 | Summerton |
| 5,093,246 A | 3/1992 | Cech |
| 5,270,163 A | 12/1993 | Gold et al. |
| 5,290,957 A | 3/1994 | Correa |
| 5,292,921 A | 3/1994 | Correa |
| 5,332,567 A | 7/1994 | Goldenberg |
| 5,438,072 A | 8/1995 | Bobee |
| 5,443,953 A | 8/1995 | Hansen |
| 5,541,297 A | 7/1996 | Hansen |
| 5,587,493 A | 12/1996 | Bouchard |

(Continued)

FOREIGN PATENT DOCUMENTS

| | | |
|---|---|---|
| EP | 0 253 738 | 1/1988 |
| WO | WO 1991/17976 | 11/1991 |

(Continued)

OTHER PUBLICATIONS

GenBank, BC085086.1, accessed on line at https://www.ncbi.nlm.nih.gov/nuccore/BC085086 on Aug. 24, 2018. (Year: 2018).*

UniProtKB—P02792, accessed online at https://www.uniprot.org/uniprot/P02792, on Aug. 24, 2018. (Year: 2018).*

Altschul et al., *Gapped BLAST and PSI-BLAST: a new generation of protein database search programs*, Nucleic Acids Res. 25(17):33893402 (1997).

Altschul et al., *Basic local alignment search tool*, J Mol Biol, 215(3):403-410 (1990).

Arora et al., *c-Myc antisense limits rat liver regeneration and indicates role for c-Myc in regulating cytochrome P-450 3A activity*, J. Pharmacol. Exp. Ther.;292(3):921-928 (2000).

(Continued)

*Primary Examiner* — Rachael E Bredefeld
*Assistant Examiner* — Kaipeen E Yang
(74) *Attorney, Agent, or Firm* — Fish & Richardson P.C.

(57) ABSTRACT

Described herein are methods of modulating autophagic targeting of ferritin in a cell, wherein the method comprises modulating the level and/or activity of nuclear receptor coactivator 4 (NCOA4) in the cell. Also provided are related methods of treatment.

8 Claims, 52 Drawing Sheets

Specification includes a Sequence Listing.

(56) References Cited

U.S. PATENT DOCUMENTS

| | | | |
|---|---|---|---|
| 5,601,825 | A | 2/1997 | Hansen |
| 5,637,288 | A | 6/1997 | Goldenberg |
| 5,637,684 | A | 6/1997 | Cook |
| 5,677,427 | A | 10/1997 | Goldenberg |
| 5,677,437 | A | 10/1997 | Teng |
| 5,686,578 | A | 11/1997 | Goldenberg |
| 5,698,178 | A | 12/1997 | Goldenberg |
| 5,780,607 | A | 7/1998 | Goodnow, Jr. |
| 5,783,682 | A | 7/1998 | Cook |
| 5,792,844 | A | 7/1998 | Sanghvi |
| 5,789,554 | A | 8/1998 | Leung |
| 5,811,234 | A | 9/1998 | Roninson |
| 5,814,500 | A | 9/1998 | Dietz |
| 5,922,302 | A | 7/1999 | Goldenberg |
| 6,004,940 | A | 12/1999 | Marasco |
| 6,187,287 | B1 | 2/2001 | Leung |
| 6,319,500 | B1 | 11/2001 | Goldenberg |
| 2001/0024831 | A1 | 9/2001 | Der Maur et al. |
| 2003/0211609 | A1 | 11/2003 | Cowsert et al. |
| 2006/0270591 | A1 | 11/2006 | Chang |

FOREIGN PATENT DOCUMENTS

| | | |
|---|---|---|
| WO | WO 1991/19813 | 12/1991 |
| WO | WO 1993/00928 | 1/1993 |
| WO | WO 1993/00929 | 1/1993 |
| WO | WO 1994/02610 | 2/1994 |
| WO | WO 1996/01815 | 1/1996 |
| WO | WO 1996/39154 | 12/1996 |
| WO | WO 1997/03211 | 1/1997 |
| WO | 2010/017257 | 2/2010 |
| WO | WO 2015/149006 | 10/2015 |

OTHER PUBLICATIONS

Asano, T. et al. *Distinct mechanisms of ferritin delivery to lysosomes in iron-depleted and iron-replete cells*, Mol Cell Biol 31(10):2040-2052 (2011).

Barringer et al., *Blunt-end and single-strand ligations by Escherichia coli ligase: influence on an in vitro amplification scheme*, Gene 89(1):117 (1990).

Battle et al., *The natural product honokiol induces caspase-dependent apoptosis in B-cell chronic lymphocytic leukemia (B-CLL) cells*, Blood, 106(2):690-697 (2005).

Beatty, et al. *CD40 agonists alter tumor stroma and show efficacy against pancreatic carcinoma in mice and humans*, Science 331(6024):1612-1616 (2011).

Behrends, et al. *Network organization of the human autophagy system*, Nature; 466(7302):68-76 (2010).

Bekker-Jensen et al., *HERC2 coordinates ubiquitin-dependent assembly of DNA repair factors on damaged chromosomes*, Nat Cell Biol 12(1):80-86 (2020).

Bernstein et al., *Role for a bidentate ribonuclease in the initiation step of RNA interference*, Nature, 409(6818):363-366 (2001).

Blomster-Hautamaa and Schlievert, *Preparation of toxic shock syndrome toxin-1*, Methods Enzymol 165:37-43 (1988).

Brady et al., *Therapeutic and diagnostic uses of modified monoclonal antibodies*, nt. J. Rad. Oncol. Biol. Phys. 13(10):1535-1544 (1987).

Brummelkamp et al., *A system for stable expression of short interfering RNAs in mammalian cells*, Science, 296(5567):550-553 (2002).

Chehab et al. *Detection of specific DNA sequences by fluorescence amplification: a color complementation assay*, Proc. Natl. Acad. Sci. USA, 86: 9178-9182 (1989).

Carpet et al., *Multiple sequence alignment with hierarchical clustering*, Nucl. Acids Res., 16(22):10881-10890 (1988).

Crinelli et al., *Locked nucleic acids (LNA): versatile tools for designing oligonucleotide decoys with high stability and affinity*, Curr. Drug Targets 5(8):745-752 (2004).

De Domenico, et al. *Ferroportin-mediated mobilization of ferritin iron precedes ferritin degradation by the proteasome*, EMBO Journal, 25(22):5396-5404 (2006).

Donzéand Picard, *RNA interference in mammalian cells using siRNAs synthesized with T7 RNA polymerase*, Nucleic Acids Res.; 30(10):e46 (2002).

Egholm, M., et al. *PNA Hybridizes to Complementary Oligonucleotides Obeying the Watson-Crick Hydrogen Bonding Rules*, Nature, 365(6446):566-568 (1993).

Elbashir et al., *RNA interference is mediated by 21- and 22-nucleotide RNAs*, Genes Dev. 15(2):188-200 (2001).

Elbashir, et al., *Duplexes of 21-nucleotide RNAs mediate RNA interference in cultured mammalian cells*, Nature; 411(6836): 494-498 (2001).

Ferris, et al. *Tumor antigen-targeted, monoclonal antibody-based immunotherapy: clinical response, cellular immunity, and immunoescape*, J. Clin. Oncol. 28(28):4390-4399 (2010).

Gao, T., et al. *RFG (ARA70, ELE1) interacts with the human androgen receptor in a ligand-dependent fashion, but functions only weakly as a coactivator in cotransfection assays*, Mol Endocrinology 13(10):1645-1656(1999).

Gao, W., et al. *Biochemical isolation and characterization of the tubulovesicular LC3-positive autophagosomal compartment*, J Biol Chem, 285(2):1371-1383 (2010).

Gautier et al., *Alpha-DNA. IV: Alpha-anomeric and beta-anomeric tetrathymidylates covalently linked to intercalating oxazolopyridocarbazole. Synthesis, physicochemical properties and poly (rA) binding*, Nucl. Acids Res. 15(16):6625-6641 (1987).

Gibson et al., *A novel method for real time quantitative RT-PCR*, Genome Research 6(10):995-1001, (1996).

Griffiths, et al. *The ins and outs of human reticulocyte maturation: autophagy and the endosome/exosome pathway*, Autophagy, 8(7):1150-1151 (2012).

Guatelli et al. *Isothermal, in vitro amplification of nucleic acids by a multienzyme reaction modeled after retroviral replication*, Proc. Nat. Acad. Sci. USA 87(5):1874-8 (1990).

Hammond et al., *Post-transcriptional gene silencing by double-stranded RNA*, Nature Genet. 2 (2): 110-119 (2001).

Haseloff and Gerlach, *Simple RNA enzymes with new and highly specific endoribonuclease activities*, Nature; 334(6183):585-591 (1988).

Heasman et al., *Beta-catenin signaling activity dissected in the early Xenopus embryo: a novel antisense approach*, Dev. Biol., 222(1):124-134 (2000).

Heid et al., *Real time quantitative PCR*, Genome Research 6(10):986-994 (1996).

Heller, MJ, *DNA microarray technology: devices, systems, and applications*, Annu Rev Biomed Eng. 4:129-53 (2002).

Higgins et al., *CLUSTAL: a package for performing multiple sequence alignment on a microcomputer*, Gene, 73(1):237-244 (1988).

Higgins et al., *Fast and sensitive multiple sequence alignments on a microcomputer*, CABIOS, 5(2):151-153 (1989).

Huang et al., *Parallelization of a local similarity algorithm*, CABIOS, 8(2):155 (1992).

Huttlin, et al. *A tissue-specific atlas of mouse protein phosphorylation and expression*, Cell 143(7): 1174-1189 (2010).

Jepsen and Wengel, *LNA-antisense rivals siRNA for gene silencing*, Curr. Opin. Drug Discov. Devel., 7(2):188-194 (2004).

Karlin and Altschul, *Methods for assessing the statistical significance of molecular sequence features by using general scoring schemes*, Proc. Natl. Acad. Sci. USA, 87(6):2264-2268 (1990).

Karlin and Altschul, *Applications and statistics for multiple high-scoring segments in molecular sequences*, Proc. Natl. Acad. Sci. USA, 90(12):5873-5877 (1993).

Kidane, et al. *Release of iron from ferritin requires lysosomal activity*, Am J Physiol. Cell Physiol 291(3):C445-455 (2006).

Kimmelman, AC, *The dynamic nature of autophagy in cancer* Genes Dev 25(19):1999-2010 (2011).

Kirkin, et al. *A role for ubiquitin in selective autophagy*, Mol Cell 34(3):259-269, (2009).

Koga, et al. FASEB Journal, *Altered lipid content inhibits autophagic vesicular fusion*, 24(8):3052-3065(2010).

(56) References Cited

OTHER PUBLICATIONS

Kurz, et al. *Intralysosomal iron chelation protects against oxidative stress-induced cellular damage*, FEBS Journal, 273(13):3106-3117 (2006).
Kwoh et al. *Transcription-based amplification system and detection of amplified human immunodeficiency virus type 1 with a bead-based sandwich hybridization format*, Proc. Natl. Acad. Sci. USA 86(4):1173-7 (1989).
Landegren et al. *A ligase-mediated gene detection technique*, Science 241(4869):1077-80 (1988).
Lo et al. *Intracellular antibodies (intrabodies) and their therapeutic potential*, Handb Exp Pharmacol.181:343-73 (2009).
Lockhart et al. *Expression monitoring by hybridization to high-density oligonucleotide arrays*, Nature Biotechnology, 14:1675-1680 (1996).
Lopes, et al. *Cytoscape Web: an interactive web-based network browser*, Bioinformatics 26(18):2347-2348 (2010).
Marasco, W.A. *Intrabodies: turning the humoral immune system outside in for intracellular immunization*, Gene Therapy 4(1):11-15 (1997).
Martinez-Noel, et al. *Identification and proteomic analysis of distinct UBE3A/E6AP protein complexes*, Mol Cell Biol 32(15):3095-3106 (2012).
Marzella, et al., *Isolation of autophagic vacuoles from rat liver: morphological and biochemical characterization*, J Cell Biol, 93(1):144-154 (1982).
Mata *A hexameric phosphorothioate oligonucleotide telomerase inhibitor arrests growth of Burkitt's lymphoma cells in vitro and in vivo*, Toxicol. Appl. Pharmacol. 144(1):189-197 (1997).
McManus et al., *Gene silencing in mammals by small interfering RNAs*, Nature Reviews Genetics, 3(10):737-47 (2002).
Milligan et al., *Current concepts in antisense drug design*, J. Med. Chem. 36(14):1923-1937 (1993).
Musolino, et al. *Immunoglobulin G fragment C receptor polymorphisms and clinical efficacy of trastuzumab-based therapy in patients with HER-2/neu positive metastatic breast cancer*, J. Clin. Oncol. 26(11):1789-1796 (2008).
Myers and Miller, *Optimal alignments in linear space*, CABIOS, 4(1):11-17 (1988).
Nasevicius and Ekker, *Effective targeted gene 'knockdown' in zebrafish*, Nat. Genet. 26(2).216-220 (2000).
Needleman and Wunsch, *A General Method Applicable to the Search for Similarities in the Amino Acid Sequence of Two Proteins*, J. Mol. Biol. 48:443-453 (1970).
Nielsen et al., *Sequence-selective recognition of DNA by strand displacement with a thymine-substituted polyamide*, Science 254(5037):1497-500 (1991).
Nielsen, P.E. *PNA Technology*, Mol Biotechnol. 26(3):233-48 (2004).
Nielsen, P.E. *Triple Helix: Designing a New Molecule of Life*, Scientific American, (Dec. 2008).
Overbye, et al., *Proteomic analysis of membrane-associated proteins from rat liver autophagosomes*, Autophagy; 3(4):300-322 (2007).
Paddison et al., *Short hairpin RNAs (shRNAs) induce sequence-specific silencing in mammalian cells*, Genes Dev. 16(8): 948-958 (2002).
Pantopoulos, et al., *Mechanisms of mammalian iron homeostasis*, Biochemistry 51(29):5705-5724 (2012).
Pastan et al. *Immunotoxins*, Cell 47(5):641-8 (1986).
Paul et al., *Effective expression of small interfering RNA in human cells*, Nature Biotechnol. 20(5):505-508 (2002).
Pearson and Lipman, *Improved tools for biological sequence comparison*, Proc. Natl. Acad. Sci. USA, 85(8):2444-2448 (1988).
Pearson et al., *Using the Fasta program to search protein and DNA sequence databases*, Meth. Mol. Biol., 24:307-331 (1994).
Qin et al., *In vivo evaluation of a morpholino antisense oligomer directed against tumor necrosis factor-alpha*, Antisense Nucleic Acid Drug Dev. 10(1):11-16 (2000).
Rademann et al., *Integrating Combinatorial Synthesis and Bioassays*, Science 151:1947-1948 (2000).

Rossi, *Practical ribozymes. Making ribozymes work in cells*, Current Biology 4(5):469-471 (1994).
Samstag, *Synthesis and properties of new antisense oligodeoxynucleotides containing benzylphosphonate linkages*, Antisense Nucleic Acid Drug Dev 6(3):153-156 (1996).
Sandilands, et al. *Autophagic targeting of SRC promotes cancer cell survival following reduced FAK signaling*, Nature Cell Biology 14(1):51-60 (2012).
Schena et al. *Parallel human genome analysis: Microarray-based expression monitoring of 1000 genes*, Proc. Nail. Acad. Sci. USA, 93:10614-10619 (1996).
Scott, et al. *A Phase I clinical trial with monoclonal antibody ch806 targeting transitional state and mutant epidermal growth factor receptors*, Proc. Natl Acad. Sci. USA, 104(10):4071-4076 (2007).
Scott et al., *Antibody therapy of cancer*, Nature Reviews Cancer, 12:278-287 (2012).
Schneider, et al. *NIH Image to ImageJ: 25 years of image analysis*, Nature Methods 9(7):671-675 (2012).
Schreiber, *Target-Oriented and Diversity-Oriented Organic synthesis in Drug Discovery*, Science; 151:1964-1969 (2000).
Sharp, *RNAi and double-strand RNA*, Genes Dev. 13(2):139-141 (1999).
Shevchenko. et al. *In-gel digestion for mass spectrometric characterization of proteins and proteomes*, Nature Protocols 1(6):2856-2860 (2006).
Smith et al., *Comparison of Biosequences*, Adv. Appl. Math., 2:482-489 (1981).
Southern, *Detection of specific sequences among DNA fragments separated by gel electrophoresis*, J. Mol. Biol. 98(3):503 (1975).
Sowa, et al. *Defining the human deubiquitinating enzyme interaction landscape*, Cell 138(2): 389-403 (2009).
Stachi-Fainaro et al., *Inhibition of vessel permeability by TNP-470 and its polymer conjugate, caplostatin*, Cancer Cell 7(3), 251-61 (2005).
Strauss-Soukup *Effects of neutralization pattern and stereochemistry on DNA bending by methylphosphonate substitutions*, Biochemistry 36(29):8692-8698 (1997).
Subramanian et al. *Gene set enrichment analysis: a knowledge-based approach for interpreting genome-wide expression profiles*, Proc Natl Acad Sci USA 102(43):15545-15550 (2005).
Sui et al., *A DNA vector-based RNAi technology to suppress gene expression in mammalian cells*, Proc. Natl. Acad. Sci. USA 99(8):5515-5520 (2002).
Summerton and Weller, *Morpholino antisense oligomers: design, preparation, and properties*, Antisense Nucleic Acid Drug Dev. 7(3):187-195 (1997).
Summerton, *Morpholino antisense oligomers: the case for an RNase H-independent structural type*, Biochim. Biophys. Acta 1489(1):141-158 (1999).
Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y.
Trump, et al. *The relationship of intracellular pathways of iron metabolism to cellular iron overload and the iron storage diseases. Cell sap and cytocavitary network pathways in relation to lysosomal storage and turnover of iron macromolecules*, Am J Pathol 72(2):295-336 (1973).
Tuschl, *RNA interference and small interfering RNAs*, Chem. Biochem, 2(4):239-245 (2001).
Vitetta et al. *Redesigning nature's poisons to create anti-tumor reagents*, Science 238(4830):1098-1104 (1987).
Von Muhlinen et al. *LC3C, bound selectively by a noncanonical HR motif in NDP52, is required for antibacterial autophagy*, Mol Cell 48(3):329-342 (2012).
Watson et al. *Technology for microarray analysis of gene expression*, Cuff Opin Biotechnol 9(6):609-14 (1998).
Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986).
Weiner, et al. *Monoclonal antibodies: versatile platforms for cancer immunotherapy*, Nature Rev. Immunol.10(5):317-327 (2010).

(56) References Cited

OTHER PUBLICATIONS

White, E. *Deconvoluting the context-dependent role for autophagy in cancer*, Nature Rev Cancer 12(6):401-410 (2012).

Wu et al. *Gene expression profiling of human breast tissue samples using SAGE-Seq*, Genome Res. 20(12):1730-17399 (2010).

Wu and Wallace, *The ligation amplification reaction (LAR)—amplification of specific DNA sequences using sequential rounds of template-dependent ligation*, Genomics 4(4):560-569 (1989).

Yang, S. et al. *Pancreatic cancers require autophagy for tumor growth*, Genes Dev 25(7):717-729 (2011).

Yeh and Chang, *Cloning and characterization of a specific coactivator, ARA70, for the androgen receptor in human prostate cells*, Proc Natl Acad Sci USA, 93(11):5517-5521 (1996).

Yu et al., *RNA interference by expression of short-interfering RNAs and hairpin RNAs in mammalian cells*, Proc. Natl. Acad. Sci. USA 99:6047-6052 (2002).

Fitzgerald, LM et al. Investigation of the Relationship Between Prostate Cancer and MSMB and NCOA4 Genetic Variants and Protein Expression. Hum Mutat. Jan. 2013, vol. 34, No. 1; pp. 149-156; DOI: 10.1002/humu.22176.

Leedman, PJ et al. Thyroid Hormone Modulates the Interaction Between Iron Regulatory Proteins and the Ferritin Mrna Iron-Responsive Element. J Biol Chem. May 17, 1996, vol. 271, No. 20; pp. 12017-12023; abstract; p. 12017, second column, first paragraph; p. 12018, first column, second paragraph; p. 12019, first column, fifth paragraph; DOI: 10.1074/jbc.271.20.12017.

Dengjel, J et al. Identification of Autophagosome-Associated Proteins and Regulators by Quantitative Proteomic Analysis and Genetic Screens. Mol Cell Proteomics. Mar. 2012, vol. 11, No. 3; 'pp. 1-17; p. 1, second column, first paragraph; p. 2, first column, second paragraph; page 7, Table 1; DOI: 10.1074/mcp.M111.014035.

Nilsson, R et al. Discovery of Genes Essential for Herne Biosynthesis Through Large-Scale Gene Expression Analysis. Cell Metab. Aug. 2009, vol. 10, No. 2; pp. 119-130; p. 120, second column, second paragraph; p. 122, Table 1; p. 124, second column, third paragraph; DOI: 10.1016/j.cmet.2009.06.012.

Dowdle, WE et al. Selective VPS34 Inhibitor Blocks Autophagy and Uncovers a Role for NCOA4 in Ferritin Degradation and Iron Homeostasis In Vivo. Nat Cell Biol. Oct. 19, 2014, vol. 16, No. 11; abstract only provided.

Goodall, M et al. Identifying Specific Receptors for Cargo-Mediated Autophagy. Cell Res. May 6, 2014, vol. 24, No. 7; pp. 783-784; DOI: 10.1038/cr.2014.56.

US Patent and Trademark Office (ISA/US)—International Search Report and Written Opinion issued for PCT/US2015/023142 (dated Oct. 1, 2015), 23 pages.

International Preliminary Report on Patentability and Written Opinion for Intl App No. PCT/US2015/23142 dated Sep. 27, 2016 (17 pages).

\* cited by examiner

NCOA4 N-terminus

NCOA4 C-terminus

Anti-FTH1

Anti-FTH1

Coomassie

| Gene Symbols | ID* | IF | PANC1 Ex.3 No. Peptides | PANC1 Ex.3 Log2(H/L) | MCF7 | 8988T SILAC | 8988T LC3-IP |
|---|---|---|---|---|---|---|---|
| SQSTM1 | R | | 78 | 5.01 | | | |
| GABARAPL2 | A | | 9 | 4.97 | | | |
| TAX1BP1 | C | Y | 50 | 4.73 | | | |
| CALCOCO2 | R | | 43 | 4.56 | | | |
| STX17 | M | | 3 | 4.50 | | | |
| MAP1LC3B | A | | 3 | 4.38 | | | |
| NCOA4 | C | Y | 11 | 4.37 | | | |
| KEAP1 | M | | 14 | 4.29 | | | |
| ITM2B | U | | 30 | 4.20 | | | |
| NBR1 | R | | 12 | 4.17 | | | |
| APP | S | | 93 | 3.99 | | | |
| APLP2 | S | | 102 | 3.99 | | | |
| ITM2C | U | | 26 | 3.93 | | | |
| CALCOCO1 | C | Y | 8 | 3.93 | | | |
| SDC4 | C | Y | 24 | 3.84 | | | |
| TMEM59 | R | | 32 | 3.80 | | | |
| CD320 | U | | 7 | 3.80 | | | |
| IFNGR1 | U | N | 10 | 3.74 | | | |
| CLU | U | | 20 | 3.65 | | | |
| FAT1 | U | | 138 | 3.57 | | | |
| SNX17 | U | | 13 | 3.56 | | | |
| NDFIP1 | C | Y | 19 | 3.52 | | | |
| OPTN | R | | 6 | 3.37 | | | |
| NOTCH2 | U | | 32 | 3.30 | | | |
| LAPTM4A | M | | 17 | 3.24 | | | |
| RNF130 | U | | 2 | 3.17 | | | |
| UGCG | U | | 17 | 3.14 | | | |
| PRKACA | M | | 4 | 2.99 | | | |
| RNF149 | C | Y | 11 | 2.98 | | | |
| ITCH | M | | 12 | 2.88 | | | |
| GPR56 | U | | 5 | 2.70 | | | |
| TMF1 | C | Y | 11 | 2.65 | | | |
| OSMR | U | | 13 | 2.63 | | | |
| FYCO1 | M | | 13 | 2.61 | | | |
| NRP1 | S | | 24 | 2.57 | | | |
| ANTXR1 | U | | 13 | 2.51 | | | |
| IL6ST | C | N | 35 | 2.46 | | | |
| JAK1 | C | N | 28 | 2.42 | | | |
| TNFRSF10B | U | | 12 | 2.25 | | | |
| VPS26A | U | | 20 | 2.16 | | | |
| LGALS8 | M | | 15 | 1.93 | | | |
| SLC38A2 | U | | 44 | 1.93 | | | |
| STX6 | U | | 19 | 1.92 | | | |
| MFGE8 | U | | 69 | 1.90 | | | |
| MGRN1 | C | N | 9 | 1.82 | | | |
| RAB7A | H | | 84 | 1.53 | | | |
| SPTLC1 | H | | 13 | 1.40 | | | |
| NAPA | H | | 37 | 1.01 | | | |
| SLC7A1 | H | | 23 | 1.00 | | | |
| ATP6V1H | H | | 17 | 0.50 | | | |

*ID (Identification)
R = cargo receptor
A = ATG8
C = candidate tested for colocalization
U = candidate not tested for colocalization
M = autophagy machinery
S = selective autophagy cargo
H = found as HCIP in autophagy interaction network Enriched / Not enriched / Not identified

FIG. 14

COMPOSITIONS AND METHODS FOR MODULATING NCOA4-MEDIATED AUTOPHAGIC TARGETING OF FERRITIN

CROSS-REFERENCE TO RELATED APPLICATIONS

This application is a U.S. national phase application of PCT/US2015/023142 (published as WO 2015/149006), which claims priority to U.S. Provisional Patent Application No. 61/971,419, filed Mar. 27, 2014, and U.S. Provisional Patent Application No. 61/990,544, filed May 8, 2014; the entire contents of each of which are herein incorporated by reference.

STATEMENT REGARDING FEDERALLY SPONSORED RESEARCH

This invention was made with government support under grant numbers CA157490, GM070565, and GM095567 awarded by The National Institutes of Health. The government has certain rights in the invention.

TECHNICAL FIELD

This invention relates to the field of molecular and cellular biology, and more particularly to nuclear receptor coactivator 4 (NCOA4)-mediated autophagic targeting of ferritin.

BACKGROUND

Autophagy, the process by which proteins and organelles are sequestered in double-membrane structures called autophagosomes and delivered to lysosomes for degradation, is critical in diseases such as cancer and neurodegeneration. Much of the present understanding of this process has emerged from analysis of bulk cytoplasmic autophagy, but the present understanding of how specific cargo including organelles, proteins, or intracellular pathogens are targeted for selective autophagy is limited.

SUMMARY

In some aspects, provided herein is a method of modulating autophagic targeting of ferritin in a cell. In some aspects, the method can include modulating the level and/or activity of nuclear receptor coactivator 4 (NCOA4) in the cell.

In some aspects, provided herein is a method of modulating the bioavailability of iron in a cell. In some aspects, the method includes modulating the level and/or activity of NCOA4 in the cell.

In some aspects, provided herein is a method of modulating an interaction between NCOA4 and ferritin in a cell. In some aspects, the method includes delivering to the interior of a cell comprising NCOA4 and ferritin an agent that modulates the interaction between NCOA4 and ferritin. In some aspects, this method is in vitro or ex vivo and the method includes culturing the cell with the agent.

In certain aspects of the above methods, the cell can be in a subject and the method can comprise administering the agent to the subject. In some aspects, the subject is administered a cell that expresses NCOA4 or a fragment thereof that can be secreted from the cell and internalized by another cell in the subject. In some aspects, the subject is administered a cell that expresses an inhibitor or antagonist of NCOA4, as described herein (e.g., a polypeptide, peptide fragment, small molecule, antisense oligonucleotide, etc.). In other aspects, the subject is administered a cell that expresses an agonist of NCOA4 (e.g., HERC2 or active fragment thereof, agonistic antibody or intrabody, etc.) including of the activity of NCOA4 (e.g., an active fragment or full length NCOA4). The cell is preferably (but not necessarily) a cell derived from the subject, or the progeny of a cell derived from the subject.

In certain aspects, provided herein is a method of protecting a cell from reactive oxygen species (ROS)-induced cell death. In some aspects, the method includes decreasing the level and/or activity of NCOA4 in a cell comprising an increased level of ROS.

In certain of the above methods, modulating the level and/or activity of NCOA4 is decreasing the level and/or activity of NCOA4. In some aspects, decreasing the level and/or activity of NCOA4 comprises decreasing the interaction between ferritin and NCOA4. In some aspects of the above methods, modulating the interaction between NCOA4 and ferritin is decreasing the interaction between NCOA4 and ferritin. In some aspects, the interaction between ferritin and NCOA4 is decreased by delivering to the interior of the cell an inhibitor comprising a peptide fragment of NCOA4 or of ferritin. In some aspects, the peptide fragment is a peptide fragment of NCOA4 comprising: SEQ ID NO: 1 (SRIADSFQVIKNSPLSEWLIRPPYKEGSPK), or the peptide comprising SEQ ID NO: 1 with no more than 10 conservative amino acid substitutions; or SEQ ID NO: 11 (SFQVIKNSPLSEWLIRPPYKEGSPK) or the peptide comprising SEQ ID NO: 11 with no more than 10 conservative amino acid substitutions, or an amino acid sequence having at least 85% identity with SEQ ID NO: 1 or SEQ ID NO: 11. In some aspects, the peptide fragment is a peptide fragment of NCOA4 comprising SEQ ID NO: 2 (KAMTPSRIADSFQVIKNSPLSEWLIRPPYKEGSPKEVPGTEDRAGKQK), or the peptide comprising SEQ ID NO: 2 with no more than 10 conservative amino acid substitutions, or an amino acid sequence having at least 85% sequence identity with SEQ ID NO: 2. In some aspects, the peptide fragment is a peptide fragment of FTH1 comprising or consisting of: amino acids 16-34 of SEQ ID NO: 6 or amino acids 16-34 of SEQ ID NO: 6 with no more than 10 conservative substitutions; amino acids 103-125 of SEQ ID NO: 6 or amino acids 103-125 of SEQ ID NO: 6 with no more than 10 conservative substitutions; amino acids 78-88 of SEQ ID NO: 6 or amino acids 78-88 of SEQ ID NO: 6 with no more than 5 conservative substitutions; or an amino acid sequence having at least 85% identity with amino acids 16-34 of SEQ ID NO: 6, amino acids 103-125 of SEQ ID NO: 6, or amino acids 78-88 of SEQ ID NO: 6.

In some aspects, decreasing the level and/or activity of NCOA4 and/or decreasing the interaction between ferritin and NCOA4 includes delivering to the interior of the cell an inhibitory agent, e.g., an inhibitory antibody or intrabody, a dominant negative form of a target polypeptide (e.g., NCOA4, HERC2, ferritin (FTH1 and/or FTL), an ATG8 paralog), a peptide fragment that binds to NCOA4 (e.g., a ferritin fragment, a HERC2 fragment, a ATG8 paralog fragment, a NCOA4 fragment, wherein the fragments are not functionally active), a small molecule (e.g., aptamer), an antisense oligonucleotide (e.g. shRNA, siRNA, etc.) that targets NCOA4, HERC2, ferritin or an ATG8 paralog described herein. In some aspects, decreasing the level and/or activity of NCOA4 comprises delivering to the interior of the cell a peptide comprising SEQ ID NO: 3 (SMVTEDWLVQNHQDPCKVEEVCRANEPCTS- FAECVCDENCEKEALYKWLLKKEG), or the peptide comprising SEQ ID NO: 3 with no more than 10 conservative amino acid substitutions, or an amino acid sequence having at least 85% sequence identity with SEQ ID NO: 3. In some aspects, decreasing the level and/or activity of NCOA4 comprises delivering to the interior of the cell a ferritin FTH1 peptide comprising or consisting of: amino acids 16-34 of SEQ ID NO: 6 or amino acids 16-34 of SEQ ID NO: 6 with no more than 10 conservative substitutions; amino acids 103-125 of SEQ ID NO: 6 or amino acids 103-125 of SEQ ID NO: 6 with no more than 10 conservative substitutions; amino acids 78-88 of SEQ ID NO: 6 or amino acids 78-88 of SEQ ID NO: 6 with no more than 5 conservative substitutions; or an amino acid sequence having at least 85% identity with amino acids 16-34 of SEQ ID NO: 6, amino acids 103-125 of SEQ ID NO: 6, or amino acids 78-88 of SEQ ID NO: 6. Non-limiting examples of antisense oligonucleotides that can be used according to the methods disclosed herein include, e.g., siRNA against NCOA4,e.g., shNCOA4-1: 5' CCCAGGAAGTATTACT-TAATT 3' (TRCN0000019724) (SEQ ID NO: 12), shN-COA4-2: 5' GCTGGCAAACAGAAGTTTAAA 3' (TRCN 0000019726) (SEQ ID NO: 13), siNCOA4-1: 5' ACAAA GAUCUAGCCAAUCA 3' (SEQ ID NO: 15) and siN-COA4-2: 5' GACCUUAUUUAUCAGCUUA 3' (SEQ ID NO: 16), and siRNA against HERC2 (Gene ID: 8924, NM_004667.5), e.g., siHERC2-1: 5' GCACAGAGUAU-CACAGGUA 3' (SEQ ID NO: 17) and siHERC2-2: 5' CGAUGAAGGUUUGGUAUUU 3' (SEQ ID NO: 18). Methods for designing suitable antisense oligonucleotides based on the known sequence of the target nucleic acid are well known in the art.

In some aspects of the above methods for decreasing autophagic targeting of ferritin in a cell and for decreasing the bioavailability of iron in a cell, the method can include decreasing the recruitment of NCOA4/ferritin complexes to autophagosomes. In some aspects, the recruitment is decreased by delivering to the interior of the cell an inhibitor of the interaction between NCOA4 and an ATG8 paralog. In some aspects, the ATG8 paralog is GABA(A) receptor-associated protein-like 2 (GABARAPL2) or microtubule-associated proteins 1A/1B light chain 3A (LC3).

In other aspects of the above methods for modulating the level and/or activity of NCOA4 and/or for modulating the interaction between NCOA4 and ferritin, the modulating is increasing. In some aspects, increasing the level and/or activity of NCOA4 or increasing the interaction between NCOA4 and ferritin comprises delivering to the interior of the cell an NCOA4 polypeptide or functionally active fragment thereof. In some aspects, the NCOA4 polypeptide or functionally active fragment thereof binds to the ferritin heavy chain (FTH1) and/or to ferritin light chain (FLT) and/or to an ATG8 paralog (e.g., GABARAPL2 and/or LC3). In some aspects, the NCOA4 polypeptide or functionally active fragment thereof comprises SEQ ID NO: 1 (SRIADSFQVIKNSPLSEWLIRPPYKEGSPK), or the peptide comprising SEQ ID NO: 1 with no more than 10 conservative amino acid substitutions, or an amino acid sequence having at least 85% sequence identity with SEQ ID NO: 1. In some aspects, the NCOA4 polypeptide or functionally active fragment thereof comprises SEQ ID NO: 11, or the peptide comprising SEQ ID NO: 11 with no more than 10 conservative amino acid substitutions, or an amino acid sequence having at least 85% sequence identity with SEQ ID NO: 11. In some aspects, the NCOA4 polypeptide or functionally active fragment thereof comprises SEQ ID NO: 2 (KAMTPSRIADSFQVIKNSPLSEWLIRPPYKEG-SPKEVPGTEDRAGKQK), or the peptide comprising SEQ ID NO: 2 with no more than 10 conservative amino acid substitutions, or an amino acid sequence having at least 85% sequence identity with SEQ ID NO: 2. In some aspects, increasing the level and/or activity of NCOA4 or increasing the interaction between NCOA4 and ferritin comprises delivering to the interior of the cell an agent that increases the expression of NCOA4 in the cell. In some aspects, increasing the level and/or activity of NCOA4 or increasing the interaction between NCOA4 and ferritin comprises increasing the level and/or activity of HERC2 in the cell. In some aspects, the method comprises delivering to the interior of the cell an agent that increases the expression and/or activity of HERC2. In some aspects, the method comprises delivering to the interior of the cell a HERC2 polypeptide or a functionally active fragment thereof. In some aspects, the HERC2 polypeptide or functionally active fragment thereof binds to a domain of NCOA4 which comprises SEQ ID NO: 3 (SMVTEDWLVQNHQDPCKVEEVCRANEPCTSFAE CVCDENCEKEALYKWLLKKEG).

In some aspects, also provided herein are methods of treating a cancer. The methods can include administering to a subject in need thereof a composition comprising an inhibitor that decreases the level and/or activity of NCOA4 in a cancer cell in the subject, and wherein the cancer is reliant on selective autophagy for growth. In some aspects, the cancer is pancreatic cancer, lung cancer, melanoma, breast cancer, glioblastoma, colorectal cancer, prostate cancer, multiple myeloma, renal cell carcinoma, chronic lymphocytic leukemia, lymphoma, or chronic myelogenous leukemia. In some aspects, the inhibitor decreases selective autophagy in the cancer cell.

In some aspects, also provided herein is a method of treating a condition or disorder associated with iron overload. The method can include administering to a subject in need thereof a composition comprising an inhibitor that decreases the level and/or activity of NCOA4 in a cell of the subject. In some aspects, the condition or disorder is hemochromatosis. In some aspects, the condition or disorder is iron overload due to transfusion. In some aspects, decreasing the level and/or activity of NCOA4 comprises decreasing the interaction between ferritin and NCOA4 in the cell of the subject.

In some aspects of the above methods of treatment, the level and/or activity of NCOA4 in a cell of the subject can be decreased by administering to the subject a composition comprising a peptide fragment of NCOA4 or of ferritin, wherein the fragment is not a functionally active fragment (i.e., the fragment does not have at least one of the functional activities of the wild-type protein that is involved in the process of NCOA4-mediated autophagic targeting of ferritin, as described herein). In some aspects, the peptide fragment is a peptide fragment of NCOA4 comprising SEQ ID NO: 1 (SRIADSFQVIKNSPLSEWLIRPPYKEGSPK), or the peptide comprising SEQ ID NO: 1 with no more than 10 conservative amino acid substitutions; or SEQ ID NO: 11 (SFQVIKNSPLSEWLIRPPYKEGSPK), or the peptide comprising SEQ ID NO: 11 with no more than 10 conservative amino acid substitutions, or an amino acid sequence having at least 85% identity with SEQ ID NO: 1 or SEQ ID NO: 11. In some aspects, the peptide fragment is a peptide fragment of NCOA4 comprising SEQ ID NO: 2 (KAMTPSRIADSFQVIKNSPLSEWLIRPPYKEGSPKEV-PGTEDRAGKQK) or the peptide comprising SEQ ID NO: 2 with no more than 10 conservative amino acid substitutions, or an amino acid sequence having at least 85% identity with SEQ ID NO: 2. In some aspects, the ferritin fragment is a fragment of FTH1 comprising or consisting of: amino acids 16-34 of SEQ ID NO: 6 or amino acids 16-34 of SEQ ID NO: 6 with no more than 10 conservative substitutions; amino acids 103-125 of SEQ ID NO: 6 or amino acids 103-125 of SEQ ID NO: 6 with no more than 10 conservative substitutions; amino acids 78-88 of SEQ ID NO: 6 or amino acids 78-88 of SEQ ID NO: 6 with no more than 5 conservative substitutions; or an amino acid sequence having at least 85% identity with amino acids 16-34 of SEQ ID NO: 6, amino acids 103-125 of SEQ ID NO: 6, or amino acids 78-88 of SEQ ID NO: 6.

In some aspects of the above methods, decreasing the level and/or activity of NCOA4 includes administering to the subject a composition comprising an inhibitory agent, e.g., an inhibitory antibody or intrabody, a dominant negative form of a target polypeptide (e.g., NCOA4, HERC2, ferritin (FTH1 and/or FTL), an ATG8 paralog), a peptide fragment that binds to NCOA4 (e.g., a ferritin fragment, a HERC2 fragment, a ATG8 paralog fragment, a NCOA4 fragment, wherein the fragments are not functionally active), a small molecule (e.g., aptamer), an antisense oligonucleotide (e.g. shRNA, siRNA, etc.) that targets NCOA4, HERC2, ferritin or an ATG8 paralog described herein. In some aspects of these methods, the ferritin fragment is a fragment of FTH1 comprising or consisting of: amino acids 16-34 of SEQ ID NO: 6 or amino acids 16-34 of SEQ ID NO: 6 with no more than 10 conservative substitutions; amino acids 103-125 of SEQ ID NO: 6 or amino acids 103-125 of SEQ ID NO: 6 with no more than 10 conservative substitutions; amino acids 78-88 of SEQ ID NO: 6 or amino acids 78-88 of SEQ ID NO: 6 with no more than 5 conservative substitutions; or an amino acid sequence having at least 85% identity with amino acids 16-34 of SEQ ID NO: 6, amino acids 103-125 of SEQ ID NO: 6, or amino acids 78-88 of SEQ ID NO: 6. Non-limiting examples of antisense oligonucleotides that can be used according to the methods disclosed herein include, e.g., siRNA against NCOA4,e.g., shNCOA4-1: 5' CCCAGGAAGTATTACT-TAATT 3' (TRCN0000019724) (SEQ ID NO: 12), shNCOA4-2: 5' GCTGGCAAACAGAAGTTTAAA 3' (TRCN 0000019726) (SEQ ID NO: 13), siNCOA4-1: 5' ACAAA GAUCUAGCCAAUCA 3' (SEQ ID NO: 15) and siNCOA4-2: 5' GACCUUAUUUAUCAGCUUA 3' (SEQ ID NO: 16), and siRNA against HERC2 (Gene ID: 8924, NM_004667.5), e.g., siHERC2-1: 5' GCACAGAGUAU-CACAGGUA 3' (SEQ ID NO: 17) and siHERC2-2: 5' CGAUGAAGGUUUGGUAUUU 3' (SEQ ID NO: 18). Methods for designing suitable antisense oligonucleotides based on the known sequence of the target nucleic acid are well known in the art. In some aspects, decreasing the level and/or activity of NCOA4 comprises delivering to the interior of the cell a peptide comprising SEQ ID NO: 3 (SMVTEDWLVQNHQDPCKVEEVCRANEPCTSFAEC VCDENCEKEALYKWLLKKEG), or the peptide comprising SEQ ID NO: 3 with no more than 10 conservative amino acid substitutions, or an amino acid sequence having at least 85% identity with SEQ ID NO: 3. In some aspects, the method includes decreasing the recruitment of NCOA4/ferritin complexes to autophagosomes in the cell of the subject. In some aspects, the recruitment is decreased by administering to the subject a composition comprising an inhibitor of the interaction of NCOA4 with an ATG8 paralog (e.g., GABARAPL2 or LC3).

In some aspects, also provided herein is a method of treating iron deficiency anemia. The methods can include administering to a subject with anemia a composition comprising an agent that increases the level and/or activity of NCOA4 in a cell of the subject. In other aspects, also provided herein is a method of increasing erythropoiesis. The method can include administering to a subject in need of increased erythropoiesis a composition comprising an agent that increases the level and/or activity of NCOA4 in a cell of the subject. In some aspects, increasing the level and/or activity of NCOA4 includes administering to the subject an NCOA4 polypeptide or functionally active fragment thereof. In some aspects, the NCOA4 polypeptide or functionally active fragment thereof binds to FTH1 and/or FTL in the cell of the subject. In some aspects, the NCOA4 polypeptide or functionally active fragment thereof interacts with an ATG8 paralog (e.g., GABARAPL2 or LC3) in the cell of the subject. In some aspects, the NCOA4 polypeptide or functionally active fragment thereof comprises SEQ ID NO: 1 (SRIADSFQVIKNSPLSEWLIRPPYKEGSPK), or the peptide comprising SEQ ID NO: 1 with no more than 10 conservative amino acid substitutions; or SEQ ID NO: 11 (SFQVIKNSPLSEWLIRPPYKEGSPK), or the peptide comprising SEQ ID NO: 11 with no more than 10 conservative amino acid substitutions; or an amino acid sequence having at least 85% identity with SEQ ID NO: 1 or SEQ ID NO: 11. In some aspects, the NCOA4 polypeptide or functionally active fragment thereof comprises SEQ ID NO: 2 (KAMTPSRIADSFQVIKNSPLSEWLIRPPYKEGSPKEV-PGTEDRAGKQK), or the NCOA4 polypeptide or fragment comprising SEQ ID NO: 2 with no more than 10 conservative amino acid substitutions, or an amino acid sequence having at least 85% identity with SEQ ID NO: 2. In some aspects, increasing the level and/or activity of NCOA4 comprises increasing the interaction between NCOA4 and ferritin. In some aspects, increasing the level and/or activity of NCOA4 comprises administering to the subject an agent that increases the expression of NCOA4 in the subject. In some aspects, increasing the level and/or activity of NCOA4 includes increasing the level and/or activity of HERC2 in the cell. In some aspects, increasing the level and/or activity of HERC2 in the cell includes administering to the subject a composition comprising an agent that increases the expression and/or activity of HERC2. In some aspects, the method comprises administering to the subject a composition comprising a HERC2 polypeptide or a functionally active fragment thereof. In some aspects, the HERC2 polypeptide or functionally active fragment thereof binds to a domain of NCOA4 which comprises SEQ ID NO: 3 (SMVTED-WLVQNHQDPCKVEEVCRANEPCTSFAECVC-DENCEKEALYKWLLKKEG).

In some aspects, also described herein is a method of identifying a compound that modulates the expression level of NCOA4. In some aspects, the method includes contacting a cell with a candidate compound, and determining the expression level of NCOA4. In some aspects, the modulating is increasing or decreasing the expression level. In some aspects, the expression level is the mRNA expression level. In some aspects, the expression level is the protein expression level.

In some aspects, also described herein is a method of identifying a compound that modulates the activity of NCOA4. The method can include:
 (a) contacting a cell with a candidate compound;
 (b) determining the level in the cell of one or more of the following:
  (i) bioavailable iron relative to a control cell;
  (ii) ferritin in autophagosomes and/or lysosomes;
  (iii) NCOA4 present in autophagosomes and/or lysosomes;
  (iv) NCOA4/ferritin complexes;

(v) NCOA4/HERC2 complexes;
(vi) NCOA4/ATG8 paralog complexes; and
(vii) degradation of ferritin via autophagy; and
(c) if the candidate compound modulates the level of one or more of (b)(i)-(b)(vii), identifying the candidate compound as a compound that modulates the activity of NCOA4. In some aspects, the method further includes selecting the identified compound for further testing and/or for formulation as a drug product (e.g., pharmaceutical formulation). In some aspects, the modulating is increasing or decreasing.

In some aspects, also provided herein is a method of identifying a compound that modulates the binding of NCOA4 to ferritin. The method can include: contacting a NCOA4 reagent with a ferritin reagent in the presence of a candidate compound; and determining whether the candidate compound modulates binding of the NCOA4 reagent to the ferritin reagent. In some aspects, the modulating is decreasing the binding. In some aspects, the modulating is increasing the binding. In some aspects, the NCOA4 reagent comprises a full-length NCOA4 polypeptide. In some aspects, the NCOA4 reagent comprises a peptide comprising or consisting of SEQ ID NO: 11, SEQ ID NO: 1 or SEQ ID NO: 2. In some aspects the ferritin reagent is purified apo-ferritin from human liver or equine spleen or produced recombinantly in E. coli as either FTH1, FTL, or a combination of FTH1 and FTL.

In some aspects, also provided herein is a method of identifying a compound that modulates the binding of NCOA4 to an ATG8 paralog. The method can include: contacting a NCOA4 reagent with an ATG8 paralog reagent in the presence of a candidate compound; and determining whether the candidate compound modulates binding of the NCOA4 reagent to the ATG8 paralog reagent. In some aspects, the modulating is decreasing the binding. In some aspects, the modulating is increasing the binding. In some aspects, the NCOA4 reagent comprises a full-length NCOA4 polypeptide or a fragment thereof which retains binding to the ATG8 paralog reagent (e,g, a GABARAPL2 reagent or LC3 reagent). In some aspects, one or more of the reagents for use in the methods of identifying compounds ("screening assays") are recombinantly expressed protein from E. coli.

In some aspects, also provided herein is a method of identifying a compound that modulates the binding of NCOA4 to HERC2. The method can include: contacting a NCOA4 reagent with a HERC2 reagent in the presence of a candidate compound; and determining whether the candidate compound modulates binding of the NCOA4 reagent to the HERC2 reagent. In some aspects, the modulating is decreasing the binding. In some aspects, the modulating is increasing the binding. In some aspects, the NCOA4 reagent comprises a full-length NCOA4 polypeptide or a fragment thereof which retains binding to HERC2 (e.g., a fragment comprising or consisting of SEQ ID NO: 3). In some aspects, one or more of the reagents for use in the methods of identifying compounds ("screening assays") are recombinantly expressed protein from E. coli.

In some aspects, also described herein is a method of diagnosing anemia in a subject, the method comprising identifying one or more of the following conditions in the subject: (a) a mutation in NCOA4; (b) a decreased level and/or activity of NCOA4; (c) a decreased level of NCOA4/ferritin complexes; and (d) a decreased level of NCOA4/ATG8 paralog complexes.

In any of the above described methods, the NCOA4 can be human NCOA4 or a fragment thereof. In any of the above aspects, the ferritin can be human ferritin (FTH1 or FTL). In any of the above aspects, the ATG8 paralog can be a human ATG8 paralog. In any of the above aspects, HERC2 can be human HERC2. Alternatively, any or all of these proteins can be mammalian, non-human (e.g., non-human primate) proteins.

In some aspects, also described herein is a composition comprising a small molecule antagonist that targets SEQ ID NO: 11, 1, 2, or 3. In other aspects, the small molecule targets a sequence in a protein that binds to SEQ ID NO: 11, 1, 2, or 3 (e.g., the corresponding sequence in the region of ferritin that binds to SEQ ID NO: 11, 1 and 2, and the corresponding sequence in HERC2 that binds to SEQ ID NO: 3 (e.g., a region in HERC2 within residues 1700-2700 of SEQ ID NO: 8).

In some aspects, also described herein is a binding molecule that binds to a sequence within SEQ ID NO: 11, 1, 2, or 3. In some aspects, the binding molecule is an antibody or intrabody.

In some aspects, also described herein is a peptide fragment of NCOA4 comprising: SEQ ID NO: 1 (SRIADSFQ-VIKNSPLSEWLIRPPYKEGSPK), or the peptide comprising SEQ ID NO: 1 with no more than 10 conservative amino acid substitutions; or SEQ ID NO: 11 (SFQVIKNSPLSEW-LIRPPYKEGSPK), or the peptide comprising SEQ ID NO: 11 with no more than 10 conservative amino acid substitutions; or an amino acid sequence having at least 85% sequence identity with SEQ ID NO: 1 or SEQ ID NO: 11. Also described herein is a peptide fragment of NCOA4 comprising SEQ ID NO: 2 or the peptide fragment comprising SEQ ID NO: 2 with no more than 10 conservative amino acid substitutions. Also described herein is a peptide fragment of NCOA4 consisting of: SEQ ID NO: 1 or the peptide fragment consisting of SEQ ID NO: 1 with no more than 10 conservative amino acid substitutions; or SEQ ID NO: 11 or the peptide fragment consisting of SEQ ID NO: 11 with no more than 10 conservative amino acid substitutions. Also described herein is a peptide fragment of NCOA4 consisting of SEQ ID NO: 2 or the peptide fragment consisting of SEQ ID NO: 2 with no more than 10 conservative amino acid substitutions, or an amino acid sequence having at least 85% sequence identity with SEQ ID NO: 2. Also described herein is a peptide fragment of NCOA4 comprising SEQ ID NO: 3, or the peptide fragment comprising SEQ ID NO: 3 with no more than 10 conservative amino acid substitutions, an amino acid sequence having at least 85% sequence identity with SEQ ID NO: 3. Also described herein is a peptide fragment of NCOA4 consisting of SEQ ID NO: 3 or the peptide fragment consisting of SEQ ID NO: 3 with no more than 10 conservative amino acid substitutions, or an amino acid sequence having at least 85% sequence identity with SEQ ID NO: 3. Also described herein is a peptide fragment of FTH1 comprising: amino acids 16-34 of SEQ ID NO: 6 or amino acids 16-34 of SEQ ID NO: 6 with no more than 10 conservative substitutions; amino acids 103-125 of SEQ ID NO: 6 or amino acids 103-125 of SEQ ID NO: 6 with no more than 10 conservative substitutions; amino acids 78-88 of SEQ ID NO: 6 or amino acids 78-88 of SEQ ID NO: 6 with no more than 5 conservative substitutions; or an amino acid sequence having at least 85% identity with amino acids 16-34 of SEQ ID NO: 6, amino acids 103-125 of SEQ ID NO: 6, or amino acids 78-88 of SEQ ID NO: 6. Also described herein is a peptide fragment of FTH1 consisting of: amino acids 16-34 of SEQ ID NO: 6 or amino acids 16-34 of SEQ ID NO: 6 with no more than 10 conservative substitutions; amino acids 103-125 of SEQ ID NO: 6 or amino acids 103-125 of SEQ ID NO: 6 with no more than 10 conservative substitutions; amino acids 78-88 of SEQ ID NO: 6 or amino acids 78-88 of SEQ ID NO: 6 with no more than 5 conservative substitutions; or an amino acid sequence having at least 85% identity with amino acids 16-34 of SEQ ID NO: 6, amino acids 103-125 of SEQ ID NO: 6, or amino acids 78-88 of SEQ ID NO: 6.

In certain above aspects, the peptide fragment is a synthetic peptide fragment.

Also provided herein are isolated nucleic acids. An isolated nucleic acid encompassed herein includes a nucleotide sequence that:

(a) encodes a peptide fragment described herein, such as:
a peptide fragment of NCOA4 comprising: SEQ ID NO: 1 (SRIADSFQVIKNSPLSEWLIRPPYKEGSPK), or the peptide comprising SEQ ID NO: 1 with no more than 10 conservative amino acid substitutions; or SEQ ID NO: 11 (SFQVIKNSPLSEWLIRPPYKEGSPK), or the peptide comprising SEQ ID NO: 11 with no more than 10 conservative amino acid substitutions; or an amino acid sequence having at least 85% sequence identity with SEQ ID NO: 1 or SEQ ID NO: 11; or a peptide fragment of NCOA4 comprising SEQ ID NO: 2, or the peptide fragment comprising SEQ ID NO: 2 with no more than 10 conservative amino acid substitutions; or a peptide fragment of NCOA4 consisting of: SEQ ID NO: 1 or the peptide fragment consisting of SEQ ID NO: 1 with no more than 10 conservative amino acid substitutions; or the peptide fragment consisting of SEQ ID NO: 11, or the peptide fragment consisting of SEQ ID NO: 11 with no more than 10 conservative amino acid substitutions; or a peptide fragment of NCOA4 consisting of SEQ ID NO: 2, or the peptide fragment consisting of SEQ ID NO: 2 with no more than 10 conservative amino acid substitutions, or an amino acid sequence having at least 85% sequence identity with SEQ ID NO: 2; or a peptide fragment of NCOA4 comprising SEQ ID NO: 3, or the peptide fragment comprising SEQ ID NO: 3 with no more than 10 conservative amino acid substitutions, or an amino acid sequence having at least 85% sequence identity with SEQ ID NO: 3; or a peptide fragment of NCOA4 consisting of SEQ ID NO: 3, or the peptide fragment consisting of SEQ ID NO: 3 with no more than 10 conservative amino acid substitutions, or an amino acid sequence having at least 85% sequence identity with SEQ ID NO: 3; or a peptide fragment of FTH1 comprising amino acids 16-34 of SEQ ID NO: 6 or amino acids 16-34 of SEQ ID NO: 6 with no more than 10 conservative substitutions; or a peptide fragment of FTH1 comprising amino acids 103-125 of SEQ ID NO: 6 or amino acids 103-125 of SEQ ID NO: 6 with no more than 10 conservative substitutions; or a peptide fragment of FTH1 comprising amino acids 78-88 of SEQ ID NO: 6 or amino acids 78-88 of SEQ ID NO: 6 with no more than 5 conservative substitutions; or a peptide fragment of FTH1 comprising an amino acid sequence having at least 85% identity with amino acids 16-34 of SEQ ID NO: 6, amino acids 103-125 of SEQ ID NO: 6, or amino acids 78-88 of SEQ ID NO: 6; or a peptide fragment of FTH1 consisting of amino acids 16-34 of SEQ ID NO: 6 or amino acids 16-34 of SEQ ID NO: 6 with no more than 10 conservative substitutions; or a peptide fragment of FTH1 consisting of amino acids 103-125 of SEQ ID NO: 6 or amino acids 103-125 of SEQ ID NO: 6 with no more than 10 conservative substitutions; or a peptide fragment of FTH1 consisting of amino acids 78-88 of SEQ ID NO: 6 or amino acids 78-88 of SEQ ID NO: 6 with no more than 5 conservative substitutions; or a peptide fragment of FTH1 consisting of an amino acid sequence having at least 85% identity with amino acids 16-34 of SEQ ID NO: 6, amino acids 103-125 of SEQ ID NO: 6, or amino acids 78-88 of SEQ ID NO: 6.

(b) hybridizes under stringent conditions to the complement of the polynucleotide that encodes the peptide fragment described in (a); or (c) is the complement of (a).

In some aspects, the isolated nucleic acid described above is cDNA.

In some aspects, the isolated nucleic acid is derived from SEQ ID NO: 5, e.g., portion thereof.

In some aspects, also provided herein is an expression vector comprising any one or more of the nucleic acids (a) and (b) described above. Also provided herein is a host cell comprising an expression vector comprising any one or more of the nucleic acids (a) and (b) described above.

Also provided herein is a method of making a peptide fragment. The method can include culturing a host cell describe herein, e.g. a host cell comprising an expression vector comprising any one or more of the nucleic acids (a) and (b) described above, under conditions suitable for expressing the peptide fragment.

Unless otherwise defined, all technical and scientific terms used herein have the same meaning as commonly understood by one of ordinary skill in the art to which this invention pertains. In case of conflict, the present document, including definitions, will control.

All publications, patent applications, patents, and other references mentioned herein are incorporated by reference in their entirety. The materials, methods, and examples disclosed herein are illustrative only and not intended to be limiting.

The details of one or more embodiments of the invention are set forth in the accompanying drawings and the description below. Preferred methods and materials are described below, although methods and materials similar or equivalent to those described herein can also be used in the practice or testing of the present invention. Other features, objects, and advantages of the invention will be apparent from the description and drawings, and from the claims.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
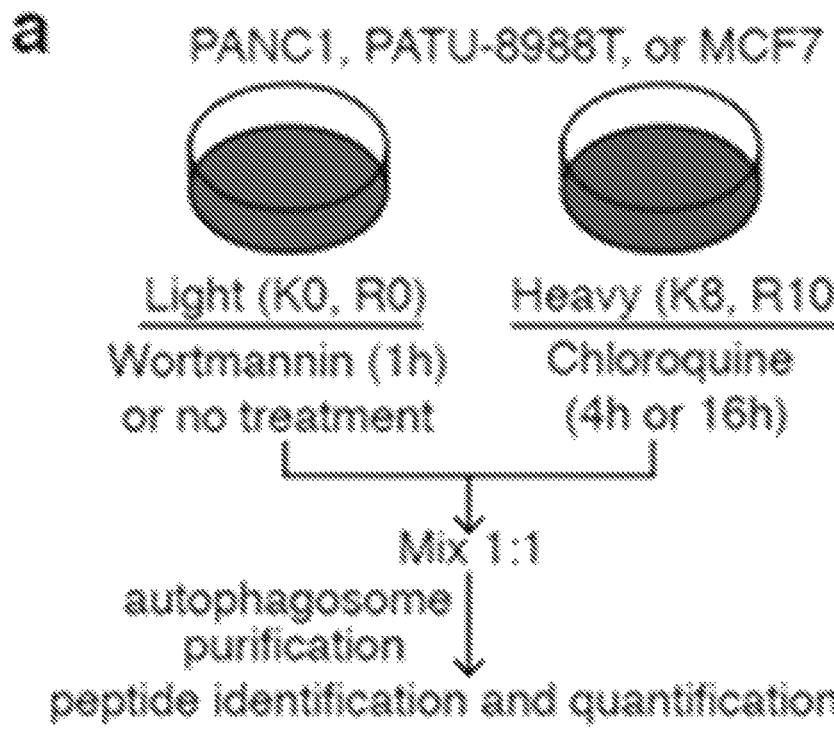
FIG. 1(a) contains a diagram illustrating autophagosome enrichment workflow using PANC1, PATU-8988T, or MCF7 cells cultured in light media ((K0) lysine (50 μg/mL) and light (R0) arginine (85 μg/mL)) or heavy media (light lysine was replaced with K8-lysine, and light arginine replaced with R10-arginine at the same concentrations). The cells were mixed and autophagosomes were purified, followed by peptide identification and quantification.
FIG. 1(b) is graph quantifying the Log 2(H:L) for autophagosome proteins from PANC1 cells (Ex. 3), overlaid with a scheme for identification of candidate autophagosome proteins.
FIG. 1(c) contains Venn diagrams showing autophagosome candidate overlap from biologic replicate experiments for PANC1 and MCF7 cells, as well as overlap between PANC1 and MCF7 datasets.
FIG. 1(d) is a Pearson correlation plot for overlapping candidates from PANC1 experiments (86 proteins, comparing Ex. 2 vs. Ex. 3 in FIG. 1(c)).
FIG. 1(e) is a Log 2(H:L) heat map of Class 1A candidates from PANC1 and MCF7 cells.
Figure 1:
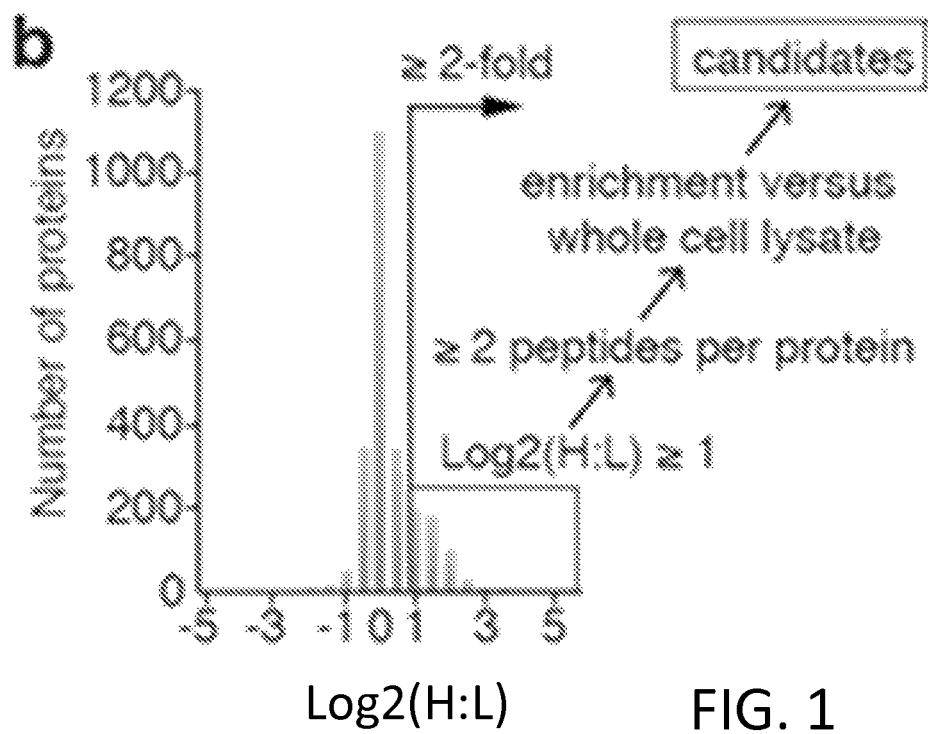
Figure 1:
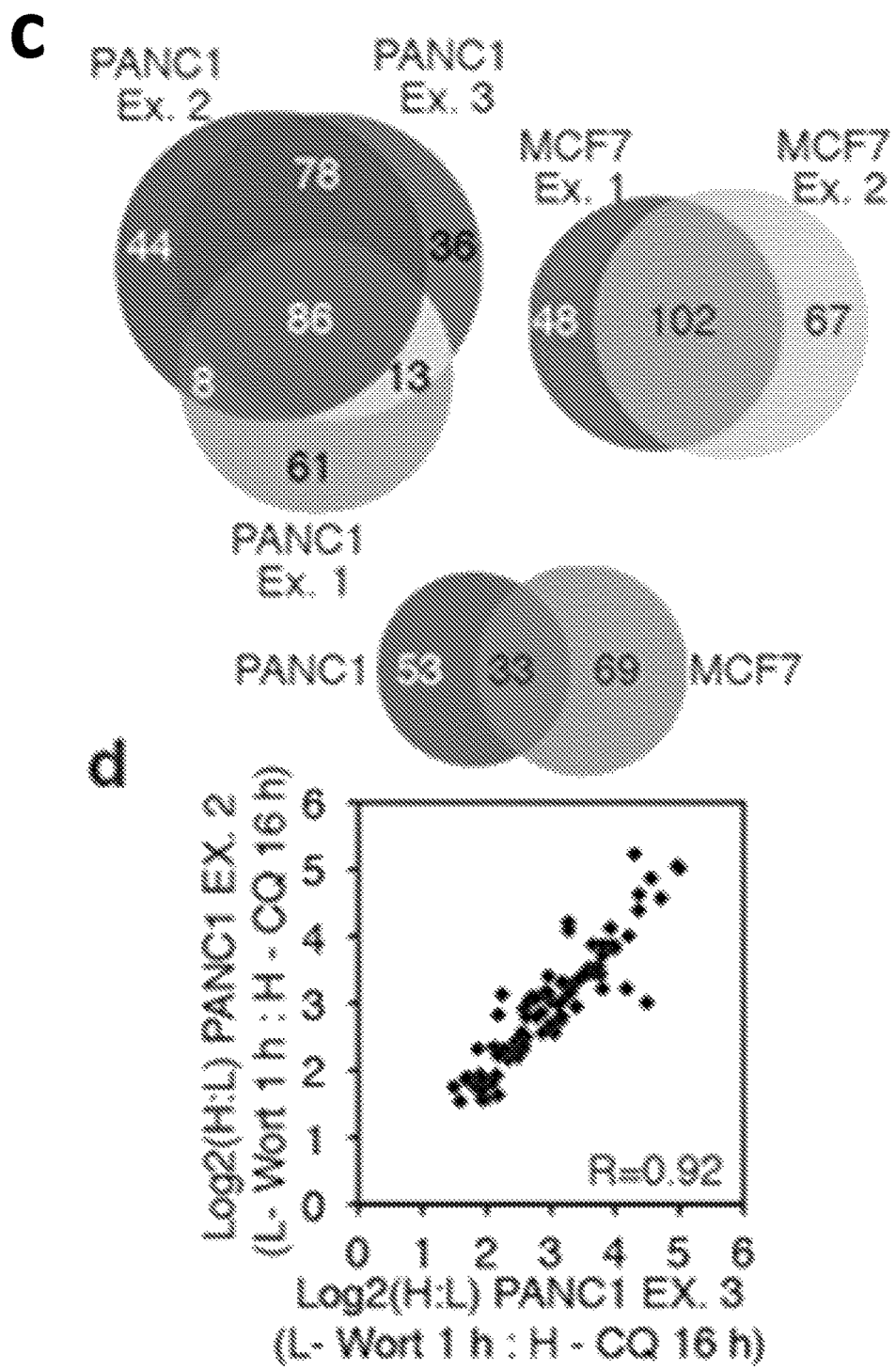
Figure 1:
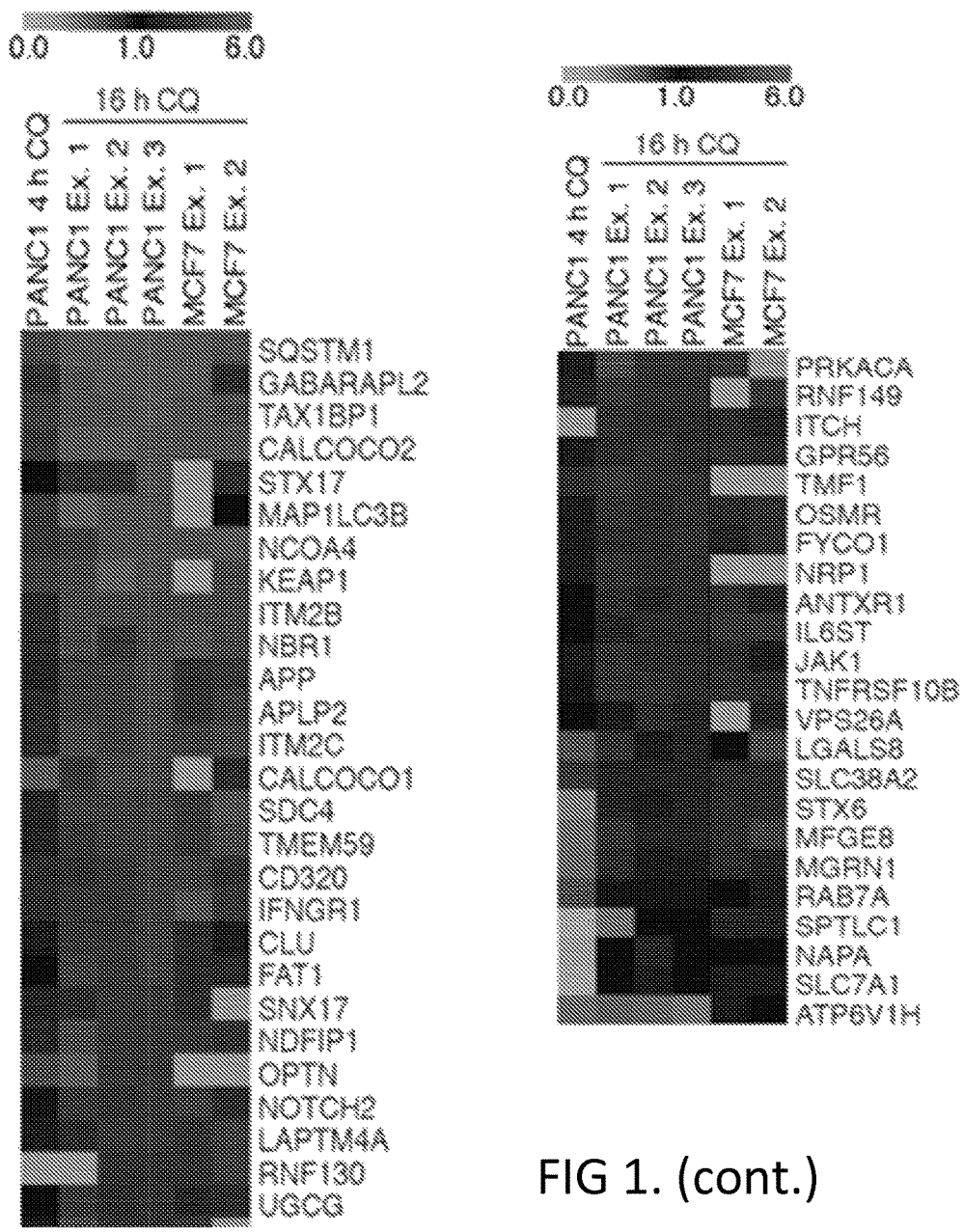

Provided herein are methods and compositions for modulating (e.g., increasing or reducing) NCOA4-mediated autophagic targeting of ferritin. These methods and compositions are also useful for, e.g., treating diseases and disorders such as cancer, anemia, and iron overload.

As described in the Examples, below, quantitative proteomics was employed to identify a cohort of novel and known autophagosome-enriched proteins, including cargo receptors. One of the novel cargo receptors identified was NOCA4. Like known cargo receptors, NCOA4 was highly enriched in autophagosomes, and associated with ATG8 proteins that recruit cargo-receptor complexes into autophagosomes. Unbiased identification of NCOA4-associated proteins revealed ferritin heavy and light chains, components of an iron-filled cage structure that protects cells from reactive iron species but is degraded via autophagy to release iron through an unknown mechanism. It was found that delivery of ferritin to lysosomes required NCOA4, and an inability of NCOA4-deficient cells to degrade ferritin led to decreased bioavailable intracellular iron. The Examples thus identify NCOA4 as a selective cargo receptor for autophagic turnover of ferritin (ferritinophagy) critical for iron homeostasis and provides a resource for further dissection of autophagosomal cargo-receptor connectivity.

As used herein, "NCOA4" is interchangeable with the term "nuclear receptor coactivator 4." "NCOA4" encompasses mammalian NCOA4, including, e.g., human NCOA4, including various genetic variants and isoforms of NCOA4. Non-human NCOA4 can be from any of species listed below for a "subject". Nucleic acid and amino acid sequences for NCOA4 are known in the art. By way of non-limiting example, a protein sequence for human NCOA4 has GenBank Accession No. NP_001138735.1:

1 mntfqdqsgs ssnrepllrc sdarrdlela iggvlraeqq ikdnlrevka qihscisrhl 61 eclrsrevwl yeqvdliyql keetlqqqaq qlysllgqfn clthqlectq nkdlanqvsv 121 clerlgsltl kpedstvllf eadtitlrqt ittfgslkti qipehlmaha ssanigpfle
181 krgcismpeq ksasgivavp fsewllgskp asgyqapyip stdpqdwltq kqtlensqts
241 sracnffnnv ggnlkglenw llksekssyq kcnshsttss fsiemekvgd qelpdqdemd
301 lsdwlvtpqe shklrkpeng sretsekfkl lfqsynvndw lvktdsctnc qgnqpkgvei
361 enlgnlkcln dhleakkpls tpsmvtedwl vqnhqdpckv eevcranepc tsfaecvcde
421 ncekealykw llkkegkdkn gmpvepkpep ekhkdslnmw lcprkevieq tkapkamtps
481 riadsfqvik nsplsewlir ppykegspke vpgtedragk qkfkspmnts wcsfntadwv
541 lpgkkmgnls qlssgedkwl lrkkaqevll nsplqeehnf ppdhyglpav cdlfacmqlk
601 vdkekwlyrt plqm (SEQ ID NO: 4).

The mRNA reference sequence for the above human amino acid sequence has GenBank® Accession No. NM_001145263 (SEQ ID NO: 5).

As used herein, the term "autophagic targeting of ferritin" means the transport of ferritin to an autophagosome by NCOA4 in a cell. The cell can be in vitro/ex vivo or in a subject (e.g. a mammal).

As used herein, the term "selective autophagy" means the selective elimination by autophagy in a cell of unwanted components such as but not limited to aberrant protein aggregates, lipid droplets, dysfunctional organelles, and invading pathogens.

As used herein, the term "modulating the level of NCOA4" means causing any increase or decrease in the mRNA and/or protein level of NCOA4 (e.g., in a cell or a subject (e.g. a mammal)).

As used herein, the term "modulating the activity of NCOA4" means causing any increase or decrease in one or more functions of NCOA4 involved in autophagic targeting of ferritin. Functions involved in autophagic targeting of ferritin include, e.g., interaction of NCOA4 with one or more of ferritin (e.g., the heavy chain of ferritin, FTH1 and/or the light chain of ferritin (FTL)), E3 ubiquitin-protein ligase HERC2 (HERC2), and an ATG8 paralog (e.g., GABARAPL2, LC3).

As used herein, the term "modulating the level of HERC2" means causing any increase or decrease in in the mRNA and/or protein level of HERC2 (e.g., in a cell or a subject (e.g. a mammal)).

As used herein, the term "modulating the activity of HERC2" means causing any increase or decrease in one or more functions of HERC2 involved in regulating expression and/or activity of NCOA4 (e.g., in a cell and/or subject (e.g., a mammal)).

The level or activity of a target gene or polypeptide (e.g., NCOA4, HERC2) is modulated (decreased or increased), if the change in the level or activity of the target gene relative to a control is at least 1.5-fold, at least 2-fold, at least 3-fold, at least 4-fold, at least 5-fold, at least 10-fold, at least 50-fold, at least 100-fold, or more, relative to a starting level of activity (e.g., control or no treatment).

Typically, when an agonist (e.g., small molecule, polypeptide, antibody, intrabody, peptide fragment, allosteric binding of an agent, etc.) is administered as a therapy (e.g., for treating anemia, and increasing red blood cell production (erythropoiesis)), the therapy is deemed effective if the level and/or activity of the target gene or polypeptide is increased by at least 1.5-fold, at least 2-fold, at least 3-fold, at least 4-fold, at least 5-fold, at least 10-fold, at least 50-fold, at least 100-fold, or more, relative to the level of the target gene or polypeptide at the beginning of or before commencement of the therapy.

As used herein, an NCOA4 peptide or NCOA4 polypeptide fragment that is an inhibitor of NCOA4, e.g., an inhibitor of the expression of NCOA4 and/or activity of NCOA4, an inhibitor of the interaction between NCOA4 and ferritin, or between NOCA4 and an ATG8 paralog or HERC2, is not a functionally active fragment of NCOA4.

Typically, when an antagonist/inhibitor (e.g., small molecule, antibody, intrabody, polypeptide, peptide fragment, etc.) is administered as a therapy (e.g., for treating cancer, treating iron overload (e.g. iron overload due to transfusion, hemochromatosis), inhibiting the interaction of NCOA4 with ferritin, inhibiting the interaction of NCOA4 with HERC2 or an ATG8 paralog (e.g., GABARAPL2 or LC3), etc.), the therapy is deemed effective if the level or activity of the target gene or polypeptide is increased by at least 1.5-fold, at least 2-fold, at least 3-fold, at least 4-fold, at least 5-fold, at least 10-fold, at least 50-fold, at least 100-fold, or more, relative to the level of the target gene or polypeptide at the beginning of or before commencement of the therapy.

As used herein, "decreasing the interaction between ferritin and NCOA4" means causing any decrease in the amount of NCOA4 bound to ferritin or the amount of ferritin bound to NCOA4, e.g., a decrease of at least 1.5-fold, at least 2-fold, at least 3-fold, at least 4-fold, at least 5-fold, at least 10-fold, at least 50-fold, at least 100-fold, or more, relative to a starting level (e.g., control or no treatment) of interaction.

Also provided herein are "peptide fragments of NCOA4." Such fragments do not encompass full-length NCOA4. In some embodiments, the peptide fragment has a length of less than 614 amino acids (e.g., 613, 612, 611, 610, etc., e.g., 600, 590, 580, 570, 560. 550, 540, 530, 520, 510, 500, 480, 460, 440, 420, 400, 380, 360, 340, 320, 300, 280, 260, 240, 220, 200, 180, 160, 140, 120, 100, 80, 60, 50, 40, 35, 30, 25 amino residues in length). In some embodiments, a peptide fragment comprises or consists of SEQ ID NO: 11 or the peptide fragment of SEQ ID NO: 11 with no more than 10 conservative amino acid substitutions. In some embodiments, a peptide fragment comprises SEQ ID NO: 1 or the peptide fragment comprising SEQ ID NO: 1 with no more than 10 conservative amino acid substitutions. In some embodiments, a peptide fragment of NCOA4 comprises SEQ ID NO: 2 or the peptide fragment comprises SEQ ID NO: 2 with no more than 10 conservative amino acid substitutions. In some embodiments, a peptide fragment of NCOA4 consists of SEQ ID NO: 1 or the peptide fragment consists of SEQ ID NO: 1 with no more than 10 conservative amino acid substitutions. In some embodiments, a peptide fragment of NCOA4 consists of SEQ ID NO: 2 or the peptide fragment consists of SEQ ID NO: 2 with no more than 10 conservative amino acid substitutions.

Also provided herein are "peptide fragments of ferritin." An exemplary human ferritin heavy chain (FTH1) sequence has GenBank® Accession No. NP_002023 (SEQ ID NO: 6) (183 amino acids). An exemplary mRNA reference sequence for human FTH1 is GenBank® Accession No. NM_002032.2 (SEQ ID NO: 21). An exemplary human ferritin light chain sequence (FTL) has GenBank Accession No. NP_000137 (SEQ ID NO: 7) (175 amino acids). An exemplary mRNA reference sequence for human FTL is GenBank® Accession No. NM_000146.3 (SEQ ID NO: 22). Such fragments do not encompass full-length ferritin (i.e., full length FTL and/or full length FTH1). In some embodiments, an FTH1 peptide fragment has, or an FTH1 nucleic acid encodes a peptide fragment that has, a length of less than 183 amino acids, e.g., 182, 181, 180, 170, 160, 150, 140, 130, 120, 110, 100, 90, 80, 70, 60, 50, 40, 35, 30, 25, 20, 19, 18, 17, 16, 15, 14, 13 12, 11, 10, 9, 8, 7, 6, or 5 amino acid residues in length). In some embodiments, a peptide fragment of FTH1 comprises or consists of amino acids 16-34 of SEQ ID NO: 6 or the peptide fragment of FTH1 comprises or consists if amino acids 16-34 of SEQ ID NO: 6 with no more than 10 conservative amino acid substitutions. Moreover, the peptide fragment of FTH1 can comprise or consist of a segment of amino acids 16-34 of SEQ ID NO: 6, the segment being 18 or fewer amino acids in length (e.g., 17, 16, 15, 14, 13, 12, 11, 10, 9, 8, 7, 6, or 5 amino acids in length) and will preferably include Arg at a position corresponding to residue 23 of SEQ ID NO: 6. In some embodiments, a peptide fragment of FTH1 comprises or consists of amino acids 103-125 of SEQ ID NO: 6 or the peptide fragment of FTH1 comprises or consists if amino acids 103-125 of SEQ ID NO: 6 with no more than 10 conservative amino acid substitutions. Moreover, the peptide fragment of FTH1 can comprise or consist of a segment of amino acids 103-125 of SEQ ID NO: 6, the segment being 22 or fewer amino acids in length (e.g., 21, 20, 19, 18, 17, 16, 15, 14, 13, 12, 11, 10, 9, 8, 7, 6, or 5 amino acids in length). In some embodiments, a peptide fragment of FTH1 comprises or consists of amino acids 78-88 of SEQ ID NO: 6 or the peptide fragment of FTH1 comprises or consists if amino acids 78-88 of SEQ ID NO: 6 with no more than 5 conservative amino acid substitutions. Moreover, the peptide fragment of FTH1 can comprise or consist of a segment of amino acids 78-88 of SEQ ID NO: 6, the segment being 10 or fewer amino acids in length (e.g., 9, 8, 7, 6, or 5 amino acids in length). In some embodiments, an FTL peptide fragment has, or an FTL nucleic acid encodes a peptide fragment that has, a length of less than 175 amino acids, e.g., 174, 173, 172, 171, 170, 160, 150, 140, 130, 120, 110, 100, 90, 80, 70, 60, 50, 40, 35, 30, 25, 20, 15, 10, etc. amino residues in length. A peptide fragment of ferritin can include a fragment of one or both of FTH1 and FTL. Such ferritin fragments can also include 20 or fewer (e.g., 19, 18, 17, 16, 15, 14, 13, 12, 11, 10, 9, 8, 7, 6, 5, 4, 3, 2 or 1) conservative amino acid substitutions.

Similar fragments of ATG8 paralogs and HERC2 are also encompassed by the present disclosure. Such fragments also do not encompass the full length, wild-type sequences.

An exemplary amino acid sequence for human HERC2 has GenBank® Accession No. NP_004658 (SEQ ID NO: 8) (4834 amino acids). An exemplary mRNA reference sequence for human HERC2 is GenBank® Accession No. NM_004667.5 (SEQ ID NO: 23). In some embodiments, a fragment of HERC2 has, or a HERC2 nucleic acid encodes a peptide fragment of HERC2 that has, a length of less than 4834 amino acids (e.g., 4833, 4832, 4800, 4700, 4600, 4500, 4400, 4300, 4200, 4100, 4000, 3500, 3000, 2500, 2000, 1500, 1000, 500, 400, 300, 200, 100, 50, 25, 20, 15, etc.). HERC2 peptide fragments can also include 20 or fewer (e.g., 19, 18, 17, 16, 15, 14, 13, 12, 11, 10, 9, 8, 7, 6, 5, 4, 3, 2 or 1) conservative amino acid substitutions. In a specific embodiment, a HERC2 fragment consists of or comprises amino acid residues 1700-2700 of SEQ ID NO: 8. In certain embodiments, a HERC2 fragment has an amino acid sequence that has at least 85% sequence identity with SEQ ID NO: 8.

An exemplary amino acid sequence for the ATG8 paralog GABARAPLR2 (gamma-aminobutyric acid receptor-associated protein-like 2) has GenBank Accession No. CAG47013 (also NP_009216) (SEQ ID NO: 9) (117 amino acids). An exemplary mRNA reference sequence for human GABARAPLR2 is GenBank® Accession No. NM_007285.6 (SEQ ID NO: 24). Peptide fragments of GABARAPLR2 have, or GABARAPLR2 nucleic acids encode peptide fragments of GABARAPLR2 that have, a length that is less than the length of the full-length wild-type sequence. Thus, in some embodiments, a peptide fragment of GABARAPLR2 has a length of less than 117 amino acids (e.g., 116, 115, 114, 113, 112, 111, 110, 105, 100, 75, 50, 25, 20, 15, etc.). GABARAPLR2 peptide fragments can also include 20 or fewer (e.g., 19, 18, 17, 16, 15, 14, 13, 12, 11, 10, 9, 8, 7, 6, 5, 4, 3, 2 or 1) conservative amino acid substitutions. In certain embodiments, a GABARAPLR2 fragment has an amino acid sequence that has at least 85% sequence identity with SEQ ID NO: 9.

An exemplary amino acid sequence for the ATG8 paralog LC3 (microtubule-associated protein 1 light chain 3 alpha (MAP1LC3A)) has GenBank Accession No. NP_852610 (SEQ ID NO: 10) (125 amino acids). An exemplary mRNA reference sequence for human LC3 is GenBank® Accession No. NM_181509.2 (SEQ ID NO: 25). Peptide fragments of LC3 have, or LC3 nucleic acid sequences encoding peptide fragments of LC3 have, a length that is less than the length of the full-length, wild-type sequence. Thus, in some embodiments, a peptide fragment of LC3 has a length of less than 125 amino acids (e.g., 124, 123, 122, 121, 120, 115, 110, 105, 100, 75, 50, 25, 20, 15, etc.). LC3 peptide fragments can also include 20 or fewer (e.g., 19, 18, 17, 16, 15, 14, 13, 12, 11, 10, 9, 8, 7, 6, 5, 4, 3, 2 or 1) conservative amino acid substitutions. In certain embodiments, a LC3 fragment has an amino acid sequence that has at least 85% sequence identity with SEQ ID NO: 10.

Also encompassed herein are peptide fragments that have at least 85% sequence identity to a peptide fragment described herein, e.g., a peptide fragment having at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or greater sequence identity to: SEQ ID NO: 1, 2, 3, 11, a fragment of SEQ ID NO: 4, 6, 7, or 8, e.g., amino acids 16-34 of SEQ ID NO: 6, amino acids 103-125 of SEQ ID NO: 6, or amino acids 78-88 of SEQ ID NO: 6.

As used herein, "sequence identity" or "identity" in the context of two nucleic acid or polypeptide sequences makes reference to a specified percentage of residues in the two sequences that are identical when aligned for maximum correspondence over a specified comparison window, as measured by sequence comparison algorithms or by visual inspection. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.). Polypeptides with substitutions will generally have not more than 50 (e.g., not more than one, two, three, four, five, six, seven, eight, nine, ten, 12, 15, 20, 25, 30, 35, 40, or 50) conservative amino acid substitutions, although more are possible. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In certain embodiments, a peptide fragment of a polypeptide disclosed herein has "substantial identity" with a reference sequence (e.g., a wild-type sequence of the polypeptide, e.g., of NCOA4, ferritin (FTL or FTH1), HERC2, GABARAPL2, or LC3)). The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Methods for alignment of sequences for comparison are well known in the art. For example, the determination of percent identity between any two sequences can be accomplished using a mathematical algorithm. Non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215: 403 (1990); *Nucl. Acids Res.*, 25:3389 (1990), are based on the algorithm of Karlin and Altschul supra.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in LAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the WorldWideWeb at ncbi.nlm.nih.gov. Alignment may also be performed manually by inspection.

Peptide fragments of ferritin (FTH1 and FTL), ATG8 paralogs, and HERC2 that are functionally active fragments retain the ability to bind to NCOA4. Determining binding to NCOA4 is routine in the art, and can be determined by any suitable method, such as, but not limited to, immunoprecipitation/immunoblot (as described herein), using instruments such as Biacore (see the WorldWideWeb at biacore.com/lifesciences/index.html) and Octet Red (see the WorldWideWeb at fortebio.com/interactions/April_2008/), and/or co-crystallization studies.

As used herein, a "peptide fragment of NCOA4" that is an inhibitor of the interaction between NCOA4 and ferritin, is capable of reducing the binding of NCOA4 to one or both of the heavy and light chains of ferritin (FTH1 and FTL, respectively), e.g., by at least 1.5-fold, at least 2-fold, at least 3-fold, at least 4-fold, at least 5-fold, at least 10-fold, at least 50-fold, at least 100-fold, or more, relative to a starting level of binding (e.g., control or no treatment). In a preferred embodiment, a peptide fragment of NCOA4 inhibits the interaction between NCOA4 and FTH1. In some embodiments, a peptide fragment of NCOA4 inhibits the interaction between NCOA4 and FTH1, e.g., by at least 1.5-fold, at least 2-fold, at least 3-fold, at least 4-fold, at least 5-fold, at least 10-fold, at least 50-fold, at least 100-fold, or more, relative to a starting level of interaction (e.g., control or no treatment).

As used herein, a "peptide fragment of ferritin" that is an inhibitor of the interaction between NCOA4 and ferritin, is capable of reducing the binding of NCOA4 to one or both of the heavy and light chains of ferritin (FTH1 and FTL, respectively), e.g., by at least 1.5-fold, at least 2-fold, at least 3-fold, at least 4-fold, at least 5-fold, at least 10-fold, at least 50-fold, at least 100-fold, or more, relative to a starting level of interaction (e.g., control or no treatment).

Each of the above-disclosed peptide fragments is contemplated for use herein as a composition or formulation.

A "decreased recruitment of NCOA4/ferritin complexes to autophagosomes" can be detected in vitro techniques known in the art, e.g., by Western blot, using antibodies specific for NCOA4 and/or ferritin.

As discussed above, "conservative amino acid substitutions" are well-known in the art and may be made generally without altering the biological activity of the resulting polypeptide (e.g., a peptide fragment of NCOA4, e.g., SEQ ID NO: 1, SEQ ID NO: 2, SEQ ID NO: 3, or SEQ ID NO: 11; or a peptide fragment of FTH1, e.g., amino acids 16-34 of SEQ ID NO: 6, amino acids 103-125 of SEQ ID NO: 6; or amino acids 78-88 of SEQ ID NO: 6). For example, such substitutions are generally made by interchanging within the groups of polar residues, charged residues, hydrophobic residues, small residues, and the like. Conservative substitutions are described above. If necessary, such substitutions may be determined empirically merely by testing the resulting modified protein for the ability to bind to and/or interact with the appropriate ligand (e.g., ferritin and/or a ATG8 paralog and/or HERC2) in in vitro biological assays (e.g., immunoassays, such as immunoprecipitation and Western blot). In some embodiments, a peptide disclosed herein (e.g., a peptide comprising SEQ ID NO:1, 2 or 3) has no more than than 30, no more than 25, no more than 20, no more than 15, no more than 10, no more than 9, no more than 8, no more than 7, no more than 6, no more than 5, no more than 4, no more than 3, no more than 2, or no more than 1 conservative amino acid substitutions. All that is required is that: (i) such variants of NCOA4 or fragments thereof have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type, full-length, NCOA4 to bind to ferritin; (ii) such variants of NCOA4 or fragments thereof have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type, full-length, NCOA4 to bind to bind to wild-type HERC2; and/or (iii) such variants of NCOA4 have at least 25% (e.g., at least: 30%; 40%; 50%; 60%; 70%; 75%; 80%; 85%; 90%; 95%; 97%; 98%; 99%; 99.5%, or 100% or even greater) of the ability of the relevant wild-type, full-length NCOA4 protein to bind to wild-type GABARAPL2 or microtubule-associated proteins 1A/1B light chain 3A (LC3). Moreover, all that is required is that such variants of FTH1 or fragments thereof have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type, full-length, FTH1 to bind to NCOA4.

As used herein, the term "delivering to the interior of the cell", e.g., of an agent, means causing an agent (e.g., antibody, intrabody, peptide fragment, polypeptide, small molecule, antisense oligonucleotide, etc.) to pass through and/or be transported through the outer cell membrane into at least the cytosol of the cell.

As used herein, a "NCOA4 reagent" contains, comprises or is: (a) full-length, wild-type NCOA4; (b) a functional fragment of NCOA4; or (c) (a) or (b) but with not more than 20 conservative substitutions (see above). In addition, "NCOA4 reagents" can include with (a), (b), or (c), internal or terminal (C or N) irrelevant amino acid sequences (e.g., sequences derived from other proteins or synthetic sequences not corresponding to any naturally occurring protein). The sequences can be, for example, an antigenic tag (e.g., FLAG, polyhistidine, hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). Heterologous sequences can be of varying length and, in some cases, can be a longer sequence than the NCOA4 polypeptide. Generally, the heterologous sequences are about 1-50 (e.g., two, four, eight, ten, 15, 20, 25, 30, 35, 40, or 45) amino acids in length. NCOA4 reagents, other than full-length, wild-type NCOA4, have at least 25% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length, wild-type, NCOA4 to bind to either or both of the heavy and light chain of ferritin and/or to an ATG8 paralog reagent (described below) and/or to a HERC2 reagent (described below).

As used herein, a "ferritin reagent", e.g., for the screening assays disclosed herein, include, e.g., (a) full-length, wild-type ferritin; (b) a functional fragment of ferritin; or (c) (a) or (b) but with not more than 20 conservative substitutions, apo-ferritin from human liver or equine spleen or produced recombinantly in *E. coli* as FTH1, FTL, or a combination of FTH1 and FTL. In functional fragments of ferritin, there can be, for example, a full length FTH1 and a fragment of FTL, a fragment of FTH1 and full length FTL, a fragment of full length of either FTH1 or FTL, or a fragment of both FTH1 and FTL. Ferritin reagents, other than full-length, wild-type, ferritin, have at least 25% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length wild-type ferritin to bind to NCOA4 (e.g., to SEQ ID NO: 11, SEQ ID NO: 1, or SEQ ID NO:2 in NCOA4). In addition, "ferritin reagents" can also include internal or terminal (C or N) irrelevant amino acid sequences (e.g., sequences derived from other proteins or synthetic sequences not corresponding to any naturally occurring protein) as described above for NCOA4 polypeptides.

As used herein, a "ATG8 paralog reagent," e.g., for the screening assays disclosed herein, include, e.g., (a) full-length, wild-type ATG8 paralog (e.g., GABARAPL2 or LC3); (b) a functional fragment of an ATG8 paralog; or (c) (a) or (b) but with not more than 10 conservative substitutions. The ATG8 paralog can be a recombinantly expressed protein from *E. coli*. ATG8 paralog reagents, other than a full-length, wild-type ATG8 paralog, have at least 25% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length wild-type ATG8 paralog to bind to NCOA4. In addition, "ATG8 paralog reagents" can also include internal or terminal (C or N) irrelevant amino acid sequences (e.g., sequences derived from other proteins or synthetic sequences not corresponding to any naturally occurring protein) as described above for NCOA4 polypeptides.

As used herein, a "HERC2 reagent," e.g., for the screening assays disclosed herein, include, e.g., (a) full-length, wild-type HERC2; (b) a functional fragment of HERC2; or (c) (a) or (b) but with not more than 10 conservative substitutions. The HERC2 can be a recombinantly expressed protein from *E. coli*. HERC2 reagents, other than a full-length, wild-type HERC2 (e.g., human HERC2), have at least 25% (e.g., at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length wild-type HERC2 to bind to NCOA4. HERC2 reagents have the ability to bind to SEQ ID NO: 3 in NCOA4. In addition, "HERC2 reagents" can also include internal or terminal (C or N) irrelevant amino acid sequences (e.g., sequences derived from other proteins or synthetic sequences not corresponding to any naturally occurring protein) as described above for NCOA4 polypeptides.

As used herein, the term "subject" means any animal, including any vertebrate, including any mammal, and, in particular, a human, and can also be referred to, e.g., as an individual or patient. A non-human mammal can be, for example, without limitation a non-human primate (such as a monkey, baboon, gorilla, or orangutan), a bovine animal, a horse, a whale, a dolphin, a sheep, a goat, a pig, a dog, a feline animal (such as a cat), a rabbit, a guinea pig, a hamster, a gerbil, a rat, or a mouse. Non-mammalian vertebrates include without limitation, a bird, a reptile, or a fish.

As used herein, "reducing" means any level of reduction up to and including full inhibition.

As used herein, a "subject in need of increased erythropoiesis" can be, for example and without limitation, a subject who has a low red blood cell count, anemia, and/or excessive blood loss.

The term "nucleic acid hybridization" refers to the pairing of complementary strands of nucleic acids. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide (oligo) inhibitors washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA or RNA molecule and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al.

(eds.), 1989, Current Protocols in Molecular Biology, Vol. I, Green Publishing Associates, Inc., and John Wiley & Sons, Inc., New York, at p. 2.10.3). An extensive guide to the hybridization of nucleic acids is found in, e.g., Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen").

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 85% sequence identity, at least 90% sequence identity, at least 95% sequence identity, or at least 99% sequence identity.

As used herein, the phrase "under hybridization conditions" means under conditions that facilitate specific hybridization of a nucleic acid sequence to a complementary sequence. The terms "hybridizing specifically to" and "specific hybridization" and "selectively hybridize to," as used herein refer to the binding, duplexing, or hybridizing of a nucleic acid molecule preferentially to a particular nucleotide sequence under at least moderately stringent conditions, and preferably, highly stringent conditions, as discussed above.

"Polypeptide" and "protein" are used interchangeably and mean any peptide-linked chain of amino acids, regardless of length or post-translational modification.

As used herein, the term "nucleic acid" or "oligonucleotide" refers to a deoxyribonucleotide or ribonucleotide in either single- or double-stranded form. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (Strauss-Soukup (1997) Biochemistry 36:8692-8698), and benzylphosphonate linkages (Samstag (1996) Antisense Nucleic Acid Drug Dev 6:153-156). The term nucleic acid is used interchangeably with cDNA, cRNA, mRNA, oligonucleotide, probe and amplification product.

In certain embodiments, it is desirable to determine (e.g., assay, measure, approximate) the level (e.g., expression or activity), e.g., one of the above-identified markers. The expression level of such markers may be determined according to any suitable method known in the art. A non-limiting example of such a method includes real-time PCR (RT-PCR), e.g., quantitative RT-PCR (QPCR), which measures the expression level of the mRNA encoding the polypeptide. Real-time PCR evaluates the level of PCR product accumulation during amplification. RNA (or total genomic DNA for detection of germline mutations) is isolated from a sample. RT-PCR can be performed, for example, using a Perkin Elmer/Applied Biosystems (Foster City, Calif.) 7700 Prism instrument. Matching primers and fluorescent probes can be designed for genes of interest using, based on the genes' nucleic acid sequences (e.g., as described above), for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.).

To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from $10-10^6$ copies of the gene of interest are generally sufficient. In addition, a standard curve is generated for the control sequence. This permits standardization of initial content of the nucleic acid of interest in a tissue sample to the amount of control for comparison purposes. Methods of QPCR using TaqMan probes are well known in the art. Detailed protocols for QPCR are provided, for example, for RNA in: Gibson et al., 1996, *Genome Res.,* 10:995-1001; and for DNA in: Heid et al., 1996, *Genome Res.,* 10:986-994; and in Innis et al. (1990) Academic Press, Inc. N.Y.

Expression of mRNA, as well as expression of peptides and other biological factors can also be determined using microarray, methods for which are well known in the art [see, e.g., Watson et al. Curr Opin Biotechnol (1998) 9: 609-14; "DNA microarray technology: Devices, Systems, and Applications" *Annual Review of Biomedical Engineering*; Vol. 4: 129-153 (2002); Chehab et al. (1989) "Detection of specific DNA sequences by fluorescence amplification: a color complementation assay" *Proc. Natl. Acad. Sci. USA,* 86: 9178-9182; Lockhart et al. (1996) "Expression monitoring by hybridization to high-density oligonucleotide arrays" *Nature Biotechnology,* 14: 1675-1680; and M. Schena et al. (1996) "Parallel human genome analysis: Microarray-based expression monitoring of 1000 genes" *Proc. Natl. Acad. Sci. USA,* 93:10614-10619; *Peptide Microarrays Methods and Protocols; Methods in Molecular Biology;* Volume 570, 2009, Humana Press; and *Small Molecule Microarrays Methods and Protocols; Series: Methods in Molecular Biology,* Vol. 669, Uttamchandani, Mahesh; Yao, Shao Q. (Eds.) 2010, 2010, Humana Press]. For example, mRNA expression profiling can be performed to identify differentially expressed genes, wherein the raw intensities determined by microarray are $\log_2$-transformed and quantile normalized and gene set enrichment analysis (GSEA) is performed according, e.g., to Subramanian et al. (2005) *Proc Natl Acad Sci USA* 102:15545-15550).

Other suitable amplification methods include, but are not limited to ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc. In another embodiment, DNA sequencing may be used to determine the presence of ER in a genome. Methods for DNA sequencing are known to those of skill in the art.

Other methods for detecting gene expression (e.g., mRNA levels) include Serial Analysis of Gene Expression applied to high-throughput sequencing (SAGEseq), as described in Wu Z J et al. Genome Res. 2010 December; 20(12):1730-9.2.

Methods for detecting the expression levels of polypeptides are also known in the art. Non-limiting examples of suitable methods for detecting expression levels of gene products (i.e., polypeptides) described herein include, e.g., flow cytometry, immunoprecipitation, Western blot (see, e.g., Battle T E, Arbiser J, & Frank D A (2005) The natural product honokiol induces caspase-dependent apoptosis in B-cell chronic lymphocytic leukemia (B-CLL) cells. Blood 106(2):690-697), ELISA (enzyme-linked immunosorbent assay) and/or immunohistochemistry.

Antisense Nucleic Acids

Antisense oligonucleotides can be used to inhibit the expression of a target polypeptide of the invention (e.g., NCOA4, HERC2, an ATG8 paralog, etc). Antisense oligonucleotides typically are about 5 nucleotides to about 30 nucleotides in length, about 10 to about 25 nucleotides in length, or about 20 to about 25 nucleotides in length. For a general discussion of antisense technology, see, e.g., Antisense DNA and RNA, (Cold Spring Harbor Laboratory, D. Melton, ed., 1988).

Appropriate chemical modifications of the inhibitors are made to ensure stability of the antisense oligonucleotide, as described below. Changes in the nucleotide sequence and/or in the length of the antisense oligonucleotide can be made to ensure maximum efficiency and thermodynamic stability of the inhibitor. Such sequence and/or length modifications are readily determined by one of ordinary skill in the art.

The antisense oligonucleotides can be DNA or RNA or chimeric mixtures, or derivatives or modified versions thereof, and can be single-stranded or double-stranded. Thus, for example, in the antisense oligonucleotides set forth in herein, when a sequence includes thymidine residues, one or more of the thymidine residues may be replaced by uracil residues and, conversely, when a sequence includes uracil residues, one or more of the uracil residues may be replaced by thymidine residues.

Antisense oligonucleotides comprise sequences complementary to at least a portion of the corresponding target polypeptide. However, 100% sequence complementarity is not required so long as formation of a stable duplex (for single stranded antisense oligonucleotides) or triplex (for double stranded antisense oligonucleotides) can be achieved. The ability to hybridize will depend on both the degree of complementarity and the length of the antisense oligonucleotides. Generally, the longer the antisense oligonucleotide, the more base mismatches with the corresponding nucleic acid target can be tolerated. One skilled in the art can ascertain a tolerable degree of mismatch by use of standard procedures to determine the melting point of the hybridized complex.

Antisense nucleic acid molecules can be encoded by a recombinant gene for expression in a cell (see, e.g., U.S. Pat. Nos. 5,814,500 and 5,811,234), or alternatively they can be prepared synthetically (see, e.g., U.S. Pat. No. 5,780,607).

The antisense oligonucleotides can be modified at the base moiety, sugar moiety, or phosphate backbone, or a combination thereof. In one embodiment, the antisense oligonucleotide comprises at least one modified sugar moiety, e.g., a sugar moiety such as arabinose, 2-fluoroarabinose, xylulose, and hexose.

In another embodiment, the antisense oligonucleotide comprises at least one modified phosphate backbone such as a phosphorothioate, a phosphorodithioate, a phosphoramidothioate, a phosphoramidate, a phosphordiamidate, a methylphosphonate, an alkyl phosphotriester, and a formacetal or analog thereof. Examples include, without limitation, phosphorothioate antisense oligonucleotides (e.g., an antisense oligonucleotide phosphothioate modified at 3' and 5' ends to increase its stability) and chimeras between methylphosphonate and phosphodiester oligonucleotides. These oligonucleotides provide good in vivo activity due to solubility, nuclease resistance, good cellular uptake, ability to activate RNase H, and high sequence selectivity.

Other examples of synthetic antisense oligonucleotides include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with CH2-NH—O—CH2, CH2-N(CH3)-O—CH2, CH2-O—N(CH3)-CH2, CH2-N(CH3)-N(CH3)-CH2 and O—N(CH3)-CH2-CH2 backbones (where phosphodiester is O—PO2-O—CH2). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds.

In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 1991; 254:1497). Other synthetic oligonucleotides may contain substituted sugar moieties comprising one of the following at the 2' position: OH, SH, SCH3, F, OCN, O(CH2)nNH2 or O(CH2)nCH3 where n is from 1 to about 10; C1 to C10 lower alkyl, substituted lower alkyl, alkaryl or aralkyl; Cl; Br; CN; CF3; OCF3; O—; S—, or N-alkyl; O—, S—, or N-alkenyl; SOCH3; SO2CH3; ONO2; NO2; N3; NH2; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties.

Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine. In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability. LNA allows the use of very short oligonucleotides (less than 10 bp) for efficient hybridization in vivo.

In one embodiment, an antisense oligonucleotide can comprise at least one modified base moiety such as a group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the antisense oligonucleotide can include α-anomeric oligonucleotides. An α-anomeric oligonucleotide forms specific double-stranded hybrids with complementary RNA in which, contrary to the usual β-units, the strands run parallel to each other (Gautier et al., Nucl. Acids Res. 1987; 15:6625-6641).

Oligonucleotides may have morpholino backbone structures (U.S. Pat. No. 5,034,506). Thus, in yet another embodiment, the antisense oligonucleotide can be a morpholino antisense oligonucleotide (i.e., an oligonucleotide in which the bases are linked to 6-membered morpholine rings, which are connected to other morpholine-linked bases via nonionic phosphorodiamidate intersubunit linkages). Morpholino oligonucleotides are highly resistant to nucleases and have good targeting predictability, high in-cell efficacy and high sequence specificity (U.S. Pat. No. 5,034,506; Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Antisense oligonucleotides may be chemically synthesized, for example using appropriately protected ribonucleoside phosphoramidites and a conventional DNA/RNA synthesizer. Antisense nucleic acid oligonucleotides can also be produced intracellularly by transcription from an exogenous sequence. For example, a vector can be introduced in vivo such that it is taken up by a cell within which the vector or a portion thereof is transcribed to produce an antisense RNA. Such a vector can remain episomal or become chromosomally integrated, so long as it can be transcribed to produce the desired antisense RNA. Such vectors can be constructed by recombinant DNA technology methods standard in the art. Vectors can be plasmid, viral, or others known in the art, used for replication and expression in mammalian cells. In another embodiment, "naked" antisense nucleic acids can be delivered to adherent cells via "scrape delivery", whereby the antisense oligonucleotide is added to a culture of adherent cells in a culture vessel, the cells are scraped from the walls of the culture vessel, and the scraped cells are transferred to another plate where they are allowed to re-adhere. Scraping the cells from the culture vessel walls serves to pull adhesion plaques from the cell membrane, generating small holes that allow the antisense oligonucleotides to enter the cytosol.

RNAi

Reversible short inhibition of a target polypeptide (e.g., NCOA4, HERC2, or an ATG8 paralog) of the invention may also be useful. Such inhibition can be achieved by use of siRNAs. RNA interference (RNAi) technology prevents the expression of genes by using small RNA molecules such as small interfering RNAs (siRNAs). This technology in turn takes advantage of the fact that RNAi is a natural biological mechanism for silencing genes in most cells of many living organisms, from plants to insects to mammals (McManus et al., Nature Reviews Genetics, 2002, 3(10) p. 737). RNAi prevents a gene from producing a functional protein by ensuring that the molecule intermediate, the messenger RNA copy of the gene is destroyed siRNAs can be used in a naked form and incorporated in a vector, as described below.

RNA interference (RNAi) is a process of sequence-specific post-transcriptional gene silencing by which double stranded RNA (dsRNA) homologous to a target locus can specifically inactivate gene function in plants, fungi, invertebrates, and vertebrates, including mammals (Hammond et al., Nature Genet. 2001; 2:110-119; Sharp, Genes Dev. 1999; 13:139-141). This dsRNA-induced gene silencing is mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245).

For mammalian systems, RNAi commonly involves the use of dsRNAs that are greater than 500 bp; however, it can also be activated by introduction of either siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

The siRNAs are preferably short double stranded nucleic acid duplexes comprising annealed complementary single stranded nucleic acid molecules. Preferably, the siRNAs are short dsRNAs comprising annealed complementary single strand RNAs. siRNAs may also comprise an annealed RNA:DNA duplex, wherein the sense strand of the duplex is a DNA molecule and the antisense strand of the duplex is a RNA molecule.

Preferably, each single stranded nucleic acid molecule of the siRNA duplex is of from about 19 nucleotides to about 27 nucleotides in length. In preferred embodiments, duplexed siRNAs have a 2 or 3 nucleotide 3' overhang on each strand of the duplex. In preferred embodiments, siRNAs have 5'-phosphate and 3'-hydroxyl groups.

RNAi molecules may include one or more modifications, either to the phosphate-sugar backbone or to the nucleoside. For example, the phosphodiester linkages of natural RNA may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Where the RNAi molecule is produced synthetically, or by in vitro transcription, a modified ribonucleoside may be introduced during synthesis or transcription. The skilled artisan will understand that many of the modifications described above for antisense oligonucleotides may also be made to RNAi molecules. Such modifications are well known in the art.

siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA.

shRNAs typically comprise a single stranded "loop" region connecting complementary inverted repeat sequences that anneal to form a double stranded "stem" region. Structural considerations for shRNA design are discussed, for example, in McManus et al., RNA 2002; 8:842-850. In certain embodiments the shRNA may be a portion of a larger RNA molecule, e.g., as part of a larger RNA that also contains U6 RNA sequences (Paul et al., supra).

In preferred embodiments, the loop of the shRNA is from about 1 to about 9 nucleotides in length. In preferred embodiments the double stranded stem of the shRNA is from about 19 to about 33 base pairs in length. In preferred embodiments, the 3' end of the shRNA stem has a 3' overhang. In particularly preferred embodiments, the 3' overhang of the shRNA stem is from 1 to about 4 nucleotides in length. In preferred embodiments, shRNAs have 5'-phosphate and 3'-hydroxyl groups.

Non-limiting examples of shRNA molecules that can be used according to the methods disclosed herein include, e.g., siRNA against NCOA4, e.g., shNCOA4-1: 5' CCCAG-GAAGTATTACTTAATT 3' (TRCN0000019724) (SEQ ID NO: 12), shNCOA4-2: 5' GCTGGCAAACAGAAGTT-TAAA 3' (TRCN0000019726) (SEQ ID NO: 13), siNCOA4-1: 5' ACAAAGAUCUAGCCAAUCA 3' (SEQ ID NO: 15) and siNCOA4-2: 5' GACCUUAUUUAUCAGCUUA 3' (SEQ ID NO: 16), and siRNA against HERC2 (Gene ID: 8924, NM_004667.5), e.g., siHERC2-1: 5' GCACAGA-GUAUCACAGGUA 3' (SEQ ID NO: 17) and siHERC2-2: 5' CGAUGAAGGUUUGGUAUUU 3' (SEQ ID NO: 18).

Although RNAi molecules preferably contain nucleotide sequences that are fully complementary to a portion of the target nucleic acid, 100% sequence complementarity between the RNAi probe and the target nucleic acid is not required.

Similar to the above-described antisense oligonucleotides, RNAi molecules can be synthesized by standard methods known in the art, e.g., by use of an automated synthesizer. RNAs produced by such methodologies tend to be highly pure and to anneal efficiently to form siRNA duplexes or shRNA hairpin stem-loop structures. Following chemical synthesis, single stranded RNA molecules are deprotected, annealed to form siRNAs or shRNAs, and purified (e.g., by gel electrophoresis or HPLC). Alternatively, standard procedures may be used for in vitro transcription of RNA from DNA templates carrying RNA polymerase promoter sequences (e.g., T7 or SP6 RNA polymerase promoter sequences). Efficient in vitro protocols for preparation of siRNAs using T7 RNA polymerase have been described (Donzé and Picard, Nucleic Acids Res. 2002; 30:e46; and Yu et al., Proc. Natl. Acad. Sci. USA 2002; 99:6047-6052). Similarly, an efficient in vitro protocol for preparation of shRNAs using T7 RNA polymerase has been described (Yu et al., supra). The sense and antisense transcripts may be synthesized in two independent reactions and annealed later, or may be synthesized simultaneously in a single reaction.

RNAi molecules may be formed within a cell by transcription of RNA from an expression construct introduced into the cell. For example, both a protocol and an expression construct for in vivo expression of siRNAs are described in Yu et al., supra. The delivery of siRNA to tumors can potentially be achieved via any of several gene delivery "vehicles" that are currently available. These include viral vectors, such as adenovirus, lentivirus, herpes simplex virus, vaccinia virus, and retrovirus, as well as chemical-mediated gene delivery systems (for example, liposomes), or mechanical DNA delivery systems (DNA guns). The oligonucleotides to be expressed for such siRNA-mediated inhibition of gene expression would be between 18 and 28 nucleotides in length. Protocols and expression constructs for in vivo expression of shRNAs have been described (Brummelkamp et al., Science 2002; 296:550-553; Sui et al., supra; Yu et al., supra; McManus et al., supra; Paul et al., supra).

The expression constructs for in vivo production of RNAi molecules comprise RNAi encoding sequences operably linked to elements necessary for the proper transcription of the RNAi encoding sequence(s), including promoter elements and transcription termination signals. Preferred promoters for use in such expression constructs include the polymerase-III HI-RNA promoter (see, e.g., Brummelkamp et al., supra) and the U6 polymerase-III promoter (see, e.g., Sui et al., supra; Paul, et al. supra; and Yu et al., supra). The RNAi expression constructs can further comprise vector sequences that facilitate the cloning of the expression constructs. Standard vectors are known in the art (e.g., pSilencer 2.0-U6 vector, Ambion Inc., Austin, Tex.).

Ribozyme Inhibition

The level of expression of a target polypeptide of the invention can also be inhibited by ribozymes designed based on the nucleotide sequence thereof.

Ribozymes are enzymatic RNA molecules capable of catalyzing the sequence-specific cleavage of RNA (for a review, see Rossi, Current Biology 1994; 4:469-471). The mechanism of ribozyme action involves sequence-specific hybridization of the ribozyme molecule to complementary target RNA, followed by an endonucleolytic cleavage event. The composition of ribozyme molecules must include: (i) one or more sequences complementary to the target RNA; and (ii) a catalytic sequence responsible for RNA cleavage (see, e.g., U.S. Pat. No. 5,093,246).

Figure 4:
FIG. 4 is a schematic diagram of the N and C-terminal regions of NCOA4, based on secondary structure predictions. Overlapping N-terminal and C-terminal fragments were designed as follows: NCOA4 N-terminal fragment, amino acids 1-245, and NCOA4 C-terminal fragment, amino acids 235-614.
Figure 4:

The use of hammerhead ribozymes is preferred. Hammerhead ribozymes cleave RNAs at locations dictated by flanking regions that form complementary base pairs with the target RNA. The sole requirement is that the target RNA has the following sequence of two bases: 5'-UG-3'. The construction of hammerhead ribozymes is known in the art, and described more fully in Myers, Molecular Biology and Biotechnology: A Comprehensive Desk Reference, VCH Publishers, New York, 1995 (see especially FIG. 4, page 833) and in Haseloff and Gerlach, Nature 1988; 334:585-591.

As in the case of antisense oligonucleotides, ribozymes can be composed of modified oligonucleotides (e.g., for improved stability, targeting, etc.). These can be delivered to cells which express the target polypeptide in vivo. A preferred method of delivery involves using a DNA construct "encoding" the ribozyme under the control of a strong constitutive pol III or pol II promoter, so that transfected cells will produce sufficient quantities of the ribozyme to catalyze cleavage of the target mRNA encoding the target polypeptide. However, because ribozymes, unlike antisense molecules, are catalytic, a lower intracellular concentration may be required to achieve an adequate level of efficacy.

Ribozymes can be prepared by any method known in the art for the synthesis of DNA and RNA molecules, as discussed above. Ribozyme technology is described further in Intracellular Ribozyme Applications: Principals and Protocols, Rossi and Couture eds., Horizon Scientific Press, 1999.

Triple Helix Forming Oligonucleotides (TFOs)

Nucleic acid molecules useful to inhibit expression level of a target polypeptide of the invention via triple helix formation are preferably composed of deoxynucleotides. The base composition of these oligonucleotides is typically designed to promote triple helix formation via Hoogsteen base pairing rules, which generally require sizeable stretches of either purines or pyrimidines to be present on one strand of a duplex. Nucleotide sequences may be pyrimidine-based, resulting in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, e.g., those containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, sequences can be targeted for triple helix formation by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Similarly to RNAi molecules, antisense oligonucleotides, and ribozymes, described above, triple helix molecules can be prepared by any method known in the art. These include techniques for chemically synthesizing oligodeoxyribonucleotides and oligoribonucleotides such as, e.g., solid phase phosphoramidite chemical synthesis. Alternatively, RNA molecules can be generated by in vitro or in vivo transcription of DNA sequences "encoding" the particular RNA molecule. Such DNA sequences can be incorporated into a wide variety of vectors that incorporate suitable RNA polymerase promoters such as the T7 or SP6 polymerase promoters. See, Nielsen, P. E. "Triple Helix: Designing a New Molecule of Life", Scientific American, December, 2008; Egholm, M., et al. "PNA Hybridizes to Complementary Oligonucleotides Obeying the Watson-Crick Hydrogen Bonding Rules." (1993) Nature, 365, 566-568; Nielsen, P. E. 'PNA Technology'. Mol Biotechnol. 2004; 26:233-48.

Antibodies and Aptamers

The polypeptide targets described herein, e.g., NCOA4, HERC2, an ATG8 paralog, etc.) can be inhibited (e.g., the level can be reduced) by the administration to or expression in a subject or a cell or tissue thereof, of blocking antibodies or aptamers against the polypeptide.

Antibodies, or their equivalents and derivatives, e.g., intrabodies, or other antagonists of the polypeptide, may be used in accordance with the present methods. Methods for engineering intrabodies (intracellular single chain antibodies) are well known. Intrabodies are specifically targeted to a particular compartment within the cell, providing control over where the inhibitory activity of the treatment is focused. This technology has been successfully applied in the art (for review, see Richardson and Marasco, 1995, TIBTECH vol. 13; Lo et al. (2009) Handb Exp Pharmacol. 181:343-73; Maraasco, W. A. (1997) Gene Therapy 4:11-15; see also, U.S. Pat. Appln. Pub. No. 2001/0024831 by Der Maur et al. and U.S. Pat. No. 6,004,940 by Marasco et al.).

Administration of a suitable dose of the antibody or the antagonist (e.g., aptamer) may serve to block the level (expression or activity) of the polypeptide in order to treat or prevent a disease or condition disclosed herein (e.g., a cancer that uses selective autophagy for growth, anemia, iron overload, etc.).

In addition to using antibodies and aptamers to inhibit the levels and/or activity of a target polypeptide, it may also be possible to use other forms of inhibitors. For example, it may be possible to identify antagonists that functionally inhibit the target polypeptide (e.g., NCOA4, HERC2, an ATG8 paralog, etc.). In addition, it may also be possible to interfere with the interaction of the polypeptide with its substrate. Other suitable inhibitors will be apparent to the skilled person.

The antibody (or other inhibitors and antagonists) can be administered by a number of methods. For example, for the administration of intrabodies, one method is set forth by Marasco and Haseltine in PCT WO 94/02610. This method discloses the intracellular delivery of a gene encoding the intrabody. In one embodiment, a gene encoding a single chain antibody is used. In another embodiment, the antibody would contain a nuclear localization sequence. By this method, one can intracellularly express an antibody, which can block activity of the target polypeptide in desired cells.

Aptamers are oligonucleic acid or peptide molecules that bind to a specific target molecule. Aptamers can be used to inhibit gene expression and to interfere with protein interactions and activity. Nucleic acid aptamers are nucleic acid species that have been engineered through repeated rounds of in vitro selection (e.g., by SELEX (systematic evolution of ligands by exponential enrichment)) to bind to various molecular targets such as small molecules, proteins, nucleic acids, and even cells, tissues and organisms. Peptide aptamers consist of a variable peptide loop attached at both ends to a protamersein scaffold. Aptamers are useful in biotechnological and therapeutic applications as they offer molecular recognition properties that rival that of antibodies. Aptamers can be engineered completely in a test tube, are readily produced by chemical synthesis, possess desirable storage properties, and elicit little or no immunogenicity in therapeutic application. Aptamers can be produced using the methodology disclosed in a U.S. Pat. No. 5,270,163 and WO 91/19813.

Small Molecules

Chemical agents, referred to in the art as "small molecule" compounds are typically organic, non-peptide molecules, having a molecular weight less than 10,000 Da, preferably less than 5,000 Da, more preferably less than 1,000 Da, and most preferably less than 500 Da. This class of modulators includes chemically synthesized molecules, for instance, compounds from combinatorial chemical libraries. Synthetic compounds may be rationally designed or identified utilizing the screening methods described below. Methods for generating and obtaining small molecules are well known in the art (Schreiber, Science 2000; 151:1964-1969; Radmann et al., Science 2000; 151:1947-1948).

In certain embodiments, the above described inhibitors and agonists can be directly targeted to a specific cell type (e.g., a cancer cell, or a red blood cell) or to a site of erythropoiesis (e.g., bone marrow). The skilled artisan will appreciate that methods for specific cell targeting are well known in the art. By way of non-limiting example, antibodies, e.g., an anti-tumor antigen antibody, may be conjugated to an inhibitor or agonist described herein, in order to target the inhibitor or agonist to, for example and without limitation, a cancer cell. Further the site of administration (e.g., direct injection into a tumor) can further increase the specificity of cell targeting.

In some embodiments, the methods can comprise recording the results (e.g., diagnostic) in a database or medical history (e.g., medical records) of the subject, selecting the subject for increased monitoring or periodically monitoring the health of the subject (e.g., for development or changes in the signs or symptoms of the cancer (e.g. pancreatic cancer, lung cancer, melanoma, breast cancer, glioblastoma, colorectal cancer, prostate cancer, multiple myeloma, renal cell carcinoma, chronic lymphocytic leukemia, lymphoma, chronic myelogenous leukemia, etc.), e.g., tumor development and/or changes in tumor size (e.g., increased or decreased size), such as e.g., clinical breast exam, mammography, MRI, or other suitable imaging or other diagnostic method(s) known in the art.

Administration and Treatment

Compositions and formulations comprising an inhibitor/antagonist or agonist (i.e., an "agent") disclosed herein (e.g., an inhibitor/antagonist or agonist of a gene or polypeptide involved in NCOA4-mediated autophagic targeting of ferritin, e.g., NCOA4, an ATG8 paralog, HERC2), can be administered topically, parenterally, orally, by inhalation, as a suppository, or by other methods known in the art. The term "parenteral" includes injection (for example, intravenous, intraperitoneal, epidural, intrathecal, intramuscular, intraluminal, intratracheal or subcutaneous). Exemplary routes of administration include, e.g., intravenous, intraductal, and intratumoral. Other exemplary routes of administration include, e.g., an implantable delivery device (e.g., subcutaneously implanted devices, intrathecal pumps, intrauterine devices, biodegradable material such as poly(lactic-co-glycolic acid) or PLGA, etc.).

While it is possible to use an agent of the invention for therapy as is, it may be preferable to administer an inhibitor or agonist as a pharmaceutical formulation, e.g., in admixture with a suitable pharmaceutical excipient, diluent, or carrier selected with regard to the intended route of administration and standard pharmaceutical practice. Pharmaceutical formulations comprise at least one active compound, or a pharmaceutically acceptable derivative thereof, in association with a pharmaceutically acceptable excipient, diluent, and/or carrier. The excipient, diluent and/or carrier must be "pharmaceutically acceptable." As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Administration of a composition or formulation can be once a day, twice a day, or more often. Frequency may be decreased during a treatment maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

It will be appreciated that the amount of an inhibitor required for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. Preliminary doses can be determined according to animal tests, and the scaling of dosages for human administration can be performed according to art-accepted practices.

Length of treatment, i.e., number of days, will be readily determined by a physician treating the subject; however the number of days of treatment may range from 1 day to about 20 days. As provided by the present methods, and discussed below, the efficacy of treatment can be monitored during the course of treatment to determine whether the treatment has been successful, or whether additional (or modified) treatment is necessary.

As used herein, "treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; and/or (2) inhibiting the state, disorder or condition, i.e., arresting, reducing or delaying the development of the disease or a relapse thereof (in case of maintenance treatment) or at least one clinical or sub-clinical symptom thereof; and/or (3) relieving the disease, i.e., causing regression of the state, disorder or condition or at least one of its clinical or sub-clinical symptoms; and/or (4) causing a decrease in the severity of one or more symptoms of the disease. The benefit to a subject to be treated is either statistically significant or at least perceptible to the patient or to the physician.

As used herein, the term "treating cancer" (e.g., a cancer that is reliant on selective autophagy for growth (such as but not limited to pancreatic cancer, lung cancer, melanoma, breast cancer, glioblastoma, colorectal cancer, prostate cancer, multiple myeloma, renal cell carcinoma, chronic lymphocytic leukemia, lymphoma, and chronic myelogenous leukemia) means causing a partial or complete decrease in the rate of growth of a tumor, and/or in the size of the tumor and/or in the rate of local or distant tumor metastasis in the presence of an inhibitor of the invention, and/or any decrease in tumor survival.

As used herein, the term "preventing a disease" (e.g., a cancer that is reliant on selective autophagy for growth, anemia, iron overload, etc., as disclosed herein) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

As used herein "combination therapy" means the treatment of a subject in need of treatment with a certain composition or drug in which the subject is treated or given one or more other compositions or drugs for the disease in conjunction with the first and/or in conjunction with one or more other therapies, such as, e.g., a cancer therapy such as chemotherapy, radiation therapy, and/or surgery. Such combination therapy can be sequential therapy wherein the patient is treated first with one treatment modality (e.g., drug or therapy), and then the other (e.g., drug or therapy), and so on, or all drugs and/or therapies can be administered simultaneously. In either case, these drugs and/or therapies are said to be "coadministered." It is to be understood that "coadministered" does not necessarily mean that the drugs and/or therapies are administered in a combined form (i.e., they may be administered separately or together to the same or different sites at the same or different times).

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol. 1: Principles and Practice, which is incorporated herein by reference to the extent of teaching such derivatives. Pharmaceutically acceptable derivatives include salts, solvates, esters, carbamates, and/or phosphate esters.

As used herein the terms "therapeutically effective" and "effective amount", used interchangeably, applied to a dose or amount refer to a quantity of a composition, compound or pharmaceutical formulation that is sufficient to result in a desired activity upon administration to an animal in need thereof. Within the context of the present invention, the term "therapeutically effective" refers to that quantity of a composition, compound or pharmaceutical formulation that is sufficient to reduce or eliminate at least one symptom of a disease or condition specified herein, e.g., cancer, anemia, iron overload, etc. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

Therapeutically effective dosages can be determined stepwise by combinations of approaches such as (i) characterization of effective doses of the composition or compound in in vitro cell culture assays using tumor cell growth and/or survival as a readout followed by (ii) characterization in animal studies using tumor growth inhibition and/or animal survival as a readout, followed by (iii) characterization in human trials using enhanced tumor growth inhibition and/or enhanced cancer survival rates as a readout.

In some embodiments, the methods and compositions disclosed herein can be used for the treatment of cancer, either as initial therapy or as a second-line option if resistance to another therapy develops.

Chemotherapeutic agents, which can be administered in a combination therapy with a method and/or composition disclosed herein, include for example: taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins. Other chemotherapeutic agents include, though are not limited to, a p38/JAK kinase inhibitor, e.g., SB203580; a phospatidyl inositol-3 kinase (PI3K) inhibitor, e.g., LY294002; a MAPK inhibitor, e.g. PD98059; a JAK inhibitor, e.g., AG490; preferred chemotherapeutics such as UCN-01, NCS, mitomycin C (MMC), NCS, and anisomycin; taxoids in addition to those describe above (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publication Nos. WO 91/17976, WO 93/00928, WO 93/00929, and WO 96/01815. In other embodiments, a cancer therapy can include but is not limited to immunotherapy such as the administration of cytokines and growth factors such as interferon (IFN)-gamma, tumor necrosis factor (TNF)-alpha, TNF-beta, and/or similar cytokines, or an antagonist of a tumor growth factor (e.g., TGF- and IL-10). Antiangiogenic agents that can be used in the therapy of cancer, include, e.g., endostatin, angiostatin, TNP-470, Caplostatin (Stachi-Fainaro et al., Cancer Cell 7(3), 251 (2005)). Drugs that interfere with intracellular protein synthesis can also be used in the methods of the present invention; such drugs are known to those skilled in the art and include puromycin, cycloheximide, and ribonuclease.

For radiation therapy, common sources of radiation used for cancer treatment include, but are not limited to, high-energy photons that come from radioactive sources such as cobalt, cesium, iodine, palladium, or a linear accelerator, proton beams; neutron beams (often used for cancers of the head, neck, and prostate and for inoperable tumors), x or gamma radiation, electron beams, etc.

It is well known that radioisotopes, drugs, and toxins can be conjugated to antibodies or antigen-binding antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986), in Immunoconjugates: Antibody Conjugates in Radioimaging and Therapy of Cancer (C. W. Vogel, ed., 3-300, Oxford University Press, N.Y., 1987), in Dillman, R. O. (CRC Critical Reviews in Oncology/Hematology 1:357, CRC Press, Inc., 1984), in Pastan et al. (Cell 47:641, 1986) in Vitetta et al. (Science 238:1098-1104, 1987) and in Brady et al. (Int. J. Rad. Oncol. Biol. Phys. 13:1535-1544, 1987). Other examples of the use of immunoconjugates for cancer and other forms of therapy have been disclosed, inter alia, in U.S. Pat. Nos. 4,331,647, 4,348,376, 4,361,544, 4,468,457, 4,444,744, 4,460,459, 4,460,561 4,624,846, 4,818,709, 4,046,722, 4,671,958, 4,046,784, 5,332,567, 5,443,953, 5,541,297, 5,601,825, 5,637,288, 5,677,427, 5,686,578, 5,698,178, 5,789,554, 5,922,302, 6,187,287, and 6,319,500. In addition, unconjugated antibodies (e.g., antibodies to epidermal growth factor receptors such a HER2/neu) can be used for the treatment of cancer. Exemplary cancer-cell specific antibodies that can be used in the combination therapies disclosed herein are described, for example, in the review by Scott et al. (Nature Reviews Cancer 12, 278-287

(April 2012)). See also, Weiner, L. M., et al. Monoclonal antibodies: versatile platforms for cancer immunotherapy. Nature Rev. Immunol. 10, 317-327 (2010); Beatty, G. L. et al. CD40 agonists alter tumor stroma and show efficacy against pancreatic carcinoma in mice and humans. Science 331, 1612-1616 (2011); Musolino, A. et al. Immunoglobulin G fragment C receptor polymorphisms and clinical efficacy of trastuzumab-based therapy in patients with HER-2/neu-positive metastatic breast cancer. J. Clin. Oncol. 26, 1789-1796 (2008); Ferris, R. L., et al. Tumor antigen-targeted, monoclonal antibody-based immunotherapy: clinical response, cellular immunity, and immunoescape. J. Clin. Oncol. 28, 4390-4399 (2010); and Scott, A. M. et al. A Phase I clinical trial with monoclonal antibody ch806 targeting transitional state and mutant epidermal growth factor receptor. Proc. Natl Acad. Sci. USA 104, 4071-4076 (2007).

Other therapies include, e.g., hematopoietic stem cell transplant (HSCT), e.g., for treatment of acute myeloid leukemia (AML) patients and many other cancers.

Peptide Preparation

The polypeptides (including peptide fragments described herein (e.g., peptide fragments of NCOA4, ferritin (FTH1 and/or FTL), ATG8 paralogs (e.g., GABARAPLR2, LC3), and HERC2) can be manufactured by standard in vitro recombinant DNA techniques and in vivo transgenesis using nucleotide sequences encoding the appropriate polypeptides, such as those nucleotide sequences described above (e.g., SEQ ID NOs: 5, 21-25 and sequences at least 85% sequence identity thereto, or that encode a peptide that has at least 85% sequence identity to a peptide having a sequence set forth in SEQ ID NO: 1, 2, 3, 4, 6, 7, 8, 9 or 10). Methods well-known to those skilled in the art can be used to introduce mutations and construct expression vectors containing relevant coding sequences and appropriate transcriptional/translational regulatory elements. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology [Green Publishing Associates and Wiley Interscience, N.Y., 1989].

The transcriptional/translational regulatory elements referred to above include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast α mating factors.

The expression systems that may be used for purposes of the invention include but are not limited to microorganisms such as bacteria (for example, E. coli and B. subtilis) transformed with recombinant bacteriophage DNA, plasmid DNA, or cosmid DNA expression vectors containing nucleic acid molecules encoding enhancing agents or immunogenic stimuli; yeast (for example, Saccharomyces and Pichia) transformed with recombinant yeast expression vectors containing a nucleic acid encoding enhancing agents or immunogenic stimuli; insect cell systems infected with recombinant virus expression vectors (for example, baculovirus) containing a nucleic acid encoding enhancing agents or immunogenic stimuli; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a nucleotide sequence encoding; or mammalian cell systems (for example, COS, CHO, BHK, 293, VERO, HeLa, MDCK, WI38, NIH 3T3, MCF7, 8988T, PANC1, PATU-8988T, and U2OS cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Cells transfected or transduced with the expression vectors described herein can then be used, for example, for large or small scale in vitro manufacture of polypeptides (e.g., peptide fragments) by methods known in the art. Such methods typically involve culturing the cells under conditions that maximize production of the polypeptide and isolating the polypeptide from the culture, i.e., the cells and/or the culture medium. Methods for purifying biological macromolecules (e.g., proteins) are known in the art. For example, polypeptides, including peptide fragments, described herein can be purified by combinations of ethanol precipitation and isoelectric focusing from culture fluids of clones containing the mutated genes. See, Blomster-Hautamaa and Schlievert, Methods Enzymol 165:37-43 (11) (1988). The degree of purity of the macromolecules can be measured by any appropriate method, e.g., column chromatography, polyacrylamide gel electrophoresis, or HPLC analysis.

In other embodiments, polypeptides, peptides, as well as salts thereof may be synthesized, e.g., using solid-phase or liquid-phase synthesis, according to any known suitable method of peptide synthesis (see, e.g., *Chemistry of Peptide Synthesis*; N. L. Benoiton; CRC Press, 2006, 290 pages).

Kits

In certain embodiments, kits are provided for diagnosing anemia in a subject.

The above kits can comprise means (e.g., reagents, dishes, solid substrates (e.g., microarray slides, ELISA plates, multiplex beads), solutions, media, buffers, etc.) for determining the level of expression or activity of one or more of the genes or proteins described herein (e.g., NCOA4, HERC2, ATG8 paralogs, ferritin, etc). Such kits can further comprise instructions for use, e.g., guidelines for determining diagnosing anemia in a subject, based on the level of expression or activity of the one or more genes detected using the kit.

Also provided are kits for the treatment of a disease or disorder described herein (e.g., cancer, anemia, iron overload, etc.). Such kits can comprise, e.g., one or more of the agents described herein, e.g., a peptide fragment (functionally active or inhibitory) of one or more of NCOA4, an ATG8 paralog (GABARAPL2 or LC3), and HERC2). In some embodiments, the kits comprise full-length sequences of the NCOA4, ATG8 paralog, ferritin (FTH1 and/or FTL), and/or HERC2. In certain embodiments, the kits can comprise an inhibitor of NCOA4 (e.g., an inhibitor of the interaction of NCOA4 with ferritin (e.g., with FTH1 and/or FTL), an inhibitor of the interaction of NCOA4 with an ATG8 paralog, an inhibitor of the interaction of NCOA4 with HERC2). Such inhibitors are described in detail herein, and include, e.g., small molecules, antisense oligonucleotides, antibodies, intrabodies, etc. In certain embodiments, the kits can comprise an agonist of NCOA4 (e.g., an agonist of the interaction of NCOA4 with ferritin (e.g., with FTH1 and/or FTL), an agonist of the interaction of NCOA4 with an ATG8 paralog, an agonist of the interaction of NCOA4 with HERC2). An agonist includes, e.g., an agonistic antibody, a recombinant polypeptide or functional fragment thereof (e.g., SEQ ID NO: 11, SEQ ID NO: 1, SEQ ID NO: 2, amino acids 16-34 of SEQ ID NO: 6, amino acids 103-125 of SEQ ID NO: 6; amino acids 78-88 of SEQ ID NO: 6, and sequences having at least 85% sequence identity thereto).

In some embodiments, the kits can comprise one or more of a peptide fragment comprising or consisting of SEQ ID NO: 11, SEQ ID NO: 1, SEQ ID NO: 2, or SEQ ID NO: 3, amino acids 16-34 of SEQ ID NO: 6, amino acids 103-125 of SEQ ID NO: 6; amino acids 78-88 of SEQ ID NO: 6, and sequences having at least 85% sequence identity thereto.

In some embodiments, the kits can comprise one or more of an NCOA4 reagent, a ferritin reagent, an ATG8 paralog reagent, a HERC2 reagent, as described above, for screening assays.

The kits, regardless of type, will generally comprise one or more containers into which the biological agents (e.g. inhibitors) are placed and, preferably, suitably aliquotted. The components of the kits may be packaged either in aqueous media or in lyophilized form. The kits can also comprise one or more pharmaceutically acceptable excipients, diluents, and/or carriers.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

EXAMPLES

Example 1: Materials and Methods

Methods Summary

Cells were grown in Lys(K)-free and Arg(R)-free DMEM/dialyzed fetal bovine serum, with light (K0, R0) or heavy (K8/R0 or K8/R10) Lys/Arg, and treated with CQ (25 µM) for 4 or 16 hours. Mixed cells were lysed and autophagosomes were purified as described [see, Marzella, L., et al. The Journal of Cell Biology; 93, 144-154 (1982); and Koga, H., et al. FASEB Journal: official publication of the Federation of American Societies for Experimental Biology 24, 3052-3065 (2010)], prior to SDS-PAGE and in-gel digestion with trypsin or Lys-C, and LC-MS/MS (see detailed methods below). Candidate autophagosomal proteins were identified by employing a multi-step filtering process including a log 2(heavy:light) ratio cut-off and enrichment in autophagosomes versus whole proteome. Interaction proteomics employed 293T, 8988T, or PANC1 cells stably expressing NCOA4 or FTH1 HA-FLAG-tagged constructs and CompPASS to identify HCIPs [Sowa, M. E., et al. Cell 138, 389-403, (2009)]. Chelation assays were performed similarly to those previously described with slight modifications [Asano, T. et al. Molecular and Cellular Biology 31, 2040-2052, (2011)]. Cells stably expressing shRNAs to NCOA4 were cultured for 24 hours in iron-enriched media (supplemental Ferric Ammonium Citrate added) and subsequently subjected to iron chelation with multiple different chelators prior to immunoblotting or immunofluorescence.

Cell Culture and Reagents

PANC1, PATU-8988T (8988T), MCF7, U2OS, IMR90, and 293T cell lines were obtained from the American Type Culture Collection or the German Collection of Microorganisms and Cell Cultures. HPDE cells were cultured as previously described [Yang, S. et al. Genes & Development 25, 717-729, (2011)]. All cell lines were tested routinely for mycoplasma contamination.

Antibodies

The following antibodies were used in these studies. Lamp 2 (Abcam Ab25631; Western 1:1000; IF 1:100); HA (Covance MMS 101P; Western blot ("Western") 1:2000; immunofluorescence ("IF"): 1:100); MAP1LC3B (LC3B) (Cell Signaling 2775; Western 1:2000); MAP1LC3B (LC3B) (Cell Signaling 3868; IF 1:200); MAP1LC3B (LC3B) (nanoTools 0231-100/LC3-5F10; IF 1:100); VDAC1 (Abcam Ab28777; Western 1:1000); ferritin (Rockland 200-401-090-0100; IF 1:400); FTH1 (Cell Signaling 3998; Western 1:1000); NCOA4 (ARA70) (Bethyl Laboratories A302-272A; Western 1:1000); NCOA4 (Sigma SAB1404569; Western 1:1000); SQSTM1 (Abnova H00008878-M01; Western 1:5000); TAX1BP1 (Cell Signaling 8182; Western 1:1000); ATG5 (Cell Signaling 2630; Western 1:1000); HERC2 (BD Transduction Laboratories 612366; Western 1:1000); FTL (Abnova Ab69090; Western 1:1000); ACTB (Sigma A2066; Western 1:5000); MYC (Santa Cruz Sc-40; Western 1:1000); IRP2 (Santa Cruz Sc-33682; Western 1:500); TFRC (BD Transduction Laboratories 612124; Western 1:2000); Mannose 6-Phosphate Receptor (Abcam ab2733; IF 1:100); GABARAPL2 (gift from Millennium Pharmaceuticals, IF 1:100). The following secondary antibodies were used: Anti-Rabbit IgG (H+L) HRP Conjugate (Western Secondary 1:7500); Anti-Mouse IgG (H+L) HRP Conjugate (Western Secondary 1:7500); Alexa Fluor® 488 anti-Mouse IgG (H+L) (IF Secondary 1:1000); Alexa Fluor® 594 anti-Rabbit IgG (H+L) (IF Secondary 1:1000), Alexa Flour® 633 anti-Rabbit IgG (H+L) (IF Secondary 1:1000). "Western" and "Western blot" are used interchangeably throughout with the term "immunoblot."

RNAi

ATG5 siRNA (Gene ID: 9474, NM_0048493) was purchased from Invitrogen as previously published [Yang, S. et al., supra]. siRNAs were transfected using a reverse transfection protocol and RNAiMax (Invitrogen). siControl was a siRNA designed against luciferase. Lentiviral shRNA plasmid clones (pLKO.1) were obtained from the RNAi Consortium collection: shNCOA4-1: 5' CCCAGGAAGT-ATTACTTAATT 3' (TRCN0000019724) (SEQ ID NO: 12), shNCOA4-2: 5' GCTGGCAAACAGAAGTTTAAA 3' (TRCN0000019726) (SEQ ID NO: 13) and shGFP: 5' GCAAGCTGACCCTGAAGTTCAT 3' (Addgene plasmid #30323) (SEQ ID NO: 14). NCOA4 Gene ID: 8031, NM_001145263.1. Lentivirus was produced as described previously [Yang, S. et al., supra]. Additional siRNAs used in this work were purchased from Invitrogen against NCOA4 (Gene ID: 8031, NM_001145263.1), siNCOA4-1: 5' ACAAAGAUCUAGCCAAUCA 3' (SEQ ID NO: 15) and siNCOA4-2: 5' GACCUUAUUUAUCAGCUUA 3' (SEQ ID NO: 16) and against HERC2 (Gene ID: 8924, NM_004667.5), siHERC2-1: 5' GCACAGAGUAUCACA-GGUA 3' (SEQ ID NO: 17) and siHERC2-2: 5' CGAUGAAGGUUUGGUAUUU 3' (SEQ ID NO: 18).

Chemicals

Ferric ammonium citrate (FAC; Fisher Scientific, 36 to 180 µM titrated for each cell line based on level of FTH1 translation at 24 h post-addition of FAC), deferoxamine mesylate (DFO; BioVision; 100 µM), bathophenanthroline disulfonate (BPS; Sigma; 300 µM), Deferiprone (DFP, Sigma, 100 µM), Deferasirox (DFX; Selleckchem; 30 µM), E64-d (Sigma; 10 µg/mL), PepstatinA (CalBiochem; 10 µg/mL), Bortezomib (BTZ; gift from Millenium Pharmaceuticals; 1 µM), Chloroquine (CQ; Sigma; 10 or 25 µM), Bafilomycin A1 (BAF; Sigma; 50 nM), hydrogen peroxide ($H_2O_2$; Sigma), CellTiter-Glo® (Promega).

SILAC-Based Density Gradient Centrifugation Autophagosome Enrichment

PANC1, 8988T, and MCF7 cells were grown in lysine and arginine free DMEM supplemented with 10% dialyzed FBS (Gibco), 2 mM L-glutamine, penicillin-streptomycin, and light (K0) lysine (50 µg/mL) and light (R0) arginine (85 µg/mL). Heavy media was the same except the light lysine was replaced with K8-lysine (Cambridge Isotopes) and the light arginine was replaced with R10-arginine at the same concentrations (PANC1 and 8988T cell lines were also grown in K8-only heavy media (K8, R0)). Where indicated, cells ($10^8$) were treated with Wortmannin (200 nM) or CQ (25 µM) for the times indicated. After the indicated treatments, heavy and light cells were mixed 1:1 by cell number. Autophagosome purification was performed as described previously [Marzella, L., et al., supra; Koga et al., supra] with slight modifications. All steps were carried out at 4° C. Briefly, cells were washed three times with PBS and resuspended in Buffer A (250 mM Sucrose, 10 mM HEPES, pH 7.4, 1 mM EDTA, protease inhibitors (EDTA-free, Roche)). Cells were lysed by nitrogen cavitation and homogenized using a potter-elvehjem homogenizer with a teflon pestle. Lysates were centrifuged at 2000×g, the supernatant was centrifuged at 17,000×g and resuspended in 0.95 mL Buffer A. Lysate was diluted with 1.45 mL 85.6% Nycodenz (Sigma-Aldrich) solution. A discontinuous Nycodenz gradient (26%, 24%, 20%, 15%) was layered on top of the lysate and spun at 24,700 rpm in a SW41 rotor (Beckman). Fractions were collected as indicated, pelleted at 24,000×g, and used for downstream applications (immunoblotting, electron microscopy, mass spectrometry).

Autophagosome Immunoisolation 8988T cells stably expressing GFP-LC3B were treated as above. Lysis and clarification centrifugation steps are as described above. GFP-based immunoisolation was performed as previously described [Gao, W. et al., supra]. Briefly, lysates were incubated with µMACS™ microbeads (magnetic beads coated with anti-GFP, MACS Miltenyi Biotec) for 1 hour at 4° C. with mixing. Lysate-bead mixture was applied to a LS Column in a MidiMACS™ Separator, washed, eluted, pelleted and prepared for downstream analysis (mass spectrometry).

Mass Spectrometry Analysis of Autophagosomes

Enriched autophagosomes were prepared for mass spectrometry analysis as described [Shevchenko, A. et al. *Nature Protocols* 1, 2856-2860, (2006)]. Briefly, pelleted autophagosomes were resuspended in 2% SDS, 50 mM Tris, pH 7.5, 2 mM EDTA, boiled for 10 minutes, and centrifuged at 16,100×g for 5 minutes at room temperature. Supernatants were subjected to SDS-PAGE followed by in-gel digestion with trypsin (K8, R10 heavy samples and 8988T K8 sample) or Lys-C (PANC1 K8 heavy samples). For generation of comparison whole cell lysate datasets, untreated heavy and light labeled cells were mixed in a 1:1 ratio, lysed as described above, and subjected to SDS-PAGE followed by in-gel digestion. Approximately 10 µg of total whole cell lysate was used for this analysis, however, multiple dilutions of whole cell lysate extract were separated by SDS-PAGE and a lane with equal intensity of overall coommassie staining to the autophagosome separations was chosen for processing. Peptides were subjected to the C18 stage-tip method and resuspended in 5% formic acid, 5% acetonitrile prior to mass spec analysis.

Peptides were separated on 100 µm×25 cm C18 reversed phase (Maccel C18 3 µm 200 Å, The Nest Group, Inc.) with a 90 min gradient of 6% to 27% acetonitrile in 0.125% formic acid. The twenty-two most intense peaks from each full MS scan acquired in the Orbitrap Velos Pro (Thermo) were selected for MS/MS (RAW files available upon request). Sequest-based identification using a Human UNI-PROT database followed by a target decoy-based linear discriminant analysis was used for peptide and protein identification as described [Huttlin, E. L. et al. *Cell* 143, 1174-1189 (2010)]. Several experiments were processed in tandem using a protein sieve and protein assembler in-house processing tool, including PANC1 CQ 4 hr with PANC1 Ex. 1 and PANC1 Ex. 2, PANC1 Ex. 3 and PANC1 WCL together. "WCL"=Whole cell lysate. MCF7 Ex. 1, MCF7 Ex. 2, and MCF7 WCL were processed together. However, all datasets were processed independently for calculation of Pearson correlation of log 2(H:L) ratios between datasets for FIG. 1*d* and FIG. 13(*j*). Other parameters used for database searching include: 50 ppm precursor mass tolerance; 1.0 Da product ion mass tolerance; tryptic or Lys-C digestion with up to three missed cleavages; and variable oxidation of Met (+15.994946). A protein level false-discovery rate of <1% was used as a threshold for protein identifications using the target decoy strategy. Quantification of each protein was determined using the peak heights for light and heavy forms for that protein. The criterion for protein quantification was a summed signal-to-noise ratio of >10. Quantification of protein level was by calculating the median value of the ratios of light to heavy. Of note, contaminants including Keratin, Lys-C, or Trypsin were removed from the data in order to avoid interference with data filtering as below. In addition, peptides identified for MAP1LC3B (Gene ID: 81631, NP_073729.1) are shared with a protein from an additional gene coding region with a gene symbol MAP1LC3B2 (Gene ID 643246, NP_001078950.1). The protein assembler program reported MAP1LC3B2 as the protein identified. However there were no peptides to discriminate the two proteins. There is one amino acid difference between MAP1LC3B and MAP1LC3B2 (C113Y). But no peptides were identified within the region of C113Y (identified peptides are as follows: $^{31}$IPVIIER$^{37}$ (SEQ ID NO: 19) and $^{52}$FLVPDHVNMSELIK$^{65}$ (SEQ ID NO: 20)). The log 2(H:L) ratios for MAP1LC3B is thus reported in the present figures, and the protein identifier is left as MAP1LC3B2.

Bioinformatic Analysis

Candidate autophagosomal proteins were identified by employing a multi-step filtering process beginning with an enrichment cut-off including proteins with log 2(heavy: light) ratios greater than 1.0 for MCF7 datasets, 1.5 for PANC1 16 h datasets and 0.5 for PANC1 and 8988T 4 h CQ datasets (0.5 was used as a cut-off in the 4 h CQ datasets given the overall relatively lower level of maximum log 2(heavy:light) ratios). To be included, proteins had to be represented by 2 or more peptides. At this point in the analysis, approximately 600 proteins remained per dataset as potential candidates. In order to remove abundant proteins that may be non-specifically captured by bulk autophagy, candidates were filtered against the relative abundance of the proteome measured independently by LC-MS by directly comparing number of peptides identified per protein.

Of note, a whole cell lysate proteome dataset was prepared from MCF7, PANC1, and 8988T cells as detailed above and was used for comparison within cell lines. In the datasets not processed together (PANC1 4 h CQ and PANC1 Ex. 1 versus PANC1 WCL (whole cell lysate) comparisons were done based on pairing of gene symbols that did not distinguish between isoforms within the same gene symbol. Finally, a two-sided Student's t-test was used as a measure of statistical confidence of the observed log 2(heavy:light) ratio taking into account the standard deviation of the log 2(heavy:light) ratio and number of peptides measured per protein. A p-value of less that 0.05 was used for inclusion as a candidate (except for the PANC1 Ex. 1 dataset that used Lys-C for digestion where a p-value of less than 0.1 was used). For each dataset, this typically left approximately 150 candidates. Subsequently, the overlap between the three PANC1 16 h CQ biological replicate datasets was determined, and 86 proteins were identified in common. The overlap between two MCF7 datasets consisted of 102 proteins. Finally, the overlap between the PANC1 and MCF7 datasets was determined (33 proteins in common, 122 proteins specific to either PANC1 or MCF7 datasets). This set of 155 proteins is referred to as Class 1 candidate autophagosomal proteins. A subset of the top 50 candidate proteins, termed Class 1A candidates, was developed based on presence in typically 3 or more independent experiments and those with known or potential links with autophagy. Finally, non-Class 1 proteins with a log 2(H:L)>2.0 in any 2 of the 5 independent PANC1 (PANC1 Ex. 1-3) or MCF7 (Ex. 1-2) profiling experiments (16 h in CQ) were also identified, and this dataset is referred to as Class 2 autophagosome-enriched proteins.

For analysis of the semi-quantitative 8988T GFP immunoisolation experiment, data was sorted by comparing log 2 ratios of peptide numbers of proteins identified in autophagosomes purified from chloroquine versus wortmannin treated cells and log 2 ratios of peptide numbers of proteins identified in autophagosomes purified from chloroquine treated cells versus peptide numbers from a whole cell lysate sample. Zero value denominators were systematically replaced with a value of 0.5 in order to generate a log 2 ratio. Candidates were qualified as enriched if both log 2 ratios were greater than 0.5.

Figure 17:
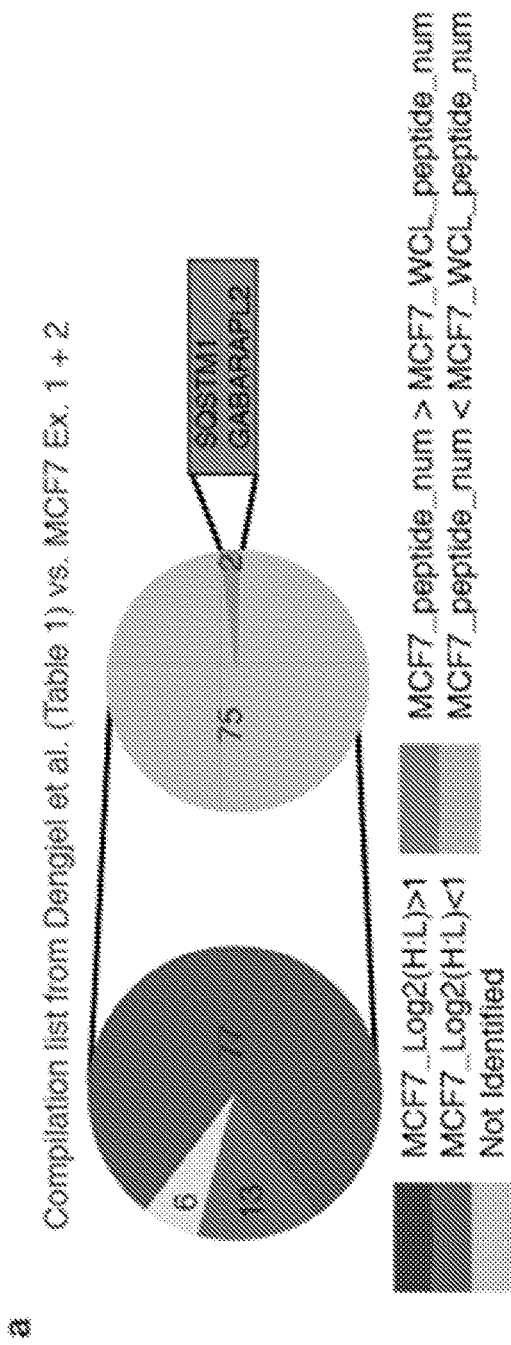
FIG. 17(a) is a schematic diagram depicting the analysis and comparison of Dengjel et al. data and candidate list with data derived from MCF7 autophagosome proteomics experiments as detailed in methods section. Shading of gene symbols denotes proteins identified as MCF7 candidates.
FIGS. 17(b)-(e) contain schematic diagrams depicting the analysis and comparison of Dengjel et al. data and candidate list with data derived from both MCF7 and PANC1 autophagosome proteomics experiments (Class 1 and 2 proteins) as detailed in the methods section (Example 1). The key for FIGS. 17(b)-(e) appears in FIG. 17(e). Orange shading of gene symbols denotes proteins identified as Class 1 or 2 candidates.
Figure 17:
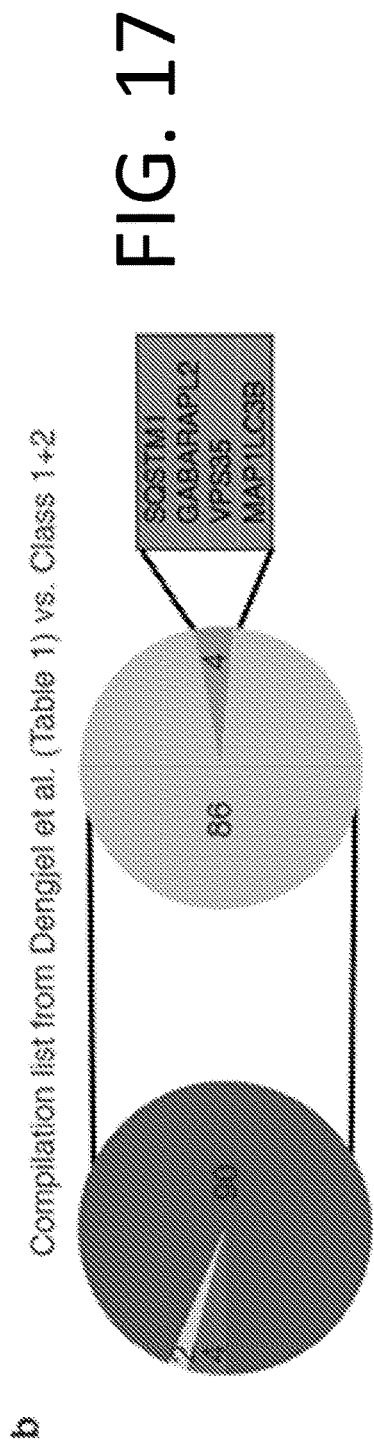
Figure 17:
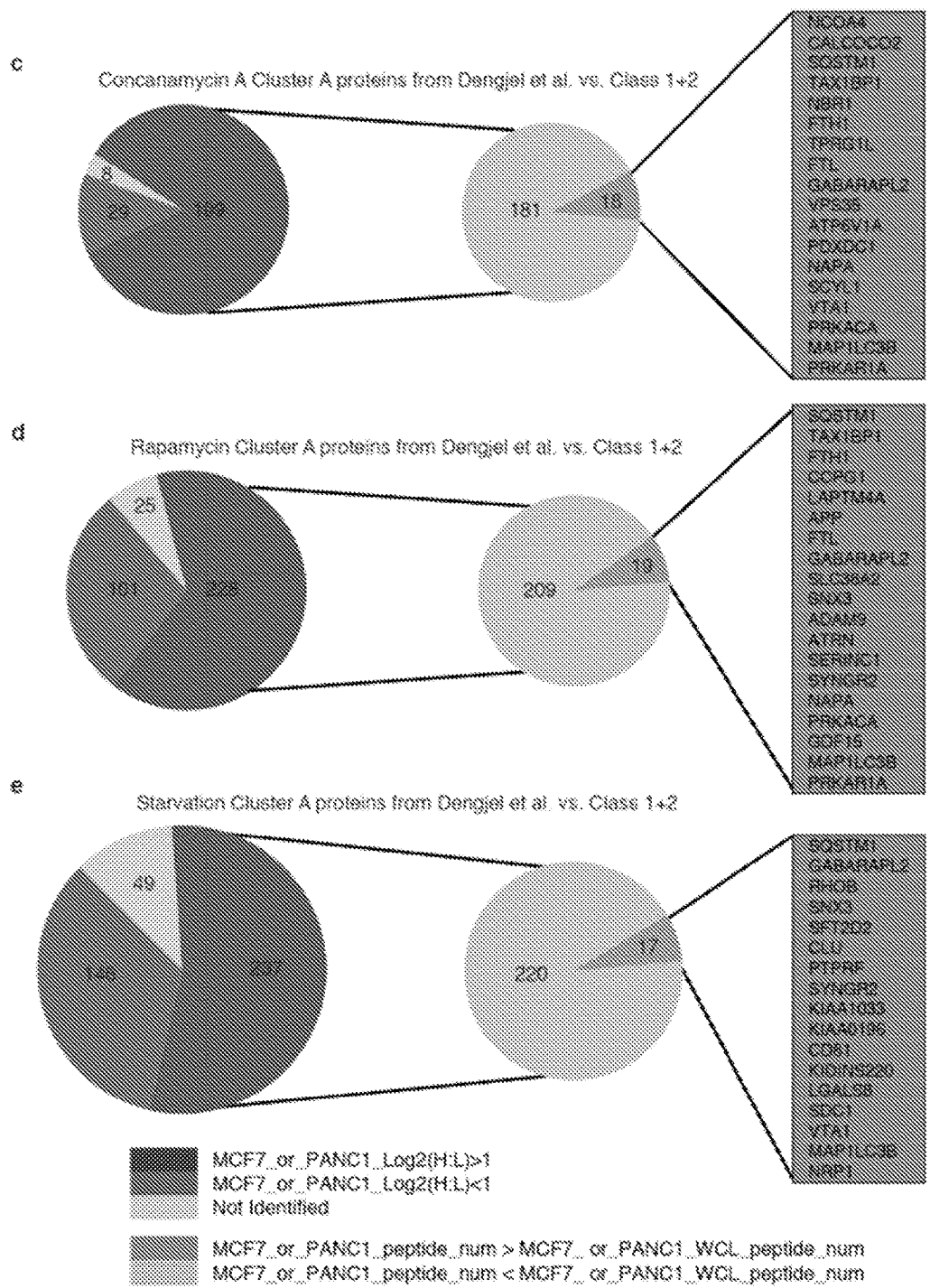

For preparation of the data shown in FIG. 17, the overlap between the MCF7 candidate proteins identified in this work and the stimulus independent autophagosomal candidates identified in Dengjel et al. [supra] was determined (Table 1 in Dengjel et al., supra). Only two proteins overlapped, namely p62/SQSTM1 and GABARAPL2. To understand the lack of overlap between the datasets, the proteins from the Dengjel et al. list were analyzed using the data from the MCF7 experiments described herein. Of note, the Dengjel et al. experiments also used the MCF7 cell line. The Dengjel datasets were curated to ensure the gene symbols published in the Dengjel et al. study matched the updated version of the database used in the present proteomics analyses. For the 96 Dengjel et al. candidate proteins, the log 2(H:L) ratio observed in both MCF7 Ex. 1 and 2 autophagosome enrichments was first determined. A majority of the proteins had a log 2(H:L) ratio greater than 1.0 (77 out of 96). However, of the 77 proteins with a log 2(H:L) ratio greater than 1.0, only 2 proteins passed the whole proteome abundance filter used in the present analysis to remove abundant proteins that may be non-specifically captured by bulk autophagy (FIG. 17(a). The 4 hour and 16 hour PANC1 autophagosome proteomics datasets used to create the final Class 1 and 2 list were subsequently included in order to obtain as much coverage and comparison of the proteins identified in the Dengjel et al. datasets as possible.

Figure 20:
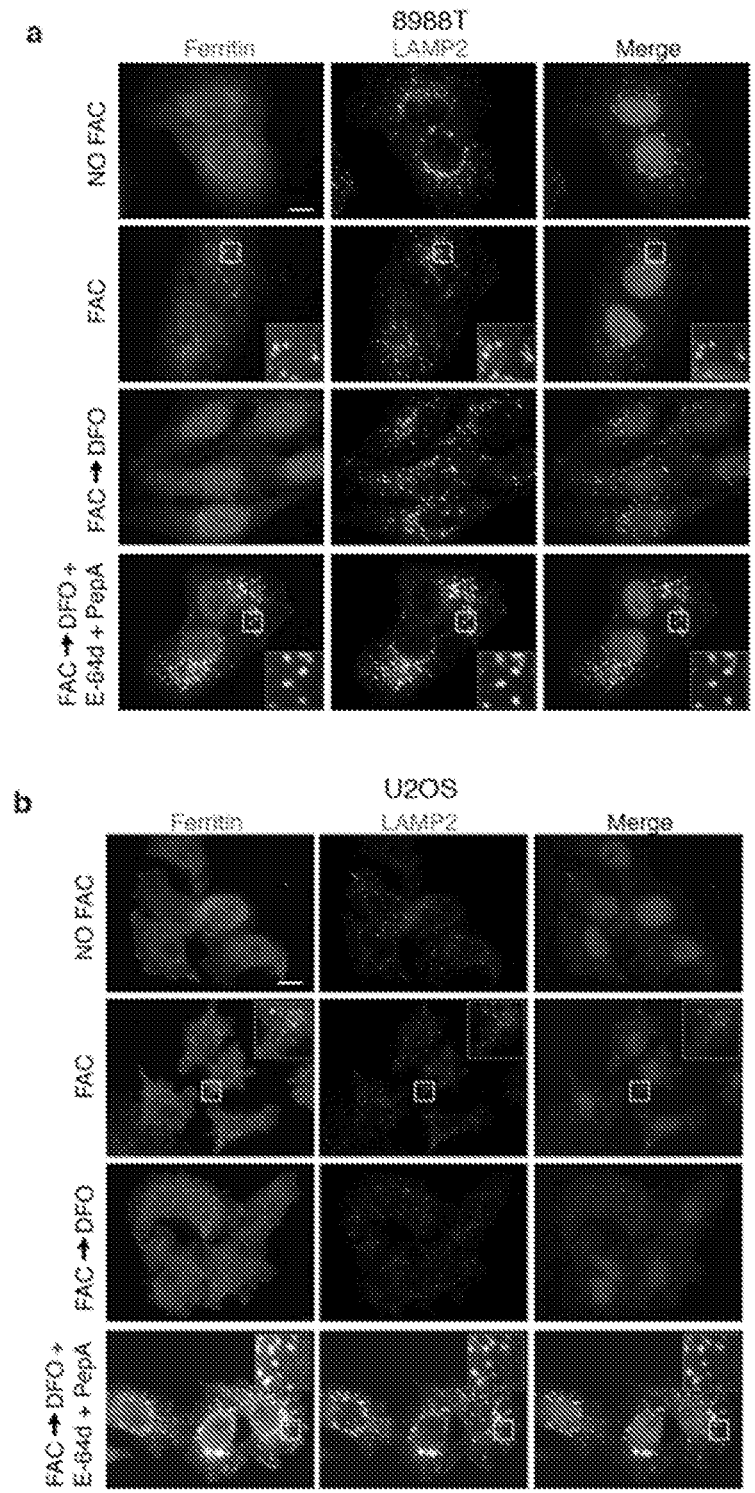
FIG. 20(a) contains fluorescent microscopy images of 8988T cells, and FIG. 20(b) contains fluorescent microscopy images of U2OS cells, cultured in the presence or absence of FAC for 24 hours, washed, and subjected to DFO chelation−/+lysosomal protease inhibitors (E-64d and PepstatinA). Cells were fixed and immunostained using antibodies to ferritin and LAMP2. Higher magnification views of the boxed areas are shown in the insets. Scale bar, 10 μm.
FIG. 20(c) contains fluorescent images of U2OS cells, FIG. 20(d) contains fluorescent images of IMR90 cells, and FIG. 20(e) contains fluorescent images of HPDE cells, expressing a control shRNA (shGFP) and two independent shRNAs to NCOA4 (shNCOA4-1 and shNCOA4-2) subjected to DFO chelation in the presence of lysosomal protease inhibitors for 9 hours and immunostained for ferritin, and LAMP2 (left panel in each figure). Scale bar, 10 μm. The right panel in FIGS. 20(c), (d) contain a bar graph quantifying the punctate ferritin fraction, in FIG. 20(c) from >75 cells per cell line from 2 independent experiments (number of U2OS cells quantitated is as follows: shGFP: 133 cells, shNCOA4-1: 103 cells, shNCOA4-2: 79 cells); and in FIG. 20(d), from >25 cells per cell line in two independent experiments and from more than 10 microscopy fields (number of IMR90 cells quantified is as follows: shGFP: 29 cells, shNCOA4-1: 26 cells, shNCOA4-2: 31 cells). Quantitation was not possible in FIG. 20(e) due to the high background signal in shGFP control cells. Bars and error bars represent mean values and s.d., respectively: *** denotes p<0.001 using a one-sided t-test.
Figure 20:
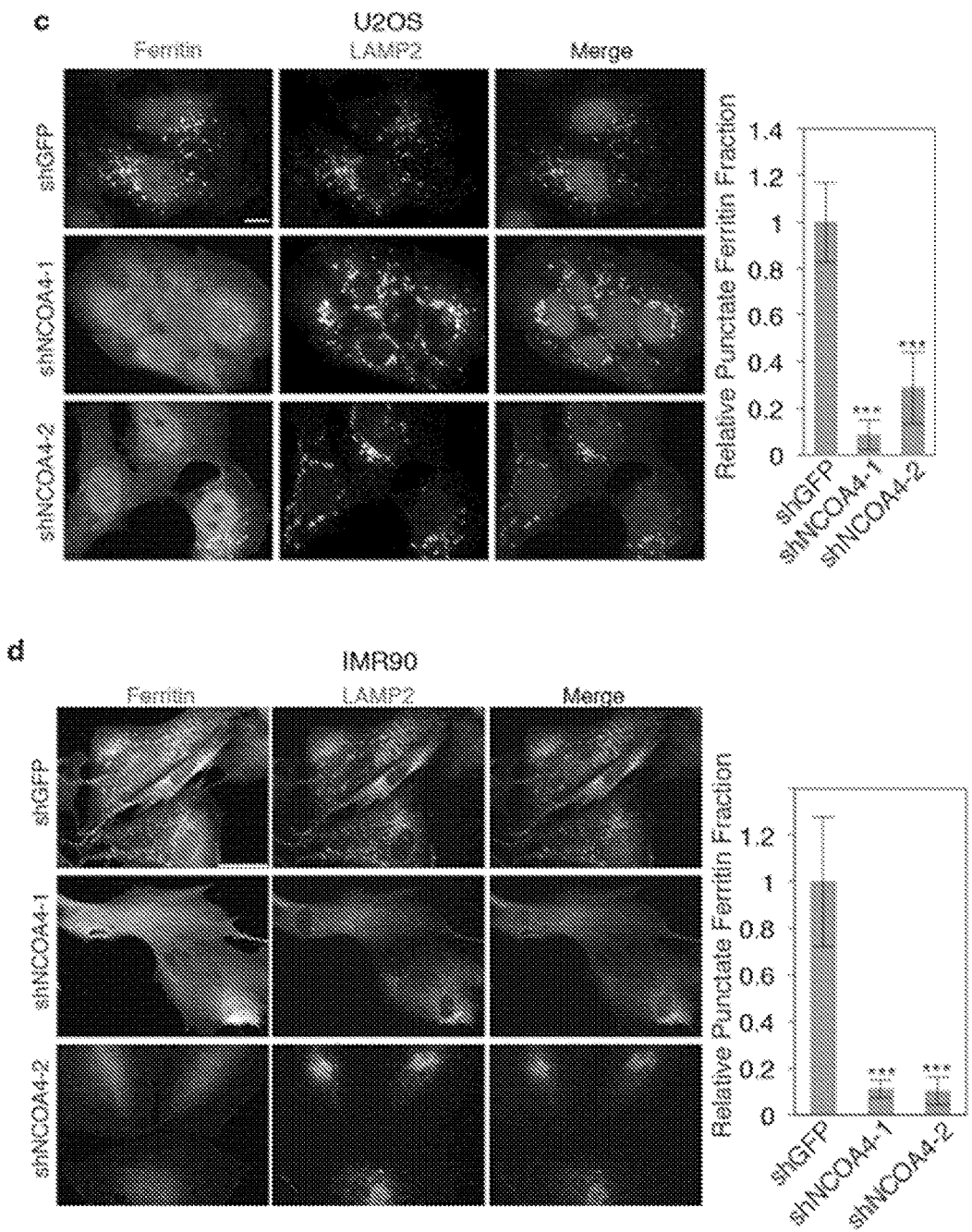
Figure 20:
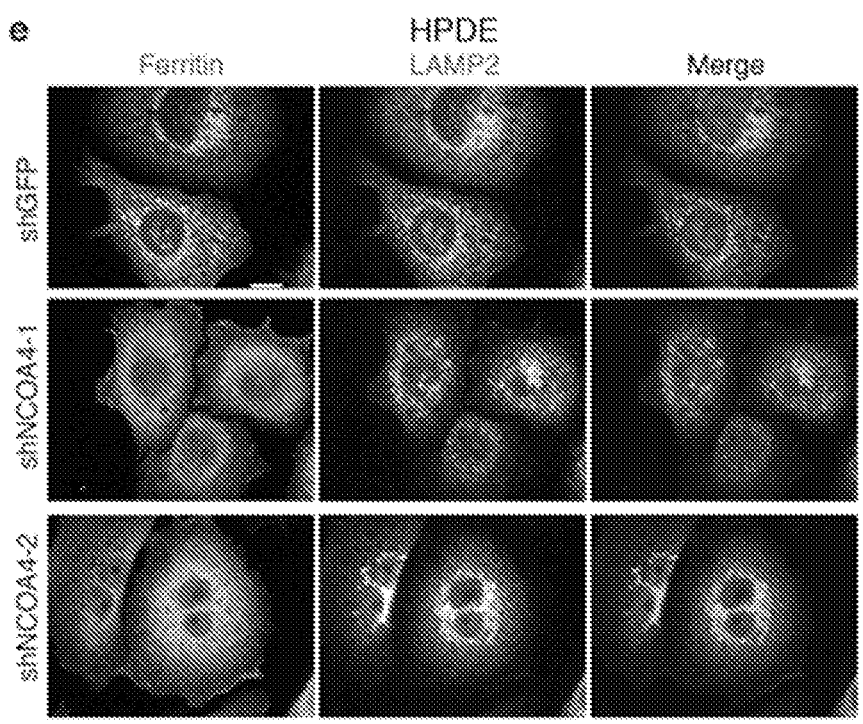

The overlap with the Dengjel et al. dataset is not significantly improved even when the data was expanded to include the PANC1 datasets (FIG. 17(b), FIG. 20) now with an overlap of 4 proteins (SQSTM1, GABARAPL2, VPS35, MAP1LC3B). Three experiments that Dengjel et al. described were analyzed independently using the same approach as above. Similarly, while a large proportion of the 'Cluster A' proteins from each experiment were enriched by log 2(H:L) ratio in the present datasets, only a small number of these proteins passed the whole proteome abundance filter and were found in the present Class 1 and 2 dataset (FIG. 17(c)-(e)). By relaxing the log 2(H:L) ratio cutoff and redundancy stringency (FIG. 17(b)-(e)) to include non-class 1 and 2 proteins in the analysis, the additional overlap only ranges from 5-15% depending on the individual dataset.

Of note, the Class 1-2 candidates that were also identified in the Dengjel et al. Concanamycin A 'Cluster A' proteins included NCOA4. The likely reason for the large number of proteins with a log 2(H:L) ratio greater than 1.0 but that did not pass the whole proteome abundance filter stems from the protein correlation profiling methodology used by Dengjel et al. Specifically, the authors of Dengjel et al. relied on an 'autophagosomal' enrichment profile that required identification and quantification of candidate proteins in all 6 iodixanol fractions for creation of an evaluable profile. This likely biased their identification towards proteins with a high abundance in the whole proteome that would be more likely to be identified in all 6 fractions. As above, abundant proteins are more likely to be captured by non-selective bulk autophagy. Finally, by using the overlap of the 3 different experiments, they further biased their candidate list towards abundant proteins captured by autophagy under all 3 conditions tested such as proteasome subunits and heat-shock proteins. It is noted that Dengjel et al. clustered all of the identified proteins from their proteomics experiments into three clusters: A, B, and C. Cluster A was defined as "autophagosome-associated proteins"; however, they did not specify these proteins as autophagic cargo receptors. The broad category of "autophagosome-associated proteins" could mean any number of things, and does not imply autophagic cargo receptor.

Electron Microscopy

Pelleted autophagosome fractions (A1) were fixed in 2.5% Glutaraldehyde, 1.25% Paraformaldehyde, and 0.03% picric acid in 0.1 M sodium cacodylate buffer (pH 7.4) for 1 hour at room temperature, washed in 0.1 M Sodium Cacodylate buffer (pH 7.4), and postfixed for 30 minutes in 1% Osmium tetroxide (OsO4)/1.5% Potassiumferrocyanide (KFeCN$_6$). Autophagosome pellets were washed in water 3 times and incubated in 1% aqueous uranyl acetate for 30 minutes followed by 2 washes in water and subsequent dehydration in grades of alcohol (5 minutes each; 50%, 70%, 95%, 2 times 100%). Autophagosome pellets were infiltrated overnight in a 1:1 mixture of propyleneoxide and TAAB Epon (Marivac Canada Inc. St. Laurent, Canada). The samples were subsequently embedded in TAAB Epon and polymerized at 60° C. for 48 hours. Ultrathin sections (about 60 nm) were cut on a Reichert Ultracut-S microtome, picked up on to copper grids stained with lead citrate and examined in a TecnaiG$^2$ Spirit BioTWIN transmission electron microscope and images were recorded with an AMT 2 k CCD camera.

Interaction Proteomics

Figure 2:
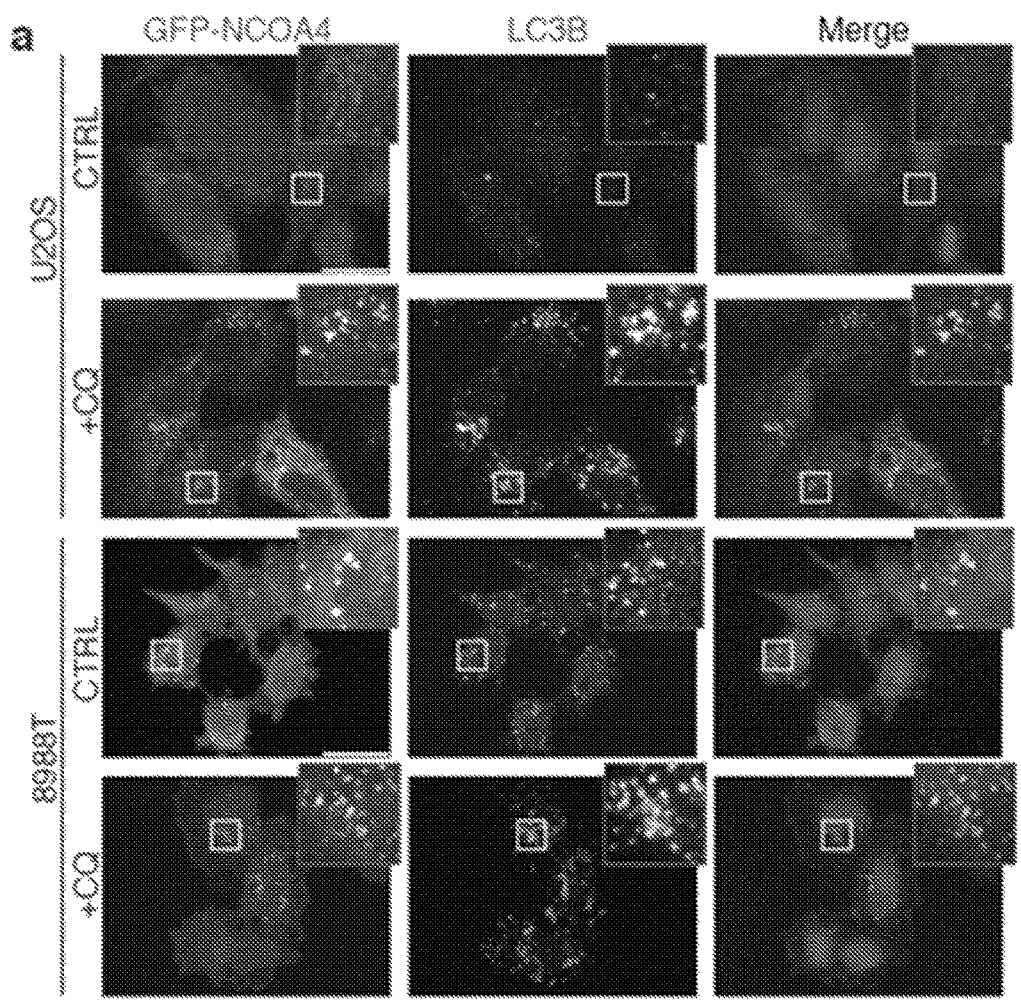
FIG. 2(a) contains fluorescent images of U2OS and 8988T cells untreated (CTRL) or treated with chloroquine (CQ). GFP-NCOA4 co-localizes with endogenous LC3 in CQ-treated cells. Scale bar, 20 μm.
FIG. 2(b) contains images of HA immunoblot results for NCOA4-HA-FLAG in a GST-pull-down assay of NCOA4-HA-FLAG from stable 293T cells using the indicated GST-ATG8 proteins.
FIG. 2(c) contains photographs of immunoblot results for lysates of 8988T cells treated with chloroquine (CQ) or BAF (8 hours) or DMSO, and immunoblotted for NCOA4, LC3B, and ACTB as a loading control; *, cross-reactive band (for discussion, see description of FIG. 19(d)-(e), below).
FIG. 2(d) photographs of immunoblot results for purified 8988T autophagosome fractions analyzed using antibodies to NCOA4 and LC3B. TAX1BP1, a newly identified autophagy receptor, was included as a positive control. LD is gradient load, A1 is autophagosome fraction, A2 is the autophagolysosome fraction, L is the lysosome fraction, M is the mitochondrial fraction.
FIG. 2(e) is a schematic diagram of the NCOA4 interaction network from cells expressing NCOA4-HA-FLAG or FTH1-HA-FLAG. Black lines (this study) depict directionality of interaction observed with line thickness weighted by WDN-score (293T dataset); dotted lines, indicate STRING database. Numbers in parentheses indicate log 2(H:L) ratio of NCOA4, FTH1, and FTL from MCF7 Ex. 1 dataset.
FIGS. 2(f), (g) contain immunoblot results from extracts from 293T cells stably expressing the indicated proteins and immunoprecipitated with an anti-FLAG antibody, and immunoblotted with the indicated antibodies. An anti-ACTB antibody was used as a loading control. The upper three blots indicate FLAG-IP results, and the lower four panels represent the input.
FIG. 2(h) contains representative fluorescent confocal images of GFP-NCOA4 and ferritin after no treatment or FAC (ferric ammonium citrate) treatment (24 h) in U2OS and 8988T cells; scale bar, 10 μm.
Figure 2:
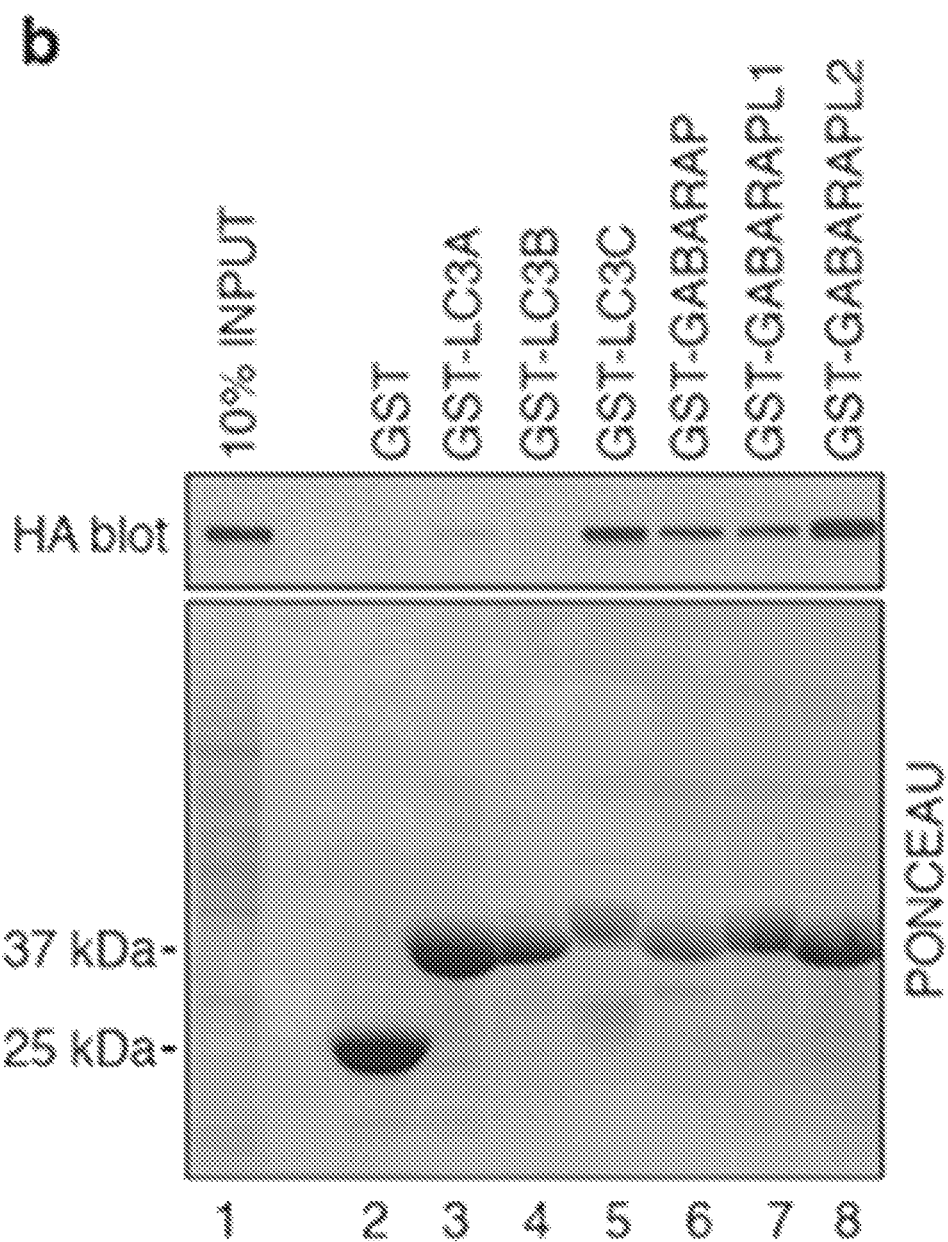
Figure 2:
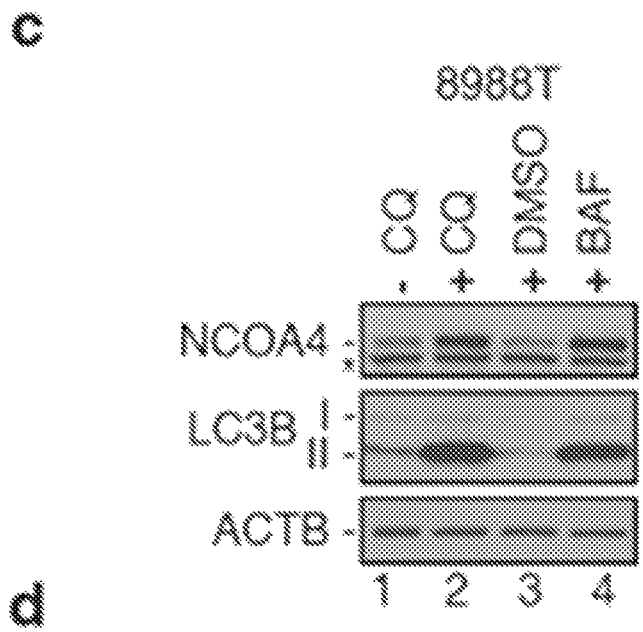
Figure 2:
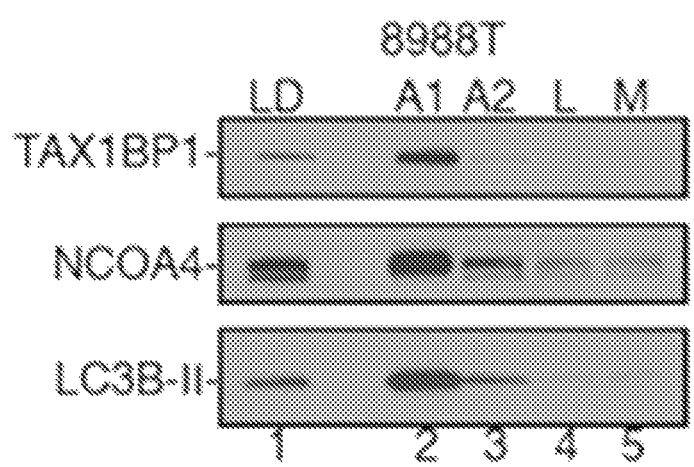
Figure 2:
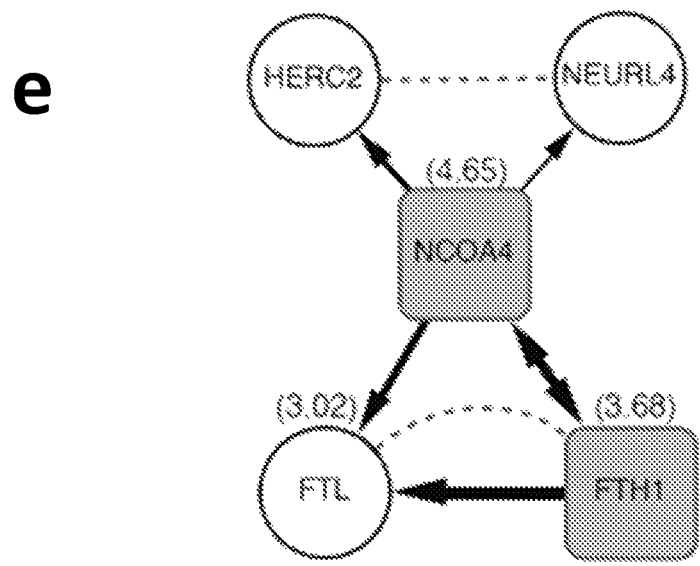
Figure 2:
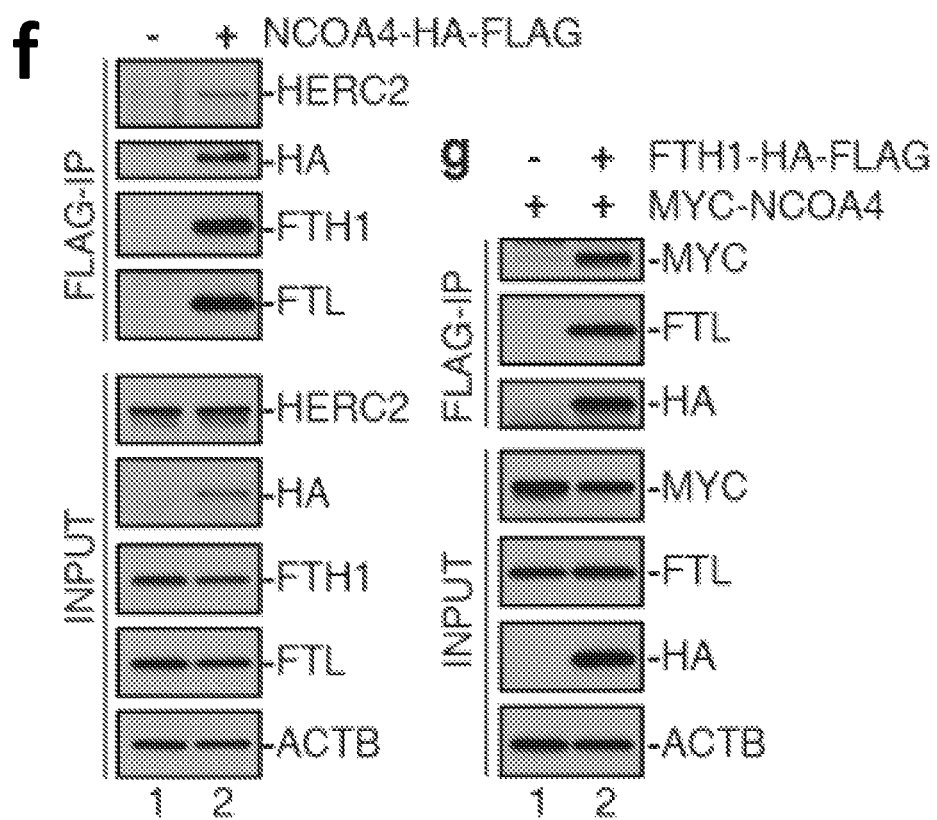
Figure 2:
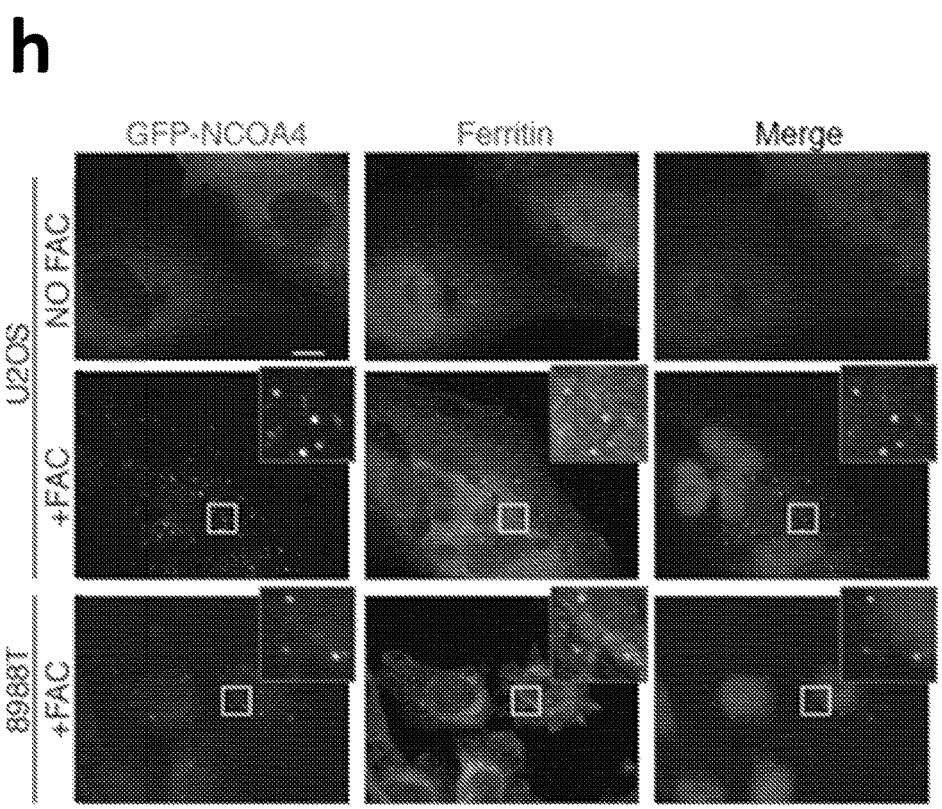

Interaction proteomics was performed essentially as described previously, but with small modifications [Sowa, M. E., et al. supra]. Briefly, 293T, PANC1, or 8988T cells were transduced with a lentiviral vector expressing NCOA4-HA-FLAG (NCOA4 amino acid sequence: NP_0011-38735.1) (SEQ ID NO: 4) or FTH1-HA-FLAG (293T only, NP_002023.2 (SEQ ID NO: 6)) and stable cell lines were selected in puromycin. Cells from 4×15 cm dishes at 80% confluence were harvested and lysed in 3 ml of 50 mM Tris-HCl (pH 7.4), 150 mM NaCl, 0.5% Nonidet P40, 2 mM DTT and protease inhibitors. Cleared lysates were filtered through 0.45 μm spin filters (Millipore Ultrafree-CL) and immunoprecipitated with 30 μl anti-HA resin (Sigma). Complexes were washed 4 times with lysis buffer, exchanged into PBS for a further 3 washes, eluted with HA peptide and precipitated with 10% TCA. TCA-precipitated proteins were trypsinized, purified with Empore C18 extraction media (3 M), and analyzed via LC-MS/MS with a LTQ-Velos linear ion trap mass spectrometer (Thermo) with an 18 cm$^3$ 125 μm (ID) C18 column and a 50 minute 8%-26% acetonitrile gradient. All AP-MS experiments in 293T cells were performed in biological duplicate and for each biological experiment, complexes were analyzed twice by LC-MS/MS to generate technical duplicates. AP-MS experiments in 8988T and PANC1 cells were performed on a single AP but with technical duplicates. Spectra were searched with Sequest against a target-decoy human tryptic UNIPROT-based peptide database, and these results were loaded into the Comparative Proteomics Analysis Software Suite (ComPASS) to identify high confidence candidate interacting proteins (HCIPs) [Sowa, M. E. et al., supra]. Here, a statistics table, derived from analogous AP-MS data for 172 unrelated proteins in 293T cells was employed to determine weighted and normalized D-scores (WDN-score) as well as Z-scores based on spectral counts. The PANC1 data was analyzed using a PANC1 specific statistics table with 12 unrelated AP-MS PANC1 experiments and the 8988T AP-MS experiment was analyzed using the 293T statistics table given no statistics table was available for the 8988T cell line. The D-score measures the reproducibility, abundance, and frequency of individual proteins detected in each individual analysis. To identify NCOA4 associated proteins, proteins were filtered at a 2% false discovery rate for those with a WDN-score ≥1.0, Z and average assembled peptide spectral matches (APSMs) ≥2 in both biological duplicates. Data presented in FIG. 2(e) are derived from the 293T AP-MS experiments and the figure was made using Cytoscape [Lopes, C. T. et al. *Bioinformatics* 26, 2347-2348 (2010)]. STRING database data are represented as previously [Sowa, M. E., et al., supra]. FTH1 and FTL interactors were confirmed in both PANC1 and 8988T AP-MS experiments and HERC2 in the 8988T AP-MS. NEURL4 was included in the interaction network given identification in the 293T AP-MS experiment and previously published data revealing a HERC2-NEURL4 interaction [Martinez-Noel, G., et al. *Molecular and Cellular Biology* 32, 3095-3106 (2012)].

Immunological Methods and Microscopy

To assess enrichment of autophagosome associated proteins in autophagosome purifications, the gradient load and autophagosome fractions were extracted in 50 mM Tris-HCl (pH 7.4), 150 mM NaCl, 1% Nonidet P40, 0.1% SDS, 2 mM EDTA, 2 mM DTT, protease inhibitors and subjected to immunoblotting with the indicated antibodies. To assess autophagosome integrity, purified autophagosome fractions (A1) were incubated in buffer A for 1 hour at 37° C. plus or minus 0.5% Triton X-100, centrifuged at 16,000×g for 10 minutes, and the supernatant and pellet were subjected to immunoblotting with the indicated antibodies. To validate interactions between NCOA4 and candidate interacting proteins, 293T cells stably expressing NCOA4-HA-FLAG were harvested at 80% confluency. Extracts (50 mM Tris-HCl (pH 7.4), 150 mM NaCl, 0.5% Nonidet P40, 2 mM DTT, and protease inhibitors) from cells were subjected to immunoprecipitation with anti-FLAG resin (M2 agarose; Sigma), and washed complexes subjected to immunoblotting with the indicated antibodies. Likewise, 293T cells stably expressing FTH1-HA-FLAG with transient expression of MYC-NCOA4 were harvested at 80% confluency, lysed as above, subjected to immunoprecipitation as above, and immunoblotted with the indicated antibodies.

Figure 3:
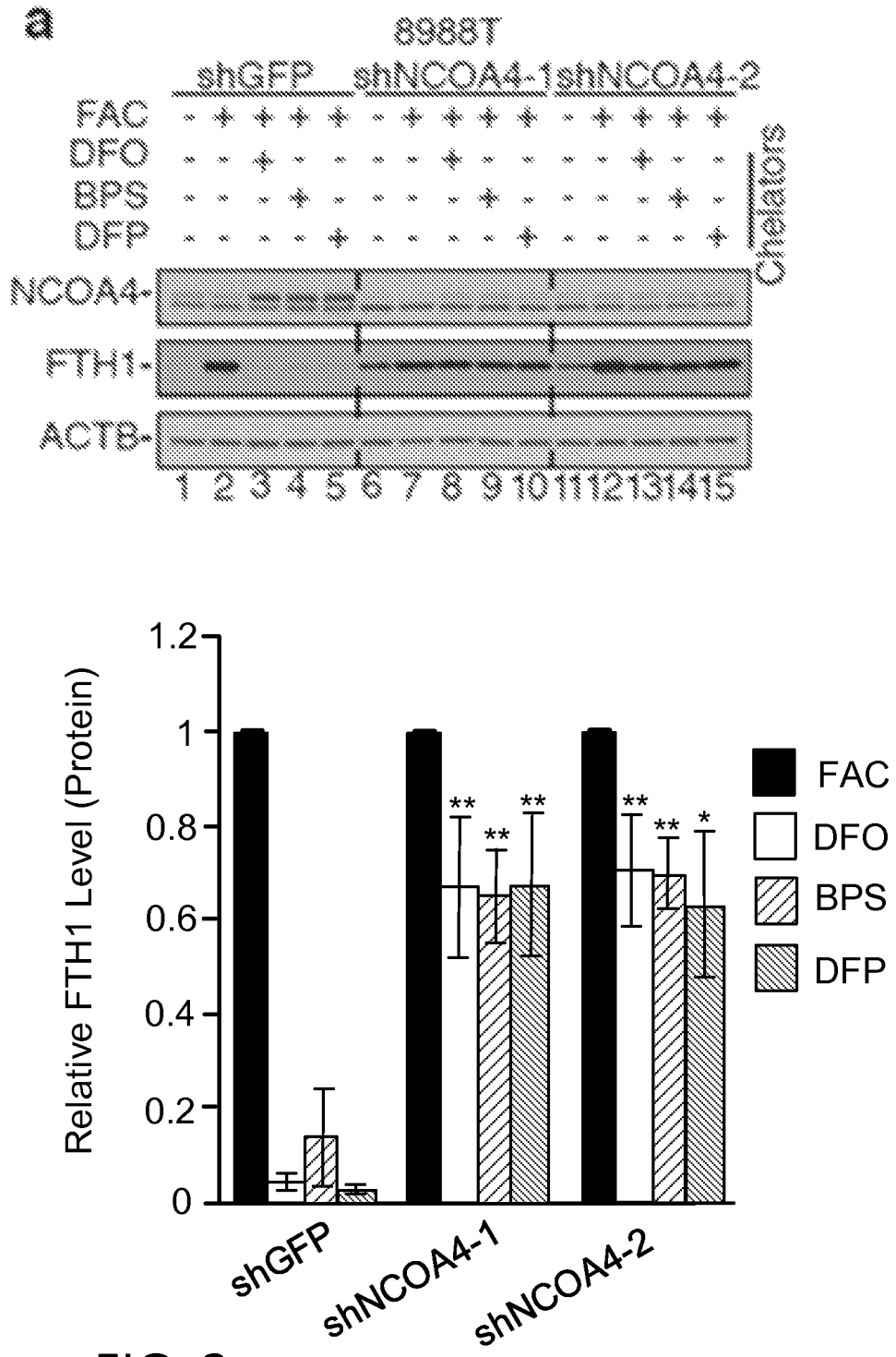
FIG. 3(a), upper panel, contains photographs of immunoblot results for lysates of 8988T cells following incubation with FAC (ferric ammonium citrate), NCOA4 depletion using shRNA, and 9 hour iron chelation with the indicated chelators (DFO (deferoxamine mesylate), BPS (bathophenanthroline disulfonate), DFP (deferiprone)). Relative FTH1 levels (n=3, biologic triplicate) for each chelator are quantified using an anti-FTH-1 antibody; an anti-ACTB antibody was used as a loading control. shGFP was a negative control for NCOA4 depletion. For each treatment groups (FAC (no iron chelation), DFO, BPS and DFP), the relative FTH1 levels in the control group (shGFP) and NCOA4-depleted groups (shNCOA4-1 and shNCOA4-2) are quantified in the graph in the lower panel; bars and error bars represent mean values and standard deviation (s.d.), respectively: ** ($p<0.01$) and * ($p<0.02$) comparing FTH1 levels between 8988T shGFP versus 8988T shNCOA4-1 or versus shNCOA4-2 (one-sided t-test). NCOA4 depletion rescued ferritin degradation.
FIG. 3(b) contains photographs of immunoblot results for lysates of U2O2 cells following incubation with FAC, in a DFO chelation time course (times are indicated "hr": hours). DFO was added at time 0; two NCOA4 antibodies were used for immunoblotting (top panel Sigma antibody, $2^{nd}$ panel Bethyl antibody). An anti-FTH1 antibody was used in the third panel and an anti-ACTB antibody was used in the fourth panel (loading control).
FIG. 3(c) contains fluorescent confocal images of U2OS cells subjected to DFO chelation in the presence of lysosomal protease inhibitors for 6 hours. GFP-NCOA4 co-localizes with endogenous LC3 and endogenous ferritin; scale bar, 20 μm. Higher magnification views of the boxed areas are shown in the insets.
FIG. 3(d), left panel, contains fluorescent confocal images of immunostained 8988T cells incubated with control shRNA (GFP) or depleted of NCOA4 by incubation with one of two different shRNAs (shRNANCOA4-1 and -2), and subjected to DFO chelation in the presence of lysosomal protease inhibitors for 9 hours. Cells were fixed and immunostained using antibodies to ferritin and LAMP2. Scale bar, 10 μm. The right panel contains a bar graph quantifying punctate ferritin fraction from >100 cells per cell line from 2 independent experiments (biologic duplicate); bars and error bars represent mean values and s.d., respectively: *** denotes $p<0.001$ using a one-sided t-test.
FIG. 3(e), left panel, contains photographs of immunoblot results from lysates from 8988T cells treated as in FIG. 3(a); the lysates were analyzed using the indicated antibodies (NCOA-4, IRP2, TFRC, and ACTB (loading control)); lanes 1-3 were untreated groups (no FAC or DFO)), lanes 4-9 were treated as indicated. The right panel contains a bar graph quantifying the relative protein level of the indicated proteins (IRP2, TFRC) based on at least 3 independent experiments (biologic triplicate); bars and error bars represent mean values and s.d., respectively: * ($p<0.05$) using a one-sided t-test.
FIG. 3(f) is a bar graph quantifying cell viability measured at 72 h in 8988T cells stably expressing shGFP or shNCOA4-1 and treated with $H_2O_2$; bars and error bars represent mean values and s.d., respectively of technical triplicates: *** ($p<0.001$) using a two-sided t-test.
Figure 3:
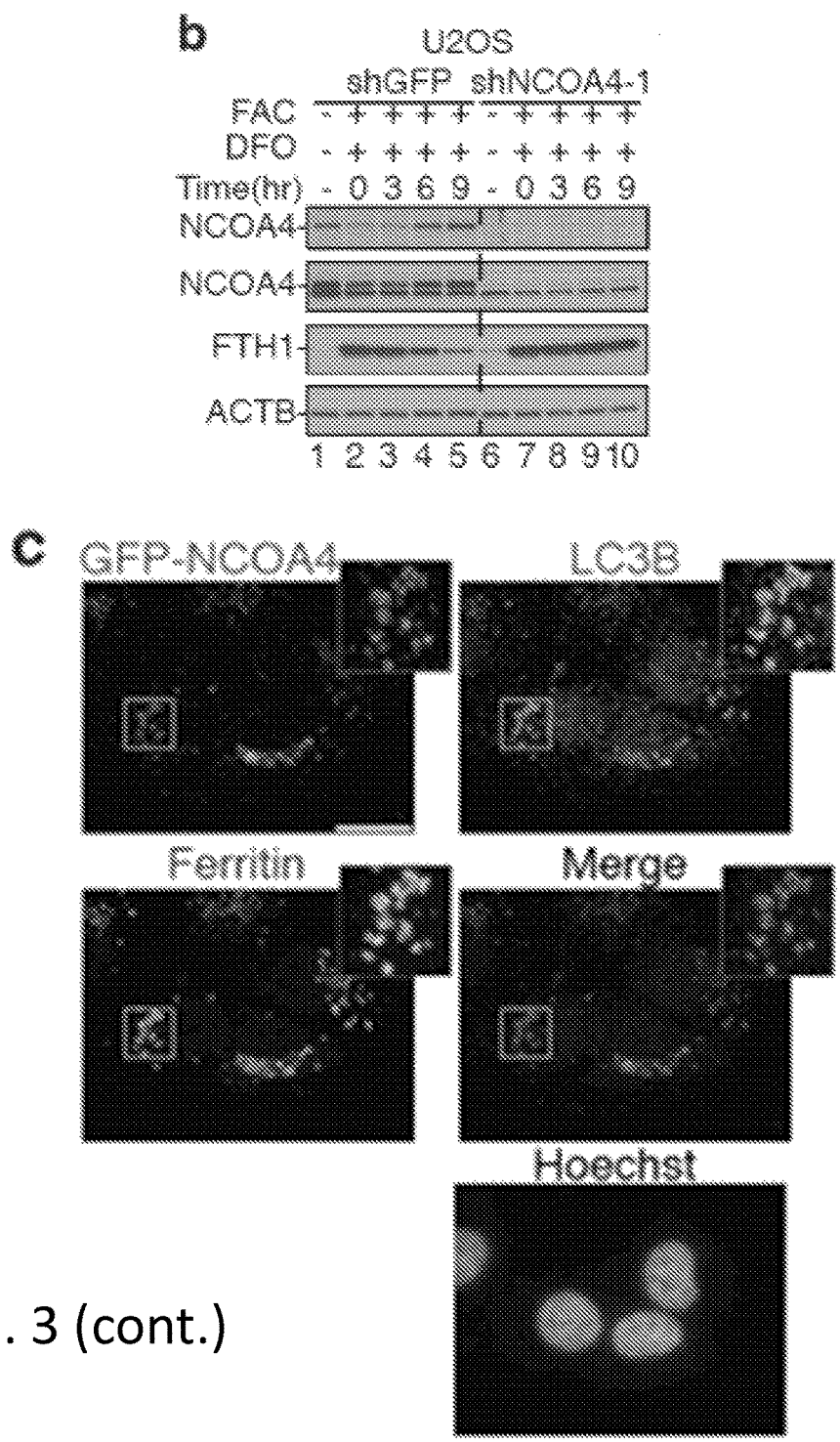
Figure 3:
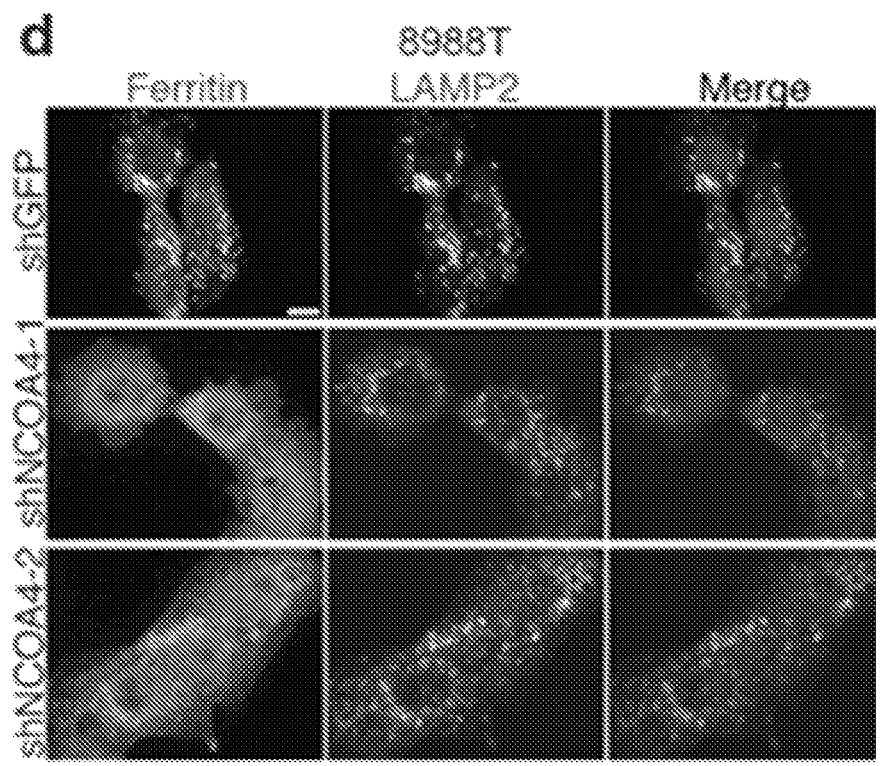
Figure 3:
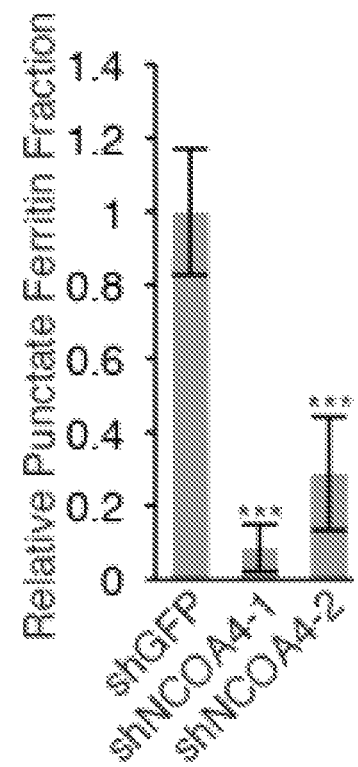
Figure 3:
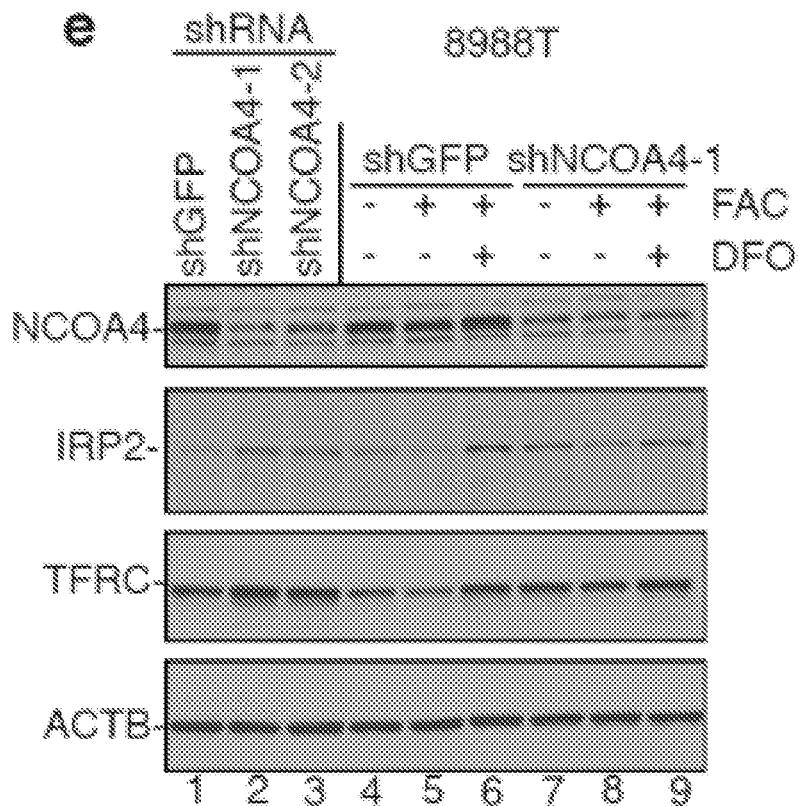
Figure 3:
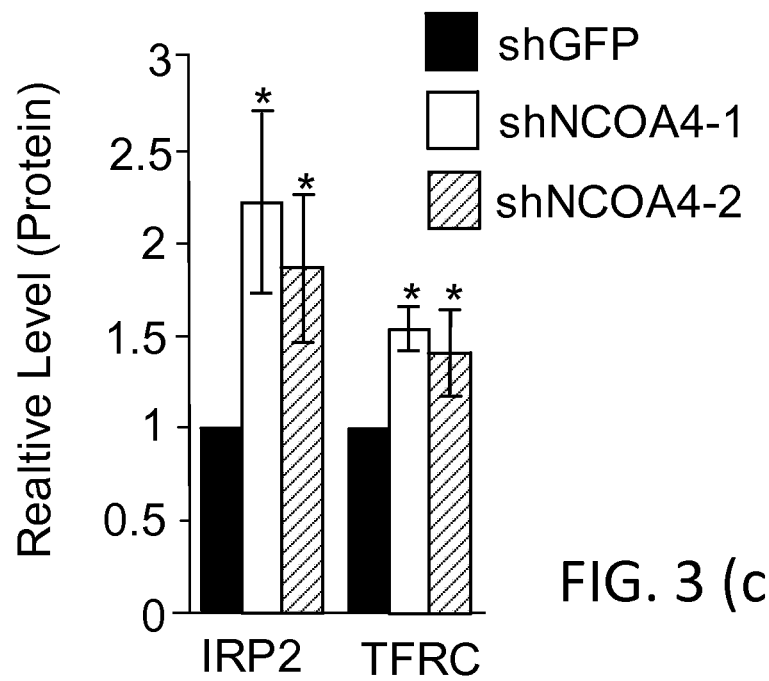
Figure 3:
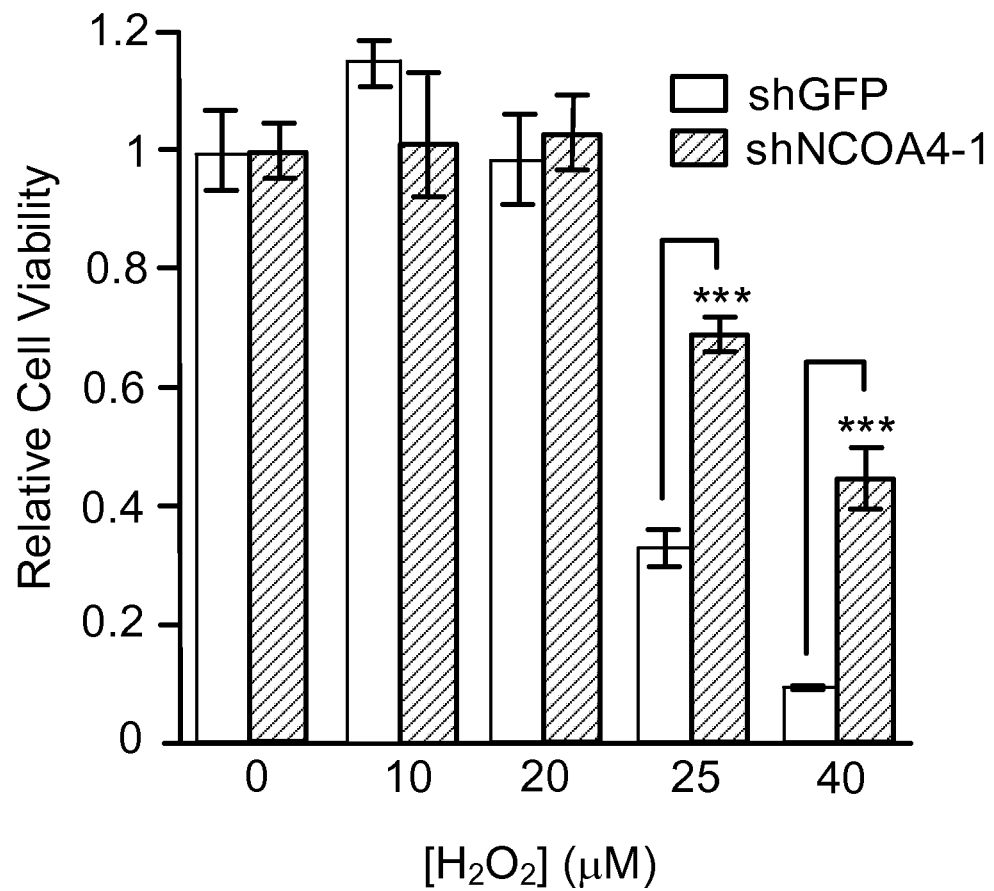
Figure 14:
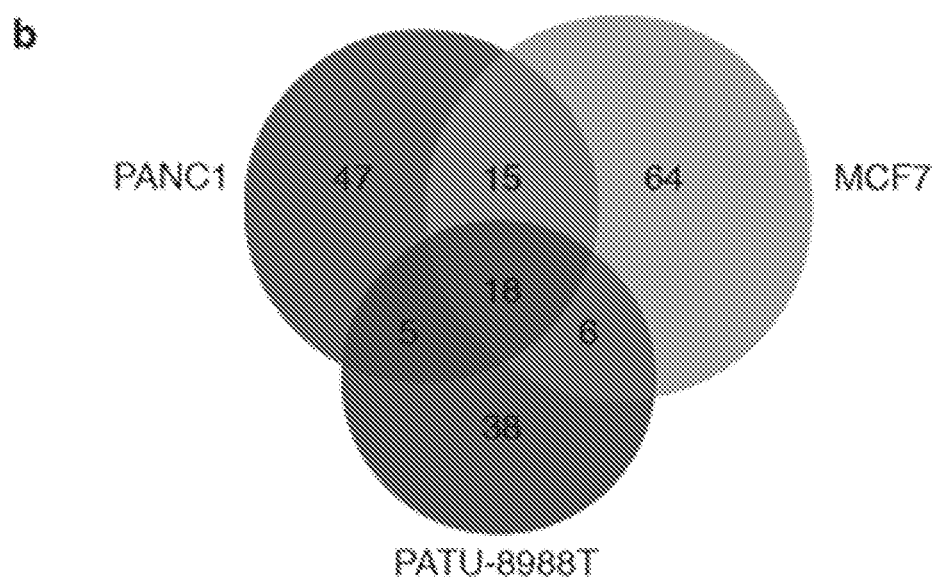
FIG. 14(a) is an autophagosome proteomics class 1A candidate list, with enriched proteins, "not enriched" proteins, and "not identified" proteins in each group indicated (MCF7, 8988T SILAC, and 8988T LC3-IP).
FIG. 14(b) is a Venn diagram showing the overlap between Class 1 candidates (MCF7 and PANC1) and candidates from 4 hr chloroquine (CQ) SILAC 8988T gradient autophagosome purification experiment.
FIG. 14(c) lists the protein expression data from 8988T SILAC gradient autophagosome for Class 1A candidates (and FTH1), with enriched proteins, "not enriched" proteins, and "not identified" proteins identified in each group. Number of peptides identified for each protein is noted (8988T peptide #) and the Log 2(Heavy:Light ratio) of each quantified protein is noted (8988T Log 2(H:L).
FIG. 14(d) is a heat map of Class 1A candidates (and FTH1) comparing PANC1 and 8988T cells treated for 4 hours (h) with chloroquine (CQ).
Figure 14:
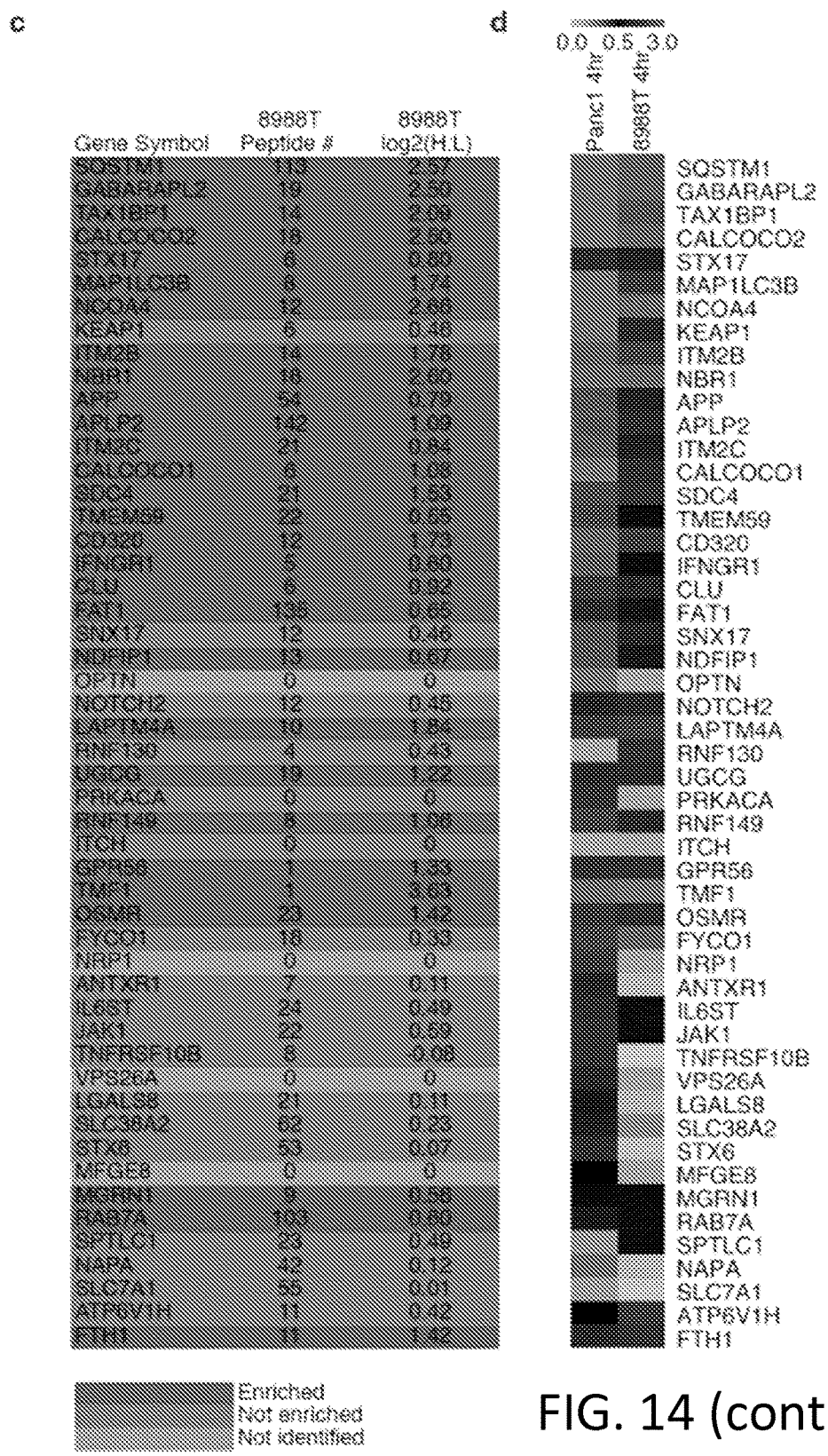

To examine localization of high-priority candidate proteins, full-length clones of the indicated candidate proteins were stably expressed as HA-FLAG fusions in 8988T and U2OS cells. Cells were plated on glass coverslips, treated with vehicle or CQ (10 μM, 4 hours (h)), and fixed with 4% paraformaldehyde prior to immunofluorescence using anti-HA to detect candidate proteins and anti-LC3B to detect autophagosomes. All images were collected with a Yokogawa CSU-X1 spinning disk confocal with Borealis modification on a Nikon Ti-E inverted microscope equipped with 100× Plan Apo NA 1.4 objective lens. HA-candidate protein fluorescence was excited with the 488 nm line (selected with an AOTF) from Spectral Applied Precision LMM-7 solid state laser launch. Emission was collected with a quad band pass polychroic mirror (Semrock) and a Chroma ET525/50 m emissions filter. LC3B fluorescence was excited with the 561 nm line from the LMM-7 launch, and emission collected with the Semrock polychroic and a Chroma ET620/60 m emission filter. For triple colocalization (FIG. 3c), ferritin fluorescence was excited with the 642 nm line from the LMM-7 launch, and emission collected with the Semrock polychroic and a Chroma ET700/75 m emission filter. Images were acquired with a Hamamatsu ORCA-AG cooled CCD camera controlled with MetaMorph 7 software. Z-series optical sections were collected with a step size of 0.2 microns, using the internal Nikon Ti-E focus motor. Co-localization was determined based on examination of single z slices using MetaMorph 7 software (results are tabulated in FIG. 14(a)).

To examine NCOA4 protein levels while blocking autophagic flux, 8988T cells were treated with vehicle (PBS or DMSO), CQ (10 μM, 8 hours), or Bafilomycin A1 (50 nM, 8 hours), extracted in 50 mM Tris-HCl (pH 7.4), 150 mM NaCl, 1% Nonidet P40, 0.1% SDS, 2 mM EDTA, 2 mM DTT, protease inhibitors and subjected to immunoblotting with the indicated antibodies.

To examine co-localization of NCOA4 with LC3B and ferritin, a N-terminal GFP fusion of NCOA4 was used. U2OS and 8988T cells stably expressing GFP-NCOA4 were treated with vehicle (PBS or DMSO), CQ (10 μM, 4 hours), Bafilomycin A1 (50 nM, 4 hours), or FAC (ferric ammonium citrate, 36 µM or 180 µM, 24 hours) and fixed with 4% paraformaldehyde prior to immunofluorescence using anti-LC3B to label autophagosomes or anti-ferritin in FAC loaded cells. Images were collected as described above with 6-10 z-series optical sections collected with a step size of 0.2 microns, using the internal Nikon Ti-E focus motor. Z-series are displayed as maximum z-projections.

GST Pull-Down

The six human paralog ATG8 proteins were produced as N-terminal GST fusions (GST-ATG8) and transformed in *E. coli* BL21 (DE3) cells. Protein expression was induced with 1 mM IPTG for 3 hours at 37° C. Cells were collected by centrifugation, re-suspended in 25 mM Tris-HCl (pH 7.4), 10% (w/v) sucrose and lysed with a single freeze-thaw cycle followed by sonication. After centrifugation, lysates were incubated with 10 µl of a 50% (v/v) slurry of glutathione Sepharose 4B beads for 30 minutes at 4° C. Beads were washed thoroughly with 150 mM NaCl, 20 mM Tris (pH 7.4), 2 mM DTT, 0.5% (w/v) Nonidet P-40, leaving 50-100 µg of GST-fusion protein bound to the beads. Beads were then mixed with 300 µg of lysate from a NCOA4-HA-FLAG stably expressing 293T cell line. The assay mix was incubated for 30 minutes at 4° C., and beads were washed four times with 1 ml wash buffer. Proteins were eluted with SDS sample buffer and analyzed by 4-20% gradient SDS-PAGE and immunoblotting with HA antibody. Pounceau stain was used to visualize GST-ATG8 bands.

Chelation Assays

Chelation assays were performed similarly to those previously described with slight modifications [Asano et al., supra]. Briefly, U2OS and 8988T cells stably expressing shRNAs as described above (shGFP, shNCOA4-1, shNCOA4-2, selected with puromycin) were plated ($2\times10^5$ cells/well) and cultured for 24 hours in FAC (36 µM or 180 µM). Cells were washed three times with PBS and subjected to iron chelation with the described chelators minus or plus lysosomal protease inhibitors (E-64d and PepstatinA) or the proteasomal inhibitor, Bortezomib. Cells were harvested at the indicated time points, washed with PBS, and lysed in 50 mM Tris-HCl (pH 7.4), 150 mM NaCl, 1% Nonidet P40, 0.1% SDS, 2 mM EDTA, 2 mM DTT, protease inhibitors and analyzed by 4-20% gradient SDS-PAGE followed by immunoblotting with the indicated antibodies. Experiments were performed at a minimum in biological triplicate. Quantitation of Western blots was performed using ImageJ [Schneider, C. A., et al. *Nature Methods* 9, 671-675 (2012)]. Cells were treated similarly for immunofluorescence experiments (including IMR90 and HPDE cells). Cells plated on glass coverslips were treated as described and fixed with 4% paraformaldehyde prior to immunofluorescence using anti-ferritin and anti-LAMP2. Data were collected as described above.

Figure 21:
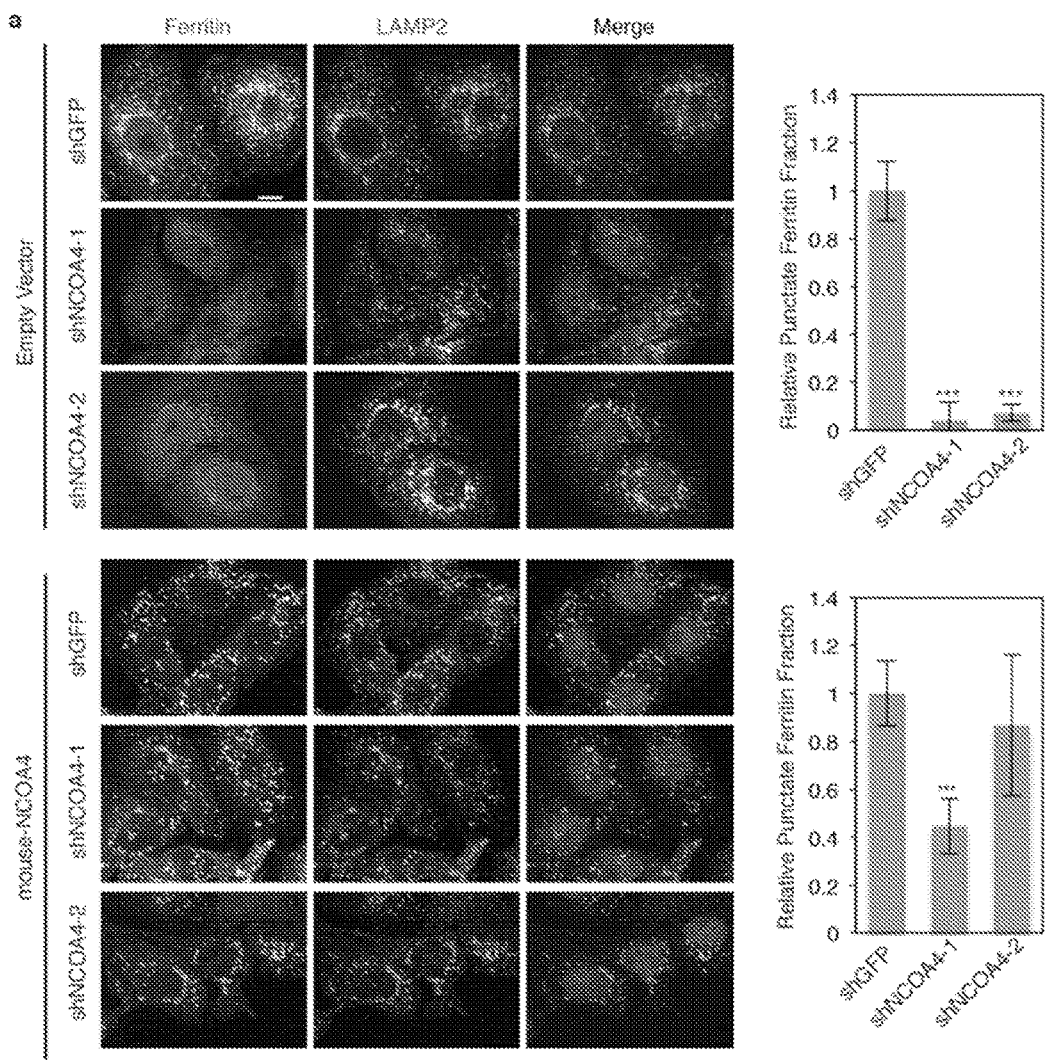
FIG. 21(a) contains fluorescent images of 8988T cells stably expressing either a control MSCV empty vector or the murine homolog of NCOA4 (selected with blasticidin) as well as stably expressing shRNAs (shGFP, shNCOA4-1, shNCOA4-2, selected with puromycin) and cultured in the presence or absence of FAC for 24 hours, washed, and subjected to DFO chelation in the presence of lysosomal protease inhibitors (E-64d and PepstatinA). Cells were fixed and immunostained using antibodies to ferritin and LAMP2. Scale bar, 10 μm (left panel). The right panel contains graphs quantifying the punctate ferritin fraction from ≥100 cells per cell line (number of 8988T cells quantified is as follows: 8988T-control MSCV-shGFP: 100 cells, 8988T-control-MSCV-shNCOA4-1: 125 cells, 8988T-control-MSCV-shNCOA4-2: 132 cells, 8988T-mouse-NCOA4-shGFP: 151 cells, 8988T-mouse-NCOA4-shNCOA4-1: 153 cells, 8988T-mouse-NCOA4-shNCOA4-2: 172 cells). Bars and error bars represent mean values and s.d., respectively: *** denotes p<0.001 using a one-sided t-test.
FIG. 21(b) contains photographs of immunoblots of lysates of 8988T cells stably expressing either a control MSCV empty vector or the murine homolog of NCOA4 (selected with blasticidin), as well as stably expressing a control shRNA (shGFP) and two independent shRNAs to NCOA4 (shNCOA4-1 and shNCOA4-2). The cells were lysed and analyzed by immunoblotting with an antibody to NCOA4 and to ACTB as a loading control. Light and dark exposures are shown. A non-specific band migrates just below the NCOA4 specific band.
FIG. 21(c) contains photographs of immunoblots of lysates of 8988T cells expressing murine HA-NCOA4 protein or control (empty vector). Cell lysates were probed with an anti-HA antibody, or an anti-ACTB antibody as a loading control.
Figure 21:
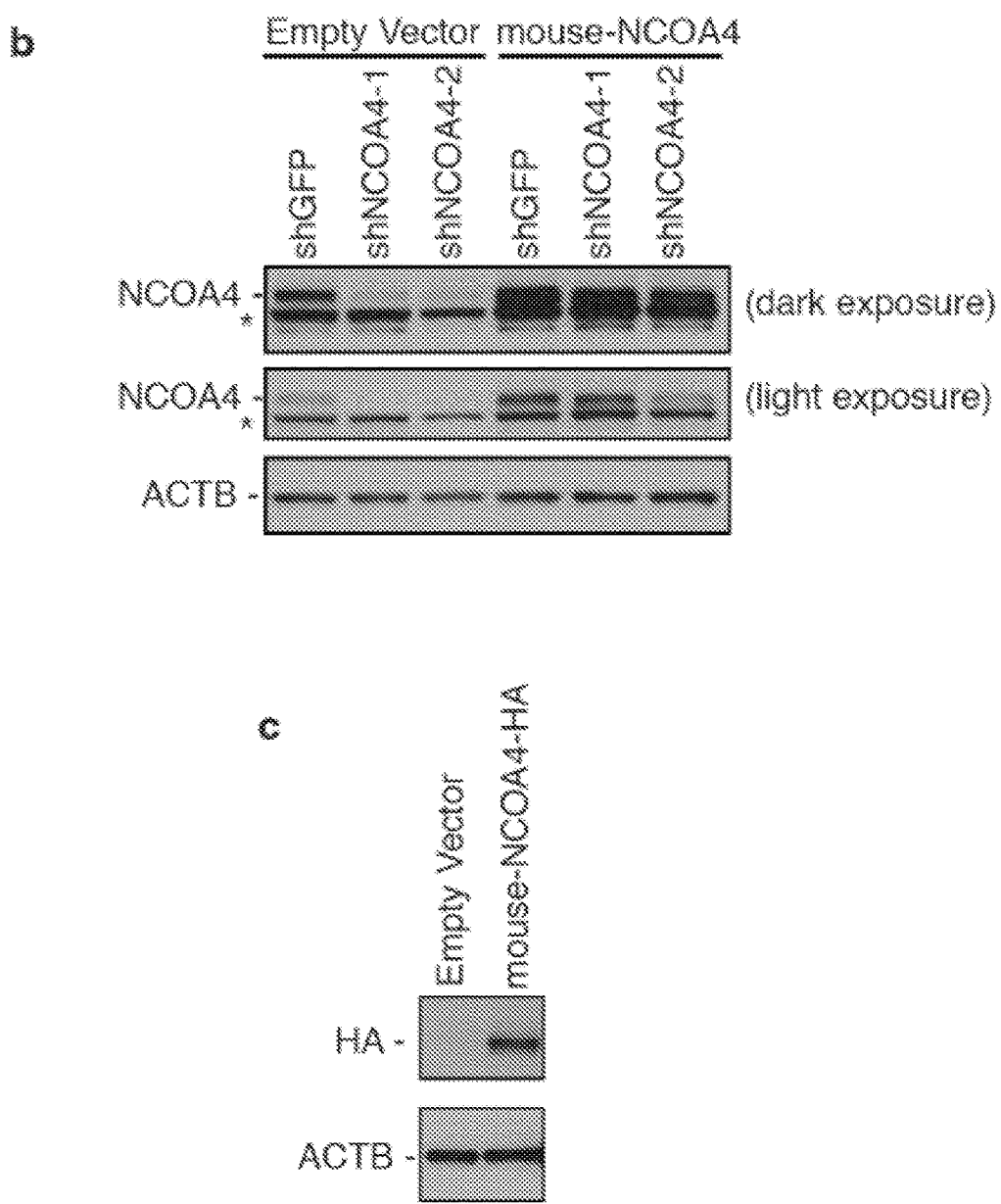

For quantitation of ferritin localization, at least 5, 40× fields were collected for biological replicate experiments. The fraction of punctate ferritin was quantitated by measuring the percentage of punctate ferritin immunofluorescence divided by total cellular ferritin immunofluorescence using MetaMorph software. At least 5 fields were quantitated from biological duplicate experiments. For FIG. 3(*d*), the number of 8988T cells quantitated expressing shGFP was 155, for 8988T cells expressing shNCOA4-1: 113, and shNCOA4-2: 138. For FIG. 20(*c*), the number of U2OS cells quantitated is as follows: shGFP: 133 cells, shNCOA4-1: 103 cells, shNCOA4-2: 79 cells. For FIG. 20(*d*), the number of IMR90 cells quantified is as follows: shGFP: 29 cells, shNCOA4-1: 26 cells, shNCOA4-2: 31 cells. For FIG. 21(*a*), the number of 8988T cells quantified is as follows: 8988T-control MSCV-shGFP: 100 cells, 8988T-control-MSCV-shNCOA4-1: 125 cells, 8988T-control-MSCV-shNCOA4-2: 132 cells, 8988T-mouse-NCOA4-shGFP: 151 cells, 8988T-mouse-NCOA4-shNCOA4-1: 153 cells, 8988T-mouse-NCOA4-shNCOA4-2: 172 cells. Exposure times were held constant between experiments. Rescue experiments were performed using retroviral (MSCV blasticidin) based expression of the murine homolog of NCOA4 (NP_001029160.1) with a N-terminal HA tag.

$H_2O_2$ Assay

Experiments were performed as described previously with slight modifications [Kurz, T., et al. *The FEBS Journal*; 273, 3106-3117, (2006)]. 8988T cells stably expressing shGFP or shNCOA4-1 were plated on a 96-well plate and treated with increasing concentrations of $H_2O_2$ as indicated for 30 minutes followed by 72 hours of culturing in complete media. Relative cell viability was measured using CellTiter-Glo®. Experiments were performed at least three times, each time in technical triplicate.

Methods for Defining NCOA4-Ferritin and NCOA4-HERC2 Interaction

NCOA-4-Ferritin Interaction Mapping

To probe the interaction between ferritin and NCOA4, initial binding assays using MYC-tagged NCOA4 full-length and truncation constructs produced using an in vitro translation ("IVT") system were conducted. MYC-NCOA4 fragments were cloned using PCR into a modified T7 cell-free expression vector (pT7CFE1-NMyc, #88863, Thermo Scientific). 1-Step Human Coupled IVT Kit—DNA from Thermo Scientific (product #88881) was used to produce MYC-tagged NCOA4 constructs as described in the product manual. Apoferritin (Sigma, A3641-100 mg) was added in a pull-down assay using anti-c-Myc Agarose Affinity Gel antibody produced in rabbit (Sigma, A7470-1 ML). Affinity purification reactions were washed thoroughly with 150 mM NaCl, 20 mM Tris (pH 7.4), and 2 mM dithiothreitol. Proteins were eluted with SDS sample buffer and analyzed by 4-20% gradient SDS-PAGE and immunoblotting with anti-FTH1 antibody (Cell Signaling 3998; Western blot 1:1,000) or anti-MYC antibody (Santa Cruz Sc-40; western blot 1:1,000).

The full-length, N-terminal (amino acids (aa) 1-245 of SEQ ID NO: 4) and C-terminal (aa 235-614 of SEQ ID NO:4) MYC-NCOA4 were incubated with ferritin purified from horse spleen (Apoferritin (Sigma, A3641-100 mg), consisting of a mixture of FTH1 and FTL subunits) and anti-MYC immunoprecipitation was performed followed by immunoblotting as described above.

GST-tagged NCOA4 constructs were also made to probe the interactions of C-terminal portions of NCOA4 with ferritin. NCOA4-truncation constructs were produced using Gateway cloning (Invitrogen, Life Technologies, catalog #11789-013 and 11791-019) into a pDEST60 N-terminal GST fusion plasmid (GST-NCOA4) from EMD Millipore (Gateway Nova pET-60-DEST, product #71851-3) and transformed in *E. coli* BL21 (DE3) cells (New England Biosciences, C2527I).

NCOA4 truncation constructs were designed based on NCBI reference sequence: NP_001138735.1 (SEQ ID NO: 4). In particular, fragments of SEQ ID NO: 4 consisting of amino acids (aa) 1-245, aa 235-614, aa 235-560, aa 235-401, aa 383-560, aa 545-614, aa 383-522, aa 510-560, aa 383-436, aa 436-485, aa 475-522, aa 475-500, aa 480-500, aa 480-504, aa 485-509, aa 490-514, aa 495-522 were designed. Protein expression in the DE3 cells was induced with 1 mM isopropyl-beta-D-thiogalactopyranoside (IPTG)

(Sigma, I6758-10 G) for 3 hours at 37° C. Cells were collected by centrifugation, re-suspended in 25 mM Tris-HCl (pH 7.4), 10% (w/v) sucrose and lysed with a single freeze-thaw cycle followed by sonication. After centrifugation, a GST pull-down assay was performed.

In the GST pull-down assay, lysates were incubated with 10 µl of a 50% (v/v) slurry of glutathione Sepharose 4B beads (GE Healthcare Lifesciences, 17-0756-01) for 30 minutes at 4° C. Beads were washed thoroughly with 150 mM NaCl, 20 mM Tris (pH 7.4), 2 mM dithiothreitol (DTT), 0.5% (w/v) Nonidet P-40, leaving 50-100 µg of GST-fusion protein bound to the beads. Beads were then mixed with 0.5-2 µg of apo-ferritin purified from equine spleen (Sigma F4503) or recombinant human FTH1 or FTL produced in Rosetta *E. coli* (EMD Millipore, 70953-3). The assay mix was incubated for 2 hours at 4° C., and beads were washed four times with 1 ml wash buffer. Proteins were eluted with SDS sample buffer and analyzed by 4-20% gradient SDS-PAGE and immunoblotting with anti-FTH1 antibody (as above) or anti-FLAG antibody (Sigma, F1804-200 UG). Pounceau stain was used to visualize GST-NCOA4 bands. (Pounceau, Sigma, P7170-1 L, protocol as per product manual).

NCOA-4-HERC2 Interaction Mapping

To map the interaction of NCOA-4 with HERC2, the GST-NCOA4 truncation constructs described above were also tested in a GST pull-down assay with HERC2-FLAG expressing 293T cell line. HERC2-FLAG fragment (F3, HERC2 amino acids 1700-2700) was produced as described in Bekker-Jensen et al., *Nature Cell Biology* (2010) 12; 80-86. The HERC2-FLAG F3 was transiently transfected into 293T cells using standard transfection procedures using PEI (Polysciences, #23966-2).

Lysates were obtained, as above, and incubated with 10 µl of a 50% (v/v) slurry of glutathione Sepharose 4B beads for 30 minutes at 4° C. Beads were washed thoroughly with 150 mM NaCl, 20 mM Tris (pH 7.4), 2 mM DTT, 0.5% (w/v) Nonidet P-40, leaving 50-100 µg of GST-fusion protein bound to the beads. Beads were then mixed with 300 µg of lysate from a HERC2-FLAG expressing 293T cell line, as above. The assay mix was incubated for 2 hours at 4° C., and beads were washed four times with 1 ml wash buffer. Proteins were eluted with SDS sample buffer and analyzed by 4-20% gradient SDS-PAGE and immunoblotting with anti-HERC2 antibody or anti-FLAG antibody, as above. Coomassie stain was used to visualize GST-NCOA4 bands as above.

Example 2: NCOA4 Modulates Autophagic Targeting of Ferritin

Autophagosomes are decorated by a family of ubiquitin-like adaptor ATG8 proteins that are conjugated to phosphatidylethanolamine through the action of an autophagy-specific E1-E2-E3 cascade. While ATG8 proteins are known to recruit a small number of cargo receptors to insipient autophagosomes, the full repertoire of selective autophagic cargo and their cognate receptor proteins remain poorly defined [Kirkin, V., et al. *Molecular Cell* 34, 259-269, (2009)]. Selective autophagy may be particularly important for the survival or growth of particular cancer cell types [Yang, S. et al. supra; Sandilands, E. et al. *Nature Cell Biology* 14, 51-60 (2012)] but in other contexts may act as a tumor suppressor to maintain normal cellular homeostasis and constrain tumor initiation [Kimmelman, A. C. *Genes & Development* 25, 1999-2010 (2011); White, E. *Nature reviews. Cancer* 12, 401-410, (2012)]. Thus, a more comprehensive understanding of autophagy cargo-receptor pairs is required for understanding autophagic mechanisms that contribute to proteostasis.

Three previous studies [Overbye, A., et al. *Autophagy;* 3, 300-322 (2007); Gao, W. et al., supra; Dengjel, J. et al., supra] described the use of mass spectrometry to identify proteins in autophagosomal preparations, but since there was a low overlap in the proteins identified between these studies (FIG. 13a), and limitations of the approaches used, it was decided to catalog resident autophagosomal proteins using quantitative proteomics. Stable isotopic labeling by amino acids in cell culture (SILAC) was combined with an established density gradient separation protocol [Marzella et al., suprap; Koga et al., supra] to quantitatively identify proteins enriched in autophagosome preparations. This analysis was performed using two pancreatic cancer cell lines (PANC1 and 8988T) that require autophagy for growth, as well as the MCF7 breast cancer cell line, which is less reliant on autophagy for growth [Yang, S., et al., supra]. Given the high basal autophagy of PANC1 and 8898T cells, light cells were briefly treated with the PI3 kinase inhibitor Wortmannin (1 hour ("h") to suppress autophagosome formation, while heavy cells were treated with the lysosomal inhibitor Chloroquine (CQ) for 4 hours, to maximize the number of autophagosomes (FIG. 1a, FIG. 13(b)). As shown in FIG. 13(b), PANC1 cells have a high level of basal autophagy (left panel), and 1 h Wortmannin (200 nM) treatment blocked autophagosome formation (middle panel), and 4 h chloroquine treatment (25 µM) caused accumulation of autophagosomes (right panel). This approach allows for robust identification of proteins intimately associated with autophagosome-enriched samples as opposed to proteins that simply co-migrate with these vesicles during gradient centrifugation.

To test for autophagosome-associated proteins, 8988T cells were lysed, mixed with Nycodenz, and placed at the bottom of a discontinuous density gradient with Nycodenz layers at the following concentrations: 15%, 20%, 24%, 26% and 85.6%. As shown in FIG. 13c, the resulting fractions A1, A2, L and M, contained the autophagosome fraction (15-20% interface), autophagolysosome fraction (20-24% interface), lysosome fraction (24-26% interface), and mitochondria fraction (26-50% interface), respectively.

Figure 13:
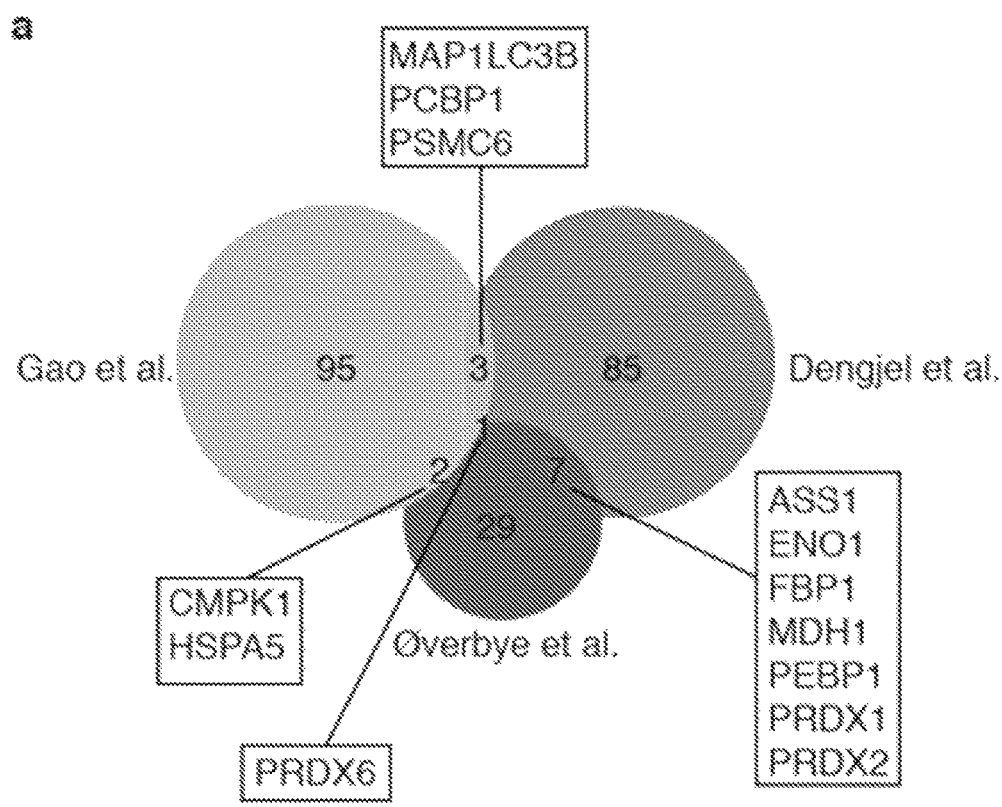
FIG. 13(a) is an area-proportional Venn diagram showing the overlap of proteins identified in three prior autophagosome proteomics studies [Overbye, A., et al., *Autophagy* 3, 300-322 (2007); Gao, W., et al. *The Journal of Biological Chemistry* 285, 1371-1383, (2010); Dengjel, J., et al. *Molecular & Cellular Proteomics*: MCP 11, M111 014035 (2012)]. Proteins overlapping between datasets are noted (MAP1LC3B: microtubule-associated protein 1 light chain 3 beta; PCBP1: poly(rC) binding protein 1; PSMC6: proteasome (prosome, macropain) 26S subunit, CMPK1: cytidine monophosphate (UMP-CMP) kinase 1, cytosolic; HSPA5: heat shock 70 kDa protein 5 (glucose-regulated protein); PRDX6: peroxiredoxin 6; ASS1: argininosuccinate synthase 1; ENO1: enolase 1; FBP1: fructose-1,6-bisphosphatase 1; MDH1: malate dehydrogenase 1, NAD; PEBP1: phosphatidylethanolamine binding protein 1; PRDX1: peroxiredoxin 1; PRDX2: peroxiredoxin 2.
FIG. 13(b) contains fluorescence microscopy images of PANC1 cells stably expressing GFP-MAP1LC3B and treated with Wormannin (1 hour ("h") or Chloroquine (4 hours ("h"), or untreated, as indicated (DAPI stain).
FIG. 13(c) contains photographs of centrifuge tubes filled with lysed 8988T cells mixed with Nycodenz and placed at the bottom of a discontinuous density gradient with Nycodenz layers at the indicated concentrations (left image). After 3 hours ("hr") centrifugation at the indicated speed, 4 bands appeared at the indicated interfaces with enrichment of the indicated organelles (A1, A2, L and M) in each interface (right image).
FIG. 13(d) contains photographs of centrifuge tubes containing lysates of 8988T cells treated with either Wortmannin (1 hour ("h"), 200 nM) or chloroquine (4 h, 25 µM) subjected to gradient centrifugation. A decreased amount of material is recovered from the A1 (autophagosome) interface (boxed) due to the effect of Wortmannin on autophagosome formation.
FIG. 13(e) contains fluorescence microscopy images of gradient load (LD) and autophagosome fraction (A1) from 8988T cells stably expressing GFP-MAP1LC3B after either chloroquine or Wortmannin treatment.
FIG. 13(f) contains fluorescence microscopy images of the indicated fractions from density gradient of 8988T cells stably expressing GFP-MAP1LC3B treated with chloroquine (A1 fraction image is also presented in panel e and gradient picture is also presented in panel c).
FIG. 13(g) contains photographs of immunoblot results for lysates PANC1 autophagosome fractions analyzed by immunoblotting using antibodies to LAMP2, VDAC1, and LC3B. LD is gradient load, A1 is autophagosome fraction from 15-20% Nycodenz interface, A2 is the autophagolysosome fraction from the 20-24% Nycodenz interface, L is the lysosome fraction from the 24-26% Nycodenz interface, M is the mitochondrial fraction from the 26%-50% nycodenz interface.
FIG. 13(h) contains photographs of immunoblot results for lysates of 8988T autophagosome fractions analyzed as in FIG. 13(g).
FIG. 13(i) contains photographs of immunoblot results using antibodies to p62 and LC3B-II on lysates of 8988T autophagosomes (A1 fraction) incubated at 37° C. for 1 hour−/+Triton X-100 and centrifuged at high speed.
FIG. 13(j) is a Pearson correlation plot for overlapping candidates from MCF7 experiments (102 proteins, comparing Log 2 ratio of Heavy Lys (H)/16 hour chloroquine treatment (CQ) to Light Lys ("L")/no treatment in Ex. 1 versus Ex. 2.
FIG. 13(k) contains photographs of electron micrographs of 8988T gradient load (LD, left panel) and 8988T autophagosome fraction (A1, right panel) at 6800× magnification, scale bar 500 nm.
FIG. 13(l) contains photographs of electron micrographs of 8988T gradient load (LD, left panel) and 8988T autophagosome fraction (A1, right panel) at 18500× magnification, scale bar 500 nm.
FIG. 13(m) contains photographs of electron micrographs of 8988T autophagosome fraction (A1) at 23000× magnification, scale bar 100 nm. Arrowhead: double-membrane autophagosome; arrow: fused autophagolysosome.
Figure 13:
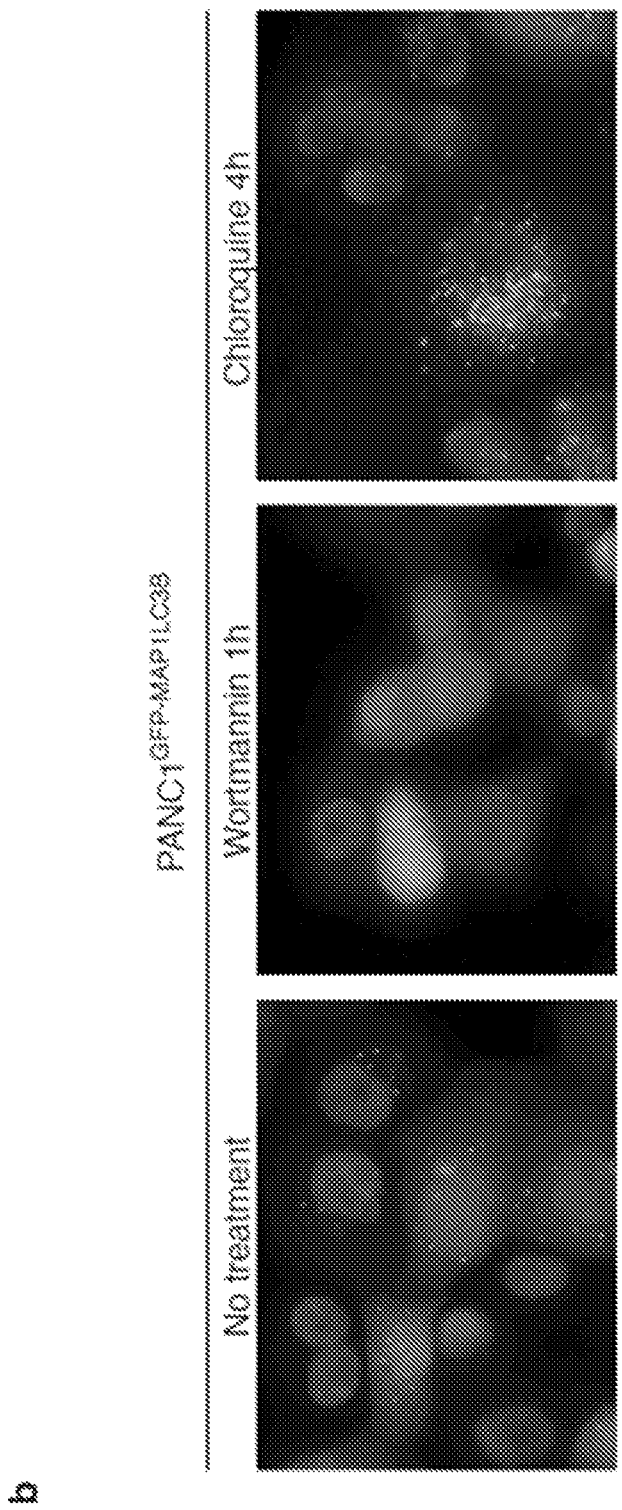
Figure 13:
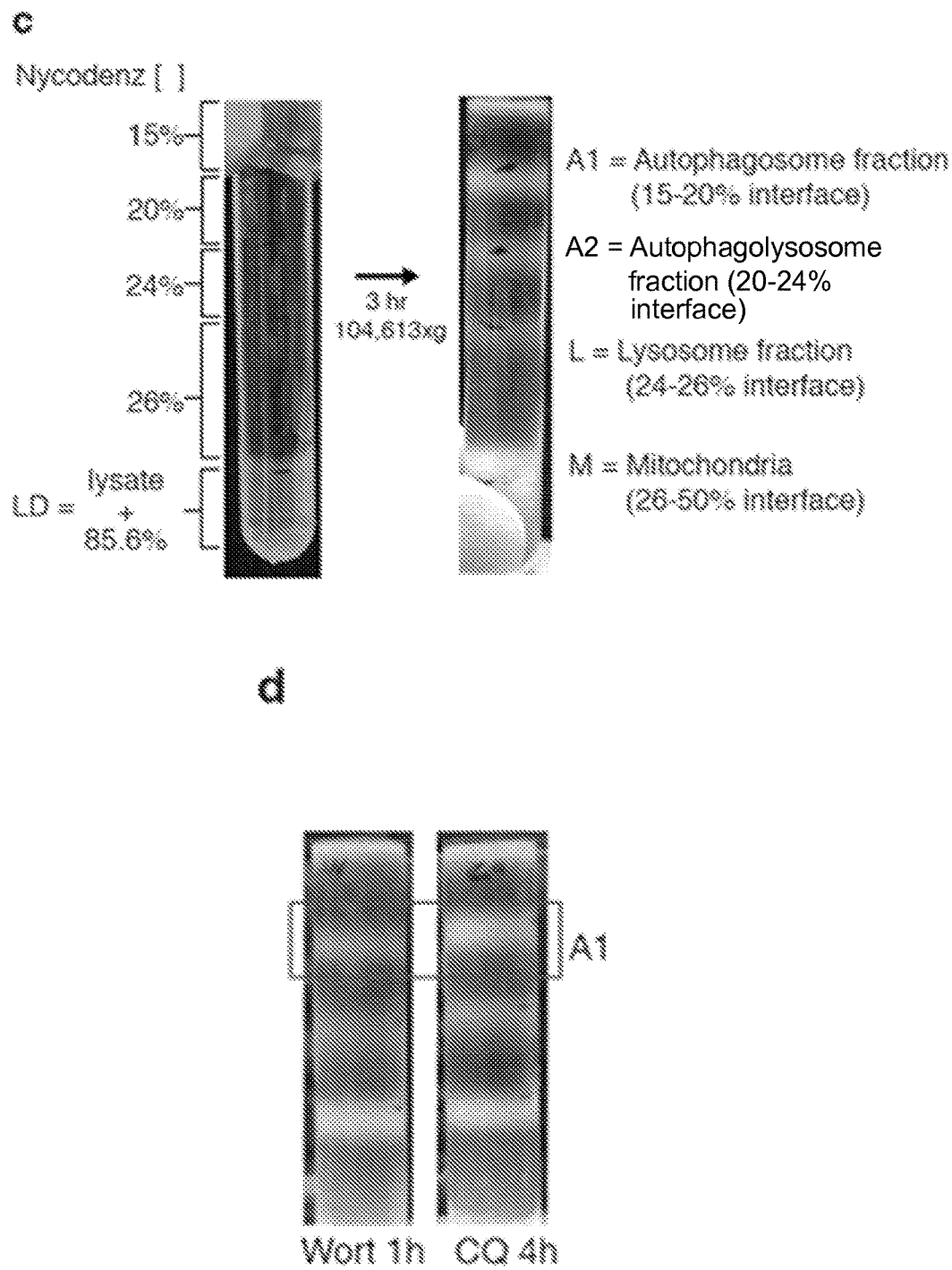
Figure 13:
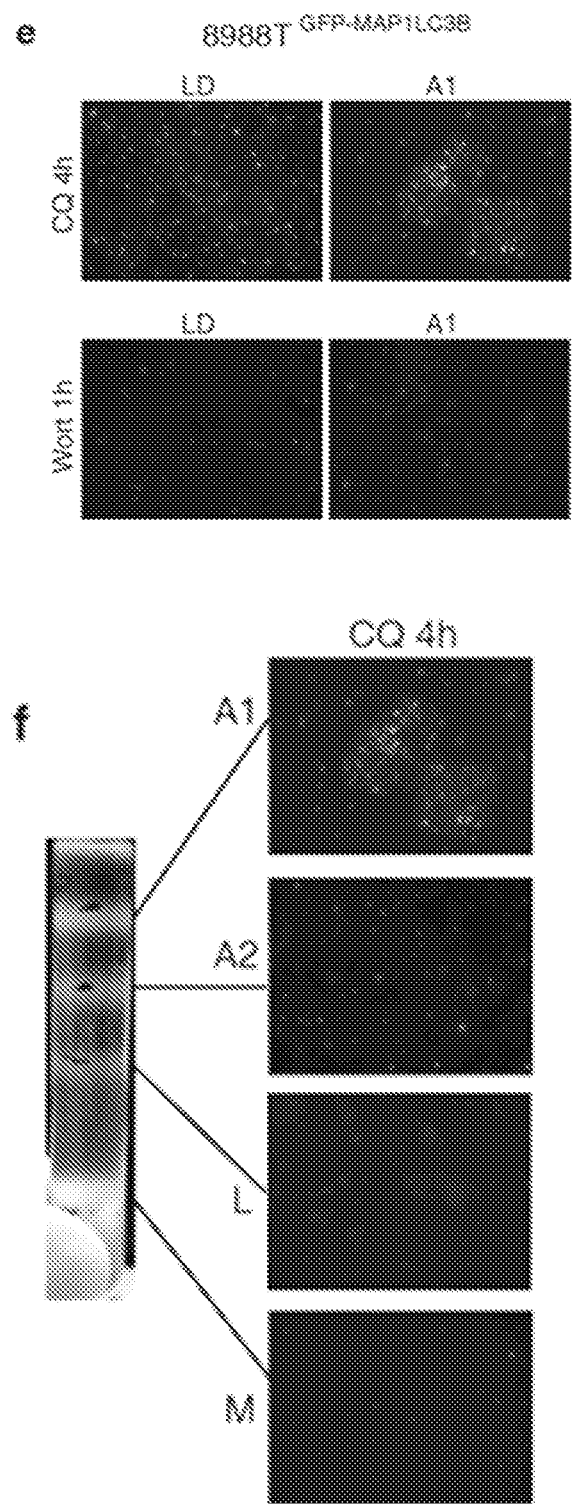
Figure 13:
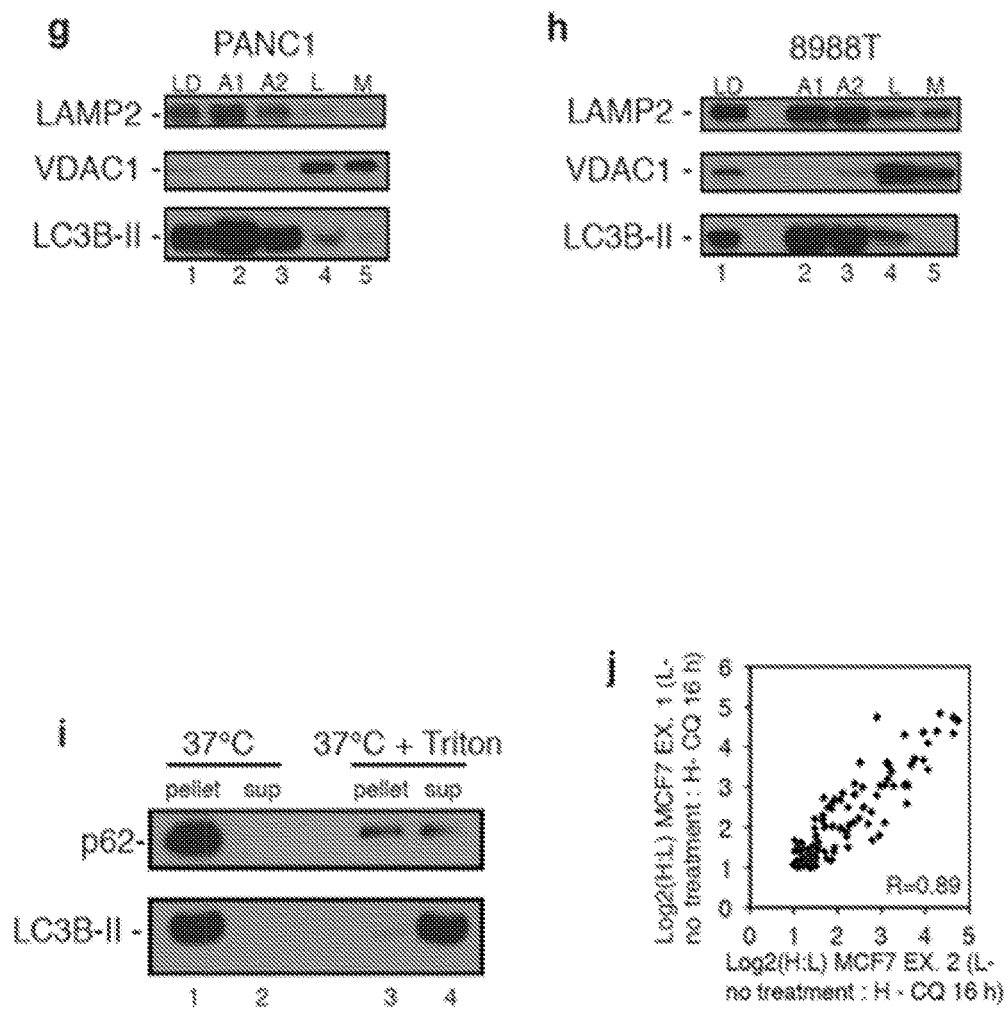
Figure 13:
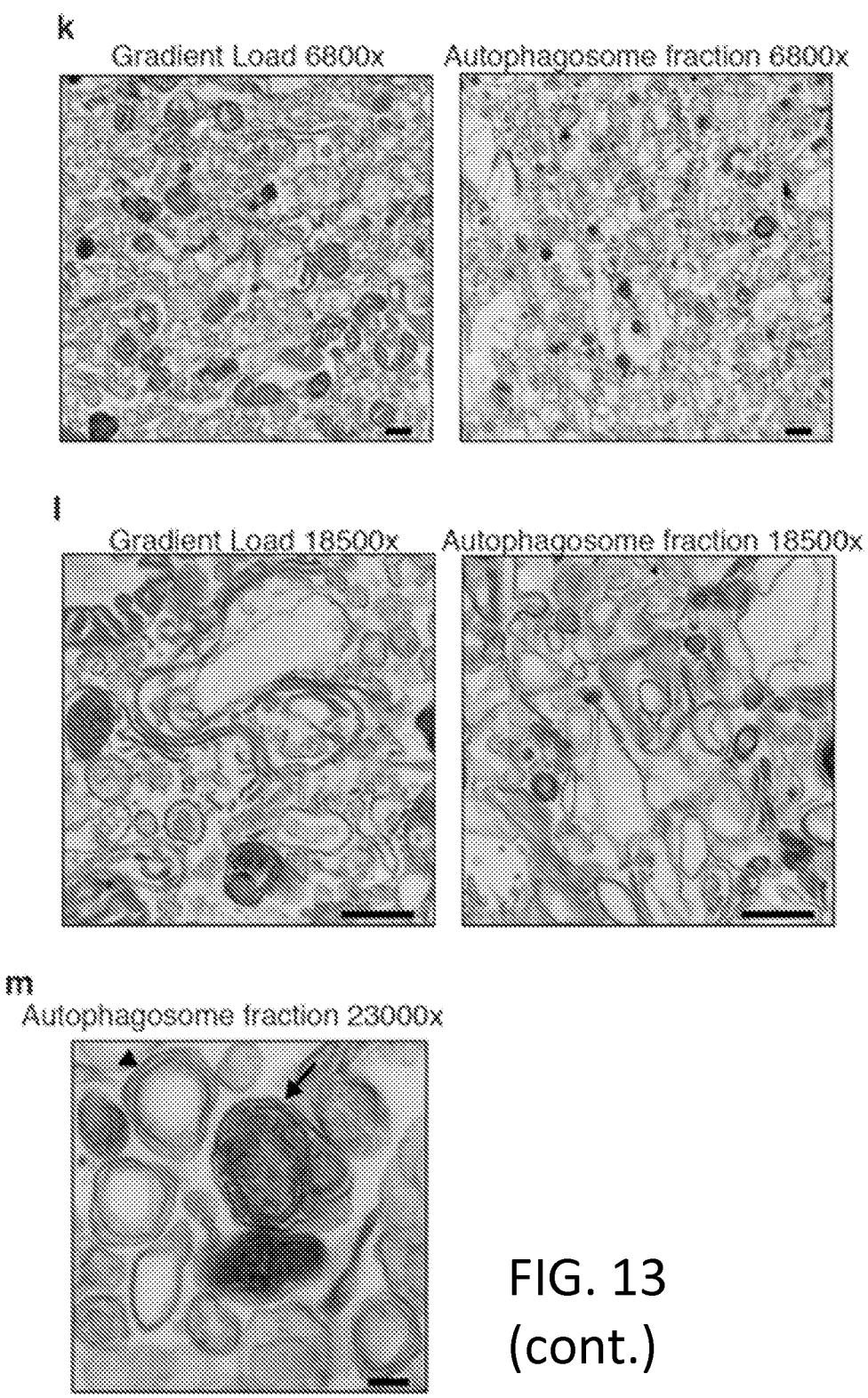

As expected, the autophagosome-enriched fraction was enriched for the ATG8 protein MAP1LC3B (LC3B) as assayed by immunoblotting (FIG. 13(e), (g), (h)) or immunofluorescence (FIGS. 13 (e), (f)), and contained characteristic double-membrane vesicles by electron microscopy (FIGS. 13(k)-(m)). To determine if the autophagosomes were intact, LC3B and p62/SQSTM1 release upon detergent treatment was tested. 8988T autophagosomes (A1 fraction) were incubated at 37° C. for 1 hour–/+Triton X-100 and centrifuged at high speed. The resulting pellet was resuspended in equal volume to supernatant and assayed by immunoblotting with antibodies to p62 and LC3B. The autophagosomes were determined to be intact (FIG. 13(i)). Autophagosomes and autophagolysosomes are heterogeneous in nature, as they form via a dynamic interplay between other membrane-rich organelles, each containing their own specific complement of proteins.

Single-label (heavy Lys) profiling of the autophagosomal fraction from PANC1 after 4 or 16 h of CQ treatment, as well as double-label (heavy Lys and Arg) profiling of PANC1 and MCF7 derived autophagosomal preparations at 16 hours of CQ treatment resulted in the quantification of >2000 proteins. Proteins were selected based on significantly increased log 2 (heavy:light) ratios and the presence of 2 or more peptides, and subsequently filtered against the relative abundance of the proteome measured independently by LC-MS (FIG. 1b), thereby removing abundant proteins that may be non-specifically captured by bulk autophagy. 86 proteins with log 2(H:L)>1.5 were identified in all 3 PANC1 replicates (Pearson correlation of 0.92 for a representative pair), and 102 proteins with log 2(H:L)>1.0 in both MCF7 replicates (Pearson correlation of 0.89) (FIG. 1(c), (d), FIG. 13(j)). The union of these two high stringency datasets are referred to as Class 1 autophagosome-enriched proteins, and a high priority subset of these proteins based on their presence in ≥3 data sets or known involvement in autophagy as Class 1A (FIG. 1e, FIG. 14(a)). Non-Class 1 proteins with a log 2(H:L)>2.0 in any 2 of the 5 PANC1 or MCF7 experiments (16 h in CQ) were also identified, and this lower stringency dataset is referred to as Class 2 autophagosome-enriched proteins. As expected, PANC1 cells treated with CQ for 16 h showed a greater accumulation of candidate proteins than PANC1 or 8988T cells treated for 4 h (FIG. 1(e), FIG. 14).

Within the Class 1A proteins, 2 ATG8 paralogs (GABARAPL2, LC3B), 4 known autophagy cargo receptors (SQSTM1/p62, CALCOCO2/NDP52, OPTN, NBR1), and 4 proteins that were previously reported to associate with ATG8 family members and/or cargo receptors, or to be involved in autophagosomal membrane fusion (KEAP1, TMEM59, FYCO1, STX17) were identified (FIG. 1(e), FIG. 14(a)). Moreover, 2 proteins reported as selective autophagy cargo (APP, NRP1), and 7 proteins identified as high-confidence interacting proteins in the previously published Autophagy Interaction Network [Behrends, C., et al. *Nature;* 466, 68-76, (2010)] were identified (FIG. 1(e), FIG. 14(a)).

Figure 15:
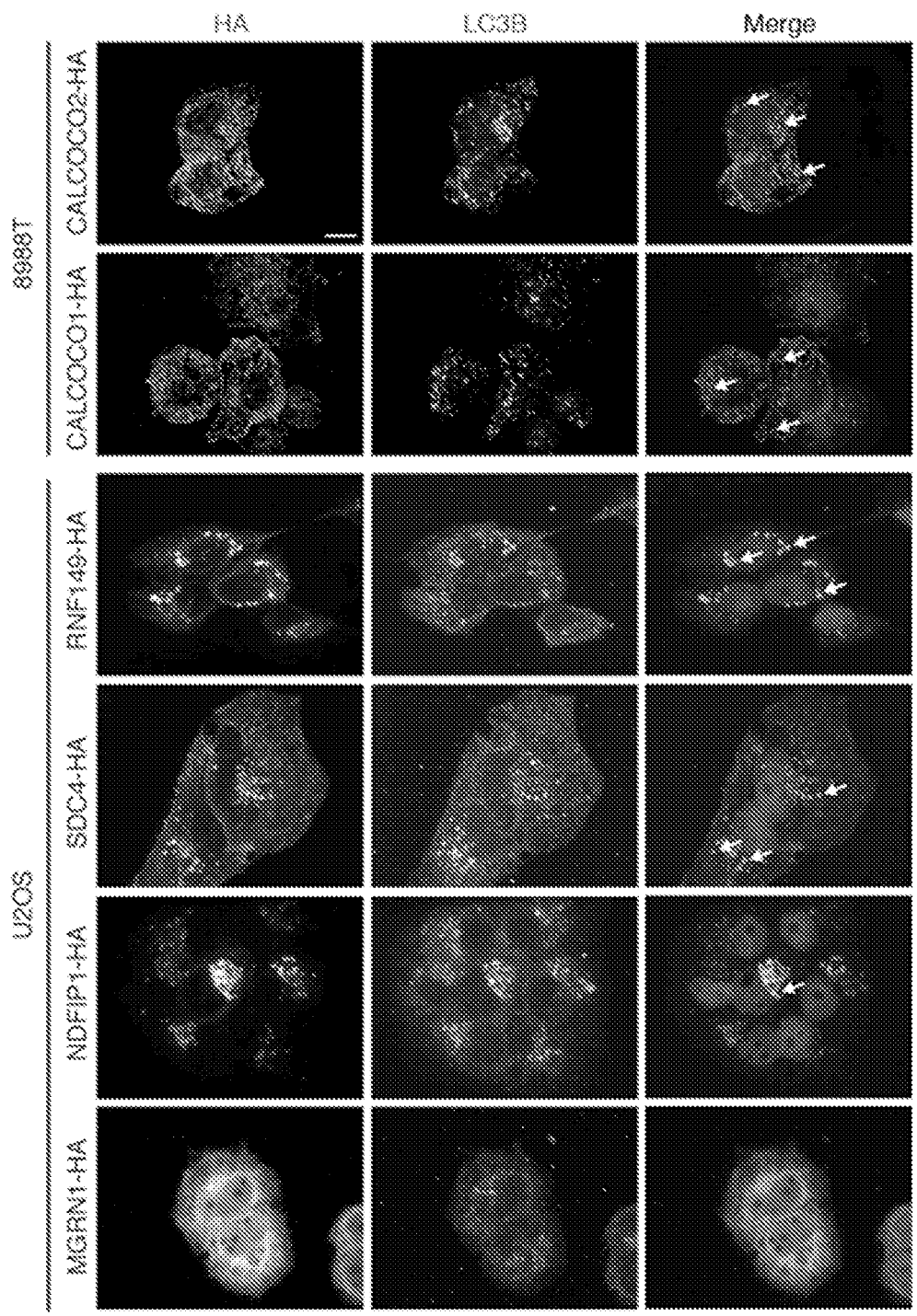
FIG. 15 contains representative confocal images of candidates from autophagosome proteomics, prepared to determine which candidates colocalize in autophagosomes after chloroquine (CQ) treatment in 8988T and U2OS cells expressing HA-tagged candidates. Autophagosomes were identified by immunostaining of endogenous LC3B. Representative colocalization is marked by white arrows. Scale bar, 10 μm. MGRN1 is included as an example of one of the candidates that did not show colocalization.
Figure 16:
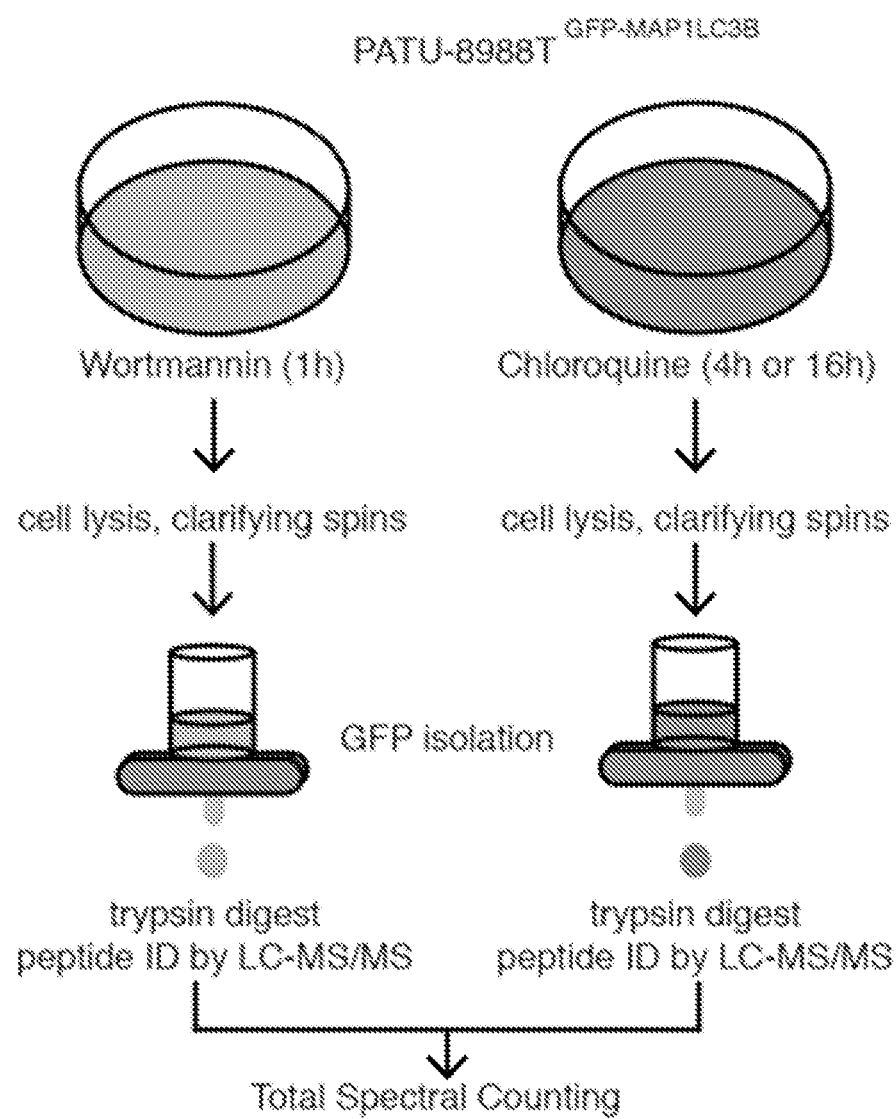
FIG. 16(a) is a schematic diagram illustrating GFP-immunoisolation of GFP-LC3B labeled autophagosomes from 8988T cells, and FIG. 16(b) contains a table of the data from GFP-immunoisolation for Class 1A candidates, with enriched proteins, "not enriched" proteins, and "not identified" proteins identified in each group. Log 2(CQ_peptide#:WORT_peptide#) represents the log$_2$ ratios of peptide numbers of proteins identified in autophagosomes purified from chloroquine versus wortmannin-treated cells and Log 2(CQ_ peptide#:WCL_peptide#) represents the log$_2$ ratios of peptide numbers of proteins identified in autophagosomes purified from chloroquine-treated cells versus peptide numbers from a whole-cell lysate sample. Zero value denominators were systematically replaced with a value of 0.5 to generate a log$_2$ ratio. Candidates were qualified as enriched if both log$_2$ ratios were greater than 0.5.
Figure 16:
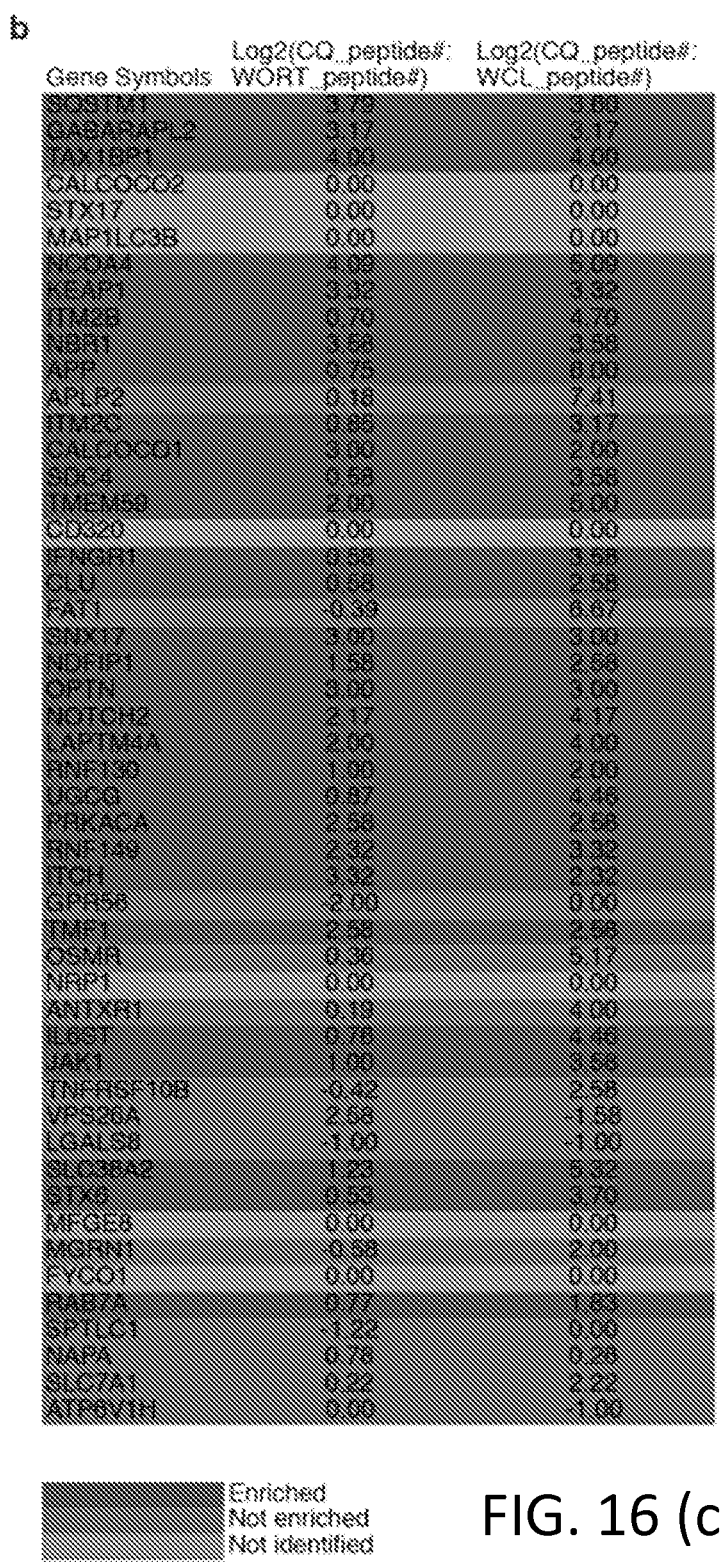

Furthermore, the autophagy pathway proteins RB1CC1, ATG9A, TBC1D15, and the OPTN-binding protein TBK1 were identified in the Class 2 dataset. The presence of several plasma membrane and endocytosis-related proteins (FIG. 1(e), FIG. 14(a)) is consistent with intermixing of these membrane sources during autophagosome maturation or lysosomal fusion. Co-localization with LC3B-positive puncta was observed for 7 of 11 Class 1A proteins tested (FIG. 14(a), FIG. 15).

As further validation, 8988T pancreatic cancer cells were subjected to both SILAC-based autophagosomal profiling using density gradient purification and a semi-quantitative proteomic approach using an immunopurification-based autophagosome enrichment scheme by immunoprecipitation of tagged GFP-LC3B (FIG. 14(b)-(d) and FIG. 16). In total, 40 proteins were identified in common between the 50 Class 1A autophagosomal proteins and those identified as enriched in autophagosomes purified from 8988T cells. Comparative analysis of the MCF7 candidate proteins with a previously reported autophagosomal quantitative proteomics analysis [Marzella et al., supra] that used the same cell line revealed 2 overlapping proteins from their final combined data set (SQSTM1 and GABARAPL2) (FIG. 17).

Expanding the analysis to also include the PANC1 datasets only increased the overlap to a total of 4 proteins from the Class 1 and 2 lists. This low rate of overlap appears to reflect the fact that a large fraction of proteins previously reported to reside in autophagosomes would have been removed upon filtering at high stringency for abundance in the total proteome (see Methods (Example 1), FIG. 17), indicating that these likely are present in autophagosomes due to non-selective bulk degradation of cytosolic contents, or are co-purifying contaminants. Likewise there was minimal overlap between the Class 1 and 2 proteins described here with two additional proteomics efforts [Overbye, A., et al., supra; Gao, W., et al., supra]. While it is understandable that there would be variation between datasets depending on cell type, autophagy stimulus, and purification technique, the present dataset represents the most robust autophagosome proteomics effort to date given the number of bona fide autophagy related proteins identified among the Class 1 and 2 candidates.

Among the most highly and consistently enriched autophagosomal proteins was NCOA4 (nuclear receptor coactivator 4) (FIG. 1(e)), which was also enriched in an independent autophagosome proteomics study, although not included in their final list of autophagosomal proteins due to the method of analysis [Dengjel et al., supra] (see, FIG. 17 and Example 1). NCOA4 was originally identified as a protein that interacts with the androgen receptor (AR), and its overexpression was reported to activate transcription of AR-regulated genes [Yeh, S. & Chang, C. *Proceedings of the National Academy of Sciences of the United States of America* 93, 5517-5521 (1996)]. However, not all studies have supported a role for NCOA4 in AR function [Gao, T., et al. *Molecular Endocrinology* 13, 1645-1656 (1999)], and the data described below reveals a previously unrecognized role for NCOA4 as an autophagy cargo receptor.

Figure 18:
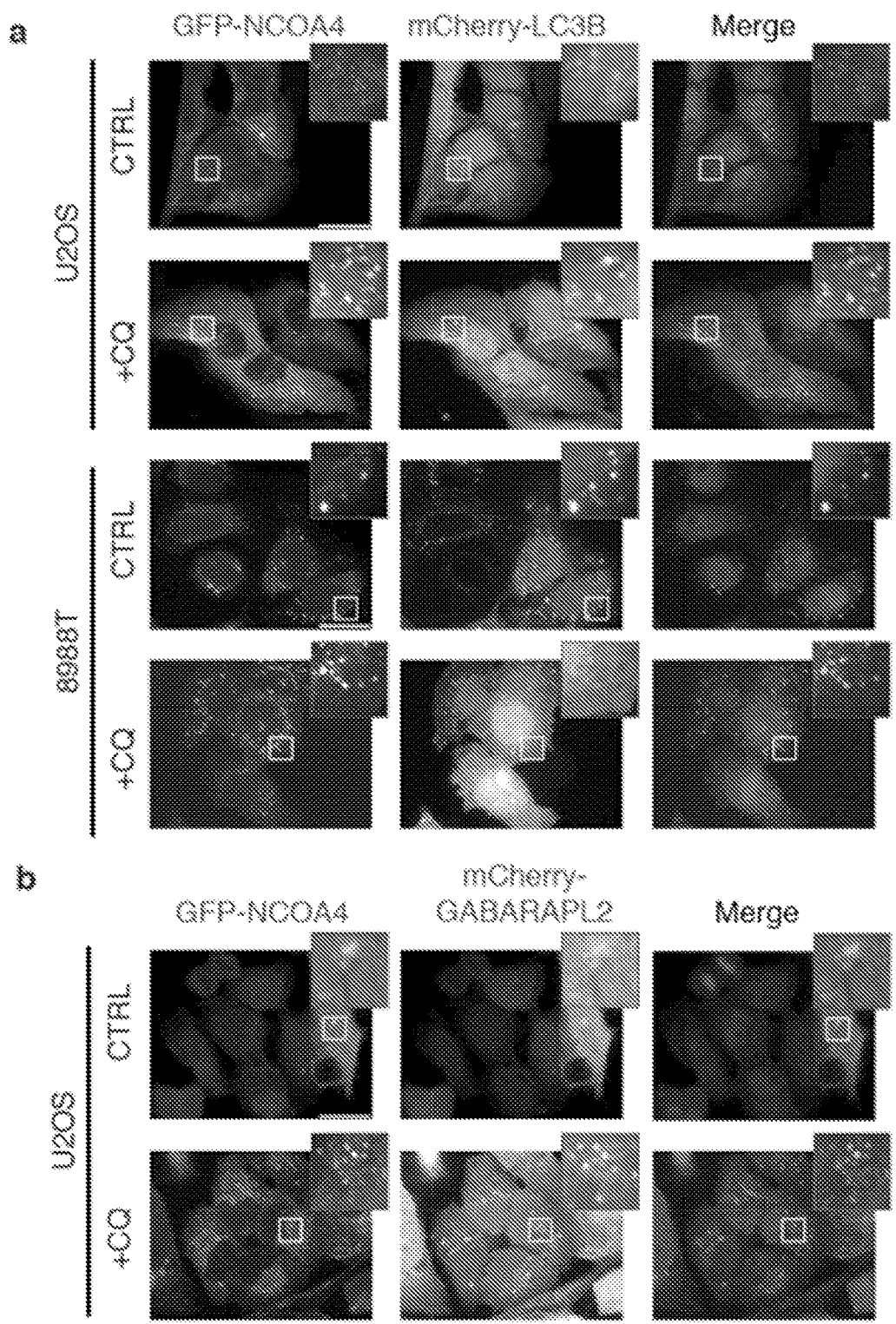
FIG. 18(a) contains fluorescent images of U2OS and 898T cells, untreated ("CTRL"), or treated with chloroquine (+CQ). GFP-NCOA4 co-localizes with mCherry-LC3B in CQ-treated cells. Scale bar, 20 μm.
FIG. 18(b) contains fluorescent images of U2OS cells, untreated, or treated with chloroquine (+CQ). GFP-NCOA4 co-localizes with mCherry-GABARAPL2 in CQ-treated cells. Scale bar, 20 μm.
FIG. 18(c) contains fluorescent images of U2OS and 898T cells, untreated ("CTRL"), or treated with chloroquine (+CQ). GFP-NCOA4 co-localizes with endogenous GABARAPL2 in CQ-treated cells. Scale bar, 20 μm.
FIG. 18(d) contains fluorescent images of 898T cells treated with chloroquine (+CQ). GFP-NCOA4 does not colocalize with endogenous Mannose 6-Phosphate Receptor (M6PR) in CQ-treated cells. Scale bar, 20 μm.
FIG. 18(e) contains fluorescent images of U2OS, untreated ("CTRL"), or treated with choloroquine (+CQ). HERC2 does not co-localize in autophagosomes. Immunostaining of U2OS cells subjected to CQ treatment, endogenous LC3B and endogenous HERC2, scale bar, 20 μm.
Figure 18:
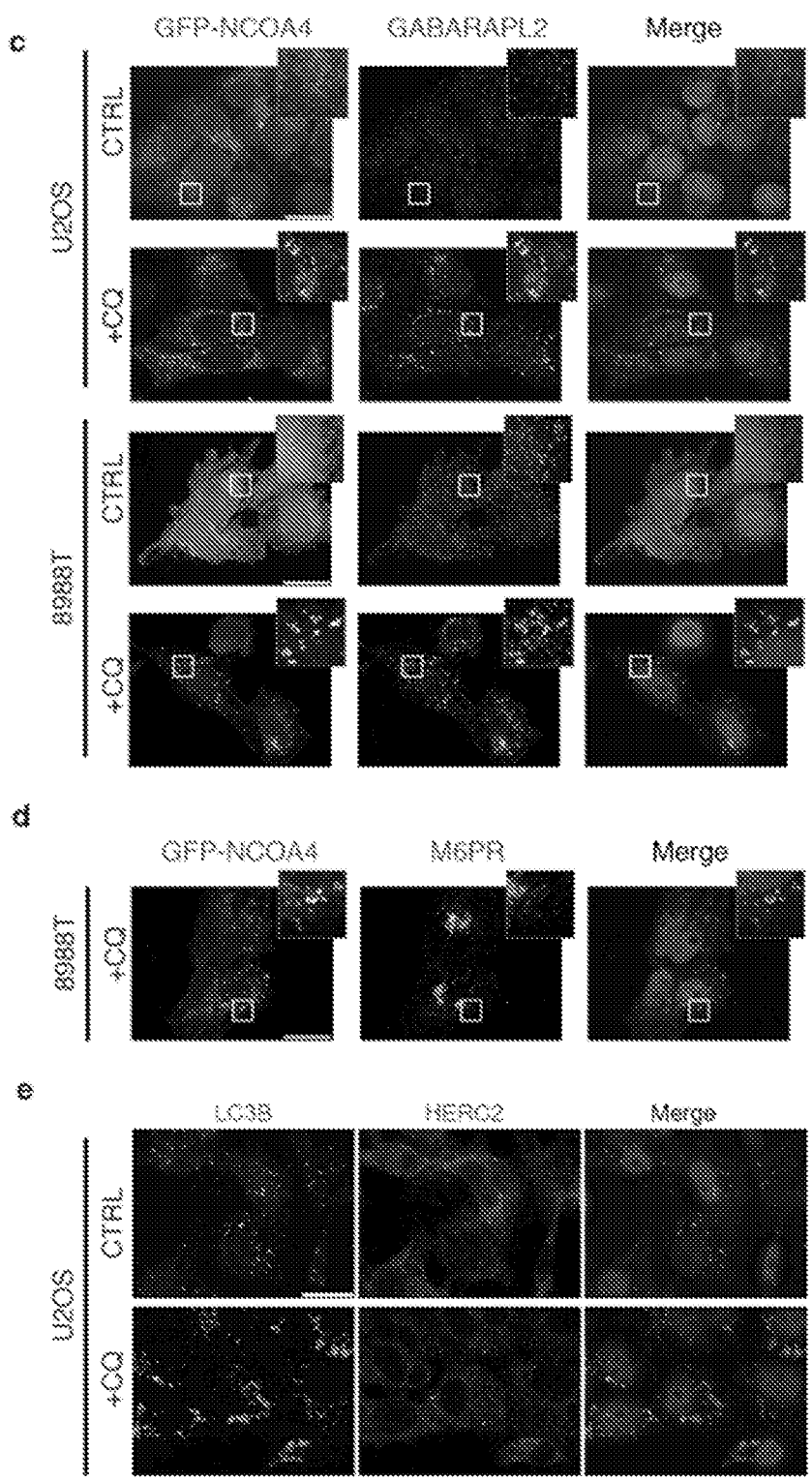

Initially, the localization of NCOA4 was examined. GFP-NCOA4 was diffusely localized in the cytoplasm in U2OS cells that have a low level of basal autophagy but accumulated in cytoplasmic puncta that are largely co-incident with LC3B-positive puncta in response to CQ in U2OS cells as well as 8988T cells, consistent with localization of GFP-NCOA4 in autophagosomes (FIG. 2(a), FIG. 18(a)). In addition, NCOA4 showed significant co-localization with GABARAPL2-positive puncta (FIG. 18(b)-(c)), which is consistent with it being amongst the strongest interactors in a GST-ATG8 binding assays performed in vitro using cell extracts (FIG. 2(b)). Consistent with the proteomic data, NCOA4 was enriched in purified autophagosomes by immunoblotting, and its levels were markedly increased in response to blockade of autophagosome degradation by CQ or Bafilomycin A1 (BAF) (FIGS. 2(c)-(d)). Moreover, NCOA4 did not co-localize with the late endosome marker Mannose 6-Phosphate Receptor (FIG. 18(d)). Together this data supports the predominantly autophagosomal localization of NCOA4 puncta. A canonical LIR (LC3-interacting region) motif was not identified in NCOA4, although the existence of non-canonical ATG8 binding motifs [von Muhlinen, N. et al. *Molecular Cell* 48, 329-342 (2012)] may suggest that NCOA4 employs such an alternative motif for interaction.

To begin to understand potential roles for NCOA4 in autophagy, affinity purification-mass spectrometry (AP-MS) of stably expressed NCOA4-HA-FLAG was performed, and the Comparative Proteomics Software Analysis Suite (CompPASS) was used to identify high confidence candidate interacting proteins (HCIPs). AP-MS of NCOA4-HA-FLAG from PANC1, 8988T, and 293T cells revealed a number of HCIPs including both the ferritin heavy chain (FTH1) and ferritin light chain (FTL), as well as HERC2 and NEURL4, which are known to associate with each other (FIG. 2(e)) [Martinez-Noel, G. et al. *Molecular and Cellular Biology* 32, 3095-3106 (2012)]. Interaction of NCOA4-HA-FLAG with selected endogenous HCIPs was verified by anti-FLAG immunoprecipitation followed by immunoblotting (FIG. 2f). FTH1-HA-FLAG reciprocally associated with endogenous NCOA4 as determined by AP-MS (FIG. 2(e)) and also associated with co-expressed MYC-NCOA4 (FIG. 2(g)). The absence of HERC2-NEURL4 in ferritin immune complexes suggested that NCOA4 makes distinct complexes with ferritin and HERC2-NEURL4. Consistent with this, neither HERC2 nor NEURL4 were enriched in autophagosomal fractions and HERC2 does not colocalize with autophagosomes (FIG. 18(e)).

FTH1 and FTL form a 24-subunit macromolecular iron-storage complex critical for iron homeostasis [Pantopoulos, K., et al., supra]. Early electron microscopy studies identified iron-laden ferritin in lysosomes and more recently, it was shown that in cells subjected to iron chelation, ferritin is delivered to the lysosome for degradation via autophagy, presumably to promote iron availability [Asano, T. et al. supra; Kidane, T. Z., et al. *American Journal of Physiology. Cell Physiology* 291, (2006); Trump, B. F., et al. *The American Journal of Pathology* 72, 295-336 (1973)]. Interestingly, FTH1 and FTL were enriched in autophagosomal fractions from MCF7 and 8988T cells based on mass spectrometry (FIG. 2(e), FIG. 14). Furthermore, ferritin and NCOA4 demonstrated extensive co-localization in puncta in several cell lines upon stimulation of ferritin expression with ferric ammonium citrate (FAC), reflecting the high level of ferritin undergoing autophagic targeting and lysosomal degradation (FIG. 2(h)). This process is referred to as "ferritinophagy."

Figure 19:
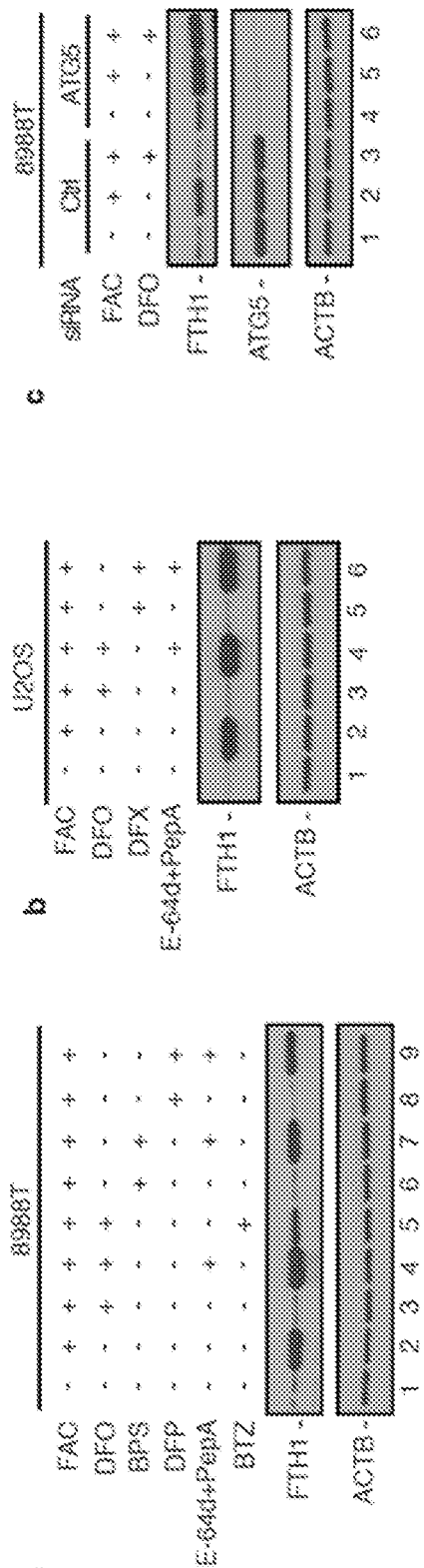
FIG. 19(a) contains photographs of immunoblots of lysates from 8988T cells cultured with FAC for 24 hours, washed, followed by chelation with the indicated combinations of chelators (DFO, BPS, DFP)−/+lysosomal protease inhibitors (E-64d and PepstatinA) or proteasomal inhibitor, Bortezomib (BTZ), (lane 5) for 8 hours. Blots were probed with antibodies to ACTB or FTH1.
FIG. 19(b) contains photographs of immunoblots of lysates from U2OS cells cultured with FAC for 24 hours, washed, followed by chelation with 2 chelators (DFO, DFX)−/+lysosomal protease inhibitors (E-64d and PepstatinA (E-64d+PepA)). Blots were probed with antibodies to ACTB or FTH1.
FIG. 19(c) contains photographs of immunoblots of lysates from 8988T cells transfected with luciferase control siRNA or validated siRNA to ATG5. The cells were cultured with FAC, washed, and subjected to DFO chelation for 9 hours. Lysates were immunoblotted using antibodies to FTH1, ATG5, and ACTB.
FIG. 19(d) contains photographs of immunoblots of lysates from 8988T cells following RNAi-mediated knockdown of NCOA4. 8988T cells stably expressing a control shRNA (shGFP) and two independent shRNAs to NCOA4 (shNCOA4-1 and shNCOA4-2) were lysed and analyzed by immunoblotting with two different antibodies to NCOA4 and ACTB as a loading control. Middle panel shows immunoblot probed with NCOA4 antibody from Bethyl Laboratories (#A302-272A). A non-specific band migrates just below the NCOA4 specific band. Top panel shows immunoblot probed with NCOA4 antibody from Sigma (SAB1404569).
FIG. 19(e) contains photographs of immunoblot results for lysates from U2OS cells stably expressing shGFP, shNCOA4-1, or shNCOA4-2. Lysates were analyzed by immunoblotting with two different antibodies to NCOA4 and ACTB as a loading control. Middle panel shows immunoblot probed with NCOA4 antibody from Bethyl Laboratories (#A302-272A).
FIG. 19(f), left panel, contains photographs of immunoblot results for lysates of U2OS cells following NCOA4 depletion and iron chelation. The right panel is a bar graph quantifying the relative FTH1 levels (n=3) for each indicated chelator. Bars and error bars represent mean values and s.d., respectively: ** ($p<0.01$) and * ($p<0.02$) comparing FTH1 levels between different cell lines to shGFP control (one-sided t-test).
FIG. 19(g) contains photographs of immunoblot results of lysates of U2OS cells stably expressing shGFP, shNCOA4-1, or shNCOA4-2 and cultured with FAC for 24 hours, washed, and subjected to DFO chelation−/+lysosomal protease inhibitors (E-64d and PepstatinA (E-64d+PepA)). Lysates were immunoblotted using antibodies to NCOA4, FTH1, and ACTB.
Figure 19:
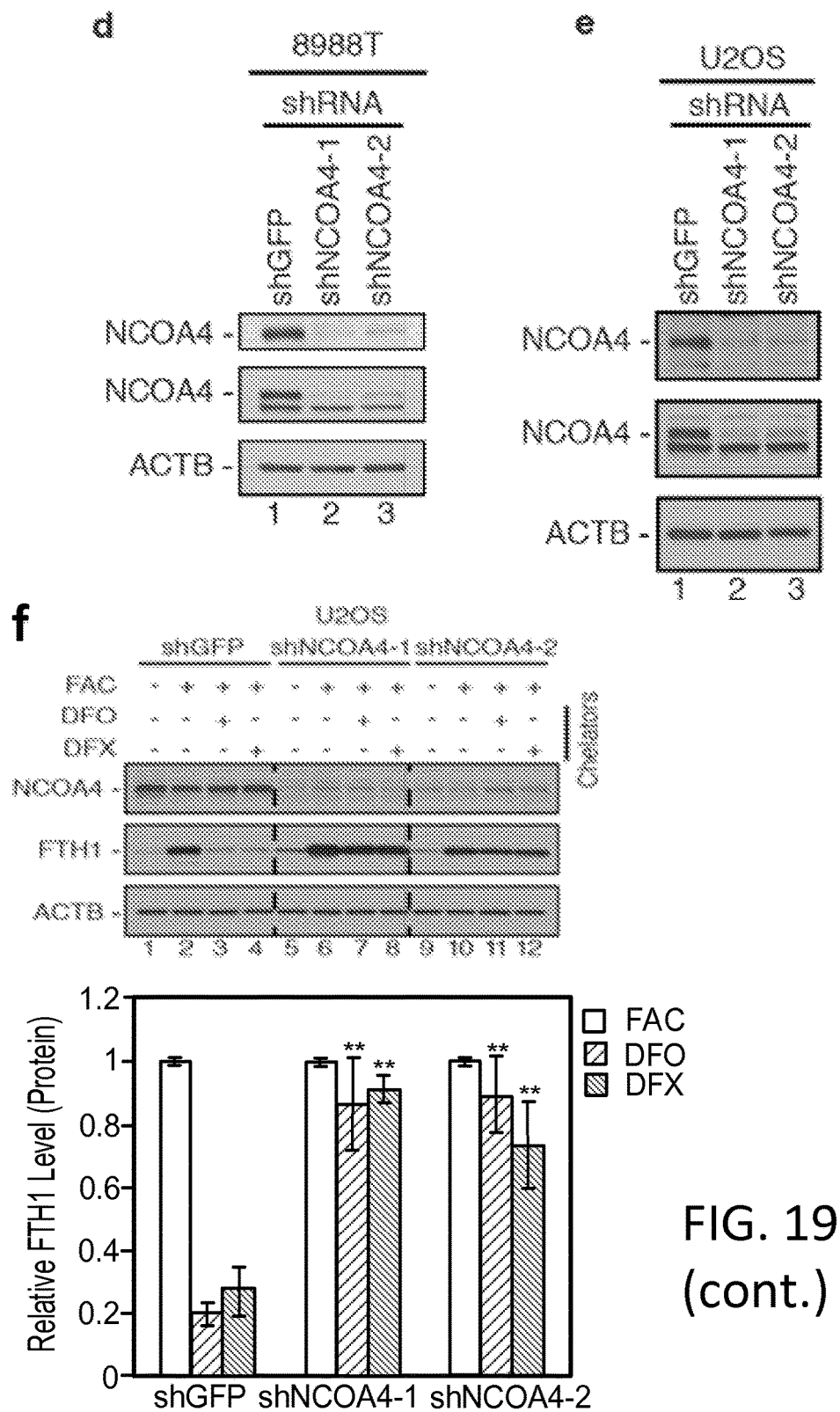
Figure 19:
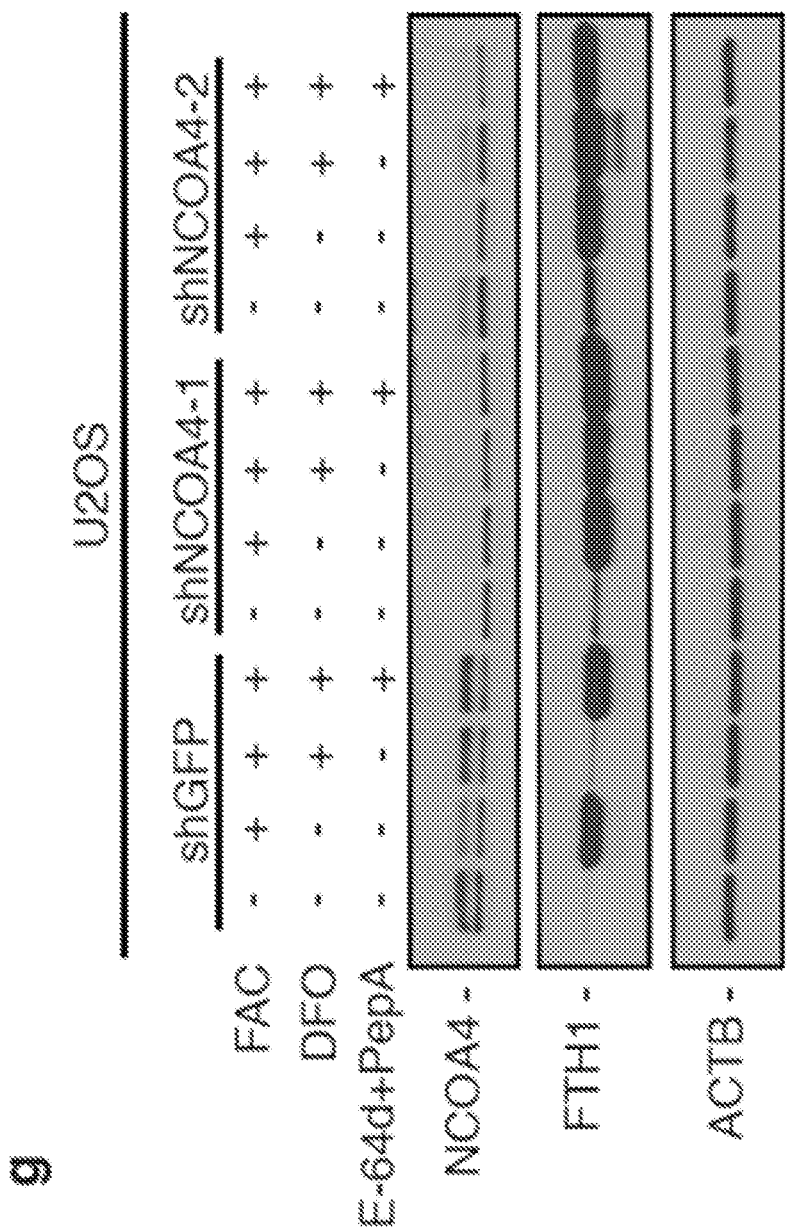
Figure 22:
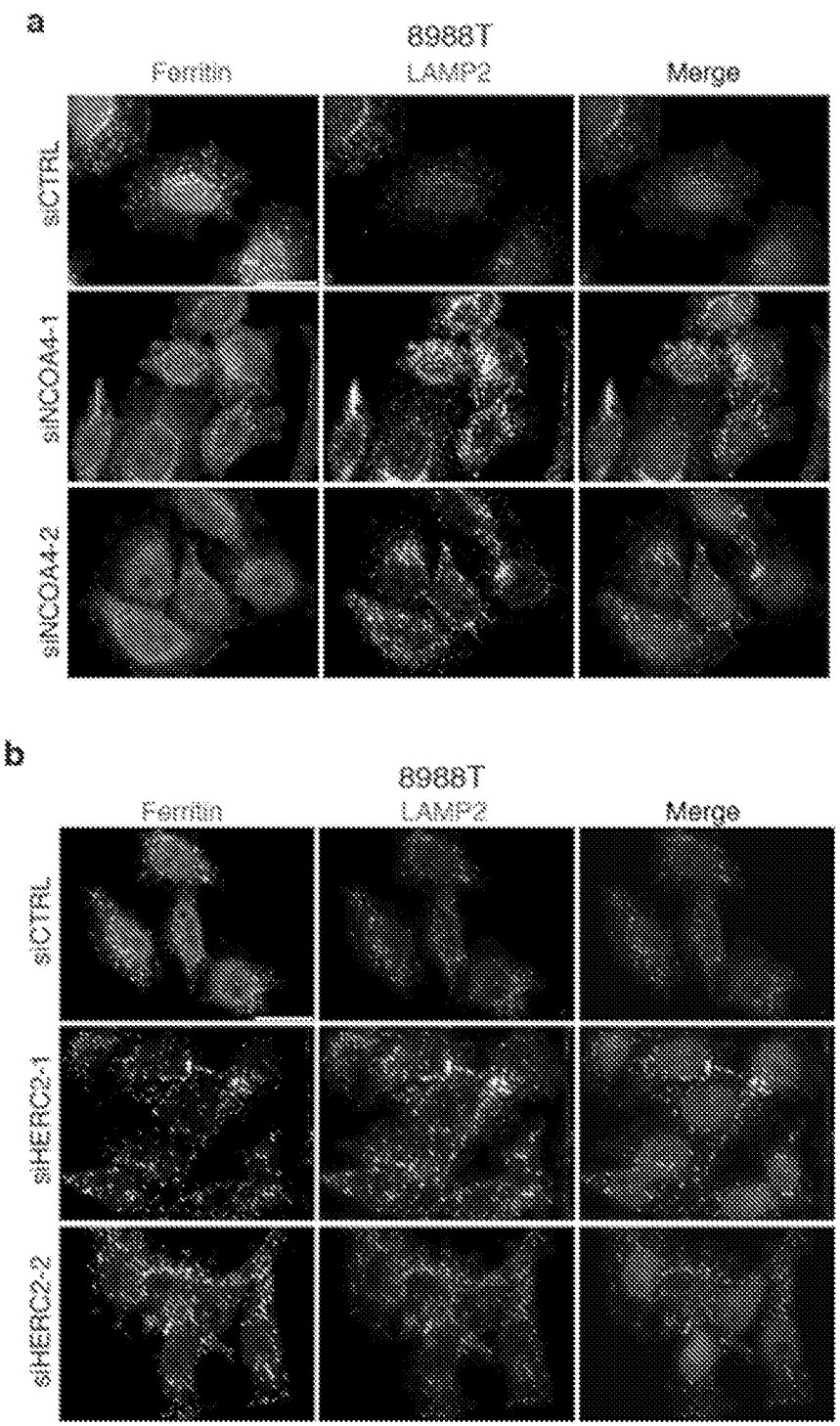
FIG. 22(a) contains fluorescent images of 8988T cells transfected with luciferase control siRNA or two independent siRNAs to NCOA4 and subjected to DFO chelation in the presence of lysosomal protease inhibitors for 9 hours. Scale bar, 20 μm. Cells were immunostained for ferritin and LAMP2.
FIG. 22(b) contains fluorescent images of 8988T cells transfected with luciferase control siRNA or two independent siRNAs to HERC2 and subjected to DFO chelation in the presence of lysosomal protease inhibitors for 9 hours. Scale bar, 20 μm. Cells were immunostained for ferritin and LAMP2.
FIG. 22(c) contains photographs of immunoblot results for lysates of 8988T cells transfected with luciferase control siRNA or two independent siRNAs to HERC2. Lysates were immunoblotted using antibodies to HERC2 and ACTB (loading control).
FIG. 22(d) contains photographs of immunoblot results for lysates of U2OS, IMR90, and 8988T cells. Cells were transfected with luciferase control siRNA or two independent siRNAs to NCOA4. Lysates were immunoblotted using antibodies to NCOA4, IRP2, TFRC, FTH1, and ACTB. Light and dark exposures are shown for TFRC.
FIG. 22(e) contains photographs of immunoblot results for lysates of 8988T cells stably expressing either a control MSCV empty vector or mouse NCOA4 and cultured in the presence of FAC for the indicated times. Cells were lysed and analyzed by immunoblotting with antibodies to NCOA4, FTH1 and ACTB as a loading control. A non-specific band migrates just below the NCOA4 specific band.
Figure 22:
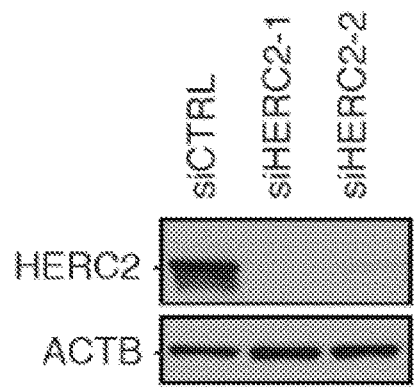
Figure 22:
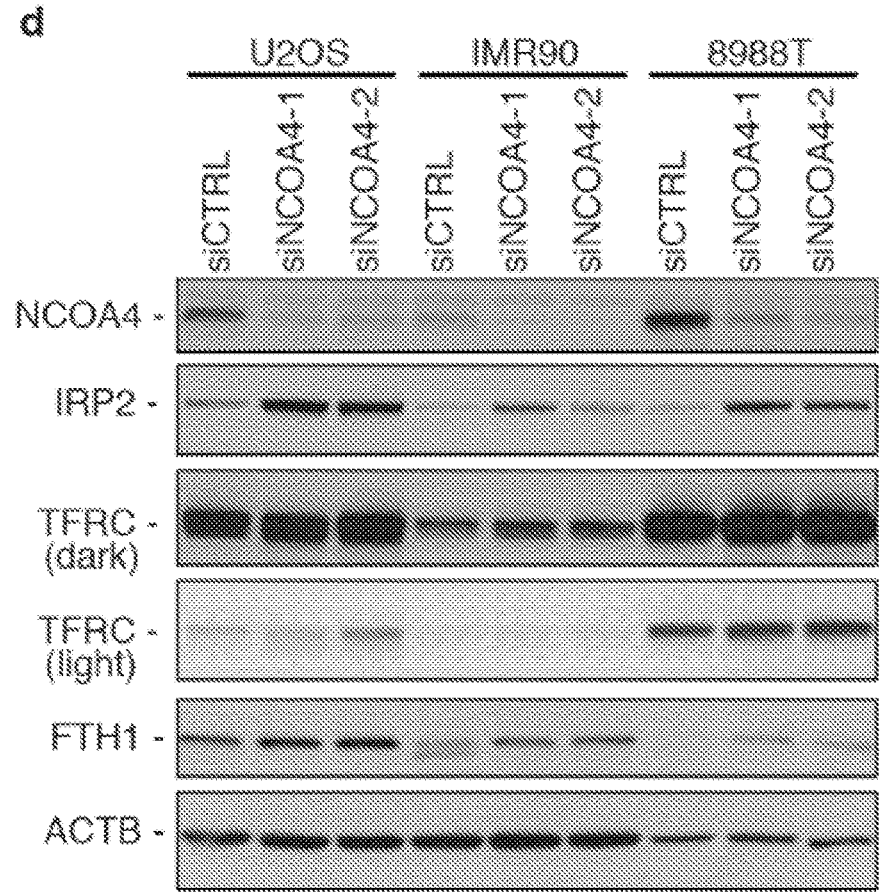
Figure 22:
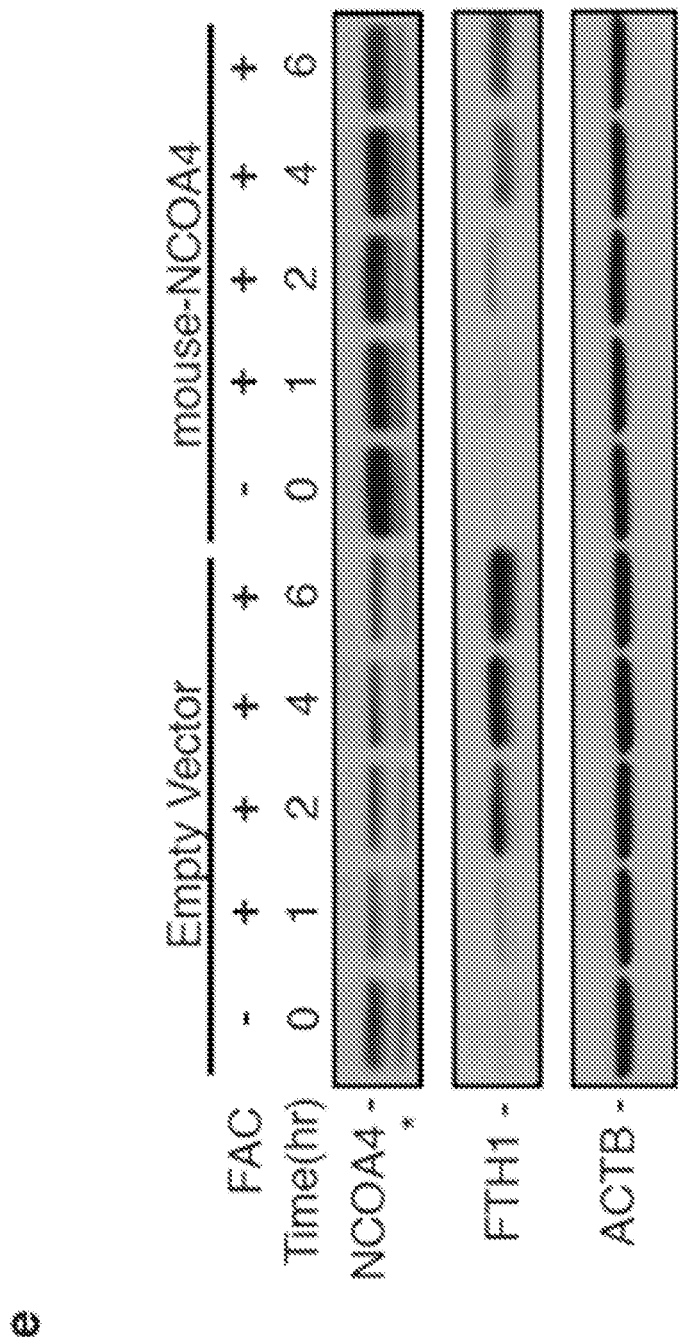
Figure 23A:
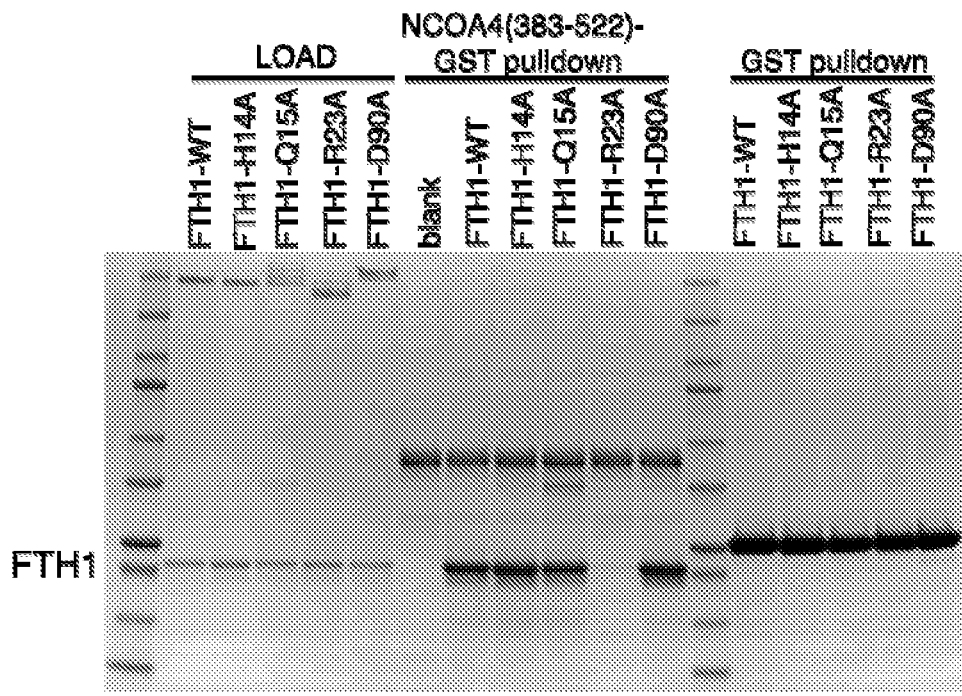
FIGS. 23(A)-(D) are photographs of a SDS-PAGE gel of a GST pull-down assay of wild type (WT) FTH1 and point mutants of FTH1 using NCOA4 (amino acids 383-522)-GST protein. Point mutants of FTH1 tested were H14A, Q15A, R23A, D90A (FIG. 23A); C91A, D92A, D93A, E95A (FIG. 23B); E102A, H106A, N110A, K120A (FIG. 23 C): and T123A, D124A, N126A, and R157A (FIG. 23D). NCOA4-GST and FTH1 bands were stained with Instant-Blue Stain (Expedeon).
Figure 23B:
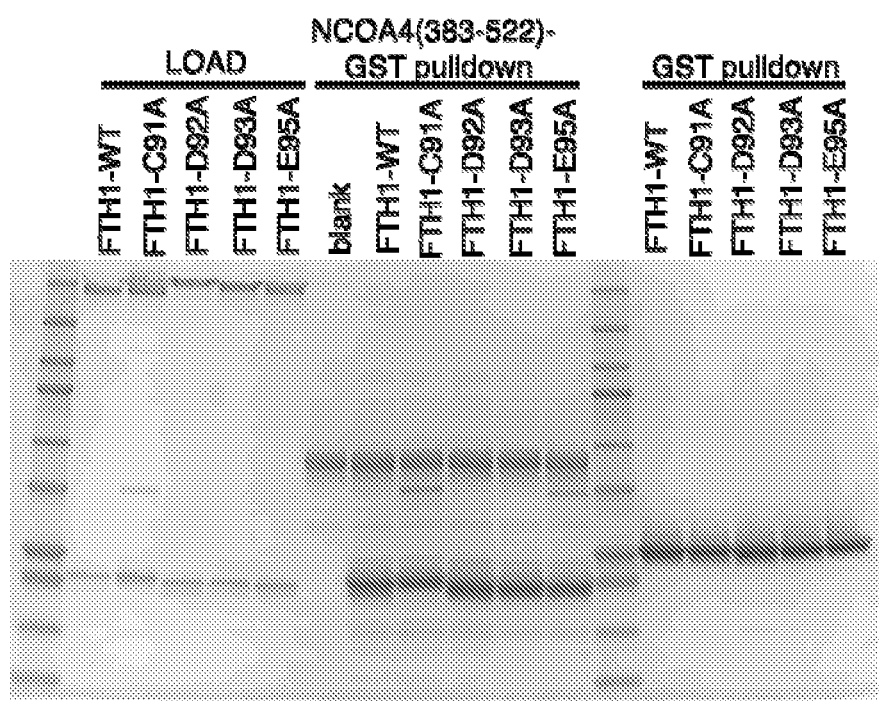
Figure 23C:
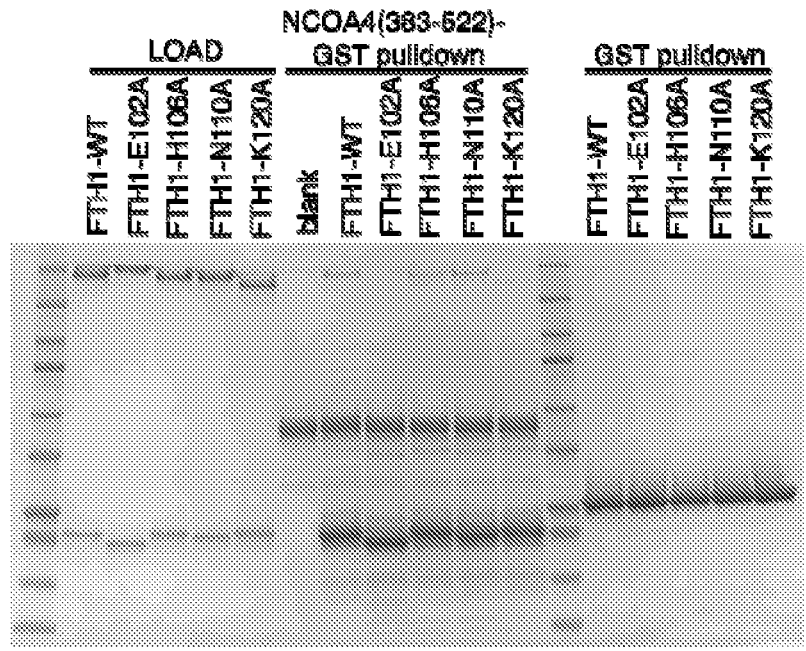
Figure 23D:
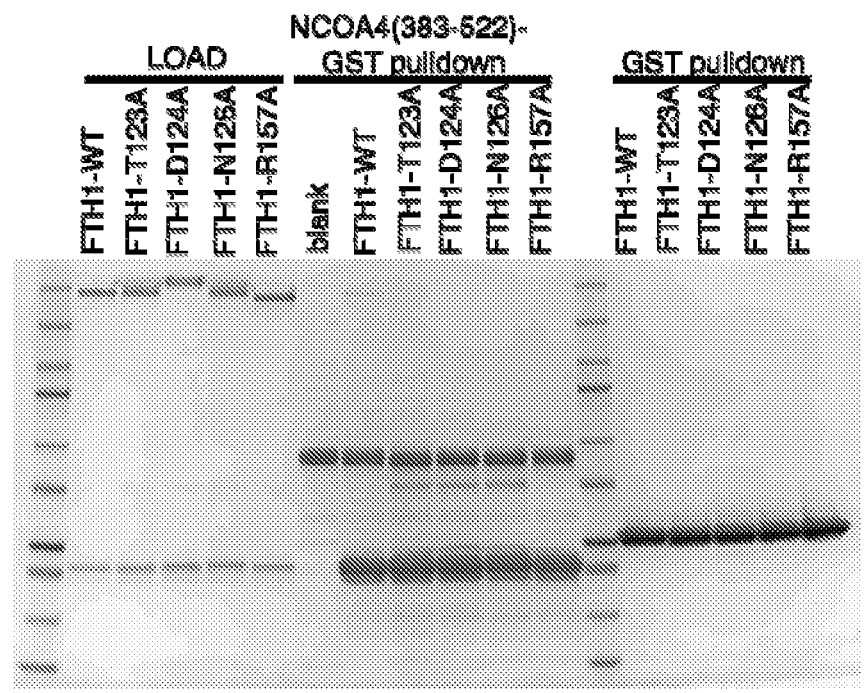

Given the interaction between NCOA4 and ferritin, and their localization in autophagosomes, the hypothesis that NCOA4 acts as an autophagy receptor for ferritinophagy was tested. In response to low intracellular iron levels, ferritin is degraded to release its iron stores. This can be stimulated experimentally by chelation of iron [Asano, T. et al., supra]. While some reports have suggested that ferritin is degraded via the proteasome [De Domenico, I., et al. *The EMBO Journal* 25, 5396-5404, (2006)], it was validated that in the cell lines examined in the studies described herein, ferritin is primarily degraded by the lysosome in response to multiple distinct chelators (FIG. 19(a)-(b)), as observed previously (Asano et al., supra). In addition, genetic inhibition of autophagy using RNAi against ATG5 reduced ferritin degradation in response to iron chelation (FIG. 19(c)). Importantly, suppression of NCOA4 expression with multiple shRNAs followed by iron chelation abrogated ferritin degradation in multiple cell lines and with chemically distinct chelators (FIG. 3a-b, FIG. 19(d)-(g)). Consistent with the above results, ferritin localized to lysosomes and accumulated to a significant degree upon lysosomal protease inhibition (FIG. 20(a)-(b)). Furthermore, ferritin simultaneously colocalizes with NCOA4 and LC3B positive puncta representing autophagosomes (FIG. 3(c)). If NCOA4 functions as an essential receptor for ferritinophagy, depletion of NCOA4 would be predicted to block ferritin localization with lysosomes. Indeed, depletion of NCOA4 blocked ferritin co-localization with lysosomes and led to a diffuse localization pattern (FIG. 3(d), FIG. 20(c)). NCOA4 is also critical in mediating the targeting of ferritin to autophagosomes in non-transformed IMR90 and HPDE cells, indicating that this is a general cellular mechanism for the degradation of ferritin by autophagy (FIG. 20(d)-(e)). As a control for the specificity of the shRNAs, a non-degradable murine NCOA4 cDNA was able to significantly rescue the ferritin lysosomal localization (FIG. 21(a)-(c)). These results were confirmed with two additional siRNAs against NCOA4 (FIG. 22(a)). Again, consistent with a distinct role for the HERC2/NCOA4 complex, HERC2 knockdown had no effect on lysosomal delivery of ferritin (FIG. 22(b)-(c)).

Iron plays an essential role in multiple cellular processes and as such iron metabolism is a tightly regulated process controlled by a network of iron-dependent proteins [Pantopoulos et al., supra]. Ferritin forms an intracellular iron storage protein complex capable of chelating up to 4500 atoms of iron, thus protecting the cell from free iron participating in the generation of free radicals via Fenton-like reactions [Kurz, T., et al., supra]. Iron stored in ferritin is utilized during periods of low iron levels and recent evidence suggests that iron can be liberated from ferritin upon degradation of ferritin in the lysosome [Asano et al, supra]. As the present evidence suggested that NCOA4 mediates the transport of ferritin to the lysosome via the autophagosome, it was next determined how NCOA4 knockdown affects the network of iron regulatory proteins. First, NCOA4 depletion increased basal ferritin levels relative to control cells (FIG. 3(a), lane 1 versus lanes 6 and 11, FIG. 19(f), lane 1 versus lanes 5 and 9). This suggested that NCOA4-deficient cells would display reduced iron bioavailability. Therefore, the levels of the iron-response protein 2 (IRP2), an RNA-binding protein that binds to iron response elements (IRE) on a set of iron-regulated mRNAs to control their translation [Pantopoulos, K. et al. *Biochemistry* 51, 5705-5724, (2012)] were examined. Cellular iron levels control IRE-binding activity of IRP2, with high and low iron levels promoting IRP2 turnover and stabilization, respectively [Pantopoulos, K. et al., supra]. It was found that NCOA4 depletion increased IRP2 abundance to an extent comparable to control cells subjected to iron chelation (FIG. 3(e), lane 7 versus lane 6). A higher IRP2 level in NCOA4-depleted cells would be anticipated to stabilize transferrin receptor mRNA and increase translation of the transferrin receptor to increase intracellular iron. Indeed, the abundance of the transferrin receptor is increased in NCOA4-depleted 8988T cells (FIG. 3(e), lane 1 versus lanes 2-3). These results were confirmed with two independent siRNAs to NCOA4 in 8988T, U2OS, and IMR90 cell lines (FIG. 22(d)). Overall, siRNA-mediated knockdown of NCOA4 in U2OS, IMR90 and, 8988T cells led to increases in IRP2, FTH1, and TFRC levels. Conversely, ectopic expression of NCOA4 in 8988T cells attenuated the increase of ferritin seen in FAC treated control cells implying that the increased NCOA4 is promoting ferritin turnover (FIG. 22(e)). The abundance of NCOA4 was altered by iron loading or chelation, although no canonical iron response element [Pantopoulos, K. et al., supra] was identified (FIG. 3(b), FIG. 22(e)).

Next, the biological consequences of reduced iron availability and lysosomal ferritin degradation in response to NCOA4 depletion were examined. Lysosomal iron has been shown to react with reactive oxygen species (ROS) leading to free radical formation via Fenton-like reactions, which results in lysosomal bursting and cell death [Kurz et al., supra]. Therefore, NCOA4 knockdown should provide protection from cell death after ROS challenge. As shown in FIG. 3(f), control cells were more sensitive to hydrogen peroxide challenge than NCOA4-depleted cells.

Selective autophagy is increasingly recognized as a regulated process through which specific cellular proteins, complexes, and organelles are degraded in the lysosome in response to diverse stimuli. Previous work suggested that delivery of the ferritin complex to lysosomes occurs via autophagy and regulates iron bioavailability [Asano et al., supra; Kidane et al., supra]. The present identification of NCOA4 as a specific cargo receptor for ferritin provides the first mechanistic understanding of how the ferritin complex is selectively delivered to autophagosomes. Flux through the pathway is regulated by iron availability, and in turn, disruption of the pathway through modulation of NCOA4 levels leads to alterations in the activity of IRP2, and altered sensitivity of cells to ROS. Moreover, NCOA4 mRNA is induced in red blood cells during erythropoiesis, and its expression correlates with genes involved in heme-biosynthesis [Nilsson, R. et al. *Cell Metabolism* 10, 119-130, (2009)], raising the possibility that NCOA4 function is important for both cellular remodeling and iron availability during differentiation [Griffiths, R. E. et al. *Autophagy;* 8, 1150-1151, (2012)]. While the present data provide compelling evidence for the role of NCOA4 as a ferritinophagy cargo receptor, it does not rule out that it may have other roles in specific cellular contexts. However, given the present findings in normal and tumor cells of diverse tissue origin, this work demonstrates that the targeting of ferritin to autophagosomes by NCOA4 is a general cellular mechanism for regulating bioavailable iron. This work also reveals the potential of quantitative autophagy proteomics to uncover receptor-cargo relationships and to further elucidate the mechanisms underlying both macro and selective autophagy.

Example 3: Mapping the Interaction Between NCOA-4 and Ferritin

Figure 5:
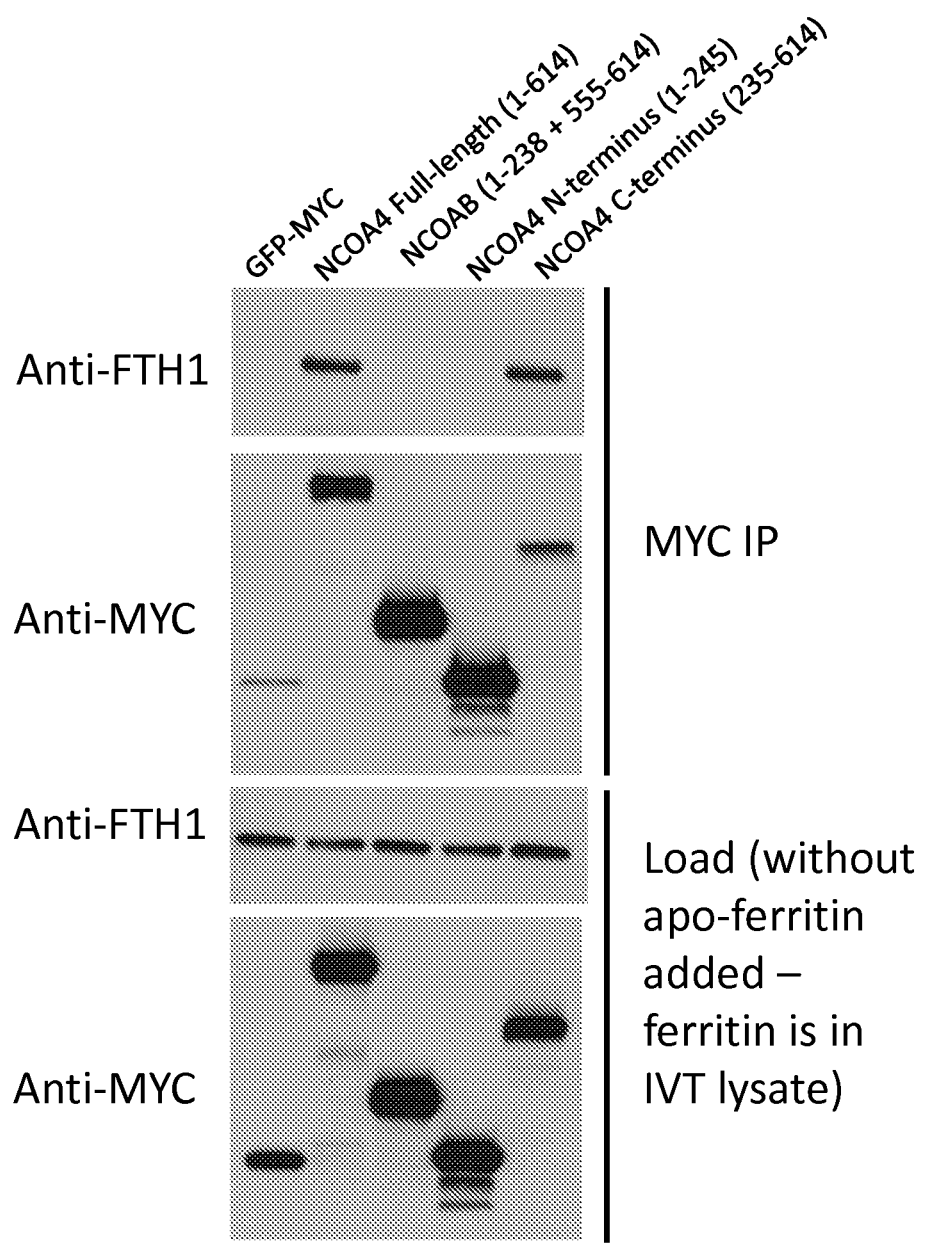
FIG. 5 contains photographs of immunoblot results. MYC-tagged versions of the full-length, N-terminal NCOA4 (amino acids (aa) 1-245) and C-terminal NCOA4 (aa 235-614 of SEQ ID NO:4) as well as a transcript variant, NCOA4B (consisting of amino acids 1-238 and 555-614 of full-length NCOA4 (SEQ ID NO: 4)), were incubated with ferritin purified from horse spleen (consisting of a mixture of FTH1 and FTL subunits). An anti-MYC antibody immunoprecipitation was performed followed by immunoblotting with the indicated antibodies. Full-length NCOA4 and C-terminal NCOA4 bind to ferritin.

To probe the interaction between ferritin and NCOA4, initial binding assays using MYC-tagged NCOA4 full-length and truncation constructs produced using an in vitro translation system were conducted according to the methods described, above. The fragments were designed based on secondary structure prediction: coiled coil domain at N-terminus and no known structure/homology with any other proteins in C-terminus. See, FIG. 4. As shown in FIG. 5, full-length (aa 1-614 of SEQ ID NO: 4) and C-terminal MYC-NCOA4 (aa 235-614 and aa 555-614) associated with ferritin but N-terminal MYC-NCOA4 did not associate with ferritin. Further, NCOAB, a naturally occurring transcript variant of NCOA4 that consists of amino acids 1-238 and 555-614 (a single construct), did not bind ferritin. The bottom two panels in FIG. 5 show the input to the immunoprecipitation assay ("IP"), i.e., there was FTH1 already in the IVT lysate (without adding the equine apoferritin) and these are the GST-NCOA4 fragments added to the IP. (Apoferritin was added to the binding reactions for which the data is shown in the upper two images in FIG. 5).

Figure 6:
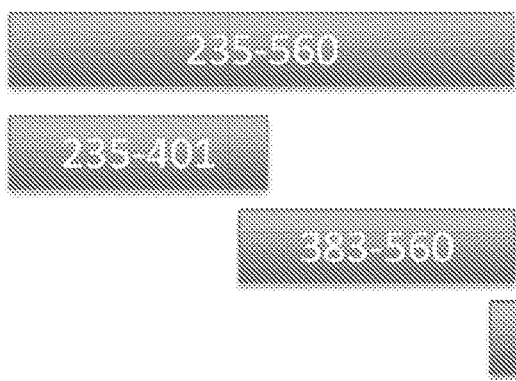
FIG. 6 is a diagram showing the design of C-terminal fragments of NCOA4, based on secondary structure predictions. Overlapping C-terminal fragments were designed as follows: NCOA4 C-terminal, amino acids 235-560, 235-401, 383-560, and 545-614.

In another set of experiments, to further probe the interaction between ferritin and NCOA4, binding assays using GST-tagged NCOA4 truncation constructs were as described, above. Briefly, portions of the C-terminal domain of NCOA4 fused to the C-terminus of GST were expressed, and then the fusion proteins were immobilized on glutathione Sepharose beads. Fragments (aa 235-614, aa 235-560, aa 383-560, aa 235-401, and aa 545-614 of SEQ ID NO: 4) were designed based on secondary structure prediction in C-terminus (see the schematic diagram in FIG. 6).

Figure 7:
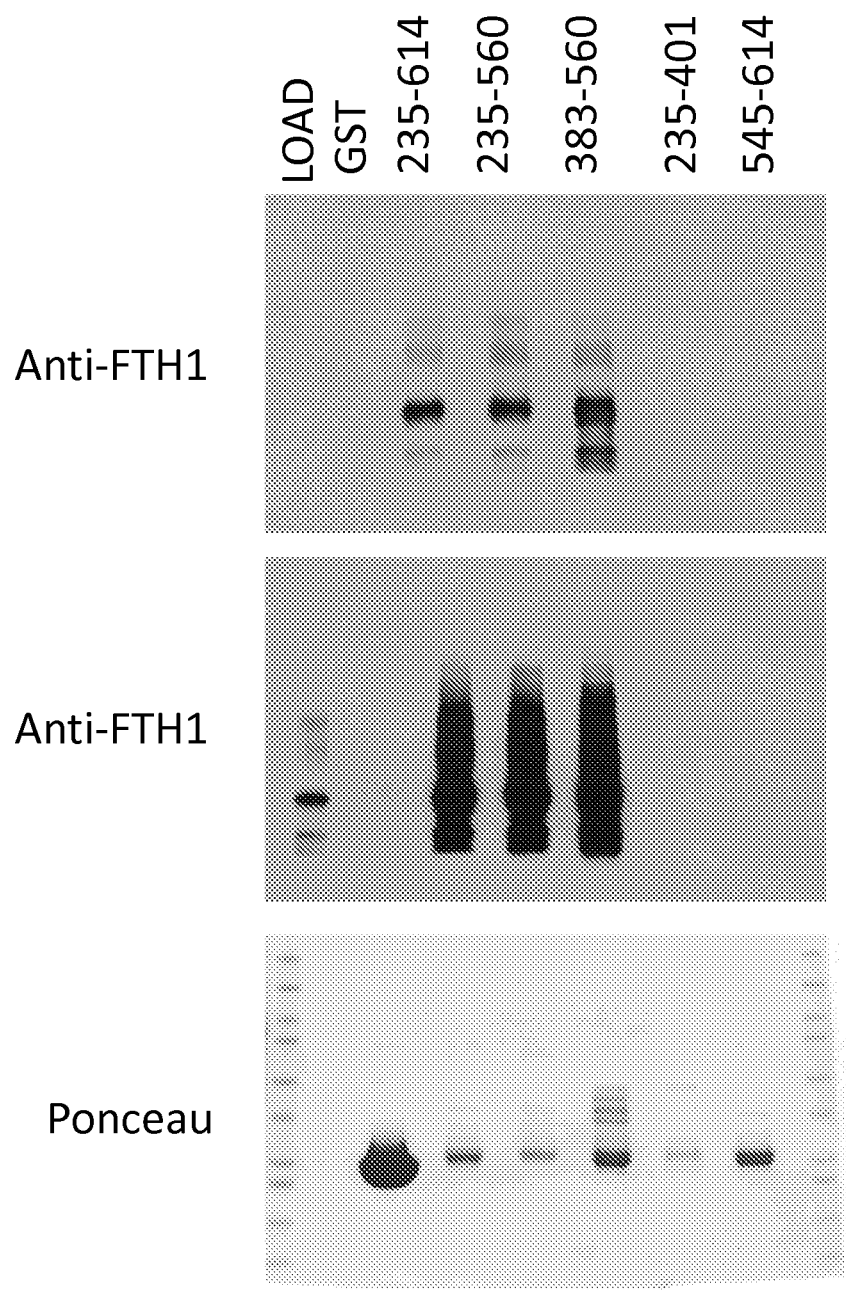
FIG. 7 contains photographs of immunoblot results from a GST pull-down assay of ferritin using GST-NCOA4 proteins, GST alone as control. FTH1 immunoblot for ferritin. Ponceau stain for loading of GST-NCOA4 fragments (there are multiple break-down products of the GST-NCOA4 fragments).

The GST pull-down assay was performed and bands were visualized with anti-FTH1 antibody or Ponceau staining, as described above. As shown in FIG. 7, C-terminal NCOA4, aa 235-560, and aa 383-560 bound to ferritin. The minimal region of NCOA4 that recapitulated binding to ferritin in this experiment was amino acid residues 383-560. Furthermore, an anti-GST antibody immunoblot showed a band at the appropriate size for the predicted size of the various GST-NCOA4 fragments, as well as breakdown products.

Figure 8:
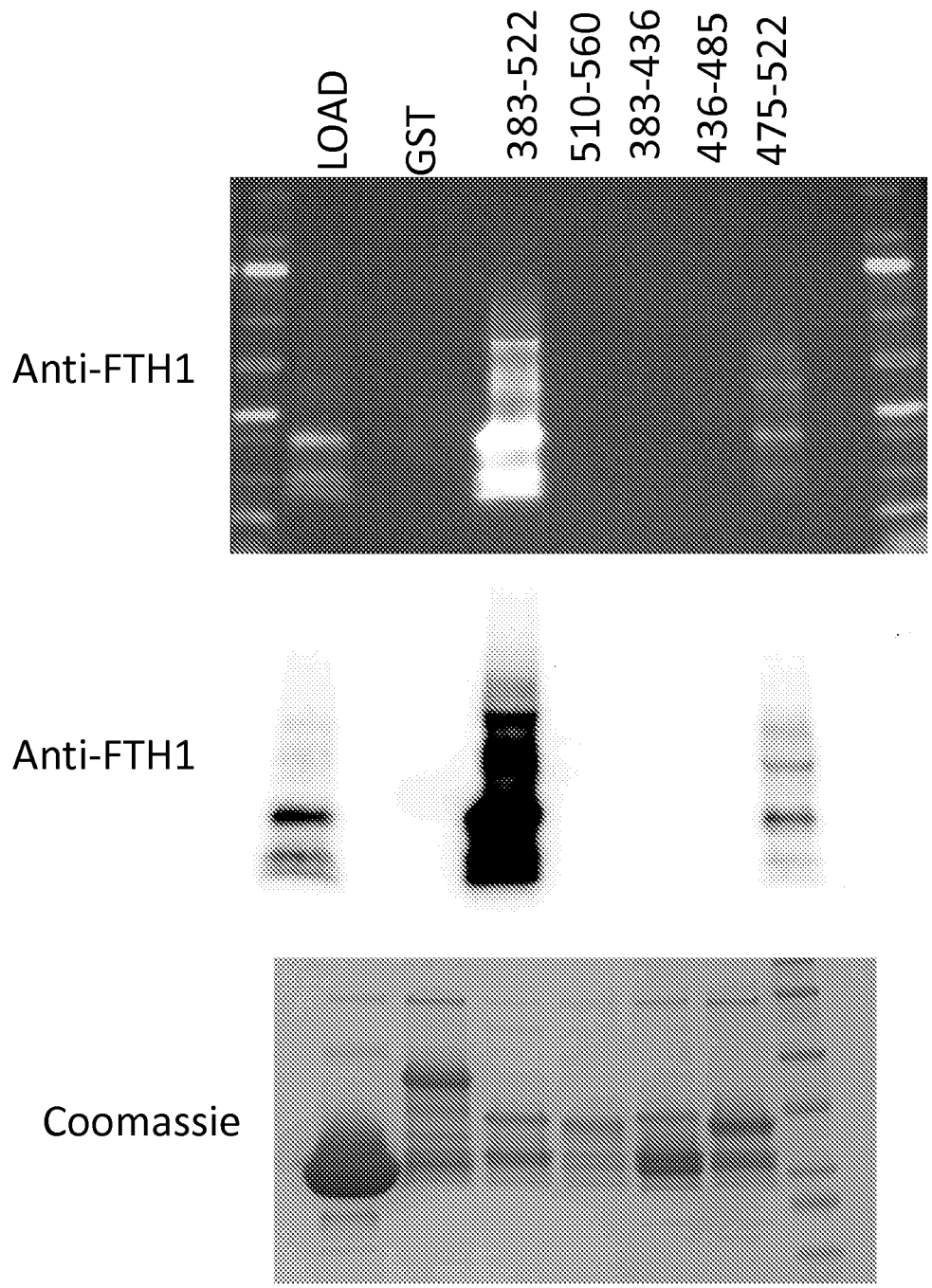
FIG. 8 contains photographs of immunoblot results (upper two images) from a GST pull-down assay of ferritin using GST-NCOA4 proteins (as labeled), and GST alone as control. The upper two images show anti-FTH1 immunoblot antibody results for ferritin. Coomassie stain for loading of GST-NCOA4 fragments (there are multiple break-down products of the GST-NCOA4 fragments) and anti-GST immunoblot show a band at the appropriate size for the predicted size of the various GST-NCOA4 fragments, as well as breakdown products (lowermost image). Fragments with amino acids 383-522 and fragments with amino acids 475-522 bind to ferritin.

Additional experiments were conducted to determine the minimal amino acid sequence of NCOA4 that was required for NCOA4 interaction with ferritin. Additional GST-tagged fragments of NCOA4 were tested (produced as described in Example 1), including aa 383-522, aa 511-560, aa 383-436, aa 401-436, aa 436-485, and aa 475-522 of SEQ ID NO:4. As shown in FIG. 8, the minimal NCOA sequence that interacted with ferritin in this experiment was aa 475-522 (corresponding to KAMTPSRIADSFQVIKNSPLSEWLIR-PPYKEGSPKEVPGTEDRAGKQK (SEQ ID NO: 2)).

Figure 9:
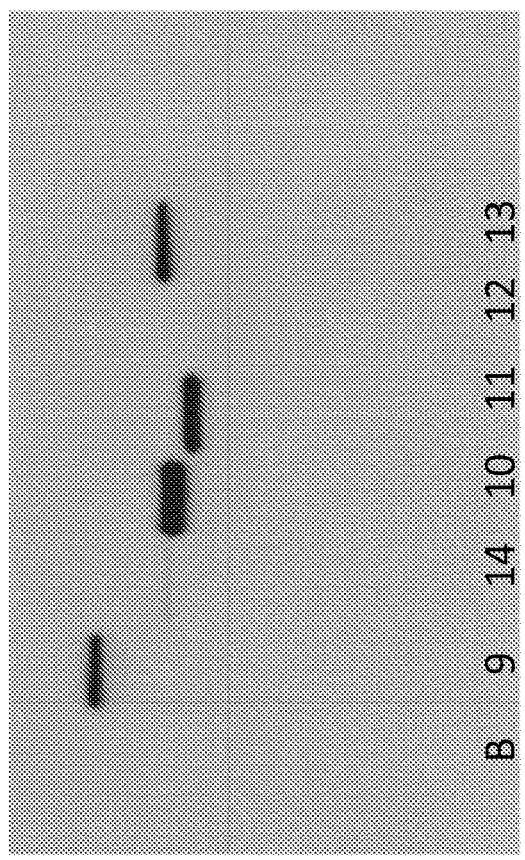
FIG. 9 contains photographs of immunoblot results from a GST pull-down assay of ferritin using GST-NCOA4 proteins (produced using an in vitro translation system). Lane B is an in vitro translation reaction with a GST-NCOA4 construct, negative control. The upper image shows the results of an anti-FTH1 antibody immunoblot for ferritin and the lower image shows the results of anti-GST antibody immunoblot for GST-NCOA4 fragments.
Figure 9:
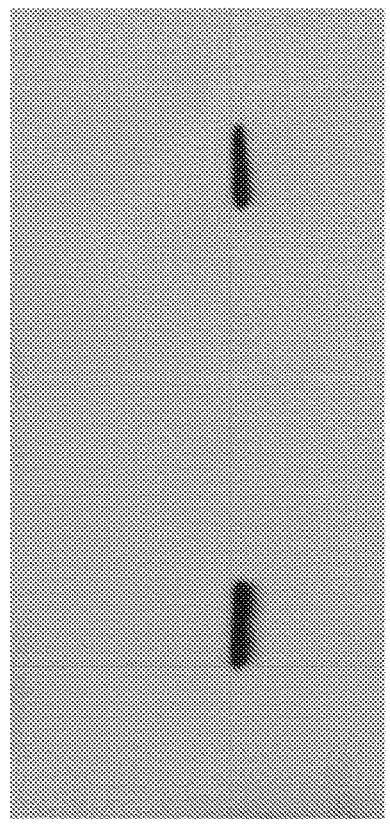

A further experiment was conducted which was an IVT-based interaction experiment using C-terminal His-GST-HA tagged NCOA4 constructs and GST pull-down (note 436-485 did not express). Data are shown in FIG. 9, and the results show that that the load for fragments of aa 383-522 and aa 475-522 were equal, and those fragments equally pulled down (bound to) FTH1.

Figure 11:
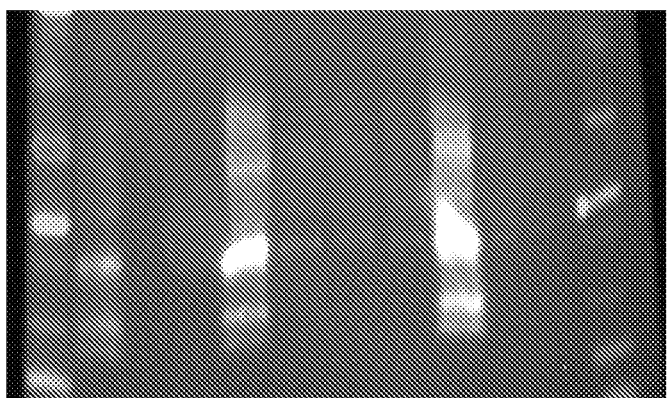
FIG. 11 contains photographs of immunoblot results (upper two images) from a GST pull-down assay of ferritin using GST-NCOA4 fragments, or GST alone as control, and of Coomassie staining. An anti-FTH1 antibody immunoblot was performed for ferritin. Coomassie stain for loading of GST-NCOA4 fragments was used (lowermost image). The following NCOA4 fragments (coupled to GST) were tested: amino acid residues (aa) 475-572 (as indicated); #15: aa 475-500; #16: aa 480-500; #17: aa 480-504; #18: aa 485-509; #19: aa 490-514; #20: aa 495-522.
Figure 11:
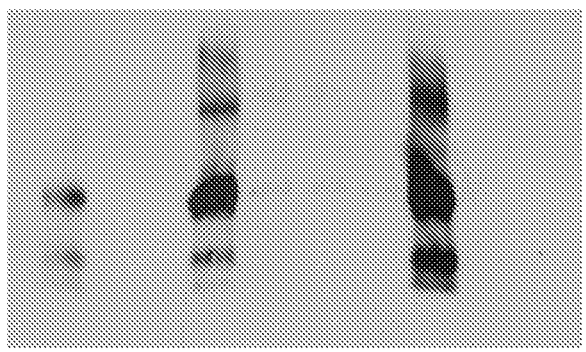
Figure 11:
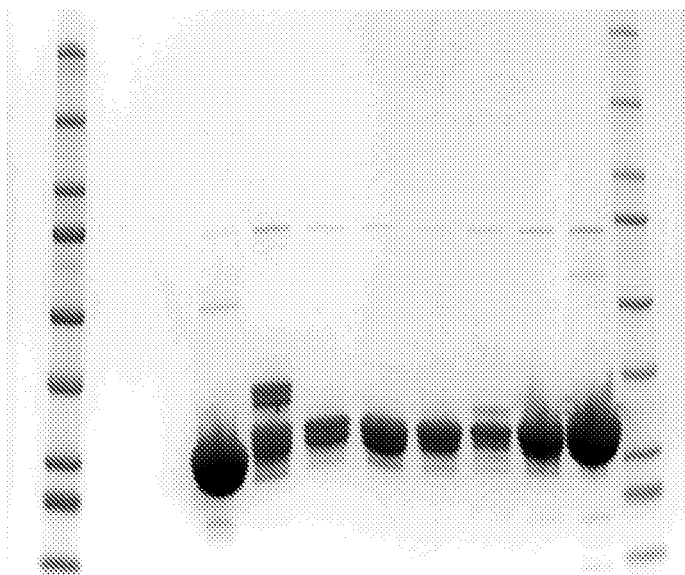

Further experiments were conducted to determine the minimal binding fragment of NCOA4 that can bind to ferritin. A GST pull-down assay of ferritin using GST-NCOA4 proteins fragments, and GST alone as control, was performed. An anti-FTH1 immunoblot was performed for ferritin. The following NCOA4 fragments (coupled to GST) were tested: amino acid residues (aa) 475-572; aa 475-500; aa 480-500; aa 480-504; aa 485-509; aa 490-514; and aa 495-522. As shown in FIG. 11, anti-GST immunoblot showed a band at the appropriate size for the predicted size of the various GST-NCOA4 fragments, as well as breakdown products, and aa 475-522 and aa 485-509 bound to ferritin. Thus, the minimal fragment of NCOA4 that binds to ferritin was aa 485-509, which corresponds to amino acids SFQVIKNSPLSEWLIRPPYKEGSPK (SEQ ID NO: 11).

Example 4: NCOA4 Binds Preferentially and Directly to FTH1

Figure 10A:
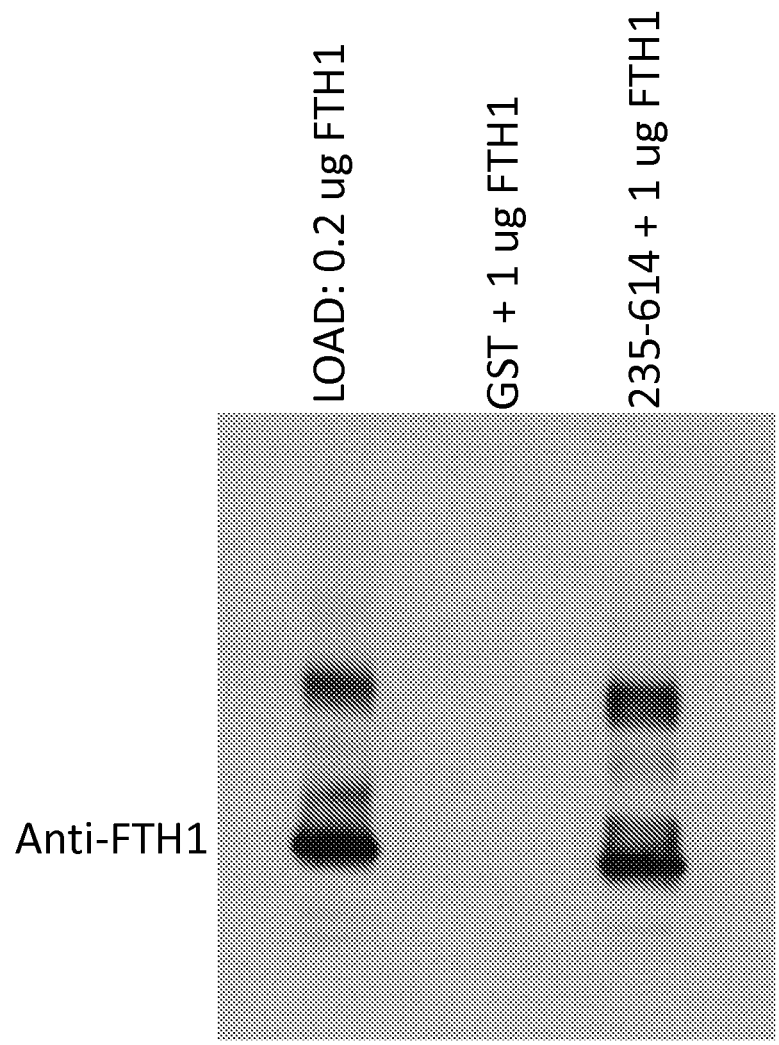
FIG. 10A contains an image of an immunoblot result of a GST pull-down assay of FTH1 using GST-NCOA4 proteins (as labeled), and GST alone as control. An anti-FTH1 antibody immunoblot was performed. GST-NCOA4 fragment binds to FTH1. Load lane is 20% of FTH1 input.
Figure 10B:
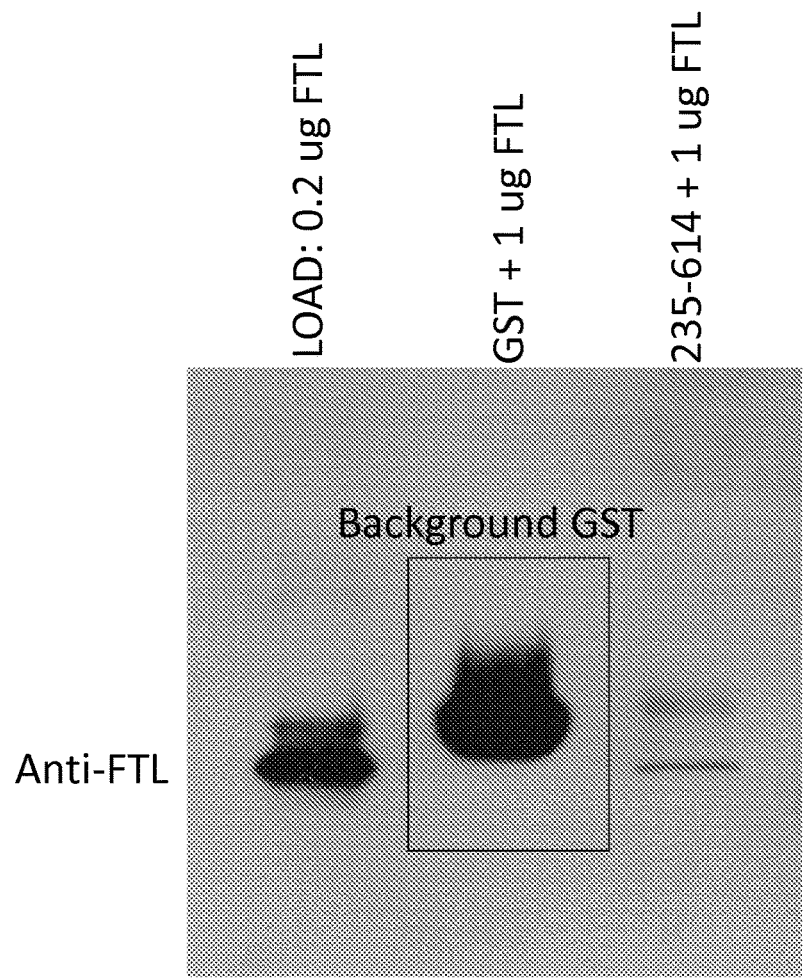
FIG. 10B contains an image of an immunoblot result of a GST pull-down assay of FTL using GST-NCOA4 proteins (as labeled), and GST alone as control. An anti-FTL antibody immunoblot was performed for FTL. GST-NCOA4 fragment binds minimally to FTL. Load lane is 20% of FTL input.

To understand if there was subunit specificity for NCOA4 binding to ferritin, the NCOA4 C-terminus (aa 235-614) fusion protein was immobilized on glutathione Sepharose beads, as described in Example 1. Recombinant purified FTH1 or FTL produced in *E. coli* was added at concentrations of 0.2 µg and 1 µg, and binding was determined using the GST pull-down assay described in Example 1, above. As shown in FIGS. 10A and 10B, FTH1 but not FTL interacted with the NCOA4 C-terminus, suggesting that NCOA4 interacts with specificity in vivo for FTH1. These results also suggest that certain cells may use ferritinophagy more than others (e.g., cells that produce more FTH1 as opposed to FTL).

Example 5: Mapping the Interaction Between NCOA4 and HERC2

Figure 12:
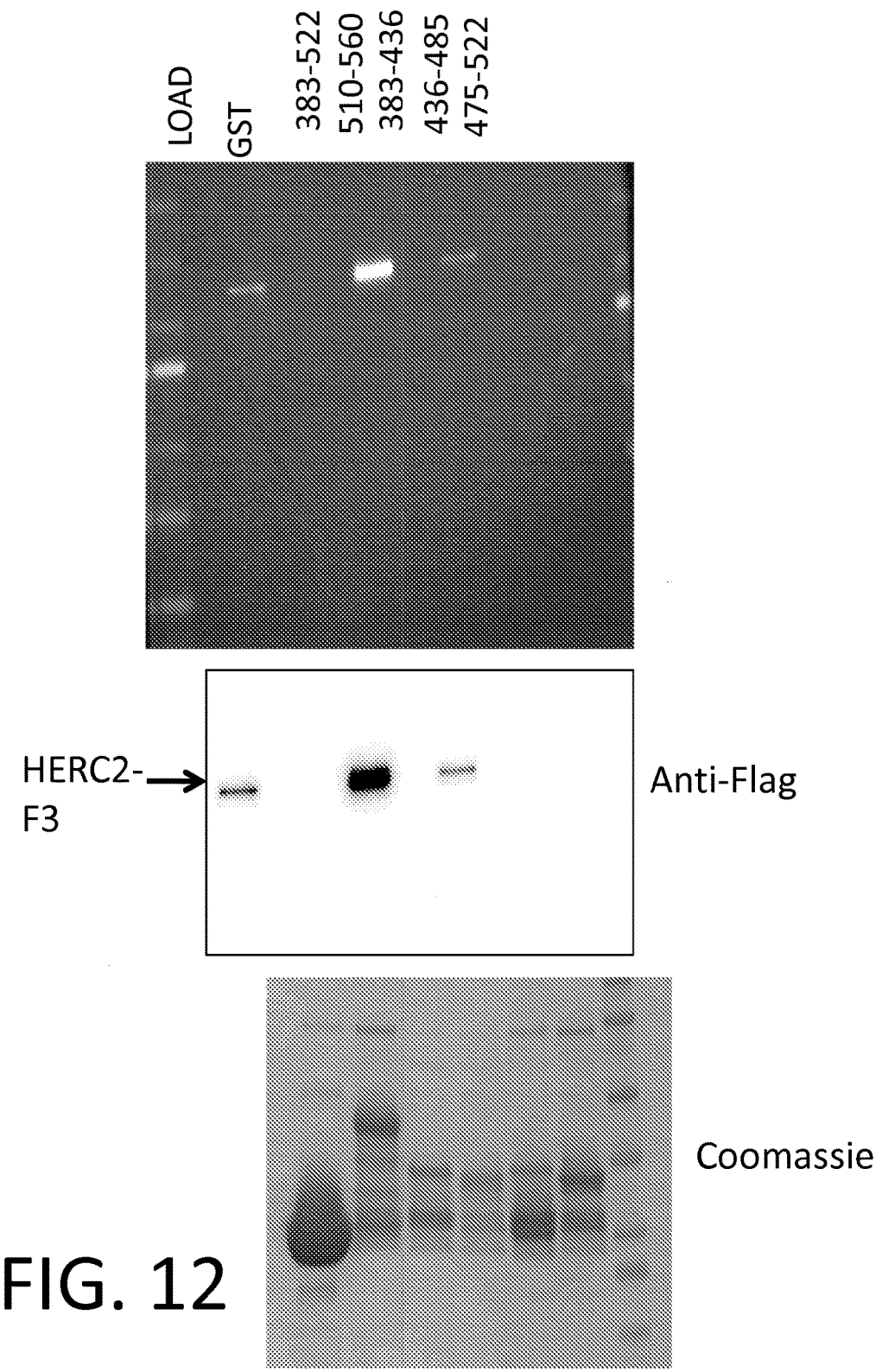
FIG. 12 contains photographs of immunoblot results from a GST pull-down assay of HERC2-FLAG Fragment 3 using GST-NCOA4 protein fragments (as labeled), or GST alone as control. An anti-FLAG immunoblot for HERC2-FLAG was performed. Coomassie stain for loading of GST-NCOA4 fragments is shown in lowermost image. The following NCOA4 fragments were tested, as indicated in the figure: aa 383-522; aa 510-560; aa 383-436; aa 436-485; and aa 475-522.

To map the interaction between NCOA4 and HERC2, it was first determined that NCOA4 (383-560) binds to HERC2 fragment "3" (amino acid residues 1700-2700 of SEQ ID NO: 8 (NP_004658)). A flag-tagged HERC2 fragment was expressed in 293T cells and cell lysates were tested in a GST-NCOA4 binding assay, using various GST-NCOA4 fragments. Anti-FLAG immunoblot for HERC2-FLAG was performed. Coomassie stain for loading of GST-NCOA4 fragments (note there are multiple breakdown products of the GST-NCOA4 fragments) was also performed. The following NCOA4 fragments were tested, amino acid residues (aa) 383-522; aa 510-560; aa 383-436; aa 436-485; and aa 475-522. Anti-GST immunoblot showed a band at the appropriate size for the predicted size of the various GST-NCOA4 fragments as well as breakdown products. As shown in FIG. 12, aa 383-522 and aa 383-436 bound to HERC2-FLAG. The minimal region of NCOA4 required for binding to HERC2 was thus determined to be aa 383-436, corresponding to SEQ ID NO: 3 (SMVTEDWLVQN-

HQDPCKVEEVCRANEPCTSFAECVC-
DENCEKEALYKWLLKKEG).

Example 6: Mapping the Interaction Between NCOA4 and FTH1

Wild-type (WT) and point mutants of FTH1 were produced recombinantly in *E. coli* and purified by chromatographic techniques including size exclusion chromatography to confirm oligomeric ferritin cage assembly (elution at 440 kDa size on Superose 6 column). In a GST pull-down assay, NCOA4(aa 383-522)-GST or GST alone was incubated with 10 µl of a 50% (v/v) slurry of glutathione Sepharose 4B beads (GE Healthcare Lifesciences, 17-0756-01) for 30 minutes at 4° C. Beads were washed thoroughly with 150 mM NaCl, 20 mM Tris (pH 7.4), 2 mM dithiothreitol (DTT), 0.5% (w/v) Nonidet P-40, leaving 50-100 µg of GST-fusion protein bound to the beads. Beads were then mixed with 40 µg of recombinant human WT or point mutant FTH1 produced in Rosetta *E. coli* (EMD Millipore, 70953-3). The assay mix was incubated for 30 minutes at 4° C., and beads were washed three times with 1 ml wash buffer. Proteins were eluted with SDS sample buffer and analyzed by 4-20% gradient SDS-PAGE. InstantBlue Stain (Expedeon: catalog #ISB1L) was used to visualize GST-NCOA4 bands and FTH1 bands. As shown in FIGS. 23A-D, the NCOA4(383-522)-GST fragment bound only very weakly to the FTH1 R23A point mutant but bound to FTH1 WT and other point mutants of FTH1 strongly. Based on this result and the known 3-dimensional structure of FTH1 (PDB: 3AJO), it is predicted that all or part of the two alpha helices of FTH1 would be involved in the interaction with NCOA4; the alpha helices include amino acids D16-V34 and C103-K125 (numbering starts from methionine encoded by start codon) of FTH1. The interaction would very likely also involve the loop structure (G78-K88) adjacent to the R23 site of FTH1.

A number of embodiments of the invention have been described. Nevertheless, it will be understood that various modifications may be made without departing from the spirit and scope of the invention. Accordingly, other embodiments are within the scope of the following claims.

What is claimed is:

1. A method of decreasing binding between nuclear receptor coactivator 4 (NCOA4) and ferritin heavy chain (FTH1) in a cell, wherein the method comprises delivering to the interior of a cell comprising NCOA4 and FTH1 an agent that decreases the binding between the C-terminus of NCOA4 and FTH1, wherein the C-terminus of NCOA4 consists of amino acids 235-614 of SEQ ID NO: 4, and
  wherein the agent is selected from the group consisting of:
  (a) an inhibitory NCOA4-specific antibody,
  (b) an inhibitory FTH1-specific antibody,
  (c) a NCOA4-specific intrabody,
  (d) a dominant negative NCOA4,
  (e) a peptide fragment of NCOA4 comprising an amino acid sequence set forth in SEQ ID NO: 11 with 0 to 3 amino acid substitutions, and
  (f) a peptide fragment of FTH1 comprising an amino acid sequence selected from the group consisting of: amino acids 16-34 of SEQ ID NO: 6 with 0 to 3 amino acid substitutions, amino acids 103-125 of SEQ ID NO: 6 with 0 to 3 amino acid substitutions, and amino acids 78-88 of SEQ ID NO: 6 with 0 to 3 amino acid substitutions.

2. The method of claim 1, wherein the agent is a peptide fragment of NCOA4 comprising an amino acid sequence set forth in SEQ ID NO: 11 with 0 to 3 amino acid substitutions.

3. The method of claim 2, wherein the peptide fragment comprises the amino acid sequence of
  SEQ ID NO: 1 (SRIADSFQVIKNSPLSEWLIRPPYKEGSPK) or
  SEQ ID NO: 11 (SFQVIKNSPLSEWLIRPPYKEGSPK).

4. The method of claim 2, wherein the peptide fragment consists of the amino acid sequence of
  SEQ ID NO: 1 (SRIADSFQVIKNSPLSEWLIRPPYKEGSPK).

5. The method of claim 2, wherein the peptide fragment consists of the amino acid sequence of
  SEQ ID NO: 11 (SFQVIKNSPLSEWLIRPPYKEGSPK).

6. The method of claim 1, wherein the agent is a peptide fragment of FTH1 comprising amino acids 16-34 of SEQ ID NO: 6 with 0 to 3 amino acid substitutions.

7. The method of claim 1, wherein the agent is a peptide fragment of FTH1 comprising amino acids 103-125 of SEQ ID NO: 6 with 0 to 3 amino acid substitutions.

8. The method of claim 1, wherein the agent is a peptide fragment of FTH1 comprising amino acids 78-88 of SEQ ID NO: 6 with 0 to 3 amino acid substitutions.

* * * * *

```
                            SEQUENCE LISTING

<160> NUMBER OF SEQ ID NOS: 25

<210> SEQ ID NO 1
<211> LENGTH: 30
<212> TYPE: PRT
<213> ORGANISM: Homo sapien

<400> SEQUENCE: 1

Ser Arg Ile Ala Asp Ser Phe Gln Val Ile Lys Asn Ser Pro Leu Ser
1               5                   10                  15

Glu Trp Leu Ile Arg Pro Pro Tyr Lys Glu Gly Ser Pro Lys
            20                  25                  30

<210> SEQ ID NO 2
<211> LENGTH: 48
<212> TYPE: PRT
<213> ORGANISM: Homo sapien

<400> SEQUENCE: 2

Lys Ala Met Thr Pro Ser Arg Ile Ala Asp Ser Phe Gln Val Ile Lys
1               5                   10                  15

Asn Ser Pro Leu Ser Glu Trp Leu Ile Arg Pro Pro Tyr Lys Glu Gly
            20                  25                  30

Ser Pro Lys Glu Val Pro Gly Thr Glu Asp Arg Ala Gly Lys Gln Lys
        35                  40                  45

<210> SEQ ID NO 3
<211> LENGTH: 54
<212> TYPE: PRT
<213> ORGANISM: Homo sapien

<400> SEQUENCE: 3

Ser Met Val Thr Glu Asp Trp Leu Val Gln Asn His Gln Asp Pro Cys
1               5                   10                  15

Lys Val Glu Glu Val Cys Arg Ala Asn Glu Pro Cys Thr Ser Phe Ala
            20                  25                  30

Glu Cys Val Cys Asp Glu Asn Cys Glu Lys Glu Ala Leu Tyr Lys Trp
        35                  40                  45

Leu Leu Lys Lys Glu Gly
    50
```

<210> SEQ ID NO 4
<211> LENGTH: 614
<212> TYPE: PRT
<213> ORGANISM: Homo sapien

<400> SEQUENCE: 4

```
Met Asn Thr Phe Gln Asp Gln Ser Gly Ser Ser Asn Arg Glu Pro
1               5                   10                  15

Leu Leu Arg Cys Ser Asp Ala Arg Arg Asp Leu Glu Leu Ala Ile Gly
            20                  25                  30

Gly Val Leu Arg Ala Glu Gln Gln Ile Lys Asp Asn Leu Arg Glu Val
        35                  40                  45

Lys Ala Gln Ile His Ser Cys Ile Ser Arg His Leu Glu Cys Leu Arg
50                  55                  60

Ser Arg Glu Val Trp Leu Tyr Glu Gln Val Asp Leu Ile Tyr Gln Leu
65                  70                  75                  80

Lys Glu Glu Thr Leu Gln Gln Ala Gln Gln Leu Tyr Ser Leu Leu
                85                  90                  95

Gly Gln Phe Asn Cys Leu Thr His Gln Leu Glu Cys Thr Gln Asn Lys
            100                 105                 110

Asp Leu Ala Asn Gln Val Ser Val Cys Leu Glu Arg Leu Gly Ser Leu
        115                 120                 125

Thr Leu Lys Pro Glu Asp Ser Thr Val Leu Leu Phe Glu Ala Asp Thr
130                 135                 140

Ile Thr Leu Arg Gln Thr Ile Thr Thr Phe Gly Ser Leu Lys Thr Ile
145                 150                 155                 160

Gln Ile Pro Glu His Leu Met Ala His Ala Ser Ser Ala Asn Ile Gly
                165                 170                 175

Pro Phe Leu Glu Lys Arg Gly Cys Ile Ser Met Pro Glu Gln Lys Ser
            180                 185                 190

Ala Ser Gly Ile Val Ala Val Pro Phe Ser Glu Trp Leu Leu Gly Ser
        195                 200                 205

Lys Pro Ala Ser Gly Tyr Gln Ala Pro Tyr Ile Pro Ser Thr Asp Pro
210                 215                 220

Gln Asp Trp Leu Thr Gln Lys Gln Thr Leu Glu Asn Ser Gln Thr Ser
225                 230                 235                 240

Ser Arg Ala Cys Asn Phe Phe Asn Asn Val Gly Gly Asn Leu Lys Gly
                245                 250                 255

Leu Glu Asn Trp Leu Leu Lys Ser Glu Lys Ser Ser Tyr Gln Lys Cys
            260                 265                 270

Asn Ser His Ser Thr Thr Ser Ser Phe Ser Ile Glu Met Glu Lys Val
        275                 280                 285

Gly Asp Gln Glu Leu Pro Asp Gln Asp Glu Met Asp Leu Ser Asp Trp
290                 295                 300

Leu Val Thr Pro Gln Glu Ser His Lys Leu Arg Lys Pro Glu Asn Gly
305                 310                 315                 320

Ser Arg Glu Thr Ser Glu Lys Phe Lys Leu Leu Phe Gln Ser Tyr Asn
                325                 330                 335

Val Asn Asp Trp Leu Val Lys Thr Asp Ser Cys Thr Asn Cys Gln Gly
            340                 345                 350

Asn Gln Pro Lys Gly Val Glu Ile Glu Asn Leu Gly Asn Leu Lys Cys
        355                 360                 365

Leu Asn Asp His Leu Glu Ala Lys Lys Pro Leu Ser Thr Pro Ser Met
```

```
                  370                 375                 380
Val Thr Glu Asp Trp Leu Val Gln Asn His Gln Asp Pro Cys Lys Val
385                 390                 395                 400

Glu Glu Val Cys Arg Ala Asn Glu Pro Cys Thr Ser Phe Ala Glu Cys
                405                 410                 415

Val Cys Asp Glu Asn Cys Glu Lys Glu Ala Leu Tyr Lys Trp Leu Leu
            420                 425                 430

Lys Lys Glu Gly Lys Asp Lys Asn Gly Met Pro Val Glu Pro Lys Pro
        435                 440                 445

Glu Pro Glu Lys His Lys Asp Ser Leu Asn Met Trp Leu Cys Pro Arg
    450                 455                 460

Lys Glu Val Ile Glu Gln Thr Lys Ala Pro Lys Ala Met Thr Pro Ser
465                 470                 475                 480

Arg Ile Ala Asp Ser Phe Gln Val Ile Lys Asn Ser Pro Leu Ser Glu
                485                 490                 495

Trp Leu Ile Arg Pro Pro Tyr Lys Glu Gly Ser Pro Lys Glu Val Pro
            500                 505                 510

Gly Thr Glu Asp Arg Ala Gly Lys Gln Lys Phe Lys Ser Pro Met Asn
        515                 520                 525

Thr Ser Trp Cys Ser Phe Asn Thr Ala Asp Trp Val Leu Pro Gly Lys
    530                 535                 540

Lys Met Gly Asn Leu Ser Gln Leu Ser Ser Gly Glu Asp Lys Trp Leu
545                 550                 555                 560

Leu Arg Lys Lys Ala Gln Glu Val Leu Leu Asn Ser Pro Leu Gln Glu
                565                 570                 575

Glu His Asn Phe Pro Pro Asp His Tyr Gly Leu Pro Ala Val Cys Asp
            580                 585                 590

Leu Phe Ala Cys Met Gln Leu Lys Val Asp Lys Glu Lys Trp Leu Tyr
        595                 600                 605

Arg Thr Pro Leu Gln Met
    610

<210> SEQ ID NO 5
<211> LENGTH: 3562
<212> TYPE: DNA
<213> ORGANISM: Homo sapien

<400> SEQUENCE: 5
agagggcagt caagggcttc tggctgaccc gagcggagat ctcgcgagac tgtcagacgt    60
atggcgagag tgtgggagg aagattgtgt tgtcgcgaga actctgcctt ggggccgtag    120
gttagtgtgg ggccgtgtct cagtccaccc aaggtctcct cggatcgcct ggagaggcac    180
tcggacctgg agcagtgagg agaatgaata ccttccaaga ccagagtggc agctccagta    240
atagagaacc ccttttgagg tgtagtgatg cacggaggga cttggagctt gctattggtg    300
gagttctccg ggctgaacag caaattaaag ataacttgcg agaggtcaaa gctcagattc    360
acagttgcat aagccgtcac ctggaatgtc ttagaagccg tgaggtatgg ctgtatgaac    420
aggtggacct tatttatcag cttaaagagg agacacttca acagcaggct cagcagctct    480
actcgttatt gggccagttc aattgtctta ctcatcaact ggagtgtacc caaaacaaag    540
atctagccaa tcaagtctct gtgtgcctgg agagactggg cagtttgacc cttaagcctg    600
aagattcaac tgtcctgctc tttgaagctg acacaattac tctgcgccag accatcacca    660
catttgggtc tctcaaaacc attcaaattc ctgagcactt gatggctcat gctagttcag    720
```

```
caaatattgg gcccttcctg gagaagagag gctgtatctc catgccagag cagaagtcag      780
catccggtat tgtagctgtc cctttcagcg aatggctcct tggaagcaaa cctgccagtg      840
gttatcaagc tccttacata cccagcaccg accccagga ctggcttacc caaaagcaga       900
ccttggagaa cagtcagact tcttccagag cctgcaattt cttcaataat gtcgggggaa      960
acctaaaggg cttagaaaac tggctcctca agagtgaaaa atcaagttat caaaagtgta     1020
acagccattc cactactagt tctttctcca ttgaaatgga aaggttgga gatcaagagc      1080 ttcctgatca agatgagatg gacctatcag attggctagt gactccccag gaatcccata     1140
agctgcggaa gcctgagaat ggcagtcgtg aaaccagtga agtttaag ctcttattcc       1200 agtcctataa tgtgaatgat tggcttgtca agactgactc ctgtaccaac tgtcagggaa     1260
accagcccaa aggtgtggag attgaaaacc tgggcaatct gaagtgcctg aatgaccact     1320
tggaggccaa gaaaccattg tccaccccca gcatggttac agaggattgg cttgtccaga     1380
accatcagga cccatgtaag gtagaggagg tgtgcagagc caatgagccc tgcacaagct     1440
ttgcagagtg tgtgtgtgat gagaattgtg agaaggaggc tctgtataag tggcttctga     1500
agaaagaagg aaaggataaa atgggatgc ctgtggaacc caaacctgag cctgagaagc      1560
ataaagattc cctgaatatg tggctctgtc ctagaaaaga agtaatagaa caaactaaag     1620
caccaaaggc aatgactcct tctagaattg ctgattcctt ccaagtcata agaacagcc      1680 ccttgtcgga gtggcttatc aggcccccat acaaagaagg aagtcccaag gaagtgcctg     1740
gtactgaaga cagagctggc aaacagaagt ttaaaagccc catgaatact tcctggtgtt     1800
cctttaacac agctgactgg gtcctgccag gaaagaagat gggcaacctc agccagttat     1860
cttctggaga agacaagtgg ctgcttcgaa agaaggccca ggaagtatta cttaattcac     1920
ctctacagga ggaacataac ttcccccag accattatgg cctccctgca gtttgtgatc     1980 tcttgcctg tatgcagctt aaagttgata agagaagtg gttatatcga actcctctac       2040
agatgtgaag gaatggacaa gagttgagca gcctttctgc tgattatcac acatcatgag     2100
ctgagtgact gcagcttgcc aaatctttgt gtttctgggt ctgaccaatt agcttagttc     2160
ttctcctgcc taattttgaa ctagtaaagc aaagtgagtc atcagattat gagttactgt     2220
ttaaaagaaa aatgctgttt attcatgctg aggtgattca gttccctcct tcttacagaa     2280
gtattttaat tcaccccaca ctagaaatgc agcatctttg tggacgtctt tttcacaagc     2340
ctccaaggct ccttagattg ggtcgttact aaaagtacat taaaacactc ttgtttatcg     2400
aagtatattg atgtattcta aagctagtaa acttccctaa cgtttaattg ccctacagat     2460
gcttctcttg ctgtgggttt tcttttgtta gtggtctgaa ataattattt tcctgttcta     2520
ttaatacata gtgtatttg cacaaaaaaa ttaacctggt caatagtgat taccaaaata     2580
tatattaata atcttggcaa ttttgacat taattatgaa acattttagc ccacgttagt      2640
tctacattat tcttcactta aactcagcta ctgcaaattt tgtctttctg taaatgttat     2700
taaaatatcc agtgagctct ttagaaggac tcagtattat ttcaagacta tttttgaggt     2760
aattctagcc tttaaaata ttctacagac ctacggggct taaaagaacc ccagtaccga      2820
ctaagcaaat aggcaaaaga catgttgaaa atgtagtata gtacttgaaa cagtcactat     2880
catagggata attggtgcat cctgtgtaaa tggaagctga gcttgacacc tggtgctttt     2940
aagtagggat aaagtcatcc tctcactgca agcacagcat acctgtacct ccaaaagtga     3000
cgttttagtg aacaggccgt tttcaacact tgtgccttgg ggtgttcatt gaagctttgt     3060
gaaaactact gatgttttct cagtctcctt aaagttacgt ccatgcttta aatgtctgt      3120
```

```
gtaggagaga agtggggttt ataatgtttt ctctaagata tctttgctgc tttccagact   3180
ttgaaactat taagcttctt aactgcctct taccggaaat acttctgggg aaacttcatg   3240
gtcccaaaat gtcattgcca tacagcttca ctagagttct ttgaaccaca gctgaaaaga   3300
gctttgtatt atttttttaat tccctcccca gatatcattt aggagtatta tataaaggtg   3360
gtgggcaaaa acaatgtaag gagcctttcc agttatcttg agttgcagct ctgtagtttc   3420
ttgaggccaa acacactgta ttttacaagt caaaatataa tttacattaa tcactatgtt   3480
aatgagtatg taaacattc ttttgcattg atgaattttg tatctgcttc cattaaaagc   3540
ataacagcca taaaaaaaaa aa                                            3562
```

<210> SEQ ID NO 6
<211> LENGTH: 183
<212> TYPE: PRT
<213> ORGANISM: Homo sapien

<400> SEQUENCE: 6

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180
```

<210> SEQ ID NO 7
<211> LENGTH: 207
<212> TYPE: PRT
<213> ORGANISM: Homo sapien

<400> SEQUENCE: 7

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Met Ser Ser Gln Ile Arg Gln Asn Tyr Ser Thr Asp Val Glu Ala Ala
        35                  40                  45

Val Asn Ser Leu Val Asn Leu Tyr Leu Gln Ala Ser Tyr Thr Tyr Leu
```

```
                    50                  55                  60
Ser Leu Gly Phe Tyr Phe Asp Arg Asp Val Ala Leu Glu Gly Val
 65                  70                  75                  80

Ser His Phe Phe Arg Glu Leu Ala Glu Glu Lys Arg Glu Gly Tyr Glu
                 85                  90                  95

Arg Leu Leu Lys Met Gln Asn Gln Arg Gly Gly Arg Ala Leu Phe Gln
                100                 105                 110

Asp Ile Lys Lys Pro Ala Glu Asp Glu Trp Gly Lys Thr Pro Asp Ala
                115                 120                 125

Met Lys Ala Ala Met Ala Leu Glu Lys Lys Leu Asn Gln Ala Leu Leu
    130                 135                 140

Asp Leu His Ala Leu Gly Ser Ala Arg Thr Asp Pro His Leu Cys Asp
145                 150                 155                 160

Phe Leu Glu Thr His Phe Leu Asp Glu Glu Val Lys Leu Ile Lys Lys
                165                 170                 175

Met Gly Asp His Leu Thr Asn Leu His Arg Leu Gly Gly Pro Glu Ala
                180                 185                 190

Gly Leu Gly Glu Tyr Leu Phe Glu Arg Leu Thr Leu Lys His Asp
                195                 200                 205

<210> SEQ ID NO 8
<211> LENGTH: 4774
<212> TYPE: PRT
<213> ORGANISM: Homo sapien

<400> SEQUENCE: 8

Arg Lys Asp Asp Ser Val Glu Pro Ser Gly Thr Lys Lys Glu Asp Leu
  1               5                  10                  15

Asn Asp Lys Glu Lys Lys Asp Glu Glu Glu Thr Pro Ala Pro Ile Tyr
                 20                  25                  30

Arg Ala Lys Ser Ile Leu Asp Ser Trp Val Trp Gly Lys Gln Pro Asp
                 35                  40                  45

Val Asn Glu Leu Lys Glu Cys Leu Ser Val Leu Val Lys Glu Gln Gln
 50                  55                  60

Ala Leu Ala Val Gln Ser Ala Thr Thr Thr Leu Ser Ala Leu Arg Leu
 65                  70                  75                  80

Lys Gln Arg Leu Val Ile Leu Glu Arg Tyr Phe Ile Ala Leu Asn Arg
                 85                  90                  95

Thr Val Phe Gln Glu Asn Val Lys Val Lys Trp Lys Ser Ser Gly Ile
                100                 105                 110

Ser Leu Pro Pro Val Asp Lys Lys Ser Ser Arg Pro Ala Gly Lys Gly
                115                 120                 125

Val Glu Gly Leu Ala Arg Val Gly Ser Arg Ala Ala Leu Ser Phe Ala
                130                 135                 140

Phe Ala Phe Leu Arg Arg Ala Trp Arg Ser Gly Glu Asp Ala Asp Leu
145                 150                 155                 160

Cys Ser Glu Leu Leu Gln Glu Ser Leu Asp Ala Leu Arg Ala Leu Pro
                165                 170                 175

Glu Ala Ser Leu Phe Asp Glu Ser Thr Val Ser Ser Val Trp Leu Glu
                180                 185                 190

Val Val Glu Arg Ala Thr Arg Phe Leu Arg Ser Val Val Thr Gly Asp
                195                 200                 205

Val His Gly Thr Pro Ala Thr Lys Gly Pro Gly Ser Ile Pro Leu Gln
                210                 215                 220
```

```
Asp Gln His Leu Ala Leu Ala Ile Leu Leu Glu Leu Ala Val Gln Arg
225                 230                 235                 240

Gly Thr Leu Ser Gln Met Leu Ser Ala Ile Leu Leu Leu Leu Gln Leu
            245                 250                 255

Trp Asp Ser Gly Ala Gln Glu Thr Asp Asn Glu Arg Ser Ala Gln Gly
            260                 265                 270

Thr Ser Ala Pro Leu Leu Pro Leu Leu Gln Arg Phe Gln Ser Ile Ile
            275                 280                 285

Cys Arg Lys Asp Ala Pro His Ser Glu Gly Asp Met His Leu Leu Ser
290                 295                 300

Gly Pro Leu Ser Pro Asn Glu Ser Phe Leu Arg Tyr Leu Thr Leu Pro
305                 310                 315                 320

Gln Asp Asn Glu Leu Ala Ile Asp Leu Arg Gln Thr Ala Val Val Val
            325                 330                 335

Met Ala His Leu Asp Arg Leu Ala Thr Pro Cys Met Pro Pro Leu Cys
            340                 345                 350

Ser Ser Pro Thr Ser His Lys Gly Ser Leu Gln Glu Val Ile Gly Trp
            355                 360                 365

Gly Leu Ile Gly Trp Lys Tyr Tyr Ala Asn Val Ile Gly Pro Ile Gln
370                 375                 380

Cys Glu Gly Leu Ala Asn Leu Gly Val Thr Gln Ile Ala Cys Ala Glu
385                 390                 395                 400

Lys Arg Phe Leu Ile Leu Ser Arg Asn Gly Arg Val Tyr Thr Gln Ala
            405                 410                 415

Tyr Asn Ser Asp Thr Leu Ala Pro Gln Leu Val Gln Gly Leu Ala Ser
            420                 425                 430

Arg Asn Ile Val Lys Ile Ala Ala His Ser Asp Gly His His Tyr Leu
            435                 440                 445

Ala Leu Ala Ala Thr Gly Glu Val Tyr Ser Trp Gly Cys Gly Asp Gly
450                 455                 460

Gly Arg Leu Gly His Gly Asp Thr Val Pro Leu Glu Glu Pro Lys Val
465                 470                 475                 480

Ile Ser Ala Phe Ser Gly Lys Gln Ala Gly Lys His Val Val His Ile
            485                 490                 495

Ala Cys Gly Ser Thr Tyr Ser Ala Ala Ile Thr Ala Glu Gly Glu Leu
            500                 505                 510

Tyr Thr Trp Gly Arg Gly Asn Tyr Gly Arg Leu Gly His Gly Ser Ser
            515                 520                 525

Glu Asp Glu Ala Ile Pro Met Leu Val Ala Gly Leu Lys Gly Leu Lys
530                 535                 540

Val Ile Asp Val Ala Cys Gly Ser Gly Asp Ala Gln Thr Leu Ala Val
545                 550                 555                 560

Thr Glu Asn Gly Gln Val Trp Ser Trp Gly Asp Gly Asp Tyr Gly Lys
            565                 570                 575

Leu Gly Arg Gly Gly Ser Asp Gly Cys Lys Thr Pro Lys Leu Ile Glu
            580                 585                 590

Lys Leu Gln Asp Leu Asp Val Val Lys Val Arg Cys Gly Ser Gln Phe
            595                 600                 605

Ser Ile Ala Leu Thr Lys Asp Gly Gln Val Tyr Ser Trp Gly Lys Gly
            610                 615                 620

Asp Asn Gln Arg Leu Gly His Gly Thr Glu Glu His Val Arg Tyr Pro
625                 630                 635                 640

Lys Leu Leu Glu Gly Leu Gln Gly Lys Lys Val Ile Asp Val Ala Ala
```

-continued

```
                645                 650                 655
Gly Ser Thr His Cys Leu Ala Leu Thr Glu Asp Ser Glu Val His Ser
            660                 665                 670
Trp Gly Ser Asn Asp Gln Cys Gln His Phe Asp Thr Leu Arg Val Thr
            675                 680                 685
Lys Pro Glu Pro Ala Ala Leu Pro Gly Leu Asp Thr Lys His Ile Val
        690                 695                 700
Gly Ile Ala Cys Gly Pro Ala Gln Ser Phe Ala Trp Ser Ser Cys Ser
705                 710                 715                 720
Glu Trp Ser Ile Gly Leu Arg Val Pro Phe Val Val Asp Ile Cys Ser
                725                 730                 735
Met Thr Phe Glu Gln Leu Asp Leu Leu Leu Arg Gln Val Ser Glu Gly
            740                 745                 750
Met Asp Gly Ser Ala Asp Trp Pro Pro Gln Glu Lys Glu Cys Val
            755                 760                 765
Ala Val Ala Thr Leu Asn Leu Leu Arg Leu Gln Leu His Ala Ala Ile
        770                 775                 780
Ser His Gln Val Asp Pro Glu Phe Leu Gly Leu Gly Leu Gly Ser Ile
785                 790                 795                 800
Leu Leu Asn Ser Leu Lys Gln Thr Val Val Thr Leu Ala Ser Ser Ala
                805                 810                 815
Gly Val Leu Ser Thr Val Gln Ser Ala Ala Gln Ala Val Leu Gln Ser
            820                 825                 830
Gly Trp Ser Val Leu Leu Pro Thr Ala Glu Arg Ala Arg Ala Leu
            835                 840                 845
Ser Ala Leu Leu Pro Cys Ala Val Ser Gly Asn Glu Val Asn Ile Ser
850                 855                 860
Pro Gly Arg Arg Phe Met Ile Asp Leu Leu Val Gly Ser Leu Met Ala
865                 870                 875                 880
Asp Gly Gly Leu Glu Ser Ala Leu His Ala Ala Ile Thr Ala Glu Ile
                885                 890                 895
Gln Asp Ile Glu Ala Lys Lys Glu Ala Gln Lys Glu Lys Glu Ile Asp
            900                 905                 910
Glu Gln Glu Ala Asn Ala Ser Thr Phe His Arg Ser Arg Thr Pro Leu
            915                 920                 925
Asp Lys Asp Leu Ile Asn Thr Gly Ile Cys Glu Ser Ser Gly Lys Gln
        930                 935                 940
Cys Leu Pro Leu Val Gln Leu Ile Gln Gln Leu Leu Arg Asn Ile Ala
945                 950                 955                 960
Ser Gln Thr Val Ala Arg Leu Lys Asp Val Ala Arg Arg Ile Ser Ser
                965                 970                 975
Cys Leu Asp Phe Glu Gln His Ser Arg Glu Arg Ser Ala Ser Leu Asp
            980                 985                 990
Leu Leu Leu Arg Phe Gln Arg Leu  Leu Ile Ser Lys Leu  Tyr Pro Gly
            995                 1000                1005
Glu Ser  Ile Gly Gln Thr Ser  Asp Ile Ser Ser Pro  Glu Leu Met
    1010                1015                1020
Gly Val  Gly Ser Leu Leu Lys  Lys Tyr Thr Ala Leu  Leu Cys Thr
    1025                1030                1035
His Ile  Gly Asp Ile Leu Pro  Val Ala Ala Ser Ile  Ala Ser Thr
    1040                1045                1050
Ser Trp  Arg His Phe Ala Glu  Val Ala Tyr Ile Val  Glu Gly Asp
    1055                1060                1065
```

```
Phe Thr Gly Val Leu Leu Pro Glu Leu Val Val Ser Ile Val Leu
    1070            1075            1080

Leu Leu Ser Lys Asn Ala Gly Leu Met Gln Glu Ala Gly Ala Val
    1085            1090            1095

Pro Leu Leu Gly Gly Leu Leu Glu His Leu Asp Arg Phe Asn His
    1100            1105            1110

Leu Ala Pro Gly Lys Glu Arg Asp Asp His Glu Leu Ala Trp
    1115            1120            1125

Pro Gly Ile Met Glu Ser Phe Phe Thr Gly Gln Asn Cys Arg Asn
    1130            1135            1140

Asn Glu Glu Val Thr Leu Ile Arg Lys Ala Asp Leu Glu Asn His
    1145            1150            1155

Asn Lys Asp Gly Gly Phe Trp Thr Val Ile Asp Gly Lys Val Tyr
    1160            1165            1170

Asp Ile Lys Asp Phe Gln Thr Gln Ser Leu Thr Gly Asn Ser Ile
    1175            1180            1185

Leu Ala Gln Phe Ala Gly Glu Asp Pro Val Val Ala Leu Glu Ala
    1190            1195            1200

Ala Leu Gln Phe Glu Asp Thr Arg Glu Ser Met His Ala Phe Cys
    1205            1210            1215

Val Gly Gln Tyr Leu Glu Pro Asp Gln Glu Ile Val Thr Ile Pro
    1220            1225            1230

Asp Leu Gly Ser Leu Ser Ser Pro Leu Ile Asp Thr Glu Arg Asn
    1235            1240            1245

Leu Gly Leu Leu Leu Gly Leu His Ala Ser Tyr Leu Ala Met Ser
    1250            1255            1260

Thr Pro Leu Ser Pro Val Glu Ile Glu Cys Ala Lys Trp Leu Gln
    1265            1270            1275

Ser Ser Ile Phe Ser Gly Gly Leu Gln Thr Ser Gln Ile His Tyr
    1280            1285            1290

Ser Tyr Asn Glu Glu Lys Asp Glu Asp His Cys Ser Ser Pro Gly
    1295            1300            1305

Gly Thr Pro Ala Ser Lys Ser Arg Leu Cys Ser His Arg Arg Ala
    1310            1315            1320

Leu Gly Asp His Ser Gln Ala Phe Leu Gln Ala Ile Ala Asp Asn
    1325            1330            1335

Asn Ile Gln Asp His Asn Val Lys Asp Phe Leu Cys Gln Ile Glu
    1340            1345            1350

Arg Tyr Cys Arg Gln Cys His Leu Thr Thr Pro Ile Met Phe Pro
    1355            1360            1365

Pro Glu His Pro Val Glu Glu Val Gly Arg Leu Leu Leu Cys Cys
    1370            1375            1380

Leu Leu Lys His Glu Asp Leu Gly His Val Ala Leu Ser Leu Val
    1385            1390            1395

His Ala Gly Ala Leu Gly Ile Glu Gln Val Lys His Arg Thr Leu
    1400            1405            1410

Pro Lys Ser Val Val Asp Val Cys Arg Val Val Tyr Gln Ala Lys
    1415            1420            1425

Cys Ser Leu Ile Lys Thr His Gln Glu Gln Gly Arg Ser Tyr Lys
    1430            1435            1440

Glu Val Cys Ala Pro Val Ile Glu Arg Leu Arg Phe Leu Phe Asn
    1445            1450            1455
```

-continued

| Glu | Leu | Arg | Pro | Ala | Val | Cys | Asn | Asp | Leu | Ser | Ile | Met | Ser | Lys |
|---|---|---|---|---|---|---|---|---|---|---|---|---|---|---|
| | 1460 | | | | 1465 | | | | 1470 | | | | | |

| Phe | Lys | Leu | Leu | Ser | Ser | Leu | Pro | Arg | Trp | Arg | Arg | Ile | Ala | Gln |
|---|---|---|---|---|---|---|---|---|---|---|---|---|---|---|
| 1475 | | | | | 1480 | | | | | 1485 | | | | |

| Lys | Ile | Ile | Arg | Glu | Arg | Arg | Lys | Lys | Arg | Val | Pro | Lys | Lys | Pro |
|---|---|---|---|---|---|---|---|---|---|---|---|---|---|---|
| | 1490 | | | | 1495 | | | | | 1500 | | | | |

| Glu | Ser | Thr | Asp | Asp | Glu | Glu | Lys | Ile | Gly | Asn | Glu | Glu | Ser | Asp |
|---|---|---|---|---|---|---|---|---|---|---|---|---|---|---|
| 1505 | | | | | 1510 | | | | | 1515 | | | | |

| Leu | Glu | Glu | Ala | Cys | Ile | Leu | Pro | His | Ser | Pro | Ile | Asn | Val | Asp |
|---|---|---|---|---|---|---|---|---|---|---|---|---|---|---|
| 1520 | | | | | 1525 | | | | | 1530 | | | | |

| Lys | Arg | Pro | Ile | Ala | Ile | Lys | Ser | Pro | Lys | Asp | Lys | Trp | Gln | Pro |
|---|---|---|---|---|---|---|---|---|---|---|---|---|---|---|
| 1535 | | | | | 1540 | | | | | 1545 | | | | |

| Leu | Leu | Ser | Thr | Val | Thr | Gly | Val | His | Lys | Tyr | Lys | Trp | Leu | Lys |
|---|---|---|---|---|---|---|---|---|---|---|---|---|---|---|
| 1550 | | | | | 1555 | | | | | 1560 | | | | |

| Gln | Asn | Val | Gln | Gly | Leu | Tyr | Pro | Gln | Ser | Pro | Leu | Leu | Ser | Thr |
|---|---|---|---|---|---|---|---|---|---|---|---|---|---|---|
| 1565 | | | | | 1570 | | | | | 1575 | | | | |

| Ile | Ala | Glu | Phe | Ala | Leu | Lys | Glu | Glu | Pro | Val | Asp | Val | Glu | Lys |
|---|---|---|---|---|---|---|---|---|---|---|---|---|---|---|
| 1580 | | | | | 1585 | | | | | 1590 | | | | |

| Met | Arg | Lys | Cys | Leu | Leu | Lys | Gln | Leu | Glu | Arg | Ala | Glu | Val | Arg |
|---|---|---|---|---|---|---|---|---|---|---|---|---|---|---|
| 1595 | | | | | 1600 | | | | | 1605 | | | | |

| Leu | Glu | Gly | Ile | Asp | Thr | Ile | Leu | Lys | Leu | Ala | Ser | Lys | Asn | Phe |
|---|---|---|---|---|---|---|---|---|---|---|---|---|---|---|
| 1610 | | | | | 1615 | | | | | 1620 | | | | |

| Leu | Leu | Pro | Ser | Val | Gln | Tyr | Ala | Met | Phe | Cys | Gly | Trp | Gln | Arg |
|---|---|---|---|---|---|---|---|---|---|---|---|---|---|---|
| 1625 | | | | | 1630 | | | | | 1635 | | | | |

| Leu | Ile | Pro | Glu | Gly | Ile | Asp | Ile | Gly | Glu | Pro | Leu | Thr | Asp | Cys |
|---|---|---|---|---|---|---|---|---|---|---|---|---|---|---|
| 1640 | | | | | 1645 | | | | | 1650 | | | | |

| Leu | Lys | Asp | Val | Asp | Leu | Ile | Pro | Pro | Phe | Asn | Arg | Met | Leu | Leu |
|---|---|---|---|---|---|---|---|---|---|---|---|---|---|---|
| 1655 | | | | | 1660 | | | | | 1665 | | | | |

| Glu | Val | Thr | Phe | Gly | Lys | Leu | Tyr | Ala | Trp | Ala | Val | Gln | Asn | Ile |
|---|---|---|---|---|---|---|---|---|---|---|---|---|---|---|
| 1670 | | | | | 1675 | | | | | 1680 | | | | |

| Arg | Asn | Val | Leu | Met | Asp | Ala | Ser | Ala | Lys | Phe | Lys | Glu | Leu | Gly |
|---|---|---|---|---|---|---|---|---|---|---|---|---|---|---|
| 1685 | | | | | 1690 | | | | | 1695 | | | | |

| Ile | Gln | Pro | Val | Pro | Leu | Gln | Thr | Ile | Thr | Asn | Glu | Asn | Pro | Ser |
|---|---|---|---|---|---|---|---|---|---|---|---|---|---|---|
| 1700 | | | | | 1705 | | | | | 1710 | | | | |

| Gly | Pro | Ser | Leu | Gly | Thr | Ile | Pro | Gln | Ala | Arg | Phe | Leu | Leu | Val |
|---|---|---|---|---|---|---|---|---|---|---|---|---|---|---|
| 1715 | | | | | 1720 | | | | | 1725 | | | | |

| Met | Leu | Ser | Met | Leu | Thr | Leu | Gln | His | Gly | Ala | Asn | Asn | Leu | Asp |
|---|---|---|---|---|---|---|---|---|---|---|---|---|---|---|
| 1730 | | | | | 1735 | | | | | 1740 | | | | |

| Leu | Leu | Leu | Asn | Ser | Gly | Met | Leu | Ala | Leu | Thr | Gln | Thr | Ala | Leu |
|---|---|---|---|---|---|---|---|---|---|---|---|---|---|---|
| 1745 | | | | | 1750 | | | | | 1755 | | | | |

| Arg | Leu | Ile | Gly | Pro | Ser | Cys | Asp | Asn | Val | Glu | Glu | Asp | Met | Asn |
|---|---|---|---|---|---|---|---|---|---|---|---|---|---|---|
| 1760 | | | | | 1765 | | | | | 1770 | | | | |

| Ala | Ser | Ala | Gln | Gly | Ala | Ser | Ala | Thr | Val | Leu | Glu | Glu | Thr | Arg |
|---|---|---|---|---|---|---|---|---|---|---|---|---|---|---|
| 1775 | | | | | 1780 | | | | | 1785 | | | | |

| Lys | Glu | Thr | Ala | Pro | Val | Gln | Leu | Pro | Val | Ser | Gly | Pro | Glu | Leu |
|---|---|---|---|---|---|---|---|---|---|---|---|---|---|---|
| 1790 | | | | | 1795 | | | | | 1800 | | | | |

| Ala | Ala | Met | Met | Lys | Ile | Gly | Thr | Arg | Val | Met | Arg | Gly | Val | Asp |
|---|---|---|---|---|---|---|---|---|---|---|---|---|---|---|
| 1805 | | | | | 1810 | | | | | 1815 | | | | |

| Trp | Lys | Trp | Gly | Asp | Gln | Asp | Gly | Pro | Pro | Pro | Gly | Leu | Gly | Arg |
|---|---|---|---|---|---|---|---|---|---|---|---|---|---|---|
| 1820 | | | | | 1825 | | | | | 1830 | | | | |

| Val | Ile | Gly | Glu | Leu | Gly | Glu | Asp | Gly | Trp | Ile | Arg | Val | Gln | Trp |
|---|---|---|---|---|---|---|---|---|---|---|---|---|---|---|
| 1835 | | | | | 1840 | | | | | 1845 | | | | |

| Asp | Thr | Gly | Ser | Thr | Asn | Ser | Tyr | Arg | Met | Gly | Lys | Glu | Gly | Lys |
|---|---|---|---|---|---|---|---|---|---|---|---|---|---|---|

-continued

```
            1850                1855                1860

Tyr  Asp  Leu  Lys  Leu  Ala  Glu  Leu  Pro  Ala  Ala  Gln  Pro  Ser
            1865                1870                1875

Ala  Glu  Asp  Ser  Asp  Thr  Glu  Asp  Ser  Glu  Ala  Glu  Gln  Thr
            1880                1885                1890

Glu  Arg  Asn  Ile  His  Pro  Thr  Ala  Met  Met  Phe  Thr  Ser  Thr  Ile
            1895                1900                1905

Asn  Leu  Leu  Gln  Thr  Leu  Cys  Leu  Ser  Ala  Gly  Val  His  Ala  Glu
            1910                1915                1920

Ile  Met  Gln  Ser  Glu  Ala  Thr  Lys  Thr  Leu  Cys  Gly  Leu  Leu  Arg
            1925                1930                1935

Met  Leu  Val  Glu  Ser  Gly  Thr  Thr  Asp  Lys  Thr  Ser  Ser  Pro  Asn
            1940                1945                1950

Arg  Leu  Val  Tyr  Arg  Glu  Gln  His  Arg  Ser  Trp  Cys  Thr  Leu  Gly
            1955                1960                1965

Phe  Val  Arg  Ser  Ile  Ala  Leu  Thr  Pro  Gln  Val  Cys  Gly  Ala  Leu
            1970                1975                1980

Ser  Ser  Pro  Gln  Trp  Ile  Thr  Leu  Leu  Met  Lys  Val  Val  Glu  Gly
            1985                1990                1995

His  Ala  Pro  Phe  Thr  Ala  Thr  Ser  Leu  Gln  Arg  Gln  Ile  Leu  Ala
            2000                2005                2010

Val  His  Leu  Leu  Gln  Ala  Val  Leu  Pro  Ser  Trp  Asp  Lys  Thr  Glu
            2015                2020                2025

Arg  Ala  Arg  Asp  Met  Lys  Cys  Leu  Val  Glu  Lys  Leu  Phe  Asp  Phe
            2030                2035                2040

Leu  Gly  Ser  Leu  Leu  Thr  Thr  Cys  Ser  Ser  Asp  Val  Pro  Leu  Leu
            2045                2050                2055

Arg  Glu  Ser  Thr  Leu  Arg  Arg  Arg  Arg  Val  Arg  Pro  Gln  Ala  Ser
            2060                2065                2070

Leu  Thr  Ala  Thr  His  Ser  Ser  Thr  Leu  Ala  Glu  Glu  Val  Val  Ala
            2075                2080                2085

Leu  Leu  Arg  Thr  Leu  His  Ser  Leu  Thr  Gln  Trp  Asn  Gly  Leu  Ile
            2090                2095                2100

Asn  Lys  Tyr  Ile  Asn  Ser  Gln  Leu  Arg  Ser  Ile  Thr  His  Ser  Phe
            2105                2110                2115

Val  Gly  Arg  Pro  Ser  Glu  Gly  Ala  Gln  Leu  Glu  Asp  Tyr  Phe  Pro
            2120                2125                2130

Asp  Ser  Glu  Asn  Pro  Glu  Val  Gly  Gly  Leu  Met  Ala  Val  Leu  Ala
            2135                2140                2145

Val  Ile  Gly  Gly  Ile  Asp  Gly  Arg  Leu  Arg  Leu  Gly  Gly  Gln  Val
            2150                2155                2160

Met  His  Asp  Glu  Phe  Gly  Glu  Gly  Thr  Val  Thr  Arg  Ile  Thr  Pro
            2165                2170                2175

Lys  Gly  Lys  Ile  Thr  Val  Gln  Phe  Ser  Asp  Met  Arg  Thr  Cys  Arg
            2180                2185                2190

Val  Cys  Pro  Leu  Asn  Gln  Leu  Lys  Pro  Leu  Pro  Ala  Val  Ala  Phe
            2195                2200                2205

Asn  Val  Asn  Asn  Leu  Pro  Phe  Thr  Glu  Pro  Met  Leu  Ser  Val  Trp
            2210                2215                2220

Ala  Gln  Leu  Val  Asn  Leu  Ala  Gly  Ser  Lys  Leu  Glu  Lys  His  Lys
            2225                2230                2235

Ile  Lys  Lys  Ser  Thr  Lys  Gln  Ala  Phe  Ala  Gly  Gln  Val  Asp  Leu
            2240                2245                2250
```

Asp Leu Leu Arg Cys Gln Gln Leu Lys Leu Tyr Ile Leu Lys Ala
2255                    2260                2265

Gly Arg Ala Leu Leu Ser His Gln Asp Lys Leu Arg Gln Ile Leu
2270                    2275                2280

Ser Gln Pro Ala Val Gln Glu Thr Gly Thr Val His Thr Asp Asp
2285                    2290                2295

Gly Ala Val Val Ser Pro Asp Leu Gly Asp Met Ser Pro Glu Gly
2300                    2305                2310

Pro Gln Pro Pro Met Ile Leu Leu Gln Gln Leu Leu Ala Ser Ala
2315                    2320                2325

Thr Gln Pro Ser Pro Val Lys Ala Ile Phe Asp Lys Gln Glu Leu
2330                    2335                2340

Glu Ala Ala Ala Leu Ala Val Cys Gln Cys Leu Ala Val Glu Ser
2345                    2350                2355

Thr His Pro Ser Ser Pro Gly Phe Glu Asp Cys Ser Ser Ser Glu
2360                    2365                2370

Ala Thr Thr Pro Val Ala Val Gln His Ile Arg Pro Ala Arg Val
2375                    2380                2385

Lys Arg Arg Lys Gln Ser Pro Val Pro Ala Leu Pro Ile Val Val
2390                    2395                2400

Gln Leu Met Glu Met Gly Phe Ser Arg Arg Asn Ile Glu Phe Ala
2405                    2410                2415

Leu Lys Ser Leu Thr Gly Ala Ser Gly Asn Ala Ser Ser Leu Pro
2420                    2425                2430

Gly Val Glu Ala Leu Val Gly Trp Leu Leu Asp His Ser Asp Ile
2435                    2440                2445

Gln Val Thr Glu Leu Ser Asp Ala Asp Thr Val Ser Asp Glu Tyr
2450                    2455                2460

Ser Asp Glu Glu Val Val Glu Asp Val Asp Asp Ala Ala Tyr Ser
2465                    2470                2475

Met Ser Thr Gly Ala Val Val Thr Glu Ser Gln Thr Tyr Lys Lys
2480                    2485                2490

Arg Ala Asp Phe Leu Ser Asn Asp Asp Tyr Ala Val Tyr Val Arg
2495                    2500                2505

Glu Asn Ile Gln Val Gly Met Met Val Arg Cys Cys Arg Ala Tyr
2510                    2515                2520

Glu Glu Val Cys Glu Gly Asp Val Gly Lys Val Ile Lys Leu Asp
2525                    2530                2535

Arg Asp Gly Leu His Asp Leu Asn Val Gln Cys Asp Trp Gln Gln
2540                    2545                2550

Lys Gly Gly Thr Tyr Trp Val Arg Tyr Ile His Val Glu Leu Ile
2555                    2560                2565

Gly Tyr Pro Pro Pro Ser Ser Ser His Ile Lys Ile Gly Asp
2570                    2575                2580

Lys Val Arg Val Lys Ala Ser Val Thr Thr Pro Lys Tyr Lys Trp
2585                    2590                2595

Gly Ser Val Thr His Gln Ser Val Gly Val Val Lys Ala Phe Ser
2600                    2605                2610

Ala Asn Gly Lys Asp Ile Ile Val Asp Phe Pro Gln Gln Ser His
2615                    2620                2625

Trp Thr Gly Leu Leu Ser Glu Met Glu Leu Val Pro Ser Ile His
2630                    2635                2640

-continued

| | | | | | | | | | | |
|---|---|---|---|---|---|---|---|---|---|---|
|Pro|Gly|Val|Thr|Cys|Asp|Gly|Cys|Gln|Met|Phe|Pro|Ile|Asn|Gly|
|2645| | | |2650| | | | |2655| | | | | |

Pro Gly Val Thr Cys Asp Gly Cys Gln Met Phe Pro Ile Asn Gly
    2645              2650              2655

Ser Arg Phe Lys Cys Arg Asn Cys Asp Asp Phe Asp Phe Cys Glu
    2660              2665              2670

Thr Cys Phe Lys Thr Lys Lys His Asn Thr Arg His Thr Phe Gly
    2675              2680              2685

Arg Ile Asn Glu Pro Gly Gln Ser Ala Val Phe Cys Gly Arg Ser
    2690              2695              2700

Gly Lys Gln Leu Lys Arg Cys His Ser Ser Gln Pro Gly Met Leu
    2705              2710              2715

Leu Asp Ser Trp Ser Arg Met Val Lys Ser Leu Asn Val Ser Ser
    2720              2725              2730

Ser Val Asn Gln Ala Ser Arg Leu Ile Asp Gly Ser Glu Pro Cys
    2735              2740              2745

Trp Gln Ser Ser Gly Ser Gln Gly Lys His Trp Ile Arg Leu Glu
    2750              2755              2760

Ile Phe Pro Asp Val Leu Val His Arg Leu Lys Met Ile Val Asp
    2765              2770              2775

Pro Ala Asp Ser Ser Tyr Met Pro Ser Leu Val Val Val Ser Gly
    2780              2785              2790

Gly Asn Ser Leu Asn Asn Leu Ile Glu Leu Lys Thr Ile Asn Ile
    2795              2800              2805

Asn Pro Ser Asp Thr Thr Val Pro Leu Leu Asn Asp Cys Thr Glu
    2810              2815              2820

Tyr His Arg Tyr Ile Glu Ile Ala Ile Lys Gln Cys Arg Ser Ser
    2825              2830              2835

Gly Ile Asp Cys Lys Ile His Gly Leu Ile Leu Gly Arg Ile
    2840              2845              2850

Arg Ala Glu Glu Glu Asp Leu Ala Ala Val Pro Phe Leu Ala Ser
    2855              2860              2865

Asp Asn Glu Glu Glu Asp Glu Lys Gly Asn Ser Gly Ser Leu
    2870              2875              2880

Ile Arg Lys Lys Ala Ala Gly Leu Glu Ser Ala Ala Thr Ile Arg
    2885              2890              2895

Thr Lys Val Phe Val Trp Gly Leu Asn Asp Lys Asp Gln Leu Gly
    2900              2905              2910

Gly Leu Lys Gly Ser Lys Ile Lys Val Pro Ser Phe Ser Glu Thr
    2915              2920              2925

Leu Ser Ala Leu Asn Val Val Gln Val Ala Gly Gly Ser Lys Ser
    2930              2935              2940

Leu Phe Ala Val Thr Val Glu Gly Lys Val Tyr Ala Cys Gly Glu
    2945              2950              2955

Ala Thr Asn Gly Arg Leu Gly Leu Gly Ile Ser Ser Gly Thr Val
    2960              2965              2970

Pro Ile Pro Arg Gln Ile Thr Ala Leu Ser Ser Tyr Val Val Lys
    2975              2980              2985

Lys Val Ala Val His Ser Gly Gly Arg His Ala Thr Ala Leu Thr
    2990              2995              3000

Val Asp Gly Lys Val Phe Ser Trp Gly Glu Gly Asp Asp Gly Lys
    3005              3010              3015

Leu Gly His Phe Ser Arg Met Asn Cys Asp Lys Pro Arg Leu Ile
    3020              3025              3030

Glu Ala Leu Lys Thr Lys Arg Ile Arg Asp Ile Ala Cys Gly Ser

```
                3035                3040                3045
Ser His Ser Ala Ala Leu Thr Ser Ser Gly Glu Leu Tyr Thr Trp
    3050                3055                3060
Gly Leu Gly Glu Tyr Gly Arg Leu Gly His Gly Asp Asn Thr Thr
    3065                3070                3075
Gln Leu Lys Pro Lys Met Val Lys Val Leu Leu Gly His Arg Val
    3080                3085                3090
Ile Gln Val Ala Cys Gly Ser Arg Asp Ala Gln Thr Leu Ala Leu
    3095                3100                3105
Thr Asp Glu Gly Leu Val Phe Ser Trp Gly Asp Gly Asp Phe Gly
    3110                3115                3120
Lys Leu Gly Arg Gly Gly Ser Glu Gly Cys Asn Ile Pro Gln Asn
    3125                3130                3135
Ile Glu Arg Leu Asn Gly Gln Gly Val Cys Gln Ile Glu Cys Gly
    3140                3145                3150
Ala Gln Phe Ser Leu Ala Leu Thr Lys Ser Gly Val Val Trp Thr
    3155                3160                3165
Trp Gly Lys Gly Asp Tyr Phe Arg Leu Gly His Gly Ser Asp Val
    3170                3175                3180
His Val Arg Lys Pro Gln Val Val Glu Gly Leu Arg Gly Lys Lys
    3185                3190                3195
Ile Val His Val Ala Val Gly Ala Leu His Cys Leu Ala Val Thr
    3200                3205                3210
Asp Ser Gly Gln Val Tyr Ala Trp Gly Asp Asn Asp His Gly Gln
    3215                3220                3225
Gln Gly Asn Gly Thr Thr Thr Val Asn Arg Lys Pro Thr Leu Val
    3230                3235                3240
Gln Gly Leu Glu Gly Gln Lys Ile Thr Arg Val Ala Cys Gly Ser
    3245                3250                3255
Ser His Ser Val Ala Trp Thr Thr Val Asp Val Ala Thr Pro Ser
    3260                3265                3270
Val His Glu Pro Val Leu Phe Gln Thr Ala Arg Asp Pro Leu Gly
    3275                3280                3285
Ala Ser Tyr Leu Gly Val Pro Ser Asp Ala Asp Ser Ser Ala Ala
    3290                3295                3300
Ser Asn Lys Ile Ser Gly Ala Ser Asn Ser Lys Pro Asn Arg Pro
    3305                3310                3315
Ser Leu Ala Lys Ile Leu Leu Ser Leu Asp Gly Asn Leu Ala Lys
    3320                3325                3330
Gln Gln Ala Leu Ser His Ile Leu Thr Ala Leu Gln Ile Met Tyr
    3335                3340                3345
Ala Arg Asp Ala Val Val Gly Ala Leu Met Pro Ala Ala Met Ile
    3350                3355                3360
Ala Pro Val Glu Cys Pro Ser Phe Ser Ser Ala Ala Pro Ser Asp
    3365                3370                3375
Ala Ser Ala Met Ala Ser Pro Met Asn Gly Glu Glu Cys Met Leu
    3380                3385                3390
Ala Val Asp Ile Glu Asp Arg Leu Ser Pro Asn Pro Trp Gln Glu
    3395                3400                3405
Lys Arg Glu Ile Val Ser Ser Glu Asp Ala Val Thr Pro Ser Ala
    3410                3415                3420
Val Thr Pro Ser Ala Pro Ser Ala Ser Ala Arg Pro Phe Ile Pro
    3425                3430                3435
```

```
Val Thr Asp Asp Leu Gly Ala Ala Ser Ile Ile Ala Glu Thr Met
    3440             3445             3450

Thr Lys Thr Lys Glu Asp Val Glu Ser Gln Asn Lys Ala Ala Gly
3455             3460             3465

Pro Glu Pro Gln Ala Leu Asp Glu Phe Thr Ser Leu Leu Ile Ala
    3470             3475             3480

Asp Asp Thr Arg Val Val Asp Leu Leu Lys Leu Ser Val Cys
3485             3490             3495

Ser Arg Ala Gly Asp Arg Gly Arg Asp Val Leu Ser Ala Val Leu
3500             3505             3510

Ser Gly Met Gly Thr Ala Tyr Pro Gln Val Ala Asp Met Leu Leu
3515             3520             3525

Glu Leu Cys Val Thr Glu Leu Glu Asp Val Ala Thr Asp Ser Gln
3530             3535             3540

Ser Gly Arg Leu Ser Ser Gln Pro Val Val Glu Ser Ser His
3545             3550             3555

Pro Tyr Thr Asp Asp Thr Ser Thr Ser Gly Thr Val Lys Ile Pro
    3560             3565             3570

Gly Ala Glu Gly Leu Arg Val Glu Phe Asp Arg Gln Cys Ser Thr
3575             3580             3585

Glu Arg Arg His Asp Pro Leu Thr Val Met Asp Gly Val Asn Arg
3590             3595             3600

Ile Val Ser Val Arg Ser Gly Arg Glu Trp Ser Asp Trp Ser Ser
    3605             3610             3615

Glu Leu Arg Ile Pro Gly Asp Glu Leu Lys Trp Lys Phe Ile Ser
3620             3625             3630

Asp Gly Ser Val Asn Gly Trp Gly Trp Arg Phe Thr Val Tyr Pro
3635             3640             3645

Ile Met Pro Ala Ala Gly Pro Lys Glu Leu Leu Ser Asp Arg Cys
    3650             3655             3660

Val Leu Ser Cys Pro Ser Met Asp Leu Val Thr Cys Leu Leu Asp
3665             3670             3675

Phe Arg Leu Asn Leu Ala Ser Asn Arg Ser Ile Val Pro Arg Leu
3680             3685             3690

Ala Ala Ser Leu Ala Ala Cys Ala Gln Leu Ser Ala Leu Ala Ala
3695             3700             3705

Ser His Arg Met Trp Ala Leu Gln Arg Leu Arg Lys Leu Leu Thr
    3710             3715             3720

Thr Glu Phe Gly Gln Ser Ile Asn Ile Asn Arg Leu Leu Gly Glu
3725             3730             3735

Asn Asp Gly Glu Thr Arg Ala Leu Ser Phe Thr Gly Ser Ala Leu
3740             3745             3750

Ala Ala Leu Val Lys Gly Leu Pro Glu Ala Leu Gln Arg Gln Phe
3755             3760             3765

Glu Tyr Glu Asp Pro Ile Val Arg Gly Gly Lys Gln Leu Leu His
    3770             3775             3780

Ser Pro Phe Phe Lys Val Leu Val Ala Leu Ala Cys Asp Leu Glu
3785             3790             3795

Leu Asp Thr Leu Pro Cys Cys Ala Glu Thr His Lys Trp Ala Trp
3800             3805             3810

Phe Arg Arg Tyr Cys Met Ala Ser Arg Val Ala Val Ala Leu Asp
3815             3820             3825
```

-continued

Lys Arg Thr Pro Leu Pro Arg Leu Phe Leu Asp Glu Val Ala Lys
3830            3835                3840

Lys Ile Arg Glu Leu Met Ala Asp Ser Glu Asn Met Asp Val Leu
3845            3850                3855

His Glu Ser His Asp Ile Phe Lys Arg Glu Gln Asp Glu Gln Leu
3860            3865                3870

Val Gln Trp Met Asn Arg Arg Pro Asp Asp Trp Thr Leu Ser Ala
3875            3880                3885

Gly Gly Ser Gly Thr Ile Tyr Gly Trp Gly His Asn His Arg Gly
3890            3895                3900

Gln Leu Gly Gly Ile Glu Gly Ala Lys Val Lys Val Pro Thr Pro
3905            3910                3915

Cys Glu Ala Leu Ala Thr Leu Arg Pro Val Gln Leu Ile Gly Gly
3920            3925                3930

Glu Gln Thr Leu Phe Ala Val Thr Ala Asp Gly Lys Leu Tyr Ala
3935            3940                3945

Thr Gly Tyr Gly Ala Gly Gly Arg Leu Gly Ile Gly Gly Thr Glu
3950            3955                3960

Ser Val Ser Thr Pro Thr Leu Leu Glu Ser Ile Gln His Val Phe
3965            3970                3975

Ile Lys Lys Val Ala Val Asn Ser Gly Gly Lys His Cys Leu Ala
3980            3985                3990

Leu Ser Ser Glu Gly Glu Val Tyr Ser Trp Gly Glu Ala Glu Asp
3995            4000                4005

Gly Lys Leu Gly His Gly Asn Arg Ser Pro Cys Asp Arg Pro Arg
4010            4015                4020

Val Ile Glu Ser Leu Arg Gly Ile Glu Val Val Asp Val Ala Ala
4025            4030                4035

Gly Gly Ala His Ser Ala Cys Val Thr Ala Ala Gly Asp Leu Tyr
4040            4045                4050

Thr Trp Gly Lys Gly Arg Tyr Gly Arg Leu Gly His Ser Asp Ser
4055            4060                4065

Glu Asp Gln Leu Lys Pro Lys Leu Val Glu Ala Leu Gln Gly His
4070            4075                4080

Arg Val Val Asp Ile Ala Cys Gly Ser Gly Asp Ala Gln Thr Leu
4085            4090                4095

Cys Leu Thr Asp Asp Asp Thr Val Trp Ser Trp Gly Asp Gly Asp
4100            4105                4110

Tyr Gly Lys Leu Gly Arg Gly Gly Ser Asp Gly Cys Lys Val Pro
4115            4120                4125

Met Lys Ile Asp Ser Leu Thr Gly Leu Gly Val Val Lys Val Glu
4130            4135                4140

Cys Gly Ser Gln Phe Ser Val Ala Leu Thr Lys Ser Gly Ala Val
4145            4150                4155

Tyr Thr Trp Gly Lys Gly Asp Tyr His Arg Leu Gly His Gly Ser
4160            4165                4170

Asp Asp His Val Arg Arg Pro Arg Gln Val Gln Gly Leu Gln Gly
4175            4180                4185

Lys Lys Val Ile Ala Ile Ala Thr Gly Ser Leu His Cys Val Cys
4190            4195                4200

Cys Thr Glu Asp Gly Glu Val Tyr Thr Trp Gly Asp Asn Asp Glu
4205            4210                4215

Gly Gln Leu Gly Asp Gly Thr Thr Asn Ala Ile Gln Arg Pro Arg

```
                4220                4225               4230

Leu Val Ala Ala Leu Gln Gly Lys Lys Val Asn Arg Val Ala Cys
            4235                4240                4245

Gly Ser Ala His Thr Leu Ala Trp Ser Thr Ser Lys Pro Ala Ser
            4250                4255                4260

Ala Gly Lys Leu Pro Ala Gln Val Pro Met Glu Tyr Asn His Leu
            4265                4270                4275

Gln Glu Ile Pro Ile Ile Ala Leu Arg Asn Arg Leu Leu Leu Leu
            4280                4285                4290

His His Leu Ser Glu Leu Phe Cys Pro Cys Ile Pro Met Phe Asp
            4295                4300                4305

Leu Glu Gly Ser Leu Asp Glu Thr Gly Leu Gly Pro Ser Val Gly
            4310                4315                4320

Phe Asp Thr Leu Arg Gly Ile Leu Ile Ser Gln Gly Lys Glu Ala
            4325                4330                4335

Ala Phe Arg Lys Val Val Gln Ala Thr Met Val Arg Asp Arg Gln
            4340                4345                4350

His Gly Pro Val Val Glu Leu Asn Arg Ile Gln Val Lys Arg Ser
            4355                4360                4365

Arg Ser Lys Gly Gly Leu Ala Gly Pro Asp Gly Thr Lys Ser Val
            4370                4375                4380

Phe Gly Gln Met Cys Ala Lys Met Ser Ser Phe Gly Pro Asp Ser
            4385                4390                4395

Leu Leu Leu Pro His Arg Val Trp Lys Val Lys Phe Val Gly Glu
            4400                4405                4410

Ser Val Asp Asp Cys Gly Gly Gly Tyr Ser Glu Ser Ile Ala Glu
            4415                4420                4425

Ile Cys Glu Glu Leu Gln Asn Gly Leu Thr Pro Leu Leu Ile Val
            4430                4435                4440

Thr Pro Asn Gly Arg Asp Glu Ser Gly Ala Asn Arg Asp Cys Tyr
            4445                4450                4455

Leu Leu Ser Pro Ala Ala Arg Ala Pro Val His Ser Ser Met Phe
            4460                4465                4470

Arg Phe Leu Gly Val Leu Leu Gly Ile Ala Ile Arg Thr Gly Ser
            4475                4480                4485

Pro Leu Ser Leu Asn Leu Ala Glu Pro Val Trp Lys Gln Leu Ala
            4490                4495                4500

Gly Met Ser Leu Thr Ile Ala Asp Leu Ser Glu Val Asp Lys Asp
            4505                4510                4515

Phe Ile Pro Gly Leu Met Tyr Ile Arg Asp Asn Glu Ala Thr Ser
            4520                4525                4530

Glu Glu Phe Glu Ala Met Ser Leu Pro Phe Thr Val Pro Ser Ala
            4535                4540                4545

Ser Gly Gln Asp Ile Gln Leu Ser Ser Lys His Thr His Ile Thr
            4550                4555                4560

Leu Asp Asn Arg Ala Glu Tyr Val Arg Leu Ala Ile Asn Tyr Arg
            4565                4570                4575

Leu His Glu Phe Asp Glu Gln Val Ala Ala Val Arg Glu Gly Met
            4580                4585                4590

Ala Arg Val Val Pro Val Pro Leu Leu Ser Leu Phe Thr Gly Tyr
            4595                4600                4605

Glu Leu Glu Thr Met Val Cys Gly Ser Pro Asp Ile Pro Leu His
            4610                4615                4620
```

```
Leu Leu Lys Ser Val Ala Thr Tyr Lys Gly Ile Glu Pro Ser Ala
            4625            4630            4635

Ser Leu Ile Gln Trp Phe Trp Glu Val Met Glu Ser Phe Ser Asn
    4640            4645            4650

Thr Glu Arg Ser Leu Phe Leu Arg Phe Val Trp Gly Arg Thr Arg
    4655            4660            4665

Leu Pro Arg Thr Ile Ala Asp Phe Arg Gly Arg Asp Phe Val Ile
    4670            4675            4680

Gln Val Leu Asp Lys Tyr Asn Pro Pro Asp His Phe Leu Pro Glu
    4685            4690            4695

Ser Tyr Thr Cys Phe Phe Leu Leu Lys Leu Pro Arg Tyr Ser Cys
    4700            4705            4710

Lys Gln Val Leu Glu Glu Lys Leu Lys Tyr Ala Ile His Phe Cys
    4715            4720            4725

Lys Ser Ile Asp Thr Asp Asp Tyr Ala Arg Ile Ala Leu Thr Gly
    4730            4735            4740

Glu Pro Ala Ala Asp Asp Ser Ser Asp Ser Asp Asn Glu Asp
    4745            4750            4755

Val Asp Ser Phe Ala Ser Asp Ser Thr Gln Asp Tyr Leu Thr Gly
    4760            4765            4770

His

<210> SEQ ID NO 9
<211> LENGTH: 117
<212> TYPE: PRT
<213> ORGANISM: Homo sapien

<400> SEQUENCE: 9

Met Lys Trp Met Phe Lys Glu Asp His Ser Leu Glu His Arg Cys Val
1               5                   10                  15

Glu Ser Ala Lys Ile Arg Ala Lys Tyr Pro Asp Arg Val Pro Val Ile
                20                  25                  30

Val Glu Lys Val Ser Gly Ser Gln Ile Val Asp Ile Asp Lys Arg Lys
            35                  40                  45

Tyr Leu Val Pro Ser Asp Ile Thr Val Ala Gln Phe Met Trp Ile Ile
        50                  55                  60

Arg Lys Arg Ile Gln Leu Pro Ser Glu Lys Ala Ile Phe Leu Phe Val
65                  70                  75                  80

Asp Lys Thr Val Pro Gln Ser Ser Leu Thr Met Gly Gln Leu Tyr Glu
                85                  90                  95

Lys Glu Lys Asp Glu Asp Gly Phe Leu Tyr Val Ala Tyr Ser Gly Glu
            100                 105                 110

Asn Thr Phe Gly Phe
        115

<210> SEQ ID NO 10
<211> LENGTH: 125
<212> TYPE: PRT
<213> ORGANISM: Homo sapien

<400> SEQUENCE: 10

Met Lys Met Arg Phe Phe Ser Ser Pro Cys Gly Lys Ala Ala Val Asp
1               5                   10                  15

Pro Ala Asp Arg Cys Lys Glu Val Gln Gln Ile Arg Asp Gln His Pro
                20                  25                  30
```

Ser Lys Ile Pro Val Ile Ile Glu Arg Tyr Lys Gly Glu Lys Gln Leu
            35                  40                  45

Pro Val Leu Asp Lys Thr Lys Phe Leu Val Pro Asp His Val Asn Met
 50                  55                  60

Ser Glu Leu Val Lys Ile Ile Arg Arg Leu Gln Leu Asn Pro Thr
65                  70                  75                  80

Gln Ala Phe Phe Leu Leu Val Asn Gln His Ser Met Val Ser Val Ser
                85                  90                  95

Thr Pro Ile Ala Asp Ile Tyr Glu Gln Glu Lys Asp Glu Asp Gly Phe
            100                 105                 110

Leu Tyr Met Val Tyr Ala Ser Gln Glu Thr Phe Gly Phe
        115                 120                 125

<210> SEQ ID NO 11
<211> LENGTH: 25
<212> TYPE: PRT
<213> ORGANISM: Homo sapien

<400> SEQUENCE: 11

Ser Phe Gln Val Ile Lys Asn Ser Pro Leu Ser Glu Trp Leu Ile Arg
1               5                   10                  15

Pro Pro Tyr Lys Glu Gly Ser Pro Lys
            20                  25

<210> SEQ ID NO 12
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 12
cccaggaagt attacttaat t                                             21

<210> SEQ ID NO 13
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 13
gctggcaaac agaagtttaa a                                             21

<210> SEQ ID NO 14
<211> LENGTH: 22
<212> TYPE: DNA
<213> ORGANISM: Artificial Sequence
<220> FEATURE:
<223> OTHER INFORMATION: antisense oligonucleotide

<400> SEQUENCE: 14
gcaagctgac cctgaagttc at                                            22

<210> SEQ ID NO 15
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 15
acaaagaucu agccaauca                                                19

```
<210> SEQ ID NO 16
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 16
gaccuuauuu aucagcuua                                                  19

<210> SEQ ID NO 17
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 17
gcacagagua ucacaggua                                                  19

<210> SEQ ID NO 18
<211> LENGTH: 19
<212> TYPE: RNA
<213> ORGANISM: Artificial Sequence
<220> FEATURE:
<223> OTHER INFORMATION: antisense oligonucleotide

<400> SEQUENCE: 18
cgaugaaggu uugguauuu                                                  19

<210> SEQ ID NO 19
<211> LENGTH: 7
<212> TYPE: PRT
<213> ORGANISM: Homo sapien

<400> SEQUENCE: 19

Ile Pro Val Ile Ile Glu Arg
1               5

<210> SEQ ID NO 20
<211> LENGTH: 14
<212> TYPE: PRT
<213> ORGANISM: Homo sapien

<400> SEQUENCE: 20

Phe Leu Val Pro Asp His Val Asn Met Ser Glu Leu Ile Lys
1               5                   10

<210> SEQ ID NO 21
<211> LENGTH: 1245
<212> TYPE: DNA
<213> ORGANISM: Homo sapien

<400> SEQUENCE: 21
ataagagacc acaagcgacc cgcagggcca gacgttcttc gccgagagtc gtcggggttt     60
cctgcttcaa cagtgcttgg acggaacccg gcgctcgttc cccacccggg ccggccgccc    120
atagccagcc ctccgtcacc tcttcaccgc acctcggac tgcccaagg ccccgccgc      180 cgctccagcg ccgcgcagcc accgccgccg ccgccgcctc tccttagtcg ccgccatgac    240
gaccgcgtcc acctcgcagg tgcgccagaa ctaccaccag gactcagagg ccgccatcaa    300
ccgccagatc aacctggagc tctacgcctc ctacgtttac ctgtccatgt cttactactt    360
```

| | |
|---|---|
| tgaccgcgat gatgtggctt tgaagaactt tgccaaatac tttcttcacc aatctcatga | 420 |
| ggagagggaa catgctgaga aactgatgaa gctgcagaac caacgaggtg gccgaatctt | 480 |
| ccttcaggat atcaagaaac cagactgtga tgactgggag agcgggctga atgcaatgga | 540 |
| gtgtgcatta catttggaaa aaaatgtgaa tcagtcacta ctggaactgc acaaactggc | 600 |
| cactgacaaa aatgaccccc atttgtgtga cttcattgag acacattacc tgaatgagca | 660 |
| ggtgaaagcc atcaaagaat gggtgacca cgtgaccaac ttgcgcaaga tgggagcgcc | 720 |
| cgaatctggc ttggcggaat atctctttga caagcacacc ctgggagaca gtgataatga | 780 |
| aagctaagcc tcgggctaat ttccccatag ccgtggggtg acttccctgg tcaccaaggc | 840 |
| agtgcatgca tgttggggtt tccttacct tttctataag ttgtaccaaa acatccactt | 900 |
| aagttctttg atttgtacca ttccttcaaa taaagaaatt tggtacccag tgttgtctt | 960 |
| tgaggtcttg ggatgaatca gaaatctatc caggctatct tccagattcc ttaagtgccg | 1020 |
| ttgttcagtt ctaatcacac taatcaaaaa gaaacgagta tttgtattta ttaaaactcat | 1080 |
| tagtttgggc agtatactaa ggtgtggctg tcttggattc agatagaact aagggttccc | 1140 |
| gactctgaat ccagagtctg agttaaatgt ttccaatggt tcagtctagc tttcacagtt | 1200 |
| tttatgaata aaaggcatta aaggctgaaa aaaaaaaaa aaaaa | 1245 |

<210> SEQ ID NO 22
<211> LENGTH: 889
<212> TYPE: DNA
<213> ORGANISM: Homo sapien

<400> SEQUENCE: 22

| | |
|---|---|
| gcagttcggc ggtcccgcgg gtctgtctct tgcttcaaca gtgtttggac ggaacagatc | 60 |
| cggggactct cttccagcct ccgaccgccc tccgatttcc tctccgcttg caacctccgg | 120 |
| gaccatcttc tcggccatct cctgcttctg ggacctgcca gcaccgtttt tgtggttagc | 180 |
| tccttcttgc caaccaacca tgagctccca gattcgtcag aattattcca ccgacgtgga | 240 |
| ggcagccgtc aacagcctgg tcaatttgta cctgcaggcc tcctacacct acctctctct | 300 |
| gggcttctat ttcgaccgcg atgatgtggc tctggaaggc gtgagccact tcttccgcga | 360 |
| attggccgag gagaagcgcg agggctacga gcgtctcctg aagatgcaaa accagcgtgg | 420 |
| cggccgcgct ctcttccagg acatcaagaa gccagctgaa gatgagtggg gtaaaacccc | 480 |
| agacgccatg aaagctgcca tggccctgga gaaaagctg aaccaggccc ttttggatct | 540 |
| tcatgccctg ggttctgccc gcacggaccc ccatctctgt gacttcctgg agactcactt | 600 |
| cctagatgag gaagtgaagc ttatcaagaa gatgggtgac cacctgacca acctccacag | 660 |
| gctgggtggc ccgaggctg gctgggcga gtatctcttc gaaaggctca ctctcaagca | 720 |
| cgactaagag ccttctgagc ccagcgactt ctgaagggcc ccttgcaaag taatagggct | 780 |
| tctgcctaag cctctccctc cagccaatag gcagctttct taactatcct aacaagcctt | 840 |
| ggaccaaatg gaaataaagc tttttgatgc aaaaaaaaaa aaaaaaaa | 889 |

<210> SEQ ID NO 23
<211> LENGTH: 15340
<212> TYPE: DNA
<213> ORGANISM: Homo sapien

<400> SEQUENCE: 23

| | |
|---|---|
| gcgccggctg agccagcggc tcttggggagg ctgcgtccgc gcgccggcga ggcgaggcgg | 60 |
| ccggggccctg cgcgtcaggc ctgagacctg ggaggaagct ggagaaaaga tgccctctga | 120 |

```
atctttctgt ttggctgccc aggctcgcct cgactccaaa tggttgaaaa cagatataca      180
gcttgcattc acaagagatg ggctctgtgg tctgtggaat gaaatggtta agatggagaa     240
aattgtatac actggaacag aatcaaccca gaacggagag ctccctccta gaaaagatga     300
tagtgtcgaa ccaagtggaa caaagaaaga agatctgaat gacaaagaga aaaagatga     360 agaagaaact cctgcaccta tatagggc caagtcaatt ctggacagct gggtatgggg      420
caagcaacca gatgtgaatg aactgaagga gtgtctttct gtgctggtta agagcagca     480 ggccctggcc gtccagtcag ccaccaccac cctctcagcc ctgcgactca agcagaggct     540
ggtgatcttg gagcgctatt tcattgcctt gaatagaacc gttttcagg agaatgtcaa     600 agttaagtgg aaaagcagcg gtatttctct gcctcctgtg acaaaaaaa gttcccggcc     660 tgcgggcaaa ggtgtggagg ggctcgccag agtgggatcc cgagcggcgc tgtcttttgc     720
ctttgccttc ctgcgcaggg cctggcgatc aggcgaggat gcggacctct gcagtgagct     780
gttgcaggag tccctggacg ccctgcgagc acttcccgag gcctcgctct ttgacgagag     840
caccgtgtcc tctgtgtggc tggaggtggt ggagagagcg accaggttcc tcaggtccgt     900
cgtgacgggg gatgttcacg gaacgccagc caccaaaggg ccaggaagca tcccctgca     960 ggaccagcac ttggccctgg ccatcctgct ggagctggct gtgcagagag gcacgctgag    1020
ccaaatgttg tctgccatcc tgttgttgct tcagctgtgg gacagcgggg cacaggagac    1080
tgacaatgag cgttccgccc agggcaccag cgccccactt ttgcccttgc tgcaaaggtt    1140
ccagagcatc atttgcagga aggatgcacc ccactccgag ggcgacatgc accttttgtc    1200
tggccctctg agccccaatg agagtttcct gaggtacctc acccttccac aagacaacga    1260
gcttgccatt gatctgcgac aaacggcggt tgttgtcatg gcccatttag accgtctggc    1320
tacgccctgt atgcctccgc tgtgtagctc tccgacatct cataagggat cattgcaaga    1380
ggtcataggt tgggggttaa taggatggaa atactatgcc aatgtgattg gtccaatcca    1440
gtgcgaaggc ctggccaacc tgggagtcac acagattgcc tgtgcagaga gcgtttcct     1500 gattctgtca cgcaatggcc gcgtgtacac acaggcctat aatagtgaca cgctggcccc    1560
acagctggtc caaggccttg cctccagaaa cattgtaaaa attgctgccc attctgatgg    1620
tcaccactac ctagccttgg ctgctactgg agaggtgtac tcctgggct gtggggacgg    1680 cggacggctg ggccatgggg acactgtgcc tttggaggag cctaaggtga tctccgcctt    1740
ctctggaaag caggccggga agcacgtggt gcacatcgct tgcgggagca cttacagtgc    1800
ggccatcact gccgaggggg agctgtacac ctggggccgc gggaactacg gccggctggg    1860
ccatggctcc agtgaggacg aggccattcc gatgctggta gccgggctta aaggactgaa    1920
ggtcatcgat gtgcgtgtg ggagtgggga tgctcaaacc ctggctgtca ctgagaacgg    1980
gcaagtgtgg tcttggggag atggtgacta tgggaaattg gcagaggtg gtagtgatgg    2040 ctgcaaaacc ccaaagctga ttgaaaagct tcaagacttg gatgtggtca agtccgctg    2100 tggaagtcag ttttccattg ctttgacgaa agatggccaa gtttattcat ggggaaaagg    2160
tgacaaccag agacttggac atggaacaga ggaacatgtt cgttatccaa aactcttaga    2220
aggcttgcaa gggaagaagg tgattgatgt ggctgcaggc tccacccact gcctggctct    2280
gactgaggac agcgaggtcc acagctgggg gagcaacgac cagtgccagc actttgacac    2340
cttgcgcgtg accaagccag aacctgcagc attgccagga ctggacacca aacacatagt    2400
gggaattgcc tgtgggcctg cccagagctt tgcttggtca tcatgttctg agtggtccat    2460
```

```
tggcctccgt gtcccttttg tggtggacat ctgctcaatg acttttgagc agctggatct   2520
cctgcttcgg caggtgagtg aggggatgga tggttccgcg gactggcccc cgccccagga   2580
gaaagagtgt gtggccgtgg caacgctgaa tcttctacga cttcagttgc atgctgccat   2640
tagtcaccag gttgacccgg aattccttgg tttaggtctg ggcagcatcc tcctgaacag   2700
cctgaagcag acggtggtga ccctggccag cagtgcgggc gtgctgagca ccgtgcagtc   2760
ggccgcccag gccgtgctgc agagtggctg gtccgtgctg ctgcccaccg cggaggagcg   2820
ggcccgggca ctctctgctc tcctgccctg cgcagtttca ggcaatgaag tgaacataag   2880
tccaggtcgt cgattcatga ttgatcttct ggtgggcagc ttgatggctg atggagggtt   2940
ggagtcagcc ttacacgcag ccattactgc agagatccag gatattgaag ccaaaaaga   3000
agcacagaag gaaaaagaaa ttgatgaaca ggaagcgaat gcctcaacat tcatagaag   3060
caggactcca ctggataaag accttattaa tacgggatc tgtgagtctt ctggcaaaca   3120
gtgtttgcct ctggttcagc tcatacaaca gcttcttaga aacattgctt ctcagactgt   3180
agccagattg aaagatgttg cccgtcggat ttcatcatgt ctggactttg agcaacacag   3240
tcgtgaaaga tctgcttcat tggatttgtt actgcgtttt caacgtttgc ttattagtaa   3300
actttatcca ggagaaagta ttggtcagac ctcagatatt tctagtccag agctaatggg   3360
tgttggttcc ttgctgaaga agtacacagc cctcctgtgc acgcacattg gagatatact   3420
gcctgtggcc gccagcattg cttctaccag ctggcggcac ttcgcggagg tggcttacat   3480
tgtggaaggg gactttactg gtgttctcct tccagaacta gtagtttcta tagtgcttct   3540
gctcagtaaa aatgctggtc tcatgcaaga ggctggagct gtacctctgc tgggtggcct   3600
gttggaacat ctggatcggt tcaaccatct ggcaccagga aggaacggg atgatcatga   3660
agagttagcc tggcctggca taatggagtc attttttaca ggtcagaact gtagaaataa   3720
tgaggaagtg acacttatac gcaaagctga tttggagaac cataataaag atggaggctt   3780
ctggactgtg attgacggga aggtgtatga tataaaggac ttccagacac agtcgttaac   3840
aggaaatagt attcttgctc agtttgcagg ggaagaccca gtggtagctt ggaagctgc   3900
tttgcagttt gaagacaccc gggaatccat gcacgcgttt tgtgttggcc agtatttgga   3960
gcctgaccaa gaaatcgtca ccataccaga tctgggagt ctctcttcac ctctgataga   4020
cacagagagg aatctgggcc tgcttctcgg attacgct tcgtatttgg caatgagcac   4080
accgctgtct cctgtcgaga ttgaatgtgc caaatggctt cagtcatcca tcttctctgg   4140
aggcctgcag accagccaga tccactacag ctacaacgag gagaaagacg aggaccactg   4200
cagctcccca gggggcacac ctgccagcaa atctcgactc tgctcccaca gacgggccct   4260
gggggaccat tcccaggcat ttctgcaagc cattgcagac aacaacattc aggatcacaa   4320
cgtgaaggac ttttgtgtc aaatagaaag gtactgtagg cagtgccatt tgaccacacc   4380
gatcatgttt ccccccgagc atcccgtgga agaggtcggt cgcttgttgt tatgttgcct   4440
cttaaaacat gaagatttag gtcatgtggc attatcttta gttcatgcag gtgcacttgg   4500
tattgagcaa gtaaagcaca gaacgttgcc taagtcagtg gtggatgttt gtagagttgt   4560
ctaccaagca aaatgttcgc tcattaagac tcatcaagaa cagggccgtt cttcaagga   4620
ggtctgcgct cctgtcatcg aacgtttgag attcctcttt aatgaattga gacctgctgt   4680
ttgtaatgac ctctctataa tgtctaagtt taaattgtta agttctttgc cccgttggag   4740
gaggatagct caaaagataa ttcgagaacg aaggaaaaag agagttccta agaagccaga   4800
atctacggat gatgaagaaa aaattggaaa cgaagagagt gatttagaag aagcttgcat   4860
```

```
tttgcctcat agtccaataa atgtggacaa gagacccatt gcaattaaat cacccaagga    4920
caaatggcag ccgctgttga gtactgttac aggtgttcac aaatacaagt ggttgaagca    4980
gaatgtgcag ggtctttatc cgcagtctcc actcctcagt acaattgctg aatttgccct    5040
taaagaagag ccagtggatg tggaaaaaat gagaaagtgc ctactaaaac agttggagag    5100
agcagaggtt cgcctggaag ggatagatac aattttaaaa ctggcgagca agaatttctt    5160
acttccatct gtgcagtatg cgatgttttg tggatggcaa agacttattc ctgagggaat    5220
cgatataggg gaacctctta ctgattgttt aaaggatgtt gatttgatcc cgccttttaa    5280
tcggatgctg ctggaagtca cctttggcaa gctgtacgct tgggctgtac agaacattcg    5340
aaatgttttg atggatgcca gtgccaaatt taaagagctt ggtatccagc cggttcccct    5400
gcaaaccatc accaatgaga acccgtcagg accgagcctg ggaccatcc cgcaagcccg    5460 cttcctcctg gtgatgctca gcatgctcac cctgcagcac ggcgcaaaca acctcgacct    5520
tctgctcaat tccggcatgc tggccctcac gcagacggca ctgcgcctga ttggccccag    5580
ttgtgacaac gttgaggaag atatgaatgc ttctgctcaa ggtgcttctg ccacagtttt    5640
ggaagaaaca aggaaggaaa cggctcctgt gcagctccct gtttcaggac cagaactggc    5700
tgccatgatg aagattggaa caagggtcat gagaggtgtg gactggaaat ggggcgatca    5760
ggatgggcct cctccaggcc taggccgcgt gattggtgag ctgggagagg acggatggat    5820
aagagtccag tgggacacag gcagcaccaa ctcctacagg atggggaaag aaggaaaata    5880
cgacctcaag ctggcagagc tgccggctgc tgcacagccc tcagcagagg attcggacac    5940
agaggatgac tctgaagccg aacaaactga aggaacatt caccccactg caatgatgtt    6000
taccagcact attaacttac tgcagactct ttgtctgtct gctggagttc atgctgagat    6060
catgcagagc gaagccacca agactttatg cggactgctg cgaatgttag tggaaagcgg    6120
aacgacggac aagacatctt ctccaaacag gctggtgtac agggagcaac accgagctg    6180 gtgcacgctg gggtttgtgc ggagcatcgc tctcacgccg caggtatgcg gcgccctcag    6240 ctcccccgcag tggatcacgc tgctcatgaa ggtcgtggaa gggcacgcac ccttcactgc    6300
cacctcgctg cagaggcaga tcttagctgt gcatttgttg caagcagtcc ttccatcatg    6360
ggacaagacc gaaagggcga gggacatgaa atgcctcgtg gagaagctgt ttgacttctt    6420
gggaagcttg ctcactacct gctcctctga cgtgccatta tcagagagt ccacgctgag    6480 gcggcgcagg gtgcgcccgc aggcctcgct gactgccacc cacagcagca cactggcgga    6540
ggaggtggtg gcactgctgc gcacgctgca ctccctgact cagtggaatg ggctcatcaa    6600
caagtacatc aactcccagc tccgctccat cacccacagc tttgtgggaa ggccttccga    6660
aggggcccag ttagaggact acttccccga ctccgagaac cctgaagtgg ggggcctcat    6720
ggcagtcctg gctgtgattg gaggcatcga tggtcgcctg cgcctgggcg tcaagttat    6780 gcacgatgag tttggagaag gcactgtgac tcgcatcacc ccaaagggca aaatcaccgt    6840
gcagttctct gacatgcgga cgtgtcgcgt ttgcccattg aatcagctga aaccactccc    6900
tgccgtggcc tttaatgtga acaacctgcc cttcacagag cccatgctgt ctgtctgggc    6960
tcagttggtg aaccctcgctg gaagcaagtt agaaaagcac aaaataaaga aatcgactaa    7020
acaggccttt gcaggacaag tggacctgga cctgctgcgg tgccagcagt tgaagctata    7080
catcctgaaa gcaggtcggg cgctgctctc ccaccaggat aaactgcggc agatcctgtc    7140
tcagccagct gttcaggaga ctggaactgt tcacacagat gatggagcag tggtatcacc    7200
```

```
tgaccttggg gacatgtctc ctgaagggcc gcagccccccc atgatcctct tgcagcagct    7260
gctggcctcg gccacccagc cgtctcctgt gaaggccata tttgataaac aggaacttga    7320
ggctgctgca ctggccgttt gccagtgctt ggctgtggag tccactcacc cttcgagccc    7380
aggatttgaa gactgcagct ccagtgaggc caccacgcct gtcgccgtgc agcacatccg    7440
ccctgccaga gtgaagaggc gcaagcagtc gcccgttccc gctctgccga tcgtggtgca    7500
gctcatggag atgggatttt ccagaaggaa catcgagttt gccctgaagt ctctcactgg    7560
tgcttccggg aatgcatcca gcttgcctgg tgtggaagcc ttggtcgggt ggctgctgga    7620
ccactccgac atacaggtca cggagctctc agatgcagac acggtgtccg acgagtattc    7680
tgacgaggag gtggtggagg acgtggatga tgccgcctac tccatgtcta ctggtgctgt    7740
tgtgacggag agccagacgt acaaaaaacg agctgatttc ttgagtaatg atgattatgc    7800
tgtatatgtg agagagaata ttcaggtggg aatgatggtt agatgctgcc gagcgtatga    7860
agaagtgtgc gaaggtgatg ttggcaaagt catcaagctg gacagagatg gattgcatga    7920
tctcaatgtg cagtgtgact ggcagcagaa agggggcacc tactgggtta ggtacattca    7980
tgtggaactt ataggctatc ctccaccaag ttcttcttct cacatcaaga ttggtgataa    8040
agtgcgggtc aaagcctctg tcaccacacc aaaatacaaa tggggatctg tgactcatca    8100
gagtgtgggg gttgtgaaag ctttcagtgc caatggaaaa gatatcattg tcgactttcc    8160
ccagcagtct cactgactg ggttgctatc agaaatggag ttggtaccca gtattcatcc    8220
tggggttacg tgtgatggat gtcagatgtt tcctatcaat ggatccagat tcaaatgcag    8280
aaactgtgat gactttgatt tttgtgaaac gtgtttcaag accaaaaaac acaataccag    8340
gcatacattt ggcagaataa atgaaccagg tcagtctgcg gtattttgtg gccgttctgg    8400
aaaacagctg aagcgttgcc acagcagcca gccaggcatg ctgctggaca gctggtcccg    8460
catggtgaag agcctgaatg tgtcgtcctc cgtgaaccag gcatcccgtc tcattgacgg    8520
cagcgagccc tgctggcagt catcggggtc gcaaggaaag cactggattc gtttgggagat    8580
tttcccagat gttcttgttc atagattaaa aatgatcgta gatcctgctg acagtagcta    8640
catgccgtcc ctggttgtag tgtcaggtgg aaattccctg aataacctta ttgaactaaa    8700
gacaatcaat attaaccctt ctgacaccac agtgcccctt ctgaatgact gcacagagta    8760
tcacaggtat attgaaattg ctataaagca gtgcaggagc tcaggaatcg attgtaaaat    8820
ccatggtctc atcctgctgg gacggatccg tgcagaagag gaagatttgg ctgcagttcc    8880
tttcttagct tcggataatg aagaggagga ggatgagaaa gcaacagcg gaagcctcat    8940
tagaaagaag gctgctgggc tggaatcagc agctacgata agaaccaagg tgtttgtgtg    9000
gggcctgaat gacaaggacc agctgggcgg gctgaaaggc tccaagataa aggttccttc    9060
gttctctgag acactgtcag ctttgaatgt ggtacaggtg gctggtggat ctaaaagttt    9120
gtttgcagtg actgtggaag ggaaggtgta tgcctgtgga gaagccacga atggccggct    9180
ggggctgggc atttccagcg ggacggtgcc catcccacgg cagatcacag ctctcagcag    9240
ctacgtggtc aagaaggtgg ctgttcactc aggtggccgg cacgcgacgg ctttaactgt    9300
cgatggaaaa gtgttttcgt ggggcgaagg tgacgatgaa aaacttggac acttcagcag    9360
aatgaactgt gacaaaccaa ggctgatcga ggccctgaaa accaagcgta tccgggatat    9420
cgcctgtggg agctcgcaca gcgcagccct cacatccagc ggagaactgt acacctgggg    9480
cctcggcgag tacggccggc tgggacatgg ggataatacg acacagctaa agcccaaaat    9540
ggtgaaagtc cttctcggtc acagagtaat ccaggttgca tgtgggagta gagacgcgca    9600
```

-continued

```
gaccctggct ctgaccgatg aaggtttggt attttcctgg ggtgatggtg actttggaaa    9660
actgggccgg ggcggaagtg aaggctgtaa cattccccag aacattgaga gactaaatgg    9720 acaggggtg  tgccagattg agtgtggagc tcagttctcc ctggcgctca ccaagtctgg    9780
agtggtgtgg acatggggaa aggggattac cttcagattg gccacggct  ctgacgtgca    9840 cgtgcggaaa ccacaggtgg tggaagggct gagagggaag aagatcgtgc atgtggctgt    9900
cggggccctg cactgcctgg cggtcacgga ctcggggcag gtgtatgctt ggggtgacaa    9960
cgaccacggc cagcagggca atggcacgac cacggttaac aggaagccca cactcgtgca   10020
aggcttagaa ggccagaaga tcacacgcgt ggcttgtggg tcgtcccaca gtgtggcgtg   10080
gacaactgtg gatgtggcca cgccctctgt ccacgagccc gtcctcttcc agactgcaag   10140
agacccttta ggtgcttcct atttaggcgt gccttcagat gctgattctt ctgctgccag   10200
taataaaata agtggtgcaa gtaattctaa gccaaatcgc ccttctcttg ccaagattct   10260
cttgtcattg gatggaaatc tggccaaaca gcaggcctta tcacatattc ttacagcatt   10320
gcaaatcatg tatgccagag atgctgttgt cggggccctg atgccggccg ccatgatcgc   10380
cccggtggag tgcccctcgt tctcctcggc ggccccttcc gacgcatctg cgatggctag   10440
tcccatgaat ggagaagaat gcatgctggc tgttgatatc gaagacagac tgagtccaaa   10500
tccatggcaa gaaagagag  agattgtttc ctctgaggac gcagtgaccc cctctgcagt   10560
gactccgtcg gccccctcag cctccgctcg gccttttatc ccagtgacgg atgacctggg   10620
agccgcaagc atcattgcag aaaccatgac caaaaccaaa gaggatgttg aaagccaaaa   10680
taaagcagca ggtccggagc tcaggccttt ggatgagttc accagtctgc tgattgcgga   10740
tgacactcgt gtggtggtag acctgctcaa gctgtcagtg tgcagccggg ccggggacag   10800
gggcagggat gtgctctccg cggtgctttc cggcatgggg accgcctacc cacaggtggc   10860
agatatgctg ttggagctct gtgtcaccga gttggaggat gtggccacag actcgcagag   10920
cggccgcctc tcttctcagc ctgtggtggt ggagagtagc caccttaca  ccgacgacac   10980 ctccaccagt ggcacagtga agataccagg tgcagaagga ctcagggtag aatttgaccg   11040
gcagtgctcc acagagaggc gccacgaccc tctcacagtc atggacggcg tcaacaggat   11100
cgtctccgtg cggtcaggcc gagagtggtc cgactggtcc agcgagctgc gcatcccagg   11160
ggatgagtta aagtggaagt tcatcagcga tgggtctgtg aatggctggg gctggcgctt   11220
caccgtctat cccatcatgc cagctgctgg ccctaaagaa ctcctctctg accgctgcgt   11280
cctctcctgt ccatccatgg acttggtgac gtgtctgtta gacttccgac tcaaccttgc   11340
ctctaacaga gcatcgtcc  ctcgccttgc ggcctcgctg gcagcttgtg cacagctgag   11400
tgccctagct gccagtcaca gaatgtgggc ccttcagaga ctgaggaagc tgcttacaac   11460
tgaatttggg cagtcaatta acataaatag gctgcttgga gaaaatgatg gggaaacaag   11520
agctttgagt tttacaggta gtgctcttgc tgctttggtg aaaggtcttc cagaagcttt   11580
gcaaaggcag tttgaatatg aagatcctat tgtgaggggt ggcaaacagc tgctccacag   11640
cccattcttt aaggtactgg tagctcttgc ttgtgacctg gagctggaca ctctgccttg   11700
ctgtgccgag acgcacaagt gggcctggtt ccggaggtac tgcatggcct cccgtgttgc   11760
tgtggccctt gacaaaagaa caccgttgcc ccgtctgttt cttgatgagg tggctaagaa   11820
aattcgtgaa ttaatggcag acagcgaaaa catggatgtt ctgcatgaga gcatgacat   11880 ttttaaaaga gagcaagacg aacaacttgt gcagtggatg aacaggcgac cagatgactg   11940
```

```
gactctctct gctggtggca gtggaacaat ttatggatgg ggacataatc acaggggcca   12000
gctcgggggc attgaaggcg caaaagtcaa agttcccact ccctgtgaag cccttgcaac   12060
tctcagaccc gtgcagttaa tcggagggga acagaccctc tttgctgtga cggctgatgg   12120
gaagctgtat gccactgggt atggtgcagg tggcagacta ggcattggag gacagagtc    12180 ggtgtccacc ccaacattgc ttgaatccat tcagcatgtg tttattaaga aagtagctgt   12240
gaactctgga ggaaagcact gccttgccct gtcttcagaa ggagaagttt actcttgggg   12300
tgaggcagaa gatgggaagt tggggcatgg caacagaagt ccgtgtgacc gccctcgtgt   12360
catcgagtct ctgagaggaa ttgaagtggt cgatgttgct gctggcggag cccacagcgc   12420
ctgtgtcaca gcagccgggg acctctacac atggggcaaa ggccgctacg gccggctggg   12480
gcacagcgac agtgaggacc agctgaagcc gaagctggtg gaggcgctgc agggccaccg   12540
tgtggttgac atcgcctgtg gcagtggaga tgcccagacc ctctgcctca cagatgacga   12600
cactgtctgg tcctgggggg acggggacta cggcaagctc ggccggggag gcagcgatgg   12660
ctgtaaagtg cctatgaaga ttgattctct tactggtctt ggagtagtta aagtggaatg   12720
cggatcccag ttttctgttg cccttaccaa atctggagct gtttatacct ggggcaaagg   12780
cgattatcac aggttgggcc atggatcaga tgaccatgtt cgaaggcctc ggcaggtcca   12840
agggttgcag gggaagaaag tcatcgccat cgccactggc tccctgcact gtgtgtgctg   12900
cacagaggat ggtgaggttt atacatgggg cgacaatgat gagggacaac tgggagacgg   12960
aaccaccaat gccatccaga ggcctcggtt ggtagctgcc cttcagggta agaaggtcaa   13020
ccgtgtggcc tgtggctcag cacatacct cgcctggtcg accagcaagc ccgccagtgc    13080
tggcaaactc cctgcacagg tccccatgga gtacaatcac ctgcaggaga tccccatcat   13140
tgcgctgagg aaccgtctgc tgctgctgca ccacctctcc gagctcttct gcccctgcat   13200
ccccatgttc gacctggaag gctcgctcga cgaaactgga ctcgggcctt ctgttgggtt   13260
cgacactctc cgaggaattc tgatatccca gggaaaggag gcggctttcc ggaaagtagt   13320
acaagcaact atggtacgcg atcgtcagca tggccccgtc gtggagctga ccgcatcca    13380 ggtcaaacga tcaaggagca aaggcgggct ggccggcccc gacggcacca agtctgtctt   13440
tgggcagatg tgtgctaaga tgagctcgtt tggtcccgac agcctcctcc ttcctcaccg   13500
tgtctggaaa gtcaagtttg tgggtgaatc tgtggatgac tgtgggggcg gctacagcga   13560
gtccatagct gagatctgtg aggagctgca gaacggactc acgcccctgc tgatcgtgac   13620
acccaacggg agggatgagt ctggggccaa ccgagactgc tacctgctca gcccggccgc   13680
cagagcaccc gtgcacagca gcatgttccg cttcctgggt gtgttgctgg gcattgccat   13740
ccgaaccggg agtcccctga gcctcaacct tgccgagcct gtctggaagc agctggctgg   13800
gatgagcctc accatcgcgg acctcagtga ggttgataag gattttattc ctggactcat   13860
gtacatccga gacaatgaag ccacctcaga ggagtttgaa gccatgagcc tgcccttcac   13920
agtgccaagt gccagtggcc aggacattca gttgagctcc aagcacacac acatcaccct   13980
ggacaaccgc gcggagtacg tgcggctggc gataaactat agactccatg aatttgatga   14040
gcaggtggct gctgttcggg aaggaatggc ccgcgttgtg cctgttcccc tcctctctct   14100
gttcaccggc tacgaactgg agacgatggt gtgtggcagc cctgacatcc cgctgcacct   14160
tctcaagtcg gtggccacct ataaaggcat cgagccttcc gcatcgctga tccagtggtt   14220
ctgggaggtg atggagtcct tctccaacac agagcgctct cttttccttc gcttcgtctg   14280
gggccggacg aggctgccca ggaccatcgc cgacttccgg ggccgagact cgtcatcca    14340
```

```
ggtgttggat aaatacaacc ctccagacca cttcctccct gagtcctaca cctgtttctt     14400
cttgctgaag ctgcccaggt attcctgcaa gcaggtgctg gaggagaagc tcaagtacgc     14460
catccacttc tgcaagtcca tagacacaga tgactacgct cgcatcgcac ttacaggaga     14520
gccagccgcc gacgacagca gcgacgattc agataacgag gatgtcgact cctttgcttc     14580
ggactctaca caagattatt taacaggaca ctaagatggg gaaacgtcct cgtgagatga     14640
gagcctgagc caggcagcag agcgctcgct gctgtgtaga ctgtaggctg cctggtgtgt     14700
ctgatgagaa gcgtccgtcc tcgagccagg cgggaggagg gagtggagag actgactggc     14760
cgtgatggga atgacagtga gaaggtccgc ctgtgcgcgt ggaacactgt ggacgctcga     14820
cttccaaggg tcttctcacc cgtaatgctg cattacatgt aggactgtgt ttactaaagt     14880
gtgtaaatgt ttatataaat accaaattgc agcatcccca aaatgaataa agcctttta      14940 cttgtgggtg caatcgattt ttttctttc tcctttcttt caagtgtcgt gagtcgtctt      15000
gattgtatat tggaaataac tgtgtaacaa atcgtattat aaatatttca attaatttta     15060
ctctgaattt gtttattaaa agactttga  acatgaaatg attagtatta cttgaatgca     15120
tccagaggat atttaaacca aaatgaaaaa ccagaaggcc atttggtgtc ccccctccca     15180
ggtgtcccct tgtagcatat gcattatgtc atctgaattg aggcctttct gtgaacagca     15240
tcataacttc tatcatggaa agtgtactat atataatgtt tgtgtcatgt atatgcctaa     15300 atttaatta tctataaata aaacatctga cataaaagtg                             15340

<210> SEQ ID NO 24
<211> LENGTH: 1031
<212> TYPE: DNA
<213> ORGANISM: Homo sapien

<400> SEQUENCE: 24
cgacagccgg aagtcccgcc tgccgtgtag tcgccgccgt cgctgccgct gccgctgccg       60
ccgtcgttgt tgttgtgctc ggtgcgctga gctccgcggc tccgcgagcc ggttccgtcc      120
ccttcccgcc gccgccatga agtggatgtt caaggaggac cactcgctgg aacacagatg      180
cgtggagtcc gcgaagattc gagcgaaata tcccgacagg gttccggtga ttgtggaaaa      240
ggtctcaggc tctcagattg ttgacattga caaacggaag tacttggttc catctgatat      300
cactgtggct cagttcatgt ggatcatcag gaaaaggatc cagcttcctt ctgaaaaggc      360
gatcttcctg tttgtggata agacagtccc acagtccagc ctaactatgg gacagcttta      420
cgagaaggaa aaagatgaag atggattctt atatgtggcc tacagcggag agaacacttt      480
tggcttctga gggccattgc tgggctaggt gcaccgtaac tgcttgtgta tcttgtaaat      540
agccagccat tttcagttat tataccagaa cctcttcaca tagacctatt agtgcatttg      600
taactggatt tatttcttaa tatattggaa ggttttgttt ccttagacta gtaaattatc      660
atacagagtt ttattttgag ttttttcttt tgtgcattgt cctcatgcct gtattctcca      720
ggaaacttgt ccttctggaa atcatattga atgatatttc tatatcgaag tgaggtaggt      780
gcggtattaa agtgaaaggg aaggtgatgc atttattctg ggttatgctt gaagtgttag      840
atggctaagt attaaaatta tccaaattaa atccttagca gtcagaacac ttgcttcact      900
agaatatgcc aactgccaat catgttggac tgagctaatt tgttcctctt tctgaaacta      960
ttaaggtaaa taattaacaa taaaaattct cttataaagg caaaaaaaaa aaaaaaaaaa     1020
aaaaaaaaaa a                                                          1031
```

```
<210> SEQ ID NO 25
<211> LENGTH: 994
<212> TYPE: DNA
<213> ORGANISM: Homo sapien

<400> SEQUENCE: 25
gccaggtgca aggagaaagg attttgagga ggggactcca tggcttccga gttgctgact        60
gaccctccac ctcagaggta gttctgacac tgtctcagtt ttgcagatga agatgagatt       120
cttcagttct ccatgtggaa aagcagctgt ggacccagcc gaccgctgta aggaggtaca       180
gcagatccgc gaccagcacc ccagcaaaat cccggtgatc atcgagcgct acaagggtga       240
gaagcagctg cccgtcctgg acaagaccaa gttttttggtc ccggaccatg tcaacatgag       300
cgagttggtc aagatcatcc ggcgccgcct gcagctgaac cccacgcagg ccttcttcct       360
gctggtgaac cagcacagca tggtgagtgt gtccacgccc atcgcggaca tctacgagca       420
ggagaaagac gaggacggct tcctctatat ggtctacgcc tcccaggaaa ccttcggctt       480
ctgagccagc agtagggggg ctcggcctgg gagtcgggcg gccccggtca ggccctgccc       540
agagagctcc tggttcctga actgagctgc ctctaccgtg gtgggctggg caggcatgtg       600
cccccctagt cagagggcac caacccacct actctgcccc tgggtggatc ctgggccggt       660
cgtgttaggg ttgtccctct gggtgctggc tggtgggatg ggggagggtg gggagcagct       720
cccagcaccc ctgctgtgtg gttcatcttt ttttttaggcc cctgcctgtc tgcccatctg       780
cccctcaccc acccgaggct ctgcccaccg cctggacctg cccacccctg aaagactggc       840
ccctggctcc ccgcccctcg gtctccacgt ggtgtatgga tctgtggtca ttgtccctct       900
gcagaataaa gattgctcag gcctgcctgg caaaaaaaaa aaaaaaaaaa aaaaaaaaaa       960
aaaaaaaaaa aaaaaaaaaa aaaaaaaaaa aaaa                                   994
```

UNITED STATES PATENT AND TRADEMARK OFFICE
CERTIFICATE OF CORRECTION

PATENT NO. : 10,350,264 B2
APPLICATION NO. : 15/126350
DATED : July 16, 2019
INVENTOR(S) : Alec C. Kimmelman, Joseph D. Mancias and Jeffrey Wade Harper Page 1 of 1

It is certified that error appears in the above-identified patent and that said Letters Patent is hereby corrected as shown below:

On the Title Page

Item (71) Applicants:
Before "Brigham" insert -- The --.

Signed and Sealed this
Fifth Day of November, 2019

Andrei Iancu
*Director of the United States Patent and Trademark Office*